(12) United States Patent
Swanson et al.

(10) Patent No.: US 11,820,812 B2
(45) Date of Patent: *Nov. 21, 2023

(54) RSV F PROTEIN COMPOSITIONS AND METHODS FOR MAKING SAME

(71) Applicant: GLAXOSMITHKLINE BIOLOGICALS SA, Rixensart (BE)

(72) Inventors: Kurt Swanson, Newton, MA (US); Philip R. Dormitzer, Weston, MA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 142 days.

This patent is subject to a terminal disclaimer.

(21) Appl. No.: 17/564,962

(22) Filed: Dec. 29, 2021

(65) Prior Publication Data

US 2022/0213177 A1 Jul. 7, 2022

Related U.S. Application Data

(63) Continuation of application No. 15/678,798, filed on Aug. 16, 2017, now Pat. No. 11,261,239, which is a continuation of application No. 12/836,931, filed on Jul. 15, 2010, now abandoned.

(60) Provisional application No. 61/294,426, filed on Jan. 12, 2010, provisional application No. 61/225,805, filed on Jul. 15, 2009.

(51) Int. Cl.
| | |
|---|---|
| *C07K 16/10* | (2006.01) |
| *A61K 39/155* | (2006.01) |
| *A61K 39/12* | (2006.01) |
| *C07K 14/005* | (2006.01) |
| *A61K 39/00* | (2006.01) |

(52) U.S. Cl.
CPC .......... *C07K 16/1027* (2013.01); *A61K 39/12* (2013.01); *A61K 39/155* (2013.01); *C07K 14/005* (2013.01); *A61K 39/00* (2013.01); *A61K 2039/5252* (2013.01); *A61K 2039/5256* (2013.01); *A61K 2039/5258* (2013.01); *A61K 2039/53* (2013.01); *A61K 2039/55505* (2013.01); *A61K 2039/55555* (2013.01); *A61K 2039/55561* (2013.01); *A61K 2039/55566* (2013.01); *A61K 2039/55572* (2013.01); *C07K 2317/76* (2013.01); *C07K 2319/00* (2013.01); *C07K 2319/21* (2013.01); *C07K 2319/50* (2013.01); *C07K 2319/73* (2013.01); *C12N 2760/18522* (2013.01); *C12N 2760/18534* (2013.01); *C12N 2770/36143* (2013.01)

(58) Field of Classification Search
None
See application file for complete search history.

(56) References Cited

U.S. PATENT DOCUMENTS

| | | | |
|---|---|---|---|
| 4,235,877 | A | 11/1980 | Fullerton |
| 4,372,945 | A | 2/1983 | Likhite |
| 4,436,727 | A | 3/1984 | Ribi |
| 4,474,757 | A | 10/1984 | Arnon et al. |
| 4,707,543 | A | 11/1987 | Zollinger et al. |
| 4,866,034 | A | 9/1989 | Ribi |
| 4,877,611 | A | 10/1989 | Cantrell |
| 4,912,094 | A | 3/1990 | Myers et al. |
| 5,057,540 | A | 10/1991 | Kensil et al. |
| 5,149,650 | A | 9/1992 | Wertz et al. |
| 5,194,595 | A | 3/1993 | Wathen |
| 5,278,302 | A | 1/1994 | Caruthers et al. |
| 5,639,853 | A | 6/1997 | Paradiso et al. |
| 5,666,153 | A | 9/1997 | Copeland |
| 5,691,449 | A | 11/1997 | Paradiso et al. |
| 5,726,292 | A | 3/1998 | Lowell |
| 5,750,110 | A | 5/1998 | Prieels et al. |
| 5,776,468 | A | 7/1998 | Hauser et al. |
| 5,856,462 | A | 1/1999 | Agrawal |
| 5,958,765 | A | 9/1999 | Brams et al. |
| 5,985,284 | A | 11/1999 | Lowell |
| 6,005,099 | A | 12/1999 | Davies et al. |
| 6,060,308 | A | 5/2000 | Parrington |
| 6,113,911 | A | 9/2000 | Binz et al. |
| 6,303,347 | B1 | 10/2001 | Johnson et al. |
| 6,764,840 | B2 | 7/2004 | Johnson et al. |
| 7,357,936 | B1 | 4/2008 | Garcon |

(Continued)

FOREIGN PATENT DOCUMENTS

| | | |
|---|---|---|
| CA | 2710600 | 6/2017 |
| EP | 0109942 B1 | 3/1991 |

(Continued)

OTHER PUBLICATIONS

US 6,008,200 A, 12/1999, Krieg (withdrawn)
Sissoeff et al., Journal of General Virology (2005), 86, 2543-2552 (Year: 2005).*
Sequence Comparison 2023 NPL (Year: 2023).*
Extended European Search Report for European Application No. 21199223.5, dated Jul. 18, 2022.
Mclellan et al., "Structural basis of respiratory syncytial virus neutralization by motavizumab," Nature Structural & Molecular Biology, vol. 17, No. 2, Feb. 2010, pp. 248-250.

(Continued)

*Primary Examiner* — Shanon A. Foley
*Assistant Examiner* — Myron G Hill
(74) *Attorney, Agent, or Firm* — Morgan, Lewis & Bockius LLP

(57) ABSTRACT

The present invention relates to immunogenic compositions comprising RSV F protein, methods for preparing compositions that contain RSV F protein ecto-domain polypeptides, and to certain engineered RSV F proteins and nucleic acids that encode the engineered RSV F proteins. Compositions prepared using the methods can contain RSV F protein ecto-domain polypeptides in a predominant or single desired form and conformation. The invention also relates to methods for inducing an immune response to RSV F.

12 Claims, 13 Drawing Sheets

Specification includes a Sequence Listing.

(56) References Cited

U.S. PATENT DOCUMENTS

| | | | |
|---|---|---|---|
| 7,368,537 | B2 | 5/2008 | Anderson et al. |
| 8,563,002 | B2 | 10/2013 | Baudoux et al. |
| 2003/0044425 | A1 | 3/2003 | Burt et al. |
| 2003/0232326 | A1 | 12/2003 | Fouchier et al. |
| 2004/0161846 | A1 | 8/2004 | Mason et al. |
| 2005/0042230 | A1 | 2/2005 | Anderson et al. |
| 2007/0178469 | A1 | 8/2007 | Mermod et al. |
| 2008/0233150 | A1 | 9/2008 | Smith et al. |
| 2008/0300382 | A1 | 12/2008 | Libon et al. |
| 2010/0261155 | A1 | 10/2010 | Peeples et al. |
| 2010/0291147 | A1 | 11/2010 | Baudoux et al. |
| 2011/0177117 | A1 | 7/2011 | Blais et al. |
| 2011/0206758 | A1 | 8/2011 | Vandepapeliere |
| 2012/0093847 | A1 | 4/2012 | Baudoux et al. |
| 2012/0135028 | A1 | 5/2012 | Blais et al. |
| 2012/0164176 | A1 | 6/2012 | Swanson et al. |

FOREIGN PATENT DOCUMENTS

| | | | |
|---|---|---|---|
| EP | 0362279 B1 | 1/1995 | |
| EP | 0689454 B1 | 9/1997 | |
| EP | 3508505 A1 | 7/2019 | |
| GB | 2220211 A | 1/1990 | |
| JP | 2001-514857 | 9/2001 | |
| WO | 1989/005823 A1 | 6/1989 | |
| WO | 1994/015968 A1 | 7/1994 | |
| WO | 1994/21292 A1 | 9/1994 | |
| WO | 1995/14026 A1 | 5/1995 | |
| WO | 1995/26204 A1 | 10/1995 | |
| WO | 1996/02555 A1 | 2/1996 | |
| WO | 1996/11711 A1 | 4/1996 | |
| WO | 1996/33739 A1 | 10/1996 | |
| WO | 1998/50399 A1 | 11/1998 | |
| WO | 99/11808 A1 | 3/1999 | |
| WO | 1999/14334 A1 | 3/1999 | |
| WO | 1999/33488 A2 | 7/1999 | |
| WO | 1999/64301 A1 | 12/1999 | |
| WO | 2000/00462 A1 | 1/2000 | |
| WO | 2001/46127 A1 | 6/2001 | |
| WO | 2002/42326 A1 | 5/2002 | |
| WO | 2002/074969 A2 | 9/2002 | |
| WO | 2002/085905 A1 | 10/2002 | |
| WO | 2003/011223 A2 | 2/2003 | |
| WO | 2003/043572 A2 | 5/2003 | |
| WO | WO 2003/083095 A1 | 10/2003 | |
| WO | 2003/099195 A2 | 12/2003 | |
| WO | 2004/071459 A2 | 8/2004 | |
| WO | WO 2006/011060 A2 | 2/2006 | |
| WO | 2006/038131 A2 | 4/2006 | |
| WO | 2006/042156 A2 | 4/2006 | |
| WO | WO 2008/061243 A2 | 5/2008 | |
| WO | 2008/114149 A2 | 9/2008 | |
| WO | WO 2008/154456 A2 | 12/2008 | |
| WO | WO 2009/079796 A1 | 7/2009 | |
| WO | WO-2009079796 A1 * | 7/2009 | ............ A61K 39/12 |
| WO | 2009/128951 A2 | 10/2009 | |
| WO | WO 2010/009277 A2 | 1/2010 | |
| WO | WO 2010/077712 A1 | 7/2010 | |
| WO | WO 2010/077717 A1 | 7/2010 | |
| WO | WO 2010/149743 A2 | 12/2010 | |
| WO | WO 2010/149745 A1 | 12/2010 | |
| WO | 2011/008974 A2 | 1/2011 | |
| WO | WO 2012/128628 A1 | 9/2012 | |
| WO | WO 2012/158613 A1 | 11/2012 | |
| WO | WO 2013/017713 A1 | 2/2013 | |
| WO | 2016/061240 A1 | 4/2016 | |
| WO | 2018/176103 A1 | 10/2018 | |

OTHER PUBLICATIONS

Sissoeff et al., "Stable trimerization of recombinant rabies virus glycoprotein ectodomain is required for interaction with the p75NTR receptor," Journal of General Virology, vol. 86, 2005, pp. 2543-2552.

Blais, N. et al., "Characterization of Pre-F-GCN4t, a Modified Human Respiratory Syncytial Virus Fusion Protein Stabilized in a Noncleaved Prefusion Conformation." Journal of virology vol. 91,13 (2017):e02437-16.

European Search Report for European Patent Application No. 22181398.3 dated Nov. 24, 2022, 8 pages.

McLellan, J. et al., "Structure of RSV fusion glycoprotein trimer bound to a prefusion-specific neutralizing antibody." Science vol. 340,6136 (2013): 1113-7.

McLellan, J. et al., "Structure-based design of a fusion glycoprotein vaccine for respiratory syncytial virus." Science vol. 342,6158 (2013): 592-8.

Sastre, P. et al., "Comparison of affinity chromatography and adsorption to vaccinia virus recombinant infected cells for depletion of antibodies directed against respiratory syncytial virus glycoproteins present in a human immunoglobulin preparation." Journal of medical virology vol. 76,2 (2005): 248-55.

Singh, S. et al., "Immunogenicity and efficacy of recombinant RSV-F vaccine in a mouse model." Vaccine vol. 25,33 (2007): 6211-23.

Van Drunen Littel-van den Hurk, S. et al., "Immunopathology of RSV infection: prospects for developing vaccines without this complication." Reviews in medical virology vol. 17,1 (2007): 5-34.

Russell, C. and Luque L., "The structural basis of paramyxovirus invasion." Trends in microbiology vol. 14,6 (2006): 243-6.

Schmidt, U. et al., "Mucosal immunization with live recombinant bovine respiratory syncytial virus (BRSV) and recombinant BRSV lacking the envelope glycoprotein G protects against challenge with wild-type BRSV." Journal of virology vol. 76,23 (2002): 12355-9.

Amdt KM et al., "Comparison of in vivo selection and rational design of heterodimeric coiled coils," Structure, 2002, pp. 1235-1248.

Blanco JC et al., "New insights of development of a safe and protective RSV vaccine," Hum Vaccin., vol. 6, 2010, pp. 482-492.

Calder LJ et al., "Electron microscopy of the human respiratory syncytial virus fusion protein and complexes that it forms with monoclonal antibodies," Virology, vol. 271, 2000, pp. 122-131.

Chao H et al., "Use of a heterodimeric coiled-coil system for biosensor application and affinity purification," J Chromatog B Biomed Sci Appl., vol. 715, No. 1, 1998, pp. 307-329.

Chen B et al., "A chimeric protein of simian immunodeficiency virus envelope glycoprotein gp140 and *Escherichia coli* aspartate transcarbamoylase," J Virol., vol. 78, 2004, pp. 4508-4516.

Connolly, SA et al., "Refolding a paramyxovirus F protein from prefusion to postfusion conformations observed by iposome binding and electron microscopy," PNAS, vol. 103, 2006, pp. 17903-17908.

Day ND et al., "Contribution of cysteine residues in the extracellular domain of the F protein of human respiratory syncytial virus to its function," Virol. J., vol. 3, No. 34, 2006.

Durbin et al., "Progress in the development of respiratory syncytial virus and parainfluenza virus vaccines," Clin Infect Dis., vol. 37, No. 12, 2003, pp. 1668-1677.

Fretzayas A and Moustaki M., "The challenges of RSV vaccines. Where do we stand?," Recent Pat Antiinfect Drug8 Discov., vol. 5, 2010, pp. 99-107.

Fusion protein UniProtKB/Swiss-Prot: 082022 dated 2006.

Gardner AE and Dutch RE, "A conserved region in the F(2) subunit of paramyxovirus fusion proteins is involved in fusion regulation," J Virol., vol. 81, 2007, pp. 8303-8314.

GI: 138250; UniProtKB: locus FUS_HRSV1, accession P13843.

GI: 138251; UniProtKB: locus FUS_HRSVA, accession P03420.

Gonzalez-Reyes et al., "Cleavage of the human respiratory syncytial virus fusion protein at two distinct sites is required for activation of membrane fusion," PNAS, vol. 98, No. 17, 2001, pp. 9859-9864.

Harbury PB et al., "A switch between two-, three-, and four-stranded colled coils in GCN4 leucine zipper mutants, " Science, vol. 262, 1993, pp. 1401-1407.

International Search Report from corresponding PCT/US2010/042161, dated Mar. 10, 2011.

(56) References Cited

OTHER PUBLICATIONS

Kammerer RA, "Alpha-helical coiled-coil oligomerization domains in extracellular proteins," Matrix Bioi., vol. 15, 1997, pp. 555-565.
Lamb, RA and Jardelzky, TS, "Structural basis of viral invasion; lessons from paramyxovirus F," Curr. Opin. Struc. Biology, vol. 17, 2007, p. 427.
Lee JK et al., "Reversible Inhibition of the Fusion Activity of Measles Virus F Protein by an Engineered Intersubunit Disulfide Bridge," J. Viral., vol. 81, 2007, pp. 8821-8826.
Liu J and Lu M, "An alanine-zipper structure determined by long range intermolecular interactions," J Bioi Chem., vol. 277, 2002, pp. 48708-48713.
Magro M et al., "Neutralizing antibodies against the preactive form of respiratory syncytial virus fusion protein offerunique possibilities for clinical intervention," PNAS, vol. 109, 2012, pp. 3089-3094.
Martinet et al., "Sequence elements of the fusion peptide of human respiratory syncytial virus fusion protein required for activity," J. General Virology, vol. 87, 2006, pp. 1649-1658.
Mclellan JS et al., "Structure of a major antigenic site on the respiratory syncytial virus fusion gycloprotein in complex with neutralizing antibody 101 F," J Viral, vol. 84, 2010, pp. 12236-12244.
Mclellan JS et al., "Structure of respiratory syncytial virus fusion glycoprotein in the postfusion conformation reveals 19 preservation of neutralizing epitopes," J Viral, vol. 85, 2011, pp. 7788-7796.
Muller KM et al., "Protein fusions to coiled-coil domains," Methods Enzymol., vol. 328, 2000, pp. 261-282.
Pancera et al., "Soluble mimetics of human immunodeficiency virus type 1 viral spikes produced by replacement of the native trimerization domain with a heterologous trimerization motif: characterization and ligand binding analysis," J. Virol., vol. 79, No. 15, 2005, pp. 9954-9969.
Rigter, A et al., "A Protective and Safe Intranasal RSV Vaccine Based on a Recombinant Prefusion-Like Form of the F Protein Bound to Bacterium-Like Particles," PlosOne, vol. 8, 2013, e71072.
Ruiz-ArgOello et al., "Effect of Proteolytic Processing at Two Distinct Sites on Shape and Aggregation of an Anchorless Fusion Protein of Human Respiratory Syncytial Virus and Fate of the Intervening Segment," Virology, vol. 298, No. 2, 2002, pp. 317-326.
Ruiz-ArgOello et al., "Thermostability of the human respiratory syncytial virus fusion protein before and after activitation: implications for the membrane-fusion mechanism," J. General Virology, vol. 85, 2004, pp. 3677-3687.
Sarmiento et al., "Characterization of a persistent respiratory syncytial virus showing a lowfusogenic activity associated to an impaired F protein," Virus Research, vol. 139, No. 1, 2009, pp. 39-47.
Schmidt, A.C., "Progress in Respiratory Virus Vaccine Development," Semin Respir Crit Care Med., vol. 32, No. 4, 2011, pp. 527-540.
Stevens J et al., "Structure of the uncleaved human H1 hemagglutinin from the extinct 1918 influenza virus," Science, vol. 303, 2004, pp. 1866-1870.
Sugrue et al., "Furin Cleavage of the Respiratory Syncytial Virus Fusion Protein is not a Requirement for Its Transport to the Surface of Virus-Infected Cells," J. General Virology, vol. 82, No. 6, 2001, pp. 1375-1386.
Swanson, KA et al., "Structural basis for immunization with postfusion respiratory syncytial virus fusion F glycoprotein (RSV F) to elicit high neutralizing antibody titers," PNAS, vol. 108, 2011, pp. 9619-9624.
Valarcher et al., "Bovine respiratory syncytial virus lacking the virokinin or with a mutation in furin cleavage site RA (R/K) R109 induces less pulmonary inflammation without impeding the induction of protective immunity in calves," J. General Virology, vol. 87, No. 6, 2006, pp. 1659-1667.
Van Braeckel-Budimir, N et al., "Bacterium-like particles for efficient immune stimulation of existing vaccines and new subunit vaccines in mucosal applications," Front. Immunol., vol. 4, 2013, p. 282.
Yang X et al., "Highly stable trimers formed by human immunodeficiency virus type 1 envelope glycoproteins fused with the trimeric motif of T4 bacteriophage fibritin," J Virol., No. 76, 2002, pp. 4634-4642.
Yin et al., "Structure of the parainfluenza virus 5 F protein in its mestastable, prefusion conformation." Nature, vol. 439, No. 5, 2006, pp. 38-44.
Yin, HS et al., "Structure of the uncleaved ectodomain of the paramyxovirus (hPIV3) fusion protein," PNAS, vol. 1, 2005, pp. 9288-9293.
Zhang Y and Chen O, "The noncollagenous domain 1 of type X collagen. A novel motif for trimer and higher order multimer formation without a triple helix," J Bioi Chem, vol. 274, 1999, pp. 22409-22413.
Zimmer et al., "Cleavage at the furin consensus sequence RAR/KR109 and presence of the intervening peptide of the respiratory syncytial virus fusion protein are dispensable for virus replication in cell culture," Journal of Virology, vol. 76, No. 18, 2002, pp. 9218-9224.
Zimmer et al., "Proteolytic activation of respiratory syncytial virus fusion protein: Cleavage at two furin consensus sequences," J. Biological Chemistry, vol. 276, No. 34, 2001, pp. 31642-31650.
Partial European Search Report for European Application No. 21199223.5, dated Mar. 14, 2022.
Bembridge, G. et al., "Priming with a secreted form of the fusion protein of respiratory syncytial virus (RSV) promotes interleukin-4 (IL-4) and IL-5 production but not pulmonary eosinophilia following RSV challenge." Journal of virology vol. 73,12 (1999): 10086-94.
Bolt, G. et al., "Cleavage of the respiratory syncytial virus fusion protein is required for its surface expression: role of furin." Virus research vol. 68,1 (2000): 25-33.
Brideau, R. and Wathen, M., "A chimeric glycoprotein of human respiratory syncytial virus termed FG induces T-cell mediated immunity in mice." Vaccine vol. 9,12 (1991): 863-4.
Connors, M. et al., "Cotton rats previously immunized with a chimeric RSV FG glycoprotein develop enhanced pulmonary pathology when infected with RSV, a phenomenon not encountered following immunization with vaccinia—RSV recombinants or RSV." Vaccine vol. 10,7 (1992): 475-84.
Dormitzer, P. et al., "Structure-based antigen design: a strategy for next generation vaccines." Trends in biotechnology vol. 26,12 (2008): 659-67.
Eckardt-Michel, J. et al., "The fusion protein of respiratory syncytial virus triggers p53-dependent apoptosis." Journal of virology vol. 82,7 (2008): 3236-49.
Elliott, S. et al., "Enhancement of therapeutic protein in vivo activities through glycoengineering." Nature biotechnology vol. 21,4 (2003): 414-21.
EP10724879: Oct. 17, 2014 Written Submission by Applicant.
EP10724879: Jun. 3, 2013 Response by Applicant.
EP10724879: Oct. 6, 2014 Written Submission by Applicant.
Ewasyshyn, M et al., "Comparative analysis of the immunostimulatory properties of different adjuvants on the immunogenicity of a prototype parainfluenza virus type 3 subunit vaccine." Vaccine vol. 10,6 (1992): 412-20.
Falsey, A. et al., "Comparison of the safety and immunogenicity of 2 respiratory syncytial virus (rsv) vaccines—nonadjuvanted vaccine or vaccine adjuvanted with alum—given concomitantly with influenza vaccine to high-risk elderly individuals." The Journal of infectious diseases vol. 198,9 (2008): 1317-26.
Hancock, G. et al., "Generation of atypical pulmonary inflammatory responses in BALB/c mice after immunization with the native attachment (G) glycoprotein of respiratory syncytial virus." Journal of virology vol. 70,11 (1996): 7783-91.
Hancock, G. et al., "Serum neutralizing antibody titers of seropositive chimpanzees immunized with vaccines coformulated with natural fusion and attachment proteins of respiratory syncytial virus." The Journal of infectious diseases vol. 181,5 (2000): 1768-71.
Harrison, R. and Jarvis, D., "Protein N-glycosylation in the baculovirus-insect cell expression system and engineering of insect cells to

(56) References Cited

OTHER PUBLICATIONS produce "mammalianized" recombinant glycoproteins." Advances in virus research vol. 68 (2006): 159-91.
Huang, Y. and Anderson, R., "Modulation of protective immunity, eosinophilia, and cytokine responses by selective mutagenesis of a recombinant G protein vaccine against respiratory syncytial virus." Journal of virology vol. 79,7 (2005): 4527-32.
Klink, H. A et al., "Influence of bovine respiratory syncytial virus F glycoprotein N-linked glycans on in vitro expression and on antibody responses in BALB/c mice." Vaccine vol. 24,16 (2006): 3388-95.
Ladunga, I. and Smith, R., "Amino acid substitutions preserve protein folding by conserving steric and hydrophobicity properties." Protein engineering vol. 10,3 (1997): 187-96.
Langley, J. et al., "A dose-ranging study of a subunit Respiratory Syncytial Virus subtype A vaccine with and without aluminum phosphate adjuvantation in adults greater than or equal to 65 years of age." Vaccine vol. 27,42 (2009): 5913-9.
Matthews, J. et al., "The core of the respiratory syncytial virus fusion protein is a trimeric coiled coil." Journal of virology vol. 74,13 (2000): 5911-20.
Mejias, A. et al., "New Approaches to reduce the burden of RSV infection," Drug Discovery Today: Therapeutic Strategies vol. 3,2 (2006): 173-181.
Melero, J., "Molecular Biology of Human Respiratory Syncytial Virus." Respiratory Syncytial Virus, Patricia Cane, Editor, Perspectives in Medical Virology, 14, (2007), p. 10-11.
Morton, C. et al., "Structural characterization of respiratory syncytial virus fusion inhibitor escape mutants: homology model of the F protein and a syncytium formation assay." Virology vol. 311,2 (2003): 275-88.
NCBI BLAST Accession No. EF566942.1.
Olmsted, R. et al., "Expression of the F glycoprotein of respiratory syncytial virus by a recombinant vaccinia virus: comparison of the individual contributions of the F and G glycoproteins to host immunity." Proceedings of the National Academy of Sciences of the United States of America vol. 83,19 (1986): 7462-6.
Olson, M. and Varga, S., "Pulmonary immunity and immunopathology: lessons from respiratory syncytial virus." Expert review of vaccines vol. 7,8 (2008): 1239-55.
Piedra, P. et al. "Immunogenicity of a new purified fusion protein vaccine to respiratory syncytial virus: a multi-center trial in children with cystic fibrosis." Vaccine vol. 21, 19-20 (2003): 2448-60.
Prince, G. et al. "Efficacy and safety studies of a recombinant chimeric respiratory syncytial virus FG glycoprotein vaccine in cotton rats." Journal of virology vol. 74,22 (2000): 10287-92.
Sakurai, H. et al., "Human antibody responses to mature and immature forms of viral envelope in respiratory syncytial virus infection: significance for subunit vaccines." Journal of virology vol. 73,4 (1999): 2956-62.
Schmidt, A. et al., "Mucosal immunization of rhesus monkeys against respiratory syncytial virus subgroups A and B and human parainfluenza virus type 3 by using a live cDNA-derived vaccine based on a host range-attenuated bovine parainfluenza virus type 3 vector backbone." Journal of virology vol. 76,3 (2002): 1089-99.
Simoes, E. et al., "Respiratory syncytial virus vaccine: a systematic overview with emphasis on respiratory syncytial virus subunit vaccines." Vaccine vol. 20,5-6 (2001): 954-60.
Sinclair, A., and Elliott, S., "Glycoengineering: the effect of glycosylation on the properties of therapeutic proteins." Journal of pharmaceutical sciences vol. 94,8 (2005): 1626-35.
Tang, R. et al., "Parainfluenza virus type 3 expressing the native or soluble fusion (F) Protein of Respiratory Syncytial Virus (RSV) confers protection from RSV infection in African green monkeys." Journal of virology vol. 78,20 (2004): 11198-207.
Ternette, N. et al., "Expression of RNA virus proteins by RNA polymerase II dependent expression plasmids is hindered at multiple steps." Virology journal vol. 4 (2007): 51.

Ternette, N. et al., "Immunogenicity and efficacy of codon optimized DNA vaccines encoding the F-protein of respiratory syncytial virus." Vaccine vol. 25,41 (2007): 7271-9.
Tian, S. et al., "A 20 Residues Motif Delineates the Furin Cleavage Site and its Physical Properties May Influence Viral Fusion." Biochemistry insights vol. 2 (2009):9-20.
Ulbrandt, N. et al., "Identification of antibody neutralization epitopes on the fusion protein of human metapneumovirus." The Journal of general virology vol. 89, Pt 12 (2008): 3113-3118.
Walsh, E. et al., "Immunization with glycoprotein subunits of respiratory syncytial virus to protect cotton rats against viral infection." The Journal of infectious diseases vol. 155,6 (1987): 1198-204.
Zhang, Z. and Henzel, W., "Signal peptide prediction based on analysis of experimentally verified cleavage sites." Protein science : a publication of the Protein Society vol. 13,10 (2004): 2819-24.
Zimmer, G. et al., "N-glycans of F protein differentially affect fusion activity of human respiratory syncytial virus." Journal of virology vol. 75,10 (2001): 4744-51.
Abstracts for oral presentations given at the "RSV 2007 Symposium" in Marco Island, FL, USA, 122 pages.
Bakkers, M. et al. "Addition of a trimerization domain (e.g. foldon) to a soluble RSV F protein," supplementary data dated Oct. 21, 2019.
Belshe, R. et al., "Immunogenicity of purified F glycoprotein of respiratory syncytial virus: clinical and immune responses to subsequent natural infection in children." The Journal of infectious diseases vol. 168,4 (1993): 1024-9.
Beran, J. et al., "Safety and Immunogenicity of 3 Formulations of an Investigational Respiratory Syncytial Virus Vaccine in Nonpregnant Women: Results From 2 Phase 2 Trials." The Journal of infectious diseases vol. 217,10 (2018): 1616-1625.
Chu, R., "CpG Oligodeoxynudeotides Act as Adjuvants that Switch on T Helper 1 (Thl) Immunity." J. Exp. Med vol. 186, 10 (1997): 1623-1631.
Connors, M. et al., "Respiratory syncytial virus (RSV) F, G, M2 (22K), and N proteins each induce resistance to RSV challenge, but resistance induced by M2 and N proteins is relatively short-lived." Journal of virology vol. 65,3 (1991): 1634-7.
Crank, M. et al., "A proof of concept for structure-based vaccine design targeting RSV in humans." Science vol. 365,6452 (2019): 505-509.
Decision from opposition division in opposition to European Patent No. 3109258 dated Jul. 8, 2021, 11 pages.
Declaration of Theodore Jardetzky, Ph.D. dated Dec. 8, 2020, 4 pages.
Doolittle, R., "The multiplicity of domains in proteins." Annual review of biochemistry vol. 64 (1995): 287-314.
Dudas, R., and Karron, R., "Respiratory syncytial virus vaccines." Clinical microbiology reviews vol. 11,3 (1998): 430-9.
Experimental data filed in opposition to European Patent No. 3109258 dated Apr. 8, 2021, 4 pages.
Gilman, M. et al., "Transient opening of trimeric prefusion RSV F proteins." Nature communications vol. 10,1 (2019):2105.
Graham, B. et al., "Novel antigens for RSV vaccines." Current opinion in immunology vol. 35 (2015): 30-8.
Jardetzky, T., "Structures of the pre- and post-entry paramyxovirus F protein: implications for RSV vaccine and therapeutic development." RSV 2007 Symposium, Oct. 26, 2007, Marco Island, FL, USA. Conference Presentation, 13 pages.
Langley, J. et al., "A Randomized, Controlled, Observer-Blinded Phase 1 Study of the Safety and Immunogenicity of a Respiratory Syncytial Virus Vaccine With or Without Alum Adjuvant." The Journal of infectious diseases vol. 215,1 (2017): 24-33.
Letter relating to appeal procedure in opposition to European Patent No. 3109258 dated Aug. 15, 2022, 8 pages.
Letter relating to oral proceedings during appeal procedure in opposition to European Patent No. 3109258 dated Nov. 29, 2022, 2 pages.
Ngwuta, J. et al., "Prefusion F-specific antibodies determine the magnitude of RSV neutralizing activity in human sera." Science translational medicine vol. 7,309 (2015): 309ra162.

(56) References Cited

OTHER PUBLICATIONS

Notice of opposition to European Patent No. 3109258 dated Oct. 23, 2019, 27 pages.
Notice of opposition to European Patent No. 3109258 dated Oct. 23, 2019, 51 pages.
Piedra, P., "Clinical experience with respiratory syncytial virus vaccines." The Pediatric infectious disease journal vol. 22,2 Suppl (2003): S94-9.
Preliminary opinion from opposition division in opposition to European Patent No. 3109258 dated Aug. 11, 2020, 9 pages.
Program for "RSV 2007 Symposium," in Marco Island, FL, USA, 2 pages.
Reply from opponent to submission of proprietor in opposition to European Patent No. 3109258 dated Jul. 2, 2020, 19 pages.
Reply to appeal in opposition to European Patent No. 3109258 dated Apr. 1, 2022, 31 pages.
Reply to appeal in opposition to European Patent No. 3109258 dated Apr. 4, 2022, 34 pages.
Reply to opposition to European Patent No. 3109258 dated Mar. 16, 2020, 36 pages.
Schwarz, T. et al., "Immunogenicity and Safety of 3 Formulations of a Respiratory Syncytial Virus Candidate Vaccine in Nonpregnant Women: A Phase 2, Randomized Trial." The Journal of infectious diseases vol. 220,11 (2019): 1816-1825.
Smith, B. et al., "Modelling the structure of the fusion protein from human respiratory syncytial virus." Protein engineering vol. 15,5 (2002): 365-71.
Statement of grounds of appeal in opposition to European Patent No. 3109258 dated Nov. 18, 2021, 36 pages.
Swanson, K. et al., "A monomeric uncleaved respiratory syncytial virus F antigen retains prefusion-specific neutralizing epitopes." Journal of virology vol. 88,20 (2014): 11802-10.
U.S. Appl. No. 60/942,456, filed Jun. 6, 2007.
U.S. Appl. No. 61/016,524, filed Dec. 24, 2007.
U.S. Appl. No. 61/056,206, filed May 27, 2008.
Wathen, M. et al., "Characterization of a novel human respiratory syncytial virus chimeric FG glycoprotein expressed using a baculovirus vector." The Journal of general virology vol. 70 (Pt 10) (1989): 2625-35.
Wertz, G. et al., "Expression of the fusion protein of human respiratory syncytial virus from recombinant vaccinia virus vectors and protection of vaccinated mice." Journal of virology vol. 61,2 (1987): 293-301.
Widjaja, I. et al., "Recombinant Soluble Respiratory Syncytial Virus F Protein That Lacks Heptad Repeat B, Contains a GCN4 Trimerization Motif and Is Not Cleaved Displays Prefusion-Like Characteristics." PloS one vol. 10,6 (2015): 1 -19.
Written submission in preparation to oral proceedings in opposition to European Patent No. 3109258 dated Apr. 8, 2021, 3 pages.
Written submission in preparation to oral proceedings in opposition to European Patent No. 3109258 dated Apr. 8, 2021, 7 pages.
Written submission in preparation to oral proceedings in opposition to European Patent No. 3109258 dated Apr. 8, 2021, 8 pages.
Written submission in preparation to oral proceedings in opposition to European Patent No. 3109258 dated Dec. 9, 2020, 4 pages.
Written submission in preparation to oral proceedings in opposition to European Patent No. 3109258 dated May 21, 2021, 4 pages.
Yang, X. et al., "Modifications that stabilize human immunodeficiency virus envelope glycoprotein trimers in solution." Journal of virology vol. 74,10 (2000): 4746-54.
Zhao, X. et al., "Structural characterization of the human respiratory syncytial virus fusion protein core." Proceedings of the National Academy of Sciences of the United States of America vol. 97,26 (2000): 14172-7.
Cseke, G. (2006). Cloning, Expression and Structural Characterization of Human Metapneumovirus Fusion Glycoprotein [Doctoral dissertation, Vanderbilt University], 140 pages.
Grounds of Invalidity in respect of EP3109258, EP2222710, and EP3178490 dated Jun. 8, 2022, 12 pages.

International Preliminary Report on Patentability of International Patent Application No. PCT/US2010/042161, dated Jan. 17, 2012, 20 pages.
McLellan, J. et al., "Structural basis of respiratory syncytial virus neutralization by motavizumab with supplementary information." Nature Structural & Molecular Biology, vol. 17,2, (2010), 17 pages.
Yang, X. et al., "Improved elicitation of neutralizing antibodies against primary human immunodeficiency viruses by soluble stabilized envelope glycoprotein trimers." Journal of virology vol. 75,3 (2001): 1165-71.
Bakkers, M. et al. "Characterization of EP3178490 designs," dated Jan. 17, 2023, 12 pages.
Harrison, Stephen C., "Viral membrane fusion." Nature Structural & Molecular Biology, vol. 15,7 (2008): 690-698.
McLellan, J. et al., "Structure-based design of a fusion glycoprotein vaccine for respiratory syncytial virus with supplementary information." Science vol. 342,6158 (2013): 592-8, 33 pages.
McLellan, J. et al., "Structure of RSV fusion glycoprotein trimer bound to a prefusion-specific neutralizing antibody with supplementary information." Science vol. 340,6136 (2013): 1113-7, 18 pages.
Gilman, M. et al., "Characterization of a prefusion-specific antibody that recognizes a quaternary, cleavage-dependent epitope on the RSV fusion glycoprotein." PLoS pathogens vol. 11,7 (2015): 1-17.
Stevens, J. et al., "Structure of the uncleaved human H1 hemagglutinin from the extinct 1918 influenza virus with supplementary information." Science, vol. 303 (2004):1866-1870, 20 pages.
Sequence Alignment of SEQ ID No. 611 of WO2009/128951 and SEQ ID No. 1 and 2 of EP3178490, 4 pages.
Meier, S. et al., "Foldon, the natural trimerization domain of T4 fibritin, dissociates into a monomeric A-state form containing a stable beta-hairpin: atomic details of trimer dissociation and local beta-hairpin stability from residual dipolar couplings." Journal of molecular biology vol. 344,4 (2004): 1051-69.
Sequence Alignment of Seq id No. 1 of EP3178490 and SEQ ID No. 2 and 6 of WO2009/079796, 5 pages.
Yang, X. et al., "Characterization of stable, soluble trimers containing complete ectodomains of human immunodeficiency virus type 1 envelope glycoproteins." Journal of virology vol. 74, 12 (2000): 5716-25.
Frank, S. et al., "Stabilization of short collagen-like triple helices by protein engineering." Journal of molecular biology vol. 308,5 (2001): 1081-9.
Tao, Y. et al., "Structure of bacteriophage T4 fibritin: a segmented coiled coil and the role of the C-terminal domain." Structure vol. 5,6 (1997): 789-98.
McLellan, J. et al., "Structure of RSV fusion glycoprotein trimer bound to a prefusion-specific neutralizing antibody with supplementary information." Science vol. 340,6136 (2013): 1113-7, 24 pages.
Notice of Opposition and Opposition Statement against EP3178490B1 dated Jan. 20, 2023, 57 pages.
Notice of Opposition and Opposition Statement against EP3178490B1 dated Jan. 19, 2023, 49 pages.
Declaration under 37 C.F.R. 1.132 of Matthew James Bottomley dated Mar. 3, 2021, 5 pages.
European Search Report for European Patent Application No. 22200670.2, dated Apr. 6, 2023 (10 pages).
European Search Report for European Patent Application No. 22214601.1, dated Jun. 2, 2023 (11 pages).
European Search Report for European Patent Application No. 22214608.6, dated Jun. 2, 2023 (11 pages).
European Search Report for European Patent Application No. 22211934.9, dated Jun. 7, 2023 (8 pages).
Examination Report for European Patent Application No. 22214601.1, dated Jun. 16, 2023 (9 pages).
Examination Report for European Patent Application No. 22211934.9, dated Jun. 19, 2023 (5 pages).
Examination Report for European Patent Application No. 22214608.6, dated Jun. 23, 2023 (9 pages).
Examination Report for European Patent Application No. 22200670.2, dated Apr. 19, 2023 (7 pages).

(56) References Cited

OTHER PUBLICATIONS

Auxillary Request 1 for European Patent Application No. 16190004.8, dated Sep. 28, 2021, 36 pages.
Chaiwatpongsakorn, Suprance et al., "Generation of Soluble Respiratory Syncytial Virus Fusion Glycoprotein" [Conference abstract]. American Society for Virology, 26th Annual Meeting, Scientific Program & Abstracts (2017), 5 pages.
Claimant's Closing Argument in connection with European Patent Nos. 3109258 and 2222710 dated Jun. 2, 2023, 116 pages.
Claimant's Opening Skeleton Argument in connection with European Patent Nos. 3109258 and 2222710 dated Jun. 2, 2023, 101 pages.
Closing Submissions on Behalf of GSK in connection with European Patent Nos. 3109258 and 2222710 dated Jun. 23, 2023, 166 pages.
Decision from opposition division in opposition to European Patent No. 3109258 dated Jul. 8, 2021, 28 pages.
Du, S. et al., "Effect of trimerization motifs on quaternary structure, antigenicity, and immunogenicity of a noncleavable HIV-1 gp140 envelope glycoprotein." Virology vol. 395,1 (2009): 33-44.
Expert Report of Dr. Teresa Rene Johnson dated Apr. 14, 2023, 104 pages.
Expert Report of Professor Winfried Weissenhorn dated Apr. 14, 2023, 108 pages.
Extended European Search Report for European Patent Application No. 23150323.6, dated Aug. 7, 2023, 9 pages.
First Examination Report for European Patent Application No. 19152924.7, dated Aug. 4, 2023, 9 pages.
First Examination Report for European Patent Application No. 23150323.6, dated Aug. 22, 2023, 8 pages.
First Expert Report of Dr. Geraldine Taylor dated Apr. 6, 2023, 57 pages.
Krarup, A. et al., "A highly stable prefusion RSV F vaccine derived from structural analysis of the fusion mechanism." Nature communications, 6 (2015): 8143.
Mörner, A. et al., "Human immunodeficiency virus type 1 env trimer immunization of macaques and impact of priming with viral vector or stabilized core protein." Journal of virology vol. 83,2 (2009): 540-551.
Opening Skeleton Argument for Trial in connection with European Patent Nos. 3109258 and 2222710 dated Jun. 2, 2023, 67 pages.
Preliminary opinion from opposition division in opposition to European Patent No. 3109258 dated Aug. 11, 2020, 22 pages.
Second (Supplemental) Expert Report of Dr. Teresa Johnson dated Apr. 24, 2023, 10 pages.
Second (Supplemental) Expert Report of Dr. Geraldine Taylor dated Apr. 24, 2023, 4 pages.
Second (Supplemental) Expert Report of Professor Winfried Weissenhorn dated Apr. 24, 2023, 9 pages.
Second Expert Report of Professor Anthony Wilkinson dated May 11, 2023, 8 pages.
Second Witness Statement of Theodore Jardetzky dated Apr. 5, 2023, 12 pages.
Supplemental Skeleton to GSK's Opening Skeleton Argument for Trial in connection with European Patent Nos. 3109258 and 2222710 dated Jun. 2, 2023, 9 pages.
Third Expert Report of Dr. Teresa Johnson dated May 12, 2023, 31 pages.
Third Expert Report of Dr. Geraldine Taylor dated May 11, 2023, 18 pages.
U.S. Appl. No. 60/896,201, filed Apr. 8, 2008.
White, J. et al., "Structures and mechanisms of viral membrane fusion proteins: multiple variations on a common theme." Critical reviews in biochemistry and molecular biology vol. 43,3 (2008): 189-219.
Witness Statement of Theodore Jardetzky dated Feb. 3, 2023, 14 pages.
Writ submitted on Mar. 23, 2023 in connection with European Patent No. 2222710, 156 pages.
Writ submitted on Mar. 23, 2023 in connection with European Patent No. 3109258, 151 pages.
Writ submitted on Mar. 23, 2023 in connection with European Patent No. 3178490, 146 pages.
Written Submissions filed in European Patent Application No. 16190004.8 dated Aug. 27, 2021, 17 pages.
Yuan, W. et al., "Oligomer-specific conformations of the human immunodeficiency virus (HIV-1) gp41 envelope glycoprotein ectodomain recognized by human monoclonal antibodies." AIDS research and human retroviruses vol. 25,3 (2009): 319-328.

\* cited by examiner

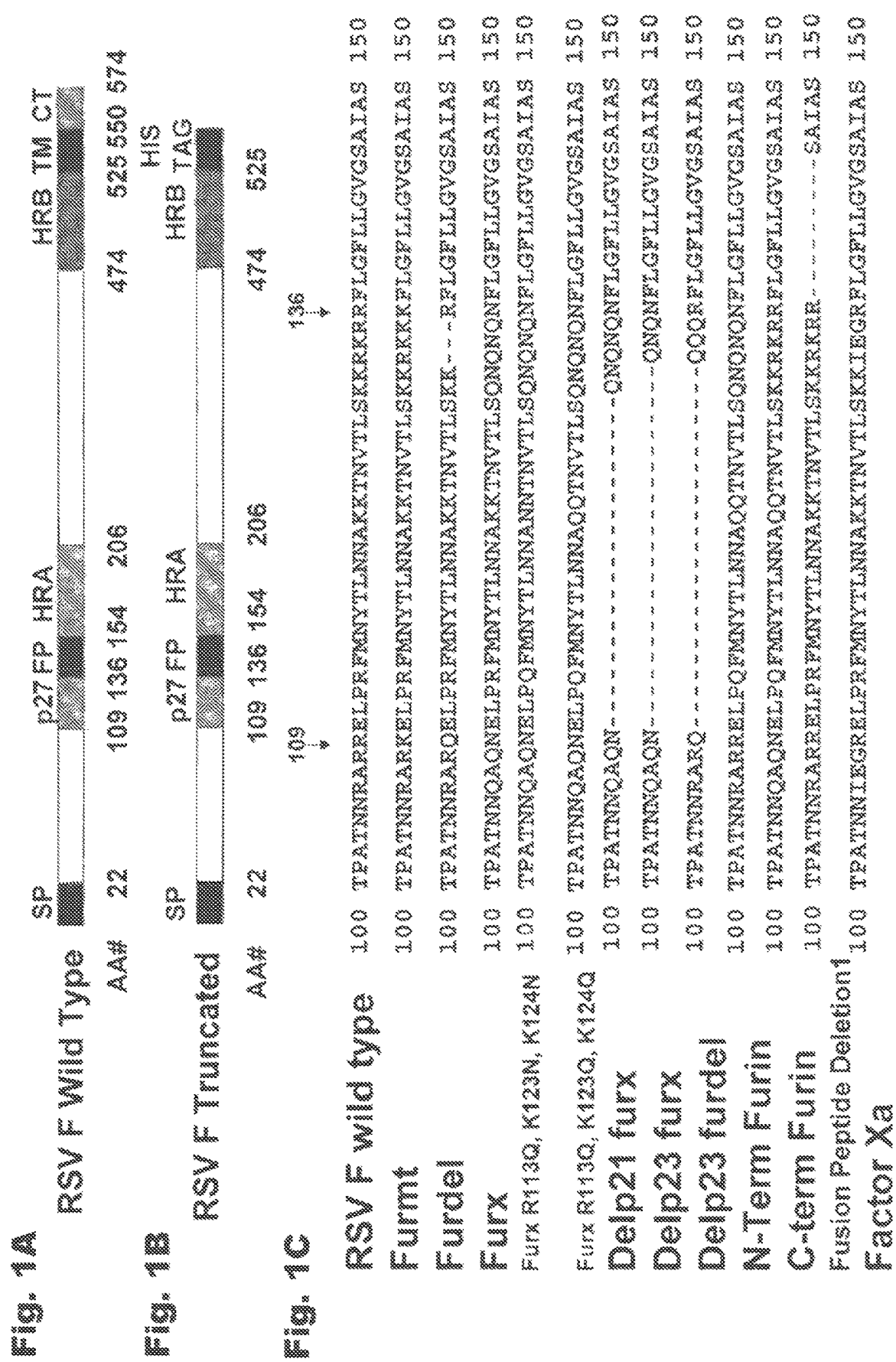

Fig. 2: Constructs to Cleave from the Cell Surface

| | | | |
|---|---|---|---|
| RSV F Wildtype | 488 | FDASISQVNEKINQSLAFIRKSDELLHNVNAGKSTTN-------------------------------- | TM-C |
| Idealized Ent | 488 | FDASISQINEKINQILAFIRKIDELLHNINAGKSTTNGSGSGDDDDKGSGSG------------------ | TM-C |
| GCN Ent | 488 | FDASISQVNEKINQSLAFIRKSDELLHNVNDKIEEILSKIYHIENEIARIKKLIGEGSGSGDDDDKGSGSG | TM-C |
| Idealized FacXa | 488 | FDASISQINEKINQILAFIRKIDELLHNINAGKSTTNGSGSGIEGRGSGSG------------------ | TM-C |
| GCN Thr | 488 | FDASISQVNEKINQSLAFIRKSDELLHNVNDKIEEILSKIYHIENEIARIKKLIGEGSGSGIEGRGSGSG | TM-C |
| Idealized Thr | 488 | FDASISQINEKINQILAFIRKIDELLHNINAGKSTTNGSGSGLVPRGSGSG------------------- | TM-C |
| GCN Thr | 488 | FDASISQVNEKINQSLAFIRKSDELLHNVNDKIEEILSKIYHIENEIARIKKLIGEGSGSGLVPRGSGSG- | TM-C |

TM-C = Transmembrane domain + C-terminal tail =
IMITTIIIVIIVILLSLIAVGLLLYCKARSTPVTLSKDQLSGINNIAFSN
Ent = Enterokinase cleavage site - DDDDK
FacXa = Factor Xa cleavage site - IEGR
Thr = Thrombin cleavage site - LVPR

```
ATAGGCGGCGCATGAGAGAAGCCCAGACCAATTACCTACCCAAAATGGAGAAAGTTCACGTTGACATCGA
GGAAGACAGCCCATTCCTCAGAGCTTTGCAGCGGAGCTTCCCGCAGTTTGAGGTAGAAGCCAAGCAGGTC
ACTGATAATGACCATGCTAATGCCAGAGCGTTTTCGCATCTGGCTTCAAAACTGATCGAAACGGAGGTGG
ACCCATCCGACACGATCCTTGACATTGGAAGTGCGCCCGCCCGCAGAATGTATTCTAAGCACAAGTATCA
TTGTATCTGTCCGATGAGATGTGCGGAAGATCCGGACAGATTGTATAAGTATGCAACTAAGCTGAAGAAA
AACTGTAAGGAAATAACTGATAAGGAATTGGACAAGAAAATGAAGGAGCTCGCCGCCGTCATGAGCGACC
CTGACCTGGAAACTGAGACTATGTGCCTCCACGACCACGAGTCGTGTCGCTACGAAGGGCAAGTCGCTGT
TTACCAGGATGTATACGCGGTTGACGGACCGACAAGTCTCTATCACCAAGCCAATAAGGGAGTTAGAGTC
GCCTACTGGATAGGCTTTGACACCACCCCTTTTATGTTTAAGAACTTGGCTGGAGCATATCCATCATACT
CTACCAACTGGGCCGACGAAACCGTGTTAACGGCTCGTAACATAGGCCTATGCAGCTCTGACGTTATGGA
GCGGTCACGTAGAGGGATGTCCATTCTTAGAAAGAAGTATTTGAAACCATCCAACAATGTTCTATTCTCT
GTTGGCTCGACCATCTACCACGAGAAGAGGGACTTACTGAGGAGCTGGCACCTGCCGTCTGTATTTCACT
TACGTGGCAAGCAAAATTACACATGTCGGTGTGAGACTATAGTTAGTTGCGACGGGTACGTCGTTAAAAG
AATAGCTATCAGTCCAGGCCTGTATGGGAAGCCTTCAGGCTATGCTGCTACGATGCACCGCGAGGGATTC
TTGTGCTGCAAAGTGACAGACACATTGAACGGGGAGAGGGTCTCTTTTCCCGTGTGCACGTATGTGCCAG
CTACATTGTGTGACCAAATGACTGGCATACTGGCAACAGATGTCAGTGCGGACGACGCGCAAAAACTGCT
GGTTGGGCTCAACCAGCGTATAGTCGTCAACGGTCGCACCCAGAGAAACACCAATACCATGAAAAATTAC
CTTTTGCCCGTAGTGGCCCAGGCATTTGCTAGGTGGGCAAAGGAATATAAGGAAGATCAAGAAGATGAAA
GGCCACTAGGACTACGAGATAGACAGTTAGTCATGGGGTGTTGTTGGGCTTTTAGAAGGCACAAGATAAC
ATCTATTTATAAGCGCCCGGATACCCAAACCATCATCAAAGTGAACAGCGATTTCCACTCATTGGTGCTG
CCCAGGATAGGCAGTAACACATTGGAGATCGGGCTGAGAACAAGAATCAGGAAAATGTTAGAGGAGCACA
AGGAGCCGTCACCTCTCATTACCGCCGAGGACGTACAAGAAGCTAAGTGCGCAGCCGATGAGGCTAAGGA
GGTGCGTGAAGCCGAGGAGTTGCGCGCAGCTCTACCACCTTTGGCAGCTGATGTTGAGGAGCCCACTCTG
GAAGCCGATGTAGACTTGATGTTACAAGAGGCTGGGGCCGGGCTCAGTGGAGACACCTGGTGGCTTGATAA
AGGTTACCAGCTACGATGGCGAGGACAAGATCGGCTCTTACGCTGTGCTTTCTCCGCAGGCTGTACTCAA
GAGTGAAAAATTATCTTGCATCCACCCTCTCGCTGAACAAGTCATAGTGATAACACACTCTGGCCGAAAA
GGGCGTTATGCCGTGGAACCATACCATGGTAAAGTAGTGGTGCCAGAGGGACATGCAATACCCGTCCAGG
ACTTTCAAGCTCTGAGTGAAAGTGCCACCATTGTGTACAACGAACGTGAGTTCGTAAACAGGTACCTGCA
CCATATTGCCACACATGGAGGAGCGCTGAACACTGATGAAGAATATTACAAAACTGTCAAGCCCAGCGAG
CACGACGGGGAATACCTGTACGACATCGACAGGAAACAGTGCGTCAAGAAAGAACTAGTCACTGGGCTAG
GGCTCACAGGCGAGCTGGTGGATCCTCCCTTCCATGAATTCGCCTACGAGAGTCTGAGAACACGACCAGC
CGCTCCTTACCAAGTACCAACCATAGGGGTGTATGGCGTGCCAGGATCAGGCAAGTCTGGCATCATTAAA
AGCGCAGTCACCAAAAAGATCTAGTGGTGAGCGCCAAGAAAGAAACTGTGCAGAAATTATAAGGGACG
TCAAGAAAATGAAAGGGCTGGACGTCAATGCCAGAACTGTGGACTCAGTGCTCTTGAATGGATGCAAACA
CCCCGTAGAGACCCTGTATATTGACGAAGCTTTTGCTTGTCATGCAGGTACTCTCAGAGCGCTCATAGCC
```

FIG. 4A

ATTATAAGACCTAAAAAGGCAGTGCTCTGCCGGGATCCCAAACAGTGCGGTTTTTTTAACATGATGTGCC
TGAAAGTGCATTTTAACCACGAGATTTGCACACAAGTCTTCCACAAAAGCATCTCTCGCCGTTGCACTAA
ATCTGTGACTTCGGTCGTCTCAACCTTGTTTACGACAAAAAAATGAGAACGACGAATCCGAAAGAGACT
AAGATTGTGATTGACACTACCGGCAGTACCAAACCTAAGCAGGACGATCTCATTCTCACTTGTTTCAGAG
GGTGGGTGAAGCAGTTGCAAATAGATTACAAAGGCAACGAAATAATGACGGCAGCTGCCTCTCAAGGGCT
GACCCGTAAAGGTGTGTATGCCGTTCGGTACAAGGTGAATGAAAATCCTCTGTACGCACCCACCTCAGAA
CATGTGAACGTCCTACTGACCCGCACGGAGGACCGCATCGTGTGGAAAACACTAGCCGGCGACCCATGGA
TAAAAACACTGACTGCCAAGTACCCTGGGAATTTCACTGCCACGATAGAGGAGTGGCAAGCAGAGCATGA
TGCCATCATGAGGCACATCTTGGAGAGACCGGACCCTACCGACGTCTTCCAGAATAAGGCAAACGTGTGT
TGGGCCAAGGCTTTAGTGCCGGTGCTGAAGACGCTGGCATAGACATGACCACTGAACAATGGAACACTG
TGGATTATTTGAAACGGACAAAGCTCACTCAGCAGAGATAGTATTGAACCAACTATGCGTGAGGTTCTT
TGGACTCGATCTGGACTCCGTCTATTTCTGCACCCACTGTTCCGTTATCCATTAGGAATAATCACTGG
GATAACTCCCCGTCGCCTAACATGTACGGGCTGAATAAAGAAGTGGTCCGTCAGCTCTCTCGCAGGTACC
CACAACTGCCTCGGGCAGTTGCCACTGGAAGAGTCTATGACATGAACACTGGTACACTGCGCAATTATGA
TCCGCGCATAAACCTAGTACCTGTAAACAGAAGACTGCCTCATGCTTTAGTCCTCCACCATAATGAACAC
CCACAGAGTGACTTTTCTTCATTCGTCAGCAAATTGAAGGGCAGAACTGTCCTGGTGGTCGGGGAAAAGT
TGTCCGTCCCAGGCAAAATGGTTGACTGGTTGTCAGACCGGCCTGAGGCTACCTTCAGAGCTCGGCTGGA
TTTAGGCATCCCAGGTGATGTGCCCAAATATGACATAATATTTGTTAATGTGAGGACCCCATATAAATAC
CATCACTATCAGCAGTGTGAAGACCATGCCATTAAGCTTAGCATGTTGACCAAGAAAGCTTGTCTGCATC
TGAATCCCGGCGGAACCTGTGTCAGCATAGGTTATGGTTACGCTGACAGGGCCAGCGAAAGCATCATTGG
TGCTATAGCGCGGCAGTTCAAGTTTTCCCGGGTATGCAAACCGAAATCCTCACTTGAAGAGACGGAAGTT
CTGTTTGTATTCATTGGGTACGATCGCAAGGCCCGTACGCACAATCCTTACAAGCTTTCATCAACCTTGA
CCAACATTTATACAGGTTCCAGACTCCACGAAGCCGGATGTGCACCCTCATATCATGTGGTGCGAGGGGA
TATTGCCACGGCCACCGAAGGAGTGATTATAAATGCTGCTAACAGCAAAGGACAACCTGGCGGAGGGGTG
TGCGGAGCGCTGTATAAGAAATTCCCGGAAAGCTTCGATTTACAGCCGATCGAAGTAGGAAAAGCGCGAC
TGGTCAAAGGTGCAGCTAAACATATCATTCATGCCGTAGGACCAAACTTCAACAAAGTTTCGGAGGTTGA
AGGTGACAAACAGTTGGCAGAGGCTTATGAGTCCATCGCTAAGATTGTCAACGATAACAATTACAAGTCA
GTAGCGATTCCACTGTTGTCCACCGGCATCTTTTCCGGGAACAAAGATCGACTAACCCAATCATTGAACC
ATTTGCTGACAGCTTTAGACACCACTGATGCAGATGTAGCCATATACTGCAGGGACAAGAAATGGGAAAT
GACTCTCAAGGAAGCAGTGGCTAGGAGAGAAGCAGTGGAGGAGATATGCATATCCGACGACTCTTCAGTG
ACAGAACCTGATCAGAGCTGGTGAGGGTGCATCCGAAGAGTTCTTTGGCTGGAAGGAAGGGCTACAGCA
CAAGCGATGGCAAAACTTTCTCATATTTGGAAGGGACCAAGTTTCACCAGGCGGCCAAGGATATAGCAGA
AATTAATGCCATGTGGCCCGTTGCAACGGAGGCCAATGAGCAGGTATGCATGTATATCCTCGGAGAAAGC
ATGAGCAGTATTAGGTCGAAATGCCCCGTCGAAGAGTCGGAAGCCTCCACACCACCTAGCACGCTGCCTT
GCTTGTGCATCCATGCCATGACTCCAGAAAGAGTACAGCGCCTAAAAGCCTCACGTCCAGAACAAATTAC

FIG. 4B

```
TGTGTGCTCATCCTTTCCATTGCCGAAGTATAGAATCACTGGTGTGCAGAAGATCCAATGCTCCCAGCCT
ATATTGTTCTCACCGAAAGTGCCTGCGTATATTCATCCAAGGAAGTATCTCGTGGAAACACCACCGGTAG
ACGAGACTCCGGAGCCATCGGCAGAGAACCAATCCACAGAGGGGACACCTGAACAACCACCACTTATAAC
CGAGGATGAGACCAGGACTAGAACGCCTGAGCCGATCATCATCGAAGAGGAAGAAGAGGATAGCATAAGT
TTGCTGTCAGATGGCCCGACCCACCAGGTGCTGCAAGTCGAGGCAGACATTCACGGGCCGCCCTCTGTAT
CTAGCTCATCCTGGTCCATTCCTCATGCATCCGACTTTGATGTGGACAGTTTATCCATACTTGACACCCT
GGAGGGAGCTAGCGTGACCAGCGGGGCAACGTCAGCCGAGACTAACTCTTACTTCGCAAAGAGTATGGAG
TTTCTGGCGCGACCGGTGCCTGCGCCTCGAACAGTATTCAGGAACCCTCCACATCCCGCTCCGCGCACAA
GAACACCGTCACTTGCACCAGCAGGGCCTGCTCGAGAACCAGCCTAGTTTCCACCCCGCCAGGCGTGAA
TAGGGTGATCACTAGAGAGGAGCTCGAGGCGCTTACCCCGTCACGCACTCCTAGCAGGTCGGTCTCGAGA
ACCAGCCTGGTCTCCAACCCGCCAGGCGTAAATAGGGTGATTACAAGAGAGGAGTTTGAGGCGTTCGTAG
CACAACAACAATGACGGTTTGATGCGGGTGCATACATCTTTCCTCCGACACCGGTCAAGGGCATTTACA
ACAAAAATCAGTAAGGCAAACGGTGCTATCCGAAGTGGTGTTGGAGACGACCGAATTGGAGATTTCGTAT
GCCCCGCGCCTCGACCAAGAAAAAGAAGAATTACTACGCAAGAAATTACAGTTAAATCCCACACCTGCTA
ACAGAAGCAGATACCAGTCCAGGAAGGTGGAGAACATGAAAGCCATAACAGCTAGACGTATTCTGCAAGG
CCTAGGGCATTATTTGAAGGCAGAAGGAAAAGTGGAGTGCTACCGAACCCTGCATCCTGTTCCTTTGTAT
TCATCTAGTGTGAACCGTGCCTTTTCAAGCCCAAGGTCGCAGTGGAAGCCTGTAACGCCATGTTGAAAG
AGAACTTTCGACTGTGGCTTCTTACTGTATTATTCCAGAGTACGATGCCTATTTGGACATGGTTGACCG
AGCTTCATGCTGCTTAGACACTGCCAGTTTTTGCCCTGCAAAGCTGCGCAGCTTTCCAAAGAAACACTCC
TATTTGGAACCCACAATACGATCGGCAGTGCCTTCAGCCATCCAGAACACGCTCCAGAACGTCCTGGCAG
CTGCCACAAAAGAAATTGCAATGTCACGCAAATGAGAGAATTGCCCGTATTGGATTCGGCGGCCTTTAA
TGTGGAATGCTTCAAGAAATATGCGTGTAATAATGAATATTGGGAAACGTTTAAAGAAAACCCCATCAGG
CTTACTGAAGAAAACGTGGTAAATTACATTACCAAATTAAAACGACCAAAAGCTGCTGCTCTTTTTGCGA
AGACACATAATTTGAATATGTTGCAGGACATACCAATGGACAGGTTTGTAATGGACTTAAAGAGAGACGT
GAAAGTGACTCCAGGAACAAAACATACTGAAGAACGGCCCAAGGTACAGGTGATCCAGGCTGCCGATCCG
CTAGCAACAGCGTATCTGTGCGGAATCCACCGAGAGCTGGTTAGGAGATTAAATGCGGTCCTGCTTCCGA
ACATTCATACACTGTTTGATATGTCGGCTGAAGACTTTGACGCTATTATAGCCGAGCACTTCCAGCCTGG
GGATTGTGTTCTGGAAACTGACATCGGCTCGTTTGATAAAAGTGAGGACGACGCCATGGCTCTGACCGCG
TTAATGATTCTGGAAGACTTAGGTGTGGACGCAGAGCTGTTGACGCTGATTGAGGCGGCTTTCGGCGAAA
TTTCATCAATACATTTGCCCACTAAAACTAAATTTAAATTCGGAGCCATGATGAAATCTGGAATGTTCCT
CACACTGTTTGTGAACACAGTCATTAACATTGTAATCGCAAGCAGAGTGTTGAGAGAACGGCTAACCGGA
TCACCATGTGCAGCATTCATTGGAGATGACAATATCGTGAAAGGAGTCAAATCGACAAATTAATGGCAG
ACAGGTGCCCCACCTGGTTGAATATGGAAGTCAAGATTATAGATGCTGTGGTGGCGAGAAAGCGCCTTA
TTTCTGTGGAGGGTTTATTTTGTGTGACTCCGTGACCGGCACAGCGTGCCGTGTGGCAGACCCCCTAAAA
AGGCTGTTTAAGCTTGGCAAACCTCTGGCAGCAGACGATGAACATGATGACAGGAGAAGGGCATTGC
```

FIG. 4C

```
ATGAAGAGTCAACACGCTGGAACCGAGTGGGTATTCTTTCAGAGCTGTGCAAGGCAGTAGAATCAAGGTA
TGAAACCGTAGGAACTTCCATCATAGTTATGGCCATGACTACTCTAGCTAGCAGTGTTAAATCATTCAGC
TACCTGAGAGGGCCCCTATAACTCTCTACGGCTAACCTGAATGGACTACGACATAGTCTAGTCGACGCC
ACCATGGAACTGCTGATCCTGAAGGCCAACGCCATCACCACCATCCTGACCGCCGTGACCTTCTGCTTCG
CCAGCGGCCAGAACATCACCGAGGAATTCTACCAGAGCACCTGCAGCGCCGTGAGCAAGGGCTACCTGAG
CGCCCTGCGGACCGGCTGGTACACCAGCGTGATCACCATCGAGCTGTCCAACATCAAAGAAAACAAGTGC
AACGGCACCGACGCCAAGGTGAAACTGATCAAGCAGGAACTGGACAAGTACAAGAACGCCGTGACCGAGC
TGCAGCTGCTGATGCAGAGCACCCCGCCACCAACAACCGGGCCAGAAGAGAGCTGCCCCGGTTCATGAA
CTACACCCTGAACAACGCCAAGAAAACCAACGTGACCCTGAGCAAGAAGCGGAAGCGGCGGTTCCTGGGC
TTCCTGCTGGGCGTGGGCAGCGGCATCGCCAGCGGGGTGGCCGTGTCCAAGGTGCTGCACCTGGAAGGCG
AGGTGAACAAGATCAAGTCCGCCCTGCTGTCCACCAACAAGGCCGTGGTGTCCCTGAGCAACGGCGTGAG
CGTGCTGACCAGCAAGGTGCTGGATCTGAAGAACTACATCGACAAGCAGCTGCTGCCCATCGTGAACAAG
CAGAGCTGCAGCATCAGCAACATCGAGACCGTGATCGAGTTCCAGCAGAAGAACAACCGGCTGCTGGAAA
TCACCCGGGAGTTCAGCGTGAACGCCGGCGTGACCACCCCCGTGAGCACCTACATGCTGACCAACAGCGA
GCTGCTGTCCCTGATCAATGACATGCCCATCACCAACGACCAGAAAAGCTGATGAGCAACAACGTGCAG
ATCGTGCGGCAGCAGAGCTACTCCATCATGAGCATCATCAAAGAAGAGGTGCTGGCCTACGTGGTGCAGC
TGCCCCTGTACGGCGTGATCGACACCCCCTGCTGGAAGCTGCACACCAGCCCCCTGTGCACCACCAACAC
CAAGAGGGCAGCAACATCTGCCTGACCCGGACCGACCGGGGCTGGTACTGCGACAACGCCGGCAGCGTG
AGCTTCTTCCCCCAAGCCGAGACCTGCAAGGTGCAGAGCAACCGGGTGTTCTGCGACACCATGAACAGCC
TGACCCTGCCCTCCGAGGTGAACCTGTGCAACGTGGACATCTTCAACCCCAAGTACGACTGCAAGATCAT
GACCTCCAAGACCGACGTGAGCAGCTCCGTGATCACCTCCCTGGGCGCCATCGTGAGCTGCTACGGCAAG
ACCAAGTGCACCGCCAGCAACAAGAACCGGGGCATCATCAAGACCTTCAGCAACGGCTGCGACTACGTGA
GCAACAAGGGCGTGGACACCGTGAGCGTGGGCAACACACTGTACTACGTGAATAAGCAGGAAGGCAAGAG
CCTGTACGTGAAGGGCGAGCCCATCATCAACTTCTACGACCCCCTGGTGTTCCCCAGCGACGAGTTCGAC
GCCAGCATCAGCCAGGTCAACGAGAAGATCAACCAGAGCCTGGCCTTCATCCGGAAGAGCGACGAGCTGC
TGCACAATGTGAATGCCGGCAAGAGCACCACCAATATCATGATCACCACAATCATCATCGTGATCATTGT
GATCCTGCTGTCTCTGATTGCCGTGGGCCTGCTGCTGTACTGCAAGGCCCCGCAGCACCCCTGTGACCCTG
TCCAAGGACCAGCTGTCCGGCATCAACAATATCGCCTTCTCCAACTGAAGTCTAGACGGCGCGCCCACCC
AGCGGCCGCATACAGCAGCAATTGGCAAGCTGCTTACATAGAACTCGCGGCGATTGGCATCCGCCTTAA
AATTTTTATTTTATTTTTCTTTTCTTTTCCGAATCGGATTTTGTTTTTAATATTTCAAAAAAAAAAAAA
AAAAAAAAAAAAAAAAAAAAAGGGTCGGCATGGCATCTCCACCTCCTCGCGGTCCGACCTGGCATCGGA
AGGAGGACGCACGTCCACTCGGATGGCTAAGGGAGAGCCACGTTTAAACCAGCTCCAATTCGCCCTATAG
TGAGTCGTATTACGCGCGCTCACTGGCCGTCGTTTTACAACGTCGTGACTGGGAAAACCCTGGCGTTACC
CAACTTAATCGCCTTGCAGCACATCCCCCTTTCGCCAGCTGGCGTAATAGCGAAGAGGCCCGCACCGATC
GCCCTTCCCAACAGTTGCGCAGCCTGAATGGCGAATGGGACGCGCCCTGTAGCGGCGCATTAAGCGCGGC
```

FIG. 4D

```
GGGTGTGGTGGTTACGCGCAGCGTGACCGCTACACTTGCCAGCGCCCTAGCGCCCGCTCCTTTCGCTTTC
TTCCCTTCCTTTCTCGCCACGTTCGCCGGCTTTCCCCGTCAAGCTCTAAATCGGGGGCTCCCTTTAGGGT
TCCGATTTAGTGCTTTACGGCACCTCGACCCCAAAAAACTTGATTAGGGTGATGGTTCACGTAGTGGGCC
ATCGCCCTGATAGACGGTTTTTCGCCCTTTGACGTTGGAGTCCACGTTCTTTAATAGTGGACTCTTGTTC
CAAACTGGAACAACACTCAACCCTATCTCGGTCTATTCTTTTGATTTATAAGGATTTTGCCCGATTTCGG
CCTATTGGTTAAAAAATGAGCTGATTTAACAAAAATTAACGCGAATTTTAACAAAATATTAACGCTTAC
AATTTAGGTGGCACTTTTCGGGGAAATGTGCGCGGAACCCCTATTTGTTTATTTTCTAAATACATTCAA
ATATGTATCCGCTCATGAGACAATAACCCTGATAAATGCTTCAATAATATTGAAAAAGGAAGAGTATGAG
TATTCAACATTTCCGTGTCGCCCTTATTCCCTTTTTTGCGGCATTTTGCCTTCCTGTTTTTGCTCACCCA
GAAACGCTGGTGAAAGTAAAAGATGCTGAAGATCAGTTGGGTGCACGAGTGGGTTACATCGAACTGGATC
TCAACAGCGGTAAGATCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGTCGCCGCATACACTAT
TCTCAGAATGACTTGGTTGAGTACTCACCAGTCACAGAAAAGCATCTTACGGATGGCATGACAGTAAGAG
AATTATGCAGTGCTGCCATAACCATGAGTGATAACACTGCGGCCAACTTACTTCTGACAACGATCGGAGG
ACCGAAGGAGCTAACCGCTTTTTTGCACAACATGGGGGATCATGTAACTCGCCTTGATCGTTGGGAACCG
GAGCTGAATGAAGCCATACCAAACGACGAGCGTGACACCACGATGCCTGTAGCAATGGCAACAACGTTGC
GCAAACTATTAACTGGCGAACTACTTACTCTAGCTTCCCGGCAACAATTAATAGACTGGATGGAGGCGGA
TAAAGTTGCAGGACCACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCCTCCCGTATCGTAGTTA
TCTACACGACGGGGAGTCAGGCAACTATGGATGAACGAAATAGACAGATCGCTGAGATAGGTGCCTCACT
GATTAAGCATTGGTAACTGTCAGACCAAGTTTACTCATATATACTTTAGATTGATTTAAAACTTCATTTT
TAATTTAAAAGGATCTAGGTGAAGATCCTTTTTGATAATCTCATGACCAAAATCCCTTAACGTGAGTTTT
CGTTCCACTGAGCGTCAGACCCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTTTGCCGGATCAAGAGCTACCA
ACTCTTTTTCCGAAGGTAACTGGCTTCAGCAGAGCGCAGATACCAAATACTGTTCTTCTAGTGTAGCCGT
AGTTAGGCCACCACTTCAAGAACTCTGTAGCACCGCCTACATACCTCGCTCTGCTAATCCTGTTACCAGT
GGCTGCTGCCAGTGGCGATAAGTCGTGTCTTACCGGGTTGGACTCAAGACGATAGTTACCGGATAAGGCG
CAGCGGTCGGGCTGAACGGGGGGTTCGTGCACACAGCCCAGCTTGGAGCGAACGACCTACACCGAACTGA
GATACCTACAGCGTGAGCTATGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGTATCTTTATAGT
CCTGTCGGGTTTCGCCACCTCTGACTTGAGCGTCGATTTTTGTGATGCTCGTCAGGGGGGCGGAGCCTAT
GGAAAAACGCCAGCAACGCGGCCTTTTTACGGTTCCTGGCCTTTTGCTGGCCTTTTGCTCACATGTTCTT
TCCTGCGTTATCCCCTGATTCTGTGGATAACCGTATTACCGCCTTTGAGTGAGCTGATACCGCTCGCCGC
AGCCGAACGACCGAGCGCAGCGAGTCAGTGAGCGAGGAAGCGGAAGAGCGCCCAATACGCAAACCGCCTC
TCCCCGCGCGTTGGCCGATTCATTAATGCAGCTGGCACGACAGGTTTCCCGACTGGAAAGCGGGCAGTGA
```

FIG. 4E

GCGCAACGCAATTAATGTGAGTTAGCTCACTCATTAGGCACCCCAGGCTTTACACTTTATGCTCCCGGCT
CGTATGTTGTGTGGAATTGTGAGCGGATAACAATTTCACACAGGAAACAGCTATGACCATGATTACGCCA
AGCGCGCAATTAACCCTCACTAAAGGGAACAAAAGCTGGGTACCGGGCCCACGCGTAATACGACTCACTA
TAG

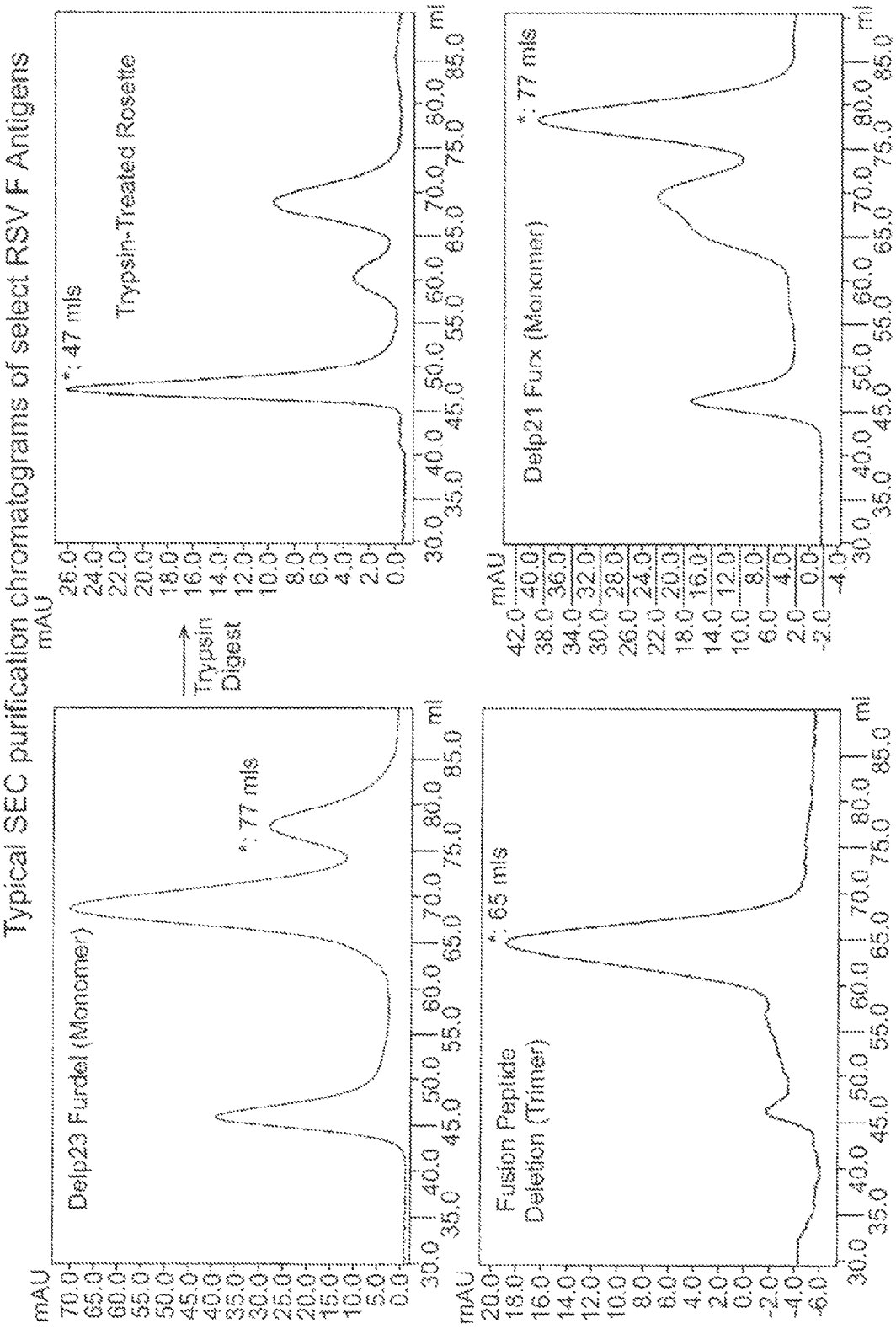

EM and SDS-PAGE analysis of RSV F antigen

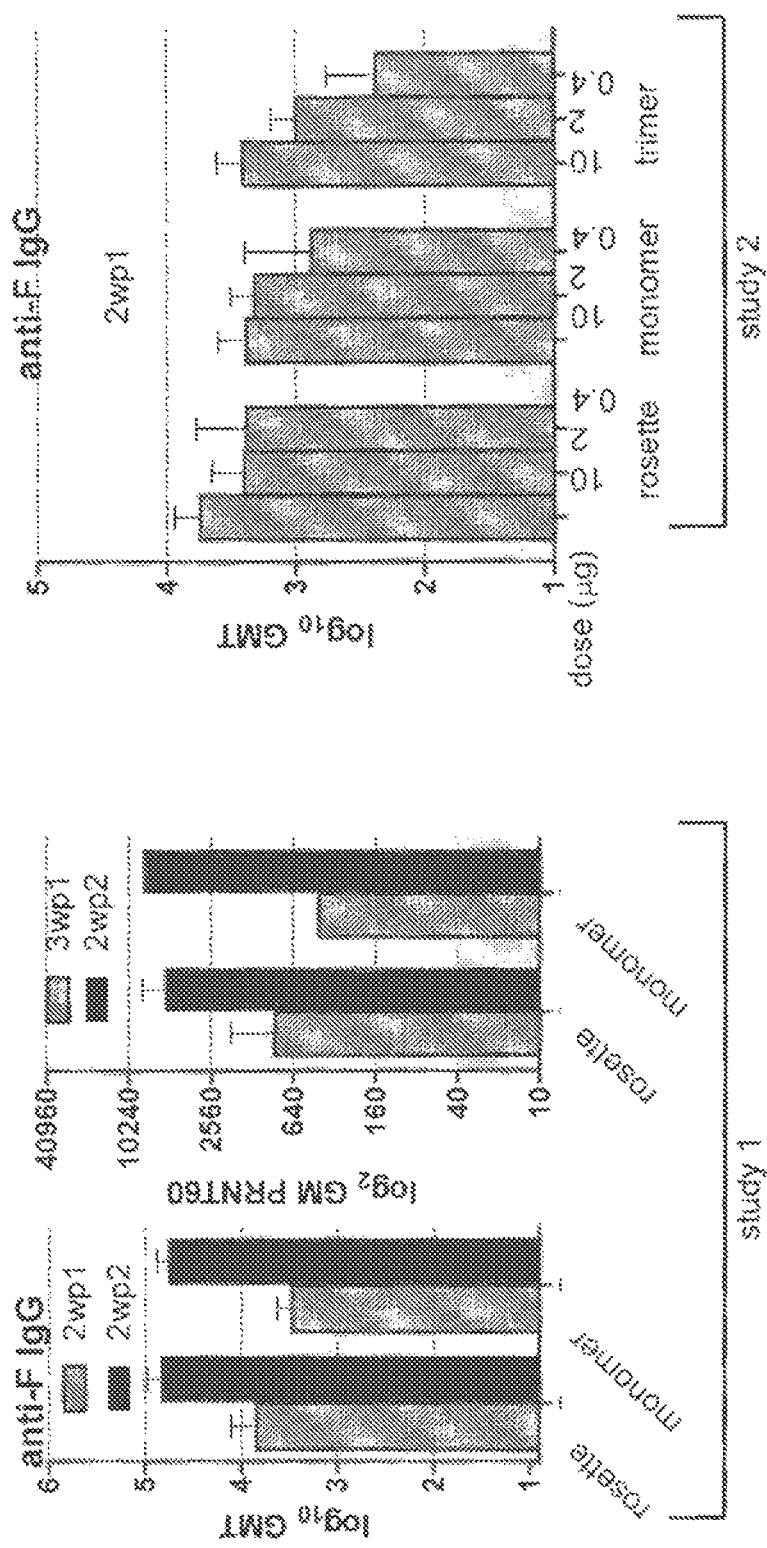

RSV F PROTEIN COMPOSITIONS AND METHODS FOR MAKING SAME

CROSS-REFERENCE TO RELATED APPLICATIONS

This application is a Continuation of U.S. patent application Ser. No. 15/678,798, filed on Aug. 16, 2017, which is a Continuation of U.S. patent application Ser. No. 12/836,931, filed on Jul. 15, 2010, which claims the benefit of U.S. Patent Application No. 61/225,805, filed on Jul. 15, 2009, and U.S. Patent Application No. 61/294,426, filed on Jan. 12, 2010. The entire teachings of the above applications are incorporated herein by reference.

BACKGROUND OF THE INVENTION

Respiratory syncytial virus (RSV) is an enveloped non-segmented negative-strand RNA virus in the family Paramyxoviridae, genus *Pneumovirus*. It is the most common cause of bronchiolitis and pneumonia among children in their first year of life. RSV also causes repeated infections including severe lower respiratory tract disease, which may occur at any age, especially among the elderly or those with compromised cardiac, pulmonary, or immune systems.

To infect a host cell, paramyxoviruses such as RSV, like other enveloped viruses such as influenza virus and HIV, require fusion of the viral membrane with a host cell's membrane. For RSV the conserved fusion protein (RSV F) fuses the viral and cellular membranes by coupling irreversible protein refolding with juxtaposition of the membranes. In current models based on paramyxovirus studies, the RSV F protein initially folds into a metastable "pre-fusion" conformation. During cell entry, the pre-fusion conformation undergoes refolding and conformational changes to its stable "post-fusion" conformation.

The RSV F protein is translated from mRNA into an approximately 574 amino acid protein designated $F_0$. Post-translational processing of $F_0$ includes removal of an N-terminal signal peptide by a signal peptidase in the endoplasmic reticulum. $F_0$ is also cleaved at two sites (approximately 109/110 and approximately 136/137) by cellular proteases (in particular furin) in the trans-Golgi. This cleavage results in the removal of a short intervening sequence and generates two subunits designated $F_1$ (~50 kDa; C-terminal; approximately residues 137-574) and $F_2$ (~20 kDa; N-terminal; approximately residues 1-109) that remain associated with each other. $F_1$ contains a hydrophobic fusion peptide at its N-terminus and also two amphipathic heptad-repeat regions (HRA and HRB). HRA is near the fusion peptide and HRB is near the transmembrane domain. Three $F_1$-$F_2$ heterodimers are assembled as homotrimers of $F_1$-$F_2$ in the virion.

A vaccine against RSV infection is not currently available, but is desired. One potential approach to producing a vaccine is a subunit vaccine based on purified RSV F protein. However, for this approach it is desirable that the purified RSV F protein is in a single form and conformation that is stable over time, consistent between vaccine lots, and conveniently purified.

The RSV F protein can be truncated, for example by deletion of the transmembrane domain and cytoplasmic tail, to permit its expression as an ectodomain, which may be soluble. In addition, although RSV F protein is initially translated as a monomer, the monomers are cleaved and assemble into trimers. When RSV F protein is in the form of cleaved trimers, the hydrophobic fusion peptide is exposed. The exposed hydrophobic fusion peptides on different trimers, e.g., soluble ecto-domain trimers, can associate with each other, resulting in the formation of rosettes. The hydrophobic fusion peptides can also associate with lipids and lipoproteins, for example from cells that are used to express recombinant soluble RSV F protein. Due to the complexity of RSV F protein processing, structure and refolding, purified, homogeneous, immunogenic preparations are difficult to obtain.

Thus, there is a need for improved RSV F protein compositions and methods for making RSV F protein compositions.

SUMMARY OF THE INVENTION

The invention relates to immunogenic compositions that contain one or more RSV F polypeptides, and to certain engineered RSV F proteins and nucleic acids that encode the engineered RSV F proteins.

In one aspect the RSV F protein is soluble. For example, the RSV F protein can have the transmembrane region and cytoplasmic tail deleted. In some aspects, the soluble RSV F contains one or more of 1) one or more mutations to one or both furin-cleavage sites, 2) one or more mutations to the fusion peptide, 3) one or more mutations to the p27 linker, 4) contains an added oligomerization sequence, and 5) contains an added amino acid sequence that provides a protease cleavage site. In additional or alternative aspects, the RSV F protein is a monomer, a trimer, or a combination of monomers and trimers. The trimer can be monodispered or in the form of a rosette. In further additional or alternative aspects, the RSV F protein can be in a prefusion conformation, an intermediate conformation or a postfusion conformation.

In one aspect, the immunogenic composition contains one or more respiratory syncytial virus F (RSV F) polypeptides in which amino acids 100-150 are replaced with the amino acid sequence of SEQ ID NO:9, SEQ ID NO:12, SEQ ID NO:3, SEQ ID NO:4, SEQ ID NO:5, SEQ ID NO:6, SEQ ID NO:7; SEQ ID NO:8, SEQ ID NO:10, SEQ ID NO:11, SEQ ID NO:13, SEQ ID NO:91 or SEQ ID NO:92. In some embodiments the RSV F polypeptide is soluble (e.g., an ectodomain).

In another aspect, the immunogenic composition contains an RSV F polypeptide in which amino acids 100-150 of the RSV F are replaced with the amino acid sequence of SEQ ID NO:12. In some embodiments the RSV F polypeptide is soluble (e.g., an ectodomain).

In yet another aspect, the immunogenic composition contains an RSV F polypeptide in which amino acids 100-150 of the RSV F are replaced with the amino acid sequence of SEQ ID NO:9, SEQ ID NO:3, SEQ ID NO:4, SEQ ID NO:5, SEQ ID NO:6, SEQ ID NO:7; SEQ ID NO:8, SEQ ID NO:10, SEQ ID NO:11, SEQ ID NO:13, or SEQ ID NO:92. In some embodiments the RSV F polypeptide is soluble (e.g., an ectodomain).

In another aspect, the immunogenic composition contains an RSV F polypeptide in which amino acids 100-150 are replaced with the amino acid sequence of SEQ ID NO:9. In some embodiments the RSV F polypeptide is soluble (e.g., an ectodomain).

In another aspect, the immunogenic composition contains an RSV F polypeptide in which RSV F contains amino acids 23-99 and 151-524 of SEQ ID NO:1 or SEQ ID NO:2. In some embodiments the RSV F polypeptide is soluble (e.g., an ectodomain).

In one aspect, the immunogenic composition contains a polypeptide selected from the group consisting of SEQ ID NO:49, SEQ ID NO:68, SEQ ID NO:71, SEQ ID NO: 25, SEQ ID NO:27, SEQ ID NO:28, SEQ ID NO:29, SEQ ID NO:31, SEQ ID NO:33, SEQ ID NO:35, SEQ ID NO:37, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:55, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:69, SEQ ID NO:70, SEQ ID NO:85, SEQ ID NO:86, SEQ ID NO:87, SEQ ID NO:88, SEQ ID NO:89, and SEQ ID NO:93. In some embodiments, the signal peptide and/or HIS tag is omitted. In some embodiments the RSV F polypeptide is soluble (e.g., an ectodomain).

In one aspect, the immunogenic composition contains SEQ ID NO:68 or alternatively, SEQ ID NO:68 in which the signal peptide, and optionally the HIS tag, is omitted.

In another aspect, the immunogenic composition contains a polypeptide selected from the group consisting of SEQ ID NO:49, SEQ ID NO:71, and any of the foregoing sequences in which the signal peptide, and optionally the HIS tag, is omitted. In some embodiments the RSV F polypeptide is soluble (e.g., an ectodomain).

In preferred embodiments, the immunogenic composition will include an adjuvant. The adjuvant is preferably an aluminum salt, a squalene-in-water emulsion (such as MF59), a benzonaphthyridine compound, a phospholipid compound (such as E6020), a small molecule immunepotentiator or a combination of any two or more of any of the foregoing.

Yet another aspect of the invention includes recombinant RSV F polypeptides. The RSV F may be in the form of a monomer, trimer, rosette of trimers, or combination of monomers and trimers. The recombinant polypeptide may include a heterologous oligomerization domain, an epitope or a signal peptide. The heterologous oligomerization domain is preferably a trimerization domain from influenza hemagglutinin, from SARS spike, or from HIV gp41, NadA, modified GCN4, or ATCase.

In one aspect, the recombinant RSV F polypeptide has amino acids 100-150 replaced with the amino acid sequence of SEQ ID NO:9, SEQ ID NO:12, SEQ ID NO:3, SEQ ID NO:4, SEQ ID NO:5, SEQ ID NO:6, SEQ ID NO:7, SEQ ID NO:8, SEQ ID NO:10, SEQ ID NO:11, SEQ ID NO:13, SEQ ID NO:91 or SEQ ID NO:92. In some embodiments the RSV F polypeptide is soluble (e.g., an ectodomain).

In another aspect, the recombinant RSV F polypeptide has amino acids 100-150 of the RSV F replaced with the amino acid sequence of SEQ ID NO:12. In some embodiments the RSV F polypeptide is soluble (e.g., an ectodomain).

In another aspect, the recombinant RSV F polypeptide has amino acids 100-150 of the RSV F replaced with the amino acid sequence of SEQ ID NO:9, SEQ ID NO:3, SEQ ID NO:4, SEQ ID NO:5, SEQ ID NO:6, SEQ ID NO:7; SEQ ID NO:8, SEQ ID NO:10, SEQ ID NO:11, SEQ ID NO:13, or SEQ ID NO:92. In some embodiments the RSV F polypeptide is soluble (e.g., an ectodomain).

In yet another aspect, the recombinant RSV F polypeptide has amino acids 100-150 of the RSV F replaced with the amino acid sequence of SEQ ID NO:9. In some embodiments the RSV F polypeptide is soluble (e.g., an ectodomain).

In one aspect, the recombinant polypeptide is selected from the group consisting of SEQ ID NO:49, SEQ ID NO:68, SEQ ID NO:71, SEQ ID NO: 25, SEQ ID NO:27, SEQ ID NO:28, SEQ ID NO:29, SEQ ID NO:31, SEQ ID NO:33, SEQ ID NO:35, SEQ ID NO:37, SEQ ID NO:41, SEQ ID NO:42, SEQ ID NO:43, SEQ ID NO:44, SEQ ID NO:45, SEQ ID NO:46, SEQ ID NO:48, SEQ ID NO:47, SEQ ID NO:50, SEQ ID NO:51, SEQ ID NO:52, SEQ ID NO:53, SEQ ID NO:54, SEQ ID NO:55, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:69, SEQ ID NO:70, SEQ ID NO:85, SEQ ID NO:86, SEQ ID NO:87, SEQ ID NO:88, SEQ ID NO:89, SEQ ID NO:93, and any combinations thereof. Optionally, the signal peptide and/or HIS tag is omitted. In some embodiments the RSV F polypeptide is soluble (e.g., an ectodomain).

Still another aspect includes nucleic acids encoding any of the foregoing polypeptides. The nucleic acid may be a self-replicating RNA molecule.

Another aspect of the invention is an immunogenic composition comprising a self-replicating RNA that encodes an RSV F polypeptide. The immunogenic composition can include a delivery system.

Another aspect of the invention includes methods of inducing an immune response to RSV F by administering any of the immunogenic compositions.

The invention relates to methods for preparing compositions and to compositions that contain RSV F protein, such as soluble RSV F ecto-domain polypeptides, including immunogenic compositions. The RSV F ecto-domain polypeptides can be in a single form, such as uncleaved monomers, uncleaved trimers, cleaved trimers, or rosettes of cleaved trimers. The RSV F ectodomain polypeptides can also be in two or more forms, for example two or more forms that exist in equilibrium, such as equilibrium between uncleaved monomers and uncleaved trimers. The invention provides several advantages. For example, the presence of a single desired form of RSV F in an immunogenic composition provides a more predictable immune response when the composition is administered to a subject, and more consistent stability and other physical and chemical characteristics when formulated into a vaccine.

In one aspect, the invention is a method for producing a composition comprising cleaved RSV F protein ecto-domain polypeptides. The method includes a) providing uncleaved RSV F protein ecto-domain polypeptides containing one or more protease cleavage sites that, when cleaved, produce $F_1$ and $F_2$ fragments, and b) cleaving the uncleaved RSV F protein ecto-domain polypeptides with a protease or proteases that recognize the protease cleavage site or sites. In general, the amino acid sequence of the uncleaved RSV F protein ecto-domain polypeptides contains altered furin cleavage sites, and the RSV F protein ecto-domain polypeptides are secreted from a host cell that produces them uncleaved at a position from amino acid 101 to amino acid 161, (e.g., is not cleaved at the furin cleavage sites at positions 106-109 and 131-136). In some embodiments, the uncleaved RSV F protein ecto-domain polypeptides provided in a) are purified.

The uncleaved RSV F protein ecto-domain polypeptides provided in a) can comprise an intact fusion peptide or an altered fusion peptide (e.g., a deleted fusion peptide or mutated fusion peptide). When the uncleaved RSV F protein ecto-domain polypeptides provided in a) contain an intact fusion peptide, the cleaving in step b) results in the formation of rosettes of trimers. When the uncleaved RSV F protein ecto-domain polypeptides provided in a) comprise an altered fusion peptide, the cleaving in step b) results in the formation of trimers.

The method can further comprise the optional step of purifying the rosettes or trimers produced by cleaving the uncleaved RSV F protein ecto-domain polypeptides. In preferred embodiments, the cleaved RSV F protein ecto-domain polypeptides produced according to the method are substantially free of lipids and lipoproteins.

In another aspect, the invention is a method for producing a composition comprising uncleaved RSV F protein ecto-domain polypeptide monomers, trimers or a combination of monomers and trimers. The method includes a) providing a biological material that contains uncleaved RSV F protein ecto-domain polypeptides; and b) purifying uncleaved RSV F protein ecto-domain polypeptide monomers or trimers from the biological material. In general, the amino acid sequence of the uncleaved RSV F protein ecto-domain polypeptides contains altered furin cleavage sites, and the RSV F protein ecto-domain polypeptides are secreted from a host cell that produces them uncleaved at a position from amino acid 101 to amino acid 161, (e.g., is not cleaved at the furin cleavage sites at positions 106-109 and 131-136). In some embodiments, the amino acid sequence of the uncleaved RSV F protein ecto-domain polypeptides further contain altered trypsin cleavage sites, and the RSV F protein ecto-domain polypeptides are not cleaved by trypsin at a site between amino acid 101 and amino acid 161. In other embodiments, the amino acid sequence of the uncleaved RSV F protein ecto-domain polypeptides further contain an altered fusion peptide.

In some embodiments, uncleaved RSV F protein ecto-domain polypeptide trimers are purified. In other embodiments, uncleaved RSV F protein ecto-domain polypeptide monomers are purified. In still other embodiments a mixture of uncleaved RSV F protein ecto-domain monomers and trimers, which may be in a dynamic equilibrium, are purified. In preferred embodiments, the cleaved RSV F protein ecto-domain polypeptides produced according to the method are substantially free of lipids and lipoproteins.

In another aspect, the invention is a method for producing a composition comprising cleaved RSV F protein ecto-domain polypeptide monomers, trimers or a combination of monomers and trimers. The method includes a) providing a biological material that contains cleaved RSV F protein ecto-domain polypeptides that contain an altered fusion peptide; and b) purifying cleaved RSV F protein ecto-domain polypeptides from the biological material.

In some embodiments, cleaved RSV F protein ecto-domain polypeptide trimers are purified. In other embodiments, cleaved RSV F protein ecto-domain polypeptide monomers are purified. In still other embodiments a mixture of cleaved RSV F protein ecto-domain monomers and trimers, which may be in a dynamic equilibrium, are purified. In preferred embodiments, the cleaved RSV F protein ecto-domain polypeptides produced according to the method are preferably substantially free of lipids and lipoproteins. In still another embodiment, a cleaved RSV F protein ectodomain trimer containing an altered fusion peptide is purified.

In other aspects, the invention provides compositions, including immunogenic compositions, produced using the methods of the invention.

BRIEF DESCRIPTION OF THE DRAWINGS

FIGS. 1A-1C shows the schematic of the wild type RSV F (FIG. 1A) and of a ectodomain construct in which the transmembrane domain and cytoplasmic tail have been removed and an optional HIS6-tag has been added to the C-terminus (FIG. 1B). For clarity, residue numbering is related to the wild type A2 strain RSV F beginning at the N-terminal signal peptide and is not altered in constructs containing amino acid deletions. Labeled in the schematics is the signal sequence or signal peptide (sp). FIG. 1A is a schematic of RSV F protein showing the signal sequence or signal peptide (SP), p27 linker region, fusion peptide (FP), HRA domain (HRA), HRB domain (HRB), transmembrane region (TM), and cytoplasmic tail (CT). The C-terminal bounds of the ectodomain can very. FIG. 1B is a general schematic of the RSV F ectodomain construct depicting the shared features with the schematics in FIG. 1A and including an optional $HIS_6$-tag (HIS TAG). Furin cleavage sites are present at amino acid positions 109/110 and 136/137. FIG. 1C also shows the amino acid sequence of amino acids 100-150 of RSV F (wild type) (SEQ ID NO:108) and several proteins (Furmt-SEQ ID NO:3; Furdel-SEQ ID NO:4; Furx-SEQ ID NO:6; Furx R113Q, K123N, K124N-SEQ ID NO:5; Furx R113Q, K123Q, K124Q-SEQ ID NO:92; Delp21 furx-SEQ ID NO:7; Delp23 furx-SEQ ID NO:8; Delp23 furdel-SEQ ID NO:9; N-Term Furin-SEQ ID NO:10; C-term Furin-SEQ ID NO:11; Fusion Peptide Deletion1-SEQ ID NO:12; and Factor Xa-SEQ ID NO:13) in which the one or both furin cleavage sites and/or fusion peptide region were mutated or deleted. In FIG. 1C, the symbol "-" indicates that the amino acid at that position is deleted.

FIG. 2 shows the amino acid sequence of the carboxy terminus from amino acid position 488 to the start of the TM region of RSV F (wild type) (SEQ ID NO:94) and several proteins (SEQ ID NOS:95-100) that contain added protease cleavage sites. In FIG. 2, the symbol "-" indicates that there is no amino acid at that position.

FIGS. 4A-4F shows the nucleotide sequence (SEQ ID NO:101) of the plasmid encoding the pT7-TC83R-FL.RSVF (A317) self-replicating RNA molecule which encodes the respiratory syncytial virus F glycoprotein (RSV-F). The nucleotide sequence encoding RSV-F is underlined.

FIG. 5 is an alignment of the amino acid sequences of F proteins from several strains of RSV. The alignment was prepared using the algorithm disclosed by Corpet, Nucleic Acids Research, 1998, 16(22):10881-10890, using default parameters (Blossum 62 symbol comparison table, gap open penalty: 12, gap extension penalty: A2, F protein of the strain A2 (accession number AF035006) (SEQ ID NO:102); CP52, F protein of the CP52 strain (accession number AF013255) (SEQ ID NO:103); B, F protein of the B strain (accession number AF013254) (SEQ ID NO:104); long, F protein of the long strain (accession number AY911262) strain (SEQ ID NO:105), and 18537strain, F protein of the 18537 strain (accession number Swiss Prot P13843) (SEQ ID NO:106). A consensus of F protein sequences is also shown (SEQ ID NO:107)

FIGS. 6A-6D shows relevant regions of size exclusion (SEC) chromatograms from select RSV F antigen purifications. The principle peak containing the indicated antigen is indicated by an asterisk with the retention time of the Superdex P200 16/60 column (GE Healthcare) is indicated in milliliters. On a calibrated column, the approximate retention times of 47 mls, 65 mls and 77 mls correspond to the column void volume, the retention of the RSV F trimer and the retention of the RSV F monomer, respectively. In FIG. 6A, the uncleaved Delp23 Furdel (Δp23 Furdel) construct is purified from the monomer peak at approximately 77 mls. When the uncleaved Delp23 Furdel RSV F antigen is treated with trypsin, the protein can form rosettes, which now migrate on SEC in the void volume at approximately 47 mls (FIG. 6B). The cleaved trimer species of RSV F fusion peptide deletion is purified from the trimer peak at approximately 65 mls retention time (FIG. 6C) while the uncleaved Delp21 Furx construct (Δp21 Furx) is purified from the monomer peak at approximately 77 mls (FIG. 6D).

FIGS. 7A-7D shows representative EM images of select RSV F antigens. FIG. 7A shows an EM image of RSV F Δp23 (Delp23) before trypsin treatment. The crutch shapes in FIG. 7A, consistent with a postfusion trimer conformation, are not always observed in the uncleaved Δp23 (Delp23) Furdel construct. When the Δp23 (Delp23) Furdel contruct is treated with trypsin and purified from the void volume of an SEC column and observed by EM the proteins are found to have adopted rosette conformations (FIG. 7B). When the RSV F fusion peptide deletion construct is purified from the trimer peak on an SEC column a monodispersed crutch shape is observed, consistent with the a postfusion trimer (FIG. 7C). Shown in FIG. 7D are three preparations of either Δp21 (Delp21) furx RSV F (labeled Monomer), Fusion peptided deletion RSV F (lanes labeled Trimer) and purified RSV F rosettes (labeled Rosettes). The gel contains several lanes of GE Full Range Standard (molecular weights standard are labeled to the left of the gel) while approximate retention times of RSV F fragments are indicated on the right of the gel.

FIGS. 8A-8C are graphs showing that monomers (uncleaved Δp21 (Delp21) furx), rosettes of trimers (cleaved Δp23 (Delp23) Furdel), and trimers (fusion peptide deletion) of RSV F ecto-domain polypeptides are immunogenic in cotton rats. Serum titers of anti-RSV F IgG and neutralizing anti-RSV antibodies were measured 2 weeks after the 1$^{st}$ vaccination (2wp1), 3 weeks after the 1$^{st}$ vaccination (3wp1), and/or 2 weeks after the 2$^{nd}$ vaccination (2wp2).

DETAILED DESCRIPTION OF THE INVENTION

Figure 3:
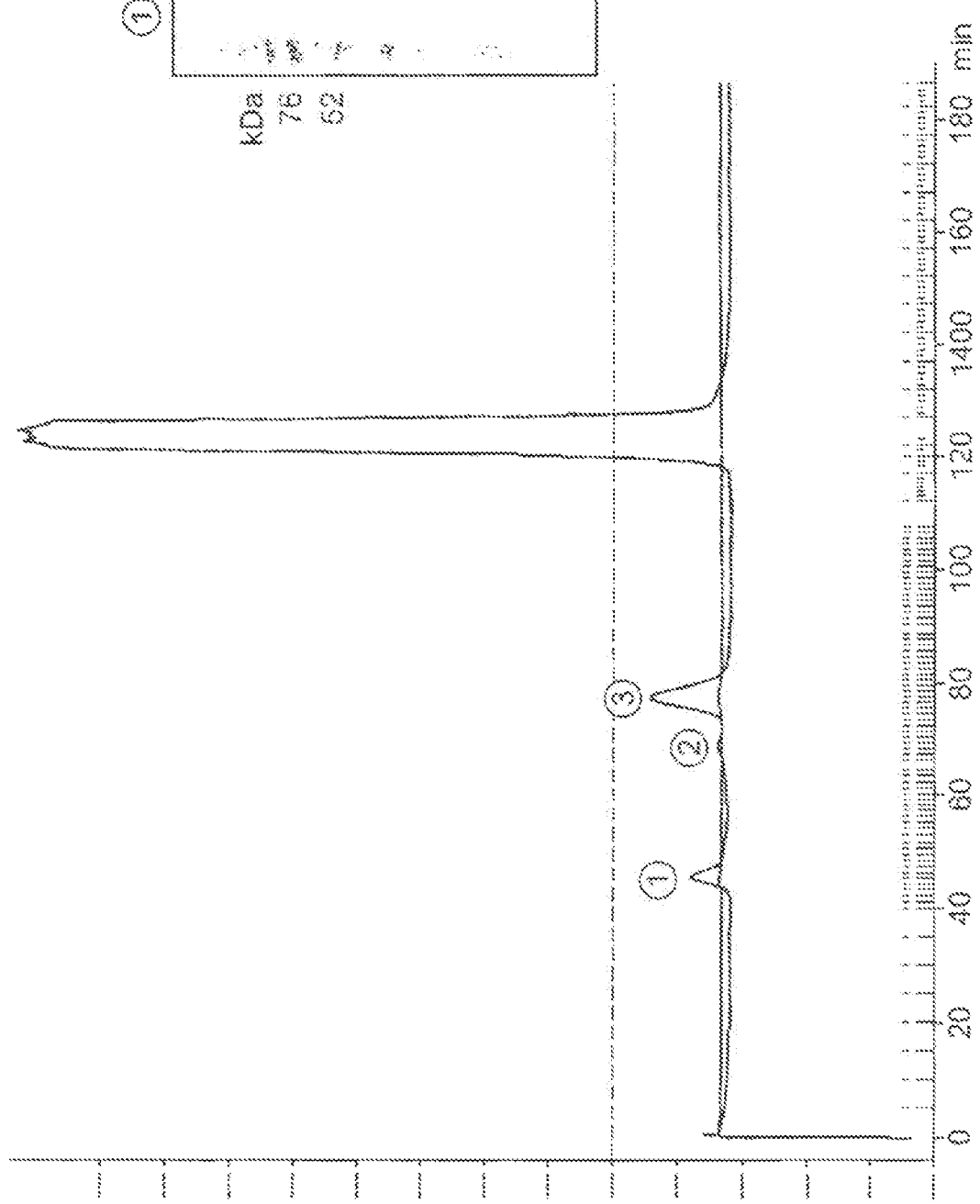
FIG. 3 is a chromatogram and image of an electrophoresis gel showing the purification of RSV F monomers (3) using size exclusion chromatography.

The invention relates to respiratory syncytial virus F (RSV F) polypeptides and/or proteins, immunogenic compositions comprising RSV F polypeptides and/or proteins, methods for producing RSV F polypeptides and/or proteins and compositions comprising RSV F polypeptides and/or proteins, and nucleic acids that encode RSV F polypeptides and/or proteins.

In general, the immunogenic compositions comprise RSV F polypeptides and/or proteins that contain mutations (e.g., amino acid replacements, deletions or additions) which provide beneficial characteristics, such as one or more of 1) stabilized prefusion or intermediate (non-post fusion) conformation, 2) reduced or eliminated exposure of the fusion peptide, 3) improved stability (e.g., reduced aggregation and/or degradation, and 4) more closely resemble active F1/F2 viral protein. These characteristics provide advantages for the immunogenic compositions and for the manufacture of the immunogenic compositions. For example, as described herein, non-post fusion conformations of RSV F protein (i.e., prefusion conformation, intermediate conformations) can be better immunogens and elicit a better neutralizing antibody response. Reducing or eliminating the exposure of the fusion peptide, e.g., by introducing mutations or deletions into the furin cleavage sites, will reduce the hydrophobicity of the polypeptide and facilitate purifications, and also reduce or eliminate the RSV F protein from associating with cell membranes in a subject to whom the protein is administered. Improved stability of the protein facilitates producing immunogenic compositions in which the protein has a decreased tendency to aggregate or degrade, which provides a more predictable immune response when the composition is administered to a subject. Finally, mutant RSV F polypeptides or proteins that resemble F1/F2 viral protein, for example by deletion of all or part of the p27 linker region, may elicit a better neutralizing antibody response. Other advantages of the invention are described herein.

The invention also relates to methods for preparing compositions that contain RSV F protein, in particular RSV F ecto-domain polypeptides, and to compositions including immunogenic compositions comprising RSV F protein. Preferably, the RSV F ecto-domain polypeptides are in a single form or in a dynamic equilibrium between known forms.

Definitions

As used herein "population" refers to more than one RSV F polypeptide or protein that is present in a composition. The population can be substantially homogenous, in which substantially all RSV F polypeptides or proteins are substantially the same (e.g., same amino acid sequence, same conformation), heterogenous, or have a desired degree of homogenicity (e.g., at least about 50%, at least about 55%, at least about 60%, at least about 65%, at least about 70%, at least about 75%, at least about 80%, at least about 85%, at least about 90%, at least about 95%, at least about 99% of the RSV F polypeptides or proteins are prefusion conformation, are postfusion conformation, are monomers, are trimers).

The "post fusion conformation" of RSV F protein is a trimer characterized by the presence of a six-helix bundle comprising 3 HRB and 3HRA regions.

The "pre-fusion conformation" of RSV F protein is a conformation characterized by a trimer that contains a triple helix comprising 3 HRB regions.

As used herein, "RSV F ecto-domain polypeptide" refers to an RSV F protein polypeptide that contains substantially the extracellular portion of mature RSV F protein, with our without the signal peptide (e.g., about amino acids 1 to about amino acid 524, or about amino acid 22 to about amino acid 524) but lacks the transmembrane domain and cytoplasmic tail of naturally occurring RSV F protein.

As used herein, "cleaved RSV F ecto-domain polypeptide" refers to a RSV F ectodomain polypeptide that has been cleaved at one or more positions from about 101/102 to about 160/161 to produce two subunits, in which one of the subunits comprises $F_1$ and the other subunit comprises $F_2$.

As used herein, "C-terminal uncleaved RSV F ecto-domain polypeptide" refers to an RSV F ectodomain polypeptide that is cleaved at one or more positions from about 101/102 to about 131/132, and is not cleaved at one or more positions from about 132/133 to about 160/161, to produce two subunits, in which one of the subunits comprises $F_1$ and the other subunit comprises $F_2$.

As used herein, "uncleaved RSV F ecto-domain polypeptide" refers to an RSV F ectodomain polypeptide that is not cleaved at one or more positions from about 101/102 to about 160/161. An uncleaved RSV F ecto-domain polypeptide can be, for example, a monomer or a trimer.

As used herein, "fusion peptide" refers to amino acids 137-154 of RSV F protein.

As used herein, "altered fusion peptide" refers to a fusion peptide in which one or more amino acids are independently replaced or deleted, including replacement or deletion of all amino acids from positions 137-154. Preferably, cleaved RSV F ecto-domain polypeptides that contain an "altered fusion peptide" do not form rosettes.

As used herein, a "purified" protein or polypeptide is a protein or polypeptide which is recombinantly or synthetically produced, or produced by its natural host, and has been isolated from other components of the recombinant or synthetic production system or natural host such that the amount of the protein relative to other macromolecular components present in a composition is substantially higher than that present in a crude preparation. In general, a purified protein will be at least about 50% homogeneous and more preferably at least about 75%, at least about 80%, at least about 85%, at least about 90%, at least about 95% or substantially homogeneous.

As used herein, "substantially free of lipids and lipoproteins" refers to compositions, proteins and polypeptides that are at least about 95% free of lipids and lipoproteins on a mass basis when protein and/or polypeptide (e.g., RSV F polypeptide) purity is observed on an SDS PAGE gel and total protein content is measured using either UV280 absorption or BCA analysis, and lipid and lipoprotein content is determined using the Phospholipase C assay (Wako, code no. 433-36201).

As used herein, "altered furin cleavage site" refers the amino acid sequence at about positions 106-109 and at about positions 133-136 in naturally occurring RSV F protein that are recognized and cleaved by furin or furin-like proteases, but in an uncleaved RSV F protein ecto-domain polypeptide contains one or more amino acid replacements, one or more amino acid deletions, or a combination of one or more amino acid replacement and one or more amino acid deletion, so that an RSV F ecto-domain polypeptide that contains an altered furin cleavage site is secreted from a cell that produces it uncleaved at the altered furin cleavage site.

Features of RSV F protein ecto-domains suitable for use in this invention are described herein with reference to particular amino acids that are identified by the position of the amino acid in the sequence of RSV F protein from the A2 strain (SEQ ID NO:1). RSV F protein ecto-domains can have the amino acid sequence of the F protein from the A2 strain or any other desired strain. When the F protein ecto-domain from a strain other than the A2 strain is used, the amino acids of the F protein are to be numbered with reference to the numbering of the F protein from the A2 strain, with the insertion of gaps as needed. This can be achieved by aligning the sequence of any desired RSV F protein with the F protein of the strain A2, as shown herein for F proteins from the A2 strain, CP52 strain, B strain, long strain, and the 18537 strain. See, FIG. 5. Sequence alignments are preferably produced using the algorithm disclosed by Corpet, Nucleic Acids Research, 1998, 16(22):10881-10890, using default parameters (Blossum 62 symbol comparison table, gap open penalty: 12, gap extension penalty: 2).

The invention provides soluble RSV F polypeptides and proteins, and immunogenic compositions comprising the soluble RSV F polypeptides and proteins, as well as compositions comprising nucleic acids (e.g., self-replicating RNA molecules) that encode the soluble RSV F polypeptides and proteins.

The RSV F polypeptides (e.g., ecto-domain polypeptides) can be in any desired form, such as in a single form, such as uncleaved monomers, uncleaved trimers, cleaved trimers, or rosettes of cleaved trimers. The RSV F ectodomain polypeptides can also be in two or more forms, for example two or more forms that exist in equilibrium, such as equilibrium between uncleaved monomers and uncleaved trimers. The invention provides several advantages. For example, the presence of a single desired form of RSV, or a dynamic equilibrium between known forms, in an immunogenic composition, provides for more predictable formulation, solubility and stability, and for a more predictable immune response when the composition is administered to a subject.

Preferably, the RSV F ecto-domain polypeptides are in a single form, such as uncleaved monomers, uncleaved trimers, cleaved trimers, rosettes of cleaved trimers, or in a dynamic equilibrium between a subset of such forms (e.g., equilibrium between uncleaved monomers and uncleaved trimers).

In one aspect of the invention, the RSV F polypeptides and proteins are in pre-fusion conformation. The epitopes of the pre-fusion conformation may be better able to elicit antibodies that can recognize and neutralize natural virions.

In one embodiment of the invention an immunogenic composition comprises a population of respiratory syncytial virus F glycoproteins in pre-fusion conformation. In another aspect of the invention, an immunogenic composition comprises a population of respiratory syncytial virus F glycoproteins which disfavor the post-fusion conformation as compared to a population of isolated RSV F glycoproteins.

The invention also provides an immunogenic composition comprising a polypeptide that displays an epitope present in a pre-fusion or an intermediate fusion conformation of respiratory syncytial virus F glycoprotein but absent the glycoprotein's post-fusion conformation.

The F Glycoprotein

The F glycoprotein of RSV directs viral penetration by fusion between the virion envelope and the host cell plasma membrane. It is a type I single-pass integral membrane protein having four general domains: N-terminal ER-translocating signal sequence (SS), ectodomain (ED), transmembrane domain (TM), and a cytoplasmic tail (CT). CT contains a single palmitoylated cysteine residue. The sequence of F protein is highly conserved among RSV isolates, but is constantly evolving (7). Unlike most paramyxoviruses, the F protein in RSV can mediate entry and syncytium formation independent of the other viral proteins (HN is usually necessary in addition to F in other paramyxoviruses).

The hRSV F mRNA is translated into a 574 amino acid precursor protein designated $F_0$, which contains a signal peptide sequence at the N-terminus that is removed by a signal peptidase in the endoplasmic reticulum. $F_0$ is cleaved at two sites (a.a. 109/110 and 136/137) by cellular proteases (in particular furin) in the trans-Golgi, removing a short glycosylated intervening sequence and generating two subunits designated $F_1$ (~50 kDa; C-terminus; residues 137-574) and $F_2$ (~20 kDa; N-terminus; residues 1-109) (See, e.g., FIGS. 1A-1C). $F_1$ contains a hydrophobic fusion peptide at its N-terminus and also two hydrophobic heptad-repeat regions (HRA and HRB). HRA is near the fusion peptide and HRB is near to the transmembrane domain (See, e.g., FIGS. 1A-1C). The $F_1$-$F_2$ heterodimers are assembled as homotrimers in the virion.

RSV exists as a single serotype but has two antigenic subgroups: A and B. The F glycoproteins of the two groups are about 90% identical. The A subgroup, the B subgroup, or a combination or hybrid of both can be used in the invention. An example sequence for the A subgroup is SEQ ID NO: 1 (A2 strain; GenBank GI: 138251; Swiss Prot P03420), and for the B subgroup is SEQ ID NO: 2 (18537 strain; GI: 138250; Swiss Prot P13843). SEQ ID NO:1 and SEQ ID NO:2 are both 574 amino acid sequences. The signal peptide in A2 strain is a.a. 1-21, but in 18537 strain it is 1-22. In both sequences the TM domain is from about a.a. 530-550, but has alternatively been reported as 525-548.

```
                                                         SEQ ID NO: 1
  1 MELLILKANAITTILTAVTFCFASGQNITEEFYQSTCSAVSKGYLSALRTGWYTSVITIE  60

61 LSNIKENKCNGTDAKVKLIKQELDKYKNAVTELQLLMQSTPPTNNRARRELPRFMNYTLN 120

121 NAKKTNVTLSKKRKRRFLGFLLGVGSAIASGVAVSKVLHLEGEVNKIKSALLSTNKAVVS 180

181 LSNGVSVLTSKVLDLKNYIDKQLLPIVNKQSCSISNIETVIEFQQKNNRLLEITREFSVN 240

241 AGVTTPVSTYMLTNSELLSLINDMPITNDQKKLMSNNVQIVRQQSYSIMSIIKEEVLAYV 300

301 VQLPLYGVIDTPCWKLHTSPLCTTNTKEGSNICLTRTDRGWYCDNAGSVSFFPQAETCKV 360

361 QSNRVFCDTMNSLTLPSEINLCNVDIFNPKYDCKIMTSKTDVSSSVITSLGAIVSCYGKT 420

421 KCTASNKNRGIIKTFSNGCDYVSNKGMDTVSVGNTLYYVNKQEGKSLYVKGEPIINFYDP 480

481 LVFPSDEFDASISQVNEKINQSLAFIRKSDELLHNVNAGKSTTNIMITTIIIVIIVILLS 540

541 LIAVGLLLYCKARSTPVTLSKDQLSGINNIAFSN                           574
                                                         SEQ ID NO: 2
  1 MELLIHRSSAIFLTLAVNALYLTSSQNITEEFYQSTCSAVSRGYFSALRTGWYTSVITIE  60

61 LSNIKETKCNGTDTKVKLIKQELDKYKNAVTELQLLMQNTPAANNRARREAPQYMNYTIN 120

121 TTKNLNVSISKKRKRRFLGFLLGVGSAIASGIAVSKVLHLEGEVNKIKNALLSTNKAVVS 180

181 LSNGVSVLTSKVLDLKNYINNRLLPIVNQQSCRISNIETVIEFQQMNSRLLEITREFSVN 240

241 AGVTTPLSTYMLTNSELLSLINDMPITNDQKKLMSSNVQIVRQQSYSIMSIIKEEVLAYV 300

301 VQLPIYGVIDTPCWKLHTSPLCTTNIKEGSNICLTRTDRGWYCDNAGSVSFFPQADTCKV 360

361 QSNRVFCDTMNSLTLPSEVSLCNTDIFNSKYDCKIMTSKTDISSSVITSLGAIVSCYGKT 420

421 KCTASNKNRGIIKTFSNGCDYVSNKGVDTVSVGNTLYYVNKLEGKNLYVKGEPIINYYDP 480

541 LIAIGLLLYCKAKNTPVTLSKDQLSGINNIAFSK                           574
```

The invention may use any desired RSV F amino acid sequence, such as the amino acid sequence of SEQ ID NO: 1 or 2, or a sequence having identity to SEQ ID NO: 1 or 2. Typically it will have at least 75% identity to SEQ ID NO: 1 or 2 e.g., at least 80%, at least 85%, at least 90%, at least 95%, at least 97%, at least 98%, at least 99%,identity to SEQ ID NO:1 or 2. The sequence may be found naturally in RSV.

Where the invention uses an ectodomain of F protein, in whole or in part, it may comprise:

(i) a polypeptide comprising about amino acid 22-525 of SEQ ID NO: 1.
(ii) a polypeptide comprising about amino acids 23-525 of SEQ ID NO: 2.
(iii) a polypeptide comprising an amino acid sequence having at least 75% identity (e.g., at least 80%, at least 85%, at least 90%, at least 95%, at least 97%, at least 98%, at least 99% identity) to (i) or (ii).
(iv) a polypeptide comprising a fragment of (i), (ii) or (iii), wherein the fragment comprises at least one F protein epitope. The fragment will usually be at least about 100 amino acids long, e.g., at least about 150, at least about 200, at least about 250, at least about 300, at least about 350, at least about 400, at least about 450 amino acids long.

The ectodomain can be an $F_0$ form with or without the signal peptide, or can comprises two separate peptide chains (e.g., an $F_1$ subunit and a $F_2$ subunit) that are associated with each other, for example, the subunits may be linked by a disulfide bridge. Accordingly, all or a portion of about amino acid 101 to about 161, such as amino acids 110-136, may be absent from the ectodomain. Thus the ectodomain, in whole or in part, can comprise:

(v) a first peptide chain and a second peptide chain that is associated with the first polypeptide chain, where the first peptide chain comprises an amino acid sequence having at least 75% identity (e.g., at least 80%, at least 85%, at least 90%, at least 95%, at least 97%, at least 98%, at least 99%, or even 100% identity) to about amino acid 22 to about amino acid 101 of SEQ ID NO: 1 or to about amino acid 23 to about amino acid 101 of SEQ ID NO: 2, and the second peptide chain comprises an amino acid sequence having at least 75% identity (e.g., at least 80%, at least 85%, at least 90%, at least 95%, at least 97%, at least 98%, at least 99%, or even 100% identity) to about amino acid 162 to about 525 of SEQ ID NO: 1 or to about amino acid 162 to 525 of SEQ ID NO: 2.

(vi) a first peptide chain and a second peptide chain that is associated with the first polypeptide chain, where the first peptide chain comprises an amino acid sequence comprising a fragment of about amino acid 22 to about amino acid 101 of SEQ ID NO: 1 or of about amino acid 23 to about amino acid 109 of SEQ ID NO: 2, and the second peptide chain comprises a fragment of about amino acid 162 to about amino acid 525 of SEQ ID NO: 1 or of about amino acid 161 to about amino acid 525 of SEQ ID NO: 2. One or both of the fragments will comprises at least one F protein epitope. The fragment in the first peptide chain will usually be at least 20 amino acids long, e.g., at least 30, at least 40, at least 50, at least 60, at least 70, at least 80 amino acids long. The fragment in the second peptide chain will usually be at least 100 amino acids long, e.g., at least 150, at least 200, at least 250, at least 300, at least 350, at least 400, at least 450 amino acids long.

(vii) a molecule obtainable by furin digestion of (i), (ii), (iii) or (iv).

Thus an amino acid sequence used with the invention may be found naturally within RSV F protein (e.g., a soluble RSV F protein lacking TM and CT, about amino acids 522-574 of SEQ ID NOS: 1 or 2), and/or it may have one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30) single amino acid mutations (insertions, deletions or substitutions) relative to a natural RSV sequence. For instance, it is known to mutate F proteins to eliminate their furin cleavage sequences, thereby preventing intracellular processing. In certain embodiments, the RSV F protein lacks TM and CT (about amino acids 522-574 of SEQ ID NOS: 1 or 2) and contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30) single amino acid mutations (insertions, deletions or substitutions) relative to a natural RSV sequence.

Furin-Cleavage, Trypsin-Cleavage and Fusion Peptide Mutations

RSV F polypeptides or proteins may contain one or more mutations that prevent cleavage at one or both of the furin cleavage sites (i.e., amino acids 109 and 136 of SEQ ID NOS: 1 and 2). These mutations can prevent aggregation of the soluble polypeptides or proteins and thereby facilitate purifications, can prevent cell-cell fusion if the RSV F protein is expressed on the surface of a cell, such as by expression from a viral replicon (e.g., alphavirus replicon particles), or if the RSV F protein is a component of a virus-like particle. These mutations, alone or in combination with other mutations described herein, may also stabilize the protein in the pre-fusion conformation.

Examples of suitable furin cleavage mutations include replacement of amino acid residues 106-109 of SEQ ID NO: 1 or 2 with RARK (SEQ ID NO:77), RARQ (SEQ ID NO:78), QAQN (SEQ ID NO:79), or IEGR (SEQ ID NO:80). Alternatively, or in addition, amino acid residues 133-136 of SEQ ID NO: 1 or 2 can be replaced with RKKK (SEQ ID NO:81), ΔΔΔR, QNQN (SEQ ID NO:82), QQQR (SEQ ID NO:83) or IEGR (SEQ ID NO:80). (Δ indicates that the amino acid residue has been deleted.) These mutations can be combined, if desired, with other mutations described herein, such as mutations in the p27 region (amino acids 110-136 of SEQ ID NOS: 1 or 2), including deletion of the p27 region in whole or in part.

These furin cleavage mutations can be combined, if desired, with other mutations described herein, such as trypsin cleavage mutations and fusion peptide mutations. Examples of suitable trypsin cleavage mutations include deletion of any lysine or arginine residue between about position 101 and position 161 of SEQ ID NO:1 or 2, or replacement of any such lysine or arginine residue with an amino acid other than lysine or arginine. For example, lysine and/or arginine residues in the p27 region (about amino acids 110-136 of SEQ ID NOS: 1 or 2) can be substituted or deleted, including deletion of the p27 region in whole or in part.

Alternatively or in addition to the furin-cleavage mutations, RSV F polypeptides or proteins may contain one or more mutations in the fusion peptide region (amino acids 137 and 153 of SEQ ID NOS: 1 or 2). For example, this region can be deleted in whole or in part.

In particular embodiments, the sequence of amino acid residue 100-150 of the RSV F polypeptide or protein, such as SEQ ID NO:1, SEQ ID NO:2, or the soluble ecto domains thereof, is

```
                                                                    (SEQ ID NO: 3)
(Furmt)                    TPATNNRARKELPRFMNYTLNNAKKTNVTLSKKRKKKFLGFLLGVGSAIAS (SEQ ID NO: 4)
(Furdel)                   TPATNNRARQELPRFMNYTLNNAKKTNVTLSKK---RFLGFLLGVGSAIAS (SEQ ID NO: 6)
(Furx)                     TPATNNQAQNELPRFMNYTLNNAKKTNVTLSQNQNQNFLGFLLGVGSAIAS (SEQ ID NO: 5)
(Furx R113Q, K123N, K124N) TPATNNQAQNELPQFMNYTLNNANNTNVTLSQNQNQNFLGFLLGVGSAIAS (SEQ ID NO: 92)
(Furx R113Q, K123Q, K124Q)) TPATNNQAQNELPQFMNYTLNNAQQTNVTLSQNQNQNFLGFLLGVGSAIAS (SEQ ID NO: 7)
(Delp21Furx)               TPATNNQAQN--------------------QNQNQNFLGFLLGVGSAIAS (SEQ ID NO: 8)
(Delp23Furx)               TPATNNQAQN----------------------QNQNFLGFLLGVGSAIAS (SEQ ID NO: 109)
(Delp21 furdel)            TPATNNRARQ--------------------QNQQQRFLGFLLGVGSAIAS (SEQ ID NO: 9)
(Delp23furdel)             TPATNNRARQ----------------------QQQRFLGFLLGVGSAIAS (SEQ ID NO: 10)
(Nterm Furin)              TPATNNRARRELPQFMNYTLNNAQQTNVTLSQNQNQNFLGFLLGVGSAIAS (SEQ ID NO: 11)
(Cterm Furin)              TPATNNQAQNELPQFMNYTLNNAQQTNVTLSKKRKRRFLGFLLGVGSAIAS (SEQ ID NO: 12)
(Fusion peptide deletion 1) TPATNNRARRELPRFMNYTLNNAKKTNVTLSKKRKRR---------SAIAS (SEQ ID NO: 91)
(Fusion peptide deletion 2) TPATNNRARRELPRFMNYTLNNAKKTNVTLSKKRKRR------GVGSAIAS,
or
                                                                    (SEQ ID NO: 13)
(Factor Xa)                TPATNNIEGRELPRFMNYTLNNAKKTNVTLSKKIEGRFLGFLLGVGSAIS;
``` wherein the symbol "-" indicates that the amino acid at that position is deleted.

In addition to furin-cleavage and fusion peptide mutations, or alternatively, soluble RSV F polypeptides or proteins, such as those that lack the transmembrane region and cytoplasmic tail, may contain one or more oligomerization sequences. When an oligomerization sequence is present, it is preferably a trimerization sequence. Suitable oligomerization sequences are well known in the art and include, for example, the coiled coil of the yeast GCN4 leucine zipper protein, trimerizing sequence from bacteriophage T4 fibritin ("foldon"), and the trimer domain of influenza HA. These and other suitable oligomerization sequences are described in greater detail herein.

In particular embodiments, the sequence of the carboxy terminus of the RSV F polypeptide or protein, starting from position 480, is structs that encode the ecto-domains in suitable recombinant host cells, although any suitable methods can be used. Suitable recombinant host cells include, for example, insect cells (e.g., *Aedes aegypti, Autographa californica, Bombyx mori, Drosophila melanogaster, Spodoptera frugiperda,* and *Trichoplusia ni*), mammalian cells (e.g., human, non-human primate, horse, cow, sheep, dog, cat, and rodent (e.g., hamster), avian cells (e.g., chicken, duck, and geese), bacteria (e.g., *E. coli, Bacillus subtilis,* and *Streptococcus* spp.), yeast cells (e.g., *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*), *Tetrahymena* cells (e.g., *Tetrahymena thermophila*) or combinations thereof. Many suitable insect cells and mammalian cells are well-known in the art. Suitable insect cells include, for example, Sf9 cells, Sf21 cells, Tn5

```
                                                                      (SEQ ID NO: 14)
(GCN)              PLVFPSDEFDASISQVNEKINQSLAFIRKSDELLHNVNDKIEEILSKIYHIENEIARIKKLIGE (SEQ ID NO: 15)
(HA)               PLVFPSDEFDASISQVNEKINQSLAFIRKSDELLHNVNEKFHQIEKEFSEVEGRIQDLEK (SEQ ID NO: 16)
(Idealized helix)  PLVFPSDEFDASISQINEKINQILAFIRKIDELLHNIN (SEQ ID NO: 17)
(foldon short)     PLVFPSDEFDASISQVNEKINQSLAFIRKSDELLHNVNGSGYIPEAPRDGQAYVRKDGEWVLLSTFL;
or (SEQ ID NO: 18)
(foldon long)      PLVFPSDEFDASISQVNEKINQSLAFIRKSDELLHNVNNKNDDKGSGYIPEAPRDGQAYVRKDGEWVLLSTFL
```

In addition to any combination of furin-cleavage mutations, fusion peptide mutations and added oligomerization sequences, or alternatively, RSV F polypeptides or proteins that contain a transmembrane region may contain an added amino acid sequence that provides a protease cleavage site. This type of RSV F polypeptide or protein can be produced by expression on the surface of a cell, and recovered in soluble form after cleavage from the cell surface using an appropriate protease. Generally, the amino acid sequence that provides a protease cleavage site will be located within about 60 amino acids, about 50 amino acids, about 40 amino acids, about 30 amino acids, about 20 amino acids, about 10 amino acids, or substantially adjacent to the amino terminus of the transmembrane domain (amino acid 525 of SEQ ID NO:1 or 2). Many suitable amino acid sequences that are cleaved by commercially available proteases are well-known in the art. For example, thrombin cleaves the sequence LVPR (SEQ ID NO:75), factor Xa cleaves the sequence IEGR and enterokinase cleaves the sequence DDDDK (SEQ ID NO:76). These amino acid sequences can be introduced into an RSV F polypeptide. In particular embodiments, the sequence of the RSV F polypeptide or protein, starting from position 488 to the TM region is a sequence shown in FIG. 2.

Immunogenic polypeptides used according to the invention will usually be isolated or purified. Thus, they will not be associated with molecules with which they are normally, if applicable, found in nature. For example, an F protein used with the invention will not be in the form of a RSV virion (although it may be in the form of an artificial virion, such as a virosome or VLP).

Polypeptides will usually be prepared by expression in a recombinant host system. Generally, they (e.g., RSV ecto-domains) are produced by expression of recombinant concells, Schneider S2 cells, and High Five cells (a clonal isolate derived from the parental Trichoplusia ni BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in *Vaccine* 27:4975-4982 (2009) and WO2005/042728), EB66 cells, and the like.

Suitable insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insert cell expression systems are commercially available in kit form from, inter alia, Invitrogen, San Diego CA Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Similarly, bacterial and mammalian cell expression systems are also known in the art and described in, e.g., *Yeast Genetic Engineering* (Barr et al., eds., 1989) Butterworths, London.

Recombinant constructs encoding RSV F protein ecto-domains can be prepared in suitable vectors using conventional methods. A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as pFastBac (Invitrogen), is used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used.

RSV F protein ecto-domain polypeptides can be purified using any suitable methods. For example, methods for purifying RSV F ecto-domain polypeptides by immunoaffinity chromatography are known in the art. Ruiz Arguello et al., *J. Gen. Virol.*, 85:3677-3687 (2004). Suitable methods for purifying desired proteins including precipitation and various types of chromatography, such as hydrophobic interaction, ion exchange, affinity, chelating and size exclusion are well-known in the art. Suitable purification schemes can be created using two or more of these or other suitable methods. If desired, the RSV F protein ecto-domain polypeptides can include a "tag" that facilitates purification, such as an epitope tag or a HIS tag. Such tagged polypeptides can conveniently be purified, for example from conditioned media, by chelating chromatography or affinity chromatography.

The RSV F polypeptides may also be produced in situ by expression of nucleic acids that encode them in the cells of a subject. For example, by expression of a self-replicating RNA described herein.

Polypeptides may include additional sequences in addition to the RSV sequences. For example, a polypeptide may include a sequence to facilitate purification (e.g., a poly-His sequence). Similarly, for expression purposes, the natural leader peptide of F protein may be substituted for a different one. For example, reference 6 used a honeybee melittin leader peptide in place of the natural one.

Form and Conformation of Polypeptides

The invention includes immunogenic compositions that include any of the forms and conformations of RSV F polypeptides and proteins disclosed herein, including any desired combination of the forms and conformations of RSV F polypeptides and proteins disclosed herein. The RSV F polypeptide can be a monomer, or the RSV F protein can be a trimer comprising three monomer polypeptides. Trimers can be monodispersed or can be in the form of a rosette, for example, due to interactions between the fusion peptides of individual timers. Immunogenic compositions may comprise polypeptides that are monomers, trimers, a combination of monomers and trimers (e.g., in dynamic equilibrium), rosettes of trimers, and any combination of the foregoing. In addition, as described further herein, the RSV F protein can be in a post-fusion conformation, a pre-fusion conformation, or intermediate conformation.

The RSV F protein can be in a pre-fusion conformation, a post-fusion conformation or an intermediate conformation. The "post fusion conformation" of RSV F protein is believed to be the low energy conformation of native RSV F, and is a trimer characterized by the presence of a six-helix bundle comprising 3 HRB and 3HRA regions. The post-fusion conformation has a characteristic "crutch" or "golf tee" shape by electron microscopy. The "pre-fusion conformation" of RSV F protein is a conformation characterized by a trimer that contains a coiled coil comprising 3 HRB regions. The fusion peptide is not exposed in the pre-fusion conformation and, therefore, prefusion conformations generally do not form rosettes, and have a "lollipop" or "ball and stem" shape by electron microscopy.

In some aspects, the RSV F protein is in the post-fusion conformation. For example, the RSV F protein can be in the form of a monodisperse trimer in the post-fusion conformation, or in the form of a rosette comprised of post-fusion trimers.

In some embodiments, the RSV F polypeptide is a monomer. In some embodiments, the RSV F polypeptide is a trimer.

In other aspects, the RSV F protein is in the pre-fusion conformation. Without wishing to be bound by any particular theory, it is believed that the pre-fusion conformation or intermediate forms of RSV F protein may contain epitopes that are the same as those on the RSV F protein expressed on natural RSV virions, and therefore provide advantages for eliciting neutralizing antibodies.

Some aspects of the invention use a polypeptide that disfavors the post-fusion conformation of the F protein. Preferably, the polypeptides (in whole or in part) will display an epitope of the pre-fusion F protein or an epitope of an intermediate conformation in the conversion from the pre-fusion conformation to the post-fusion conformation. These polypeptides may be native or mutated F proteins in a pre-fusion state, may be native or mutated F proteins in an intermediate conformation, or may be a population of native or mutated proteins where the post-fusion conformation has been disfavored or preferentially excluded. In certain instances the native or mutated protein may be combined with one or more additional molecules that assist in maintaining the polypeptides in one of the foregoing states such as a monoclonal antibody that preferentially binds the pre-fusion conformation or an intermediate conformation. In addition, the polypeptides may be derivatives of native F proteins. Such derivatives include polypeptides comprising one or more fragments of a native F protein, fusion polypeptides comprising a native F protein (or fragment thereof) and a heterologous sequence, and polypeptides comprising a native F protein sequence having one or more mutations. These (or other) modifications may disfavor the post-fusion conformation. Exemplary approaches to disfavor the post-fusion conformation include stabilizing the pre-fusion conformation, stabilizing an intermediate conformation, destabilizing the post-fusion conformation or increasing the activation barrier of one or more steps leading to the post fusion conformation.

In another embodiment, the invention is a polypeptide that displays at least one epitope that is specific to the pre-fusion conformation F protein or an intermediate conformation F protein. An epitope that is specific to the pre-fusion conformation F protein or an intermediate conformation F protein is an epitope that is not presented in the post-fusion conformation. It is preferred that the at least one epitope is stably presented, e.g., the epitope is stably presented in solution for at least twelve hours, at least one day, at least two days, at least four days, at least six days, at least one week, at least two weeks, at least four weeks, or at least six weeks.

Such polypeptides may be native or mutated F proteins in the pre-fusion state, an intermediate state or a population of states where the post-fusion state is underrepresented or at a lower percentage than for isolated native F proteins, or it may be a derivative of a native F protein. Such derivatives include polypeptides comprising one or more fragments of a native F protein, fusion polypeptides comprising a native F protein (or fragment thereof) and a heterologous sequence, and polypeptides comprising a native F protein sequence having one or more mutations. These (or other) modifications may stabilize an F protein amino acid sequence in its pre-fusion conformation, stabilize an F protein amino acid sequence in an intermediate conformation, destabilize the post fusion conformation of an F protein amino acid sequence, increase the energy barrier in a transition leading to the post-fusion conformation of an F protein amino acid sequence, or a combination of two or more of the foregoing.

The TM and/or CT domains of F proteins are important for the stability of the pre-fusion conformation (8). Thus these domains may usefully be retained in immunogens of the invention. As it may be desirable not to include transmembrane domains in soluble immunogens, though, the functional effect of TM may be achieved by other means. For instance, the pre- and post-fusion behavior of F protein of parainfluenza virus 5 has been studied in some detail (6), and the authors stabilized the ED's pre-fusion structure by fusing a heterologous trimerization domain to the C-terminus of the ED.

Oligomerization Domain

In another embodiment of the invention, the composition may comprise a polypeptide (e.g., recombinant polypeptide) that comprises a first domain and a second domain, wherein (i) the first domain comprises the RSV F protein (e.g. RSV ectodomain, in whole or part), and (ii) the second domain comprises a heterologous oligomerization domain. The second domain permits oligomerization of the polypeptide, thereby facilitating the first domain to adopt a pre-fusion state or an intermediate state. The polypeptide preferably will be present as an oligomer, and in particular as a trimer.

Various oligomerization domains are available to the skilled person. These are sequences of amino acids that can form a structure that can interact with oligomerization domains (whether the same or different) in other polypeptides (whether the same or different) such that the multiple polypeptides can associate (usually non-covalently) to form oligomers, e.g., trimers. For instance, trimerization of the F protein of HIV (i.e., gp160) has been achieved by fusing it to the catalytic subunit of *E. coli* aspartate transcarbamoylase (ATCase), which is naturally a stable trimer (9). Thus this subunit of ATCase may be used with the present invention. Similarly, trimerization of the F proteins of HIV (10) and PIV5 (6) has been achieved by fusing their ectodomains to GCNt. Thus the oligomerization domain used with the present invention may comprise the coiled coil of the yeast GCN4 leucine zipper protein (11). Trimerization of the ectodomain of HA protein from influenza A virus has been achieved by using a trimerizing sequence ('foldon') from the bacteriophage T4 fibritin (GSGYIPEAPRDGQ AYVRKDGEWVLLSTFL—SEQ ID NO:19) (12). Thus the oligomerization domain used with the present invention may comprise such a foldon.

Naturally-occurring protein oligomers (both hetero-oligomers and homo-oligomers) associate in a variety of different ways, e.g., by association of β-sheets in different monomers, by association of α-helices in different monomers, by association of hydrophobic surface patches, etc. One common structural motif involved in protein oligomerization is the coiled-coil domain. The coiled α-helix structural motif can itself form coils, and two, three, four or five α-helices can wrap around each other to form a left-handed super-helix known as the "coiled coil" though artificial right-handed super helices have been designed (13-19). The simplicity of the coiled-coil domain has made it a popular choice for designing chimeric proteins with defined oligomerization states (16).

In a coiled-coil structure the α-helices interact through hydrophobic residues that form an apolar stripe along one side of each helix, and there may also be stabilizing electrostatic interactions between side chains on either side of this stripe. Within the abcdefg heptad repeat of an α-helix, the apolar stripe is defined by hydrophobic side chains at residues a and d, with any electrostatic interactions being primarily at residues e and g. Position a is most frequently Leu, Ile or Ala and position d is usually Leu or Ala. Residues e and g are often Glu or Gln, with Arg and Lys also prominent at position g. Charged residues are common at positions b, c and f as these residues are in contact with solvent. There are exceptions to this general heptad pattern, however, and Pro residues are sometimes found within the heptad. Such exceptions usually have functional significance including, by way of example, destabilization of the oligomerization domain to allow refolding and rearrangement such as occurs in the F protein.

Hundreds of coiled-coil domain sequences are known in the art, and any suitable sequence can be used as an oligomerization domain with the invention, provided that it retains the ability to oligomerize with other coiled-coil domains and that it does not destroy the function of the other domains within the polypeptide. It is preferred to use a coiled-coil domain which is found extracellularly (20) and which naturally acts as an oligomerization domain. As an alternative to using a natural coiled-coil domain, artificial coiled-coil domains can be used (21, 22). Owing to the highly repetitive structure of a coiled-coil domain, the domain is particularly amenable to computer modeling as the backbone portions of each amino acid residue may be parameterized rather than treating each backbone portion of a residue as a unique unit with its own variables. Domain (b) may include a leucine zipper sequence or an alanine zipper sequence (23).

The coiled-coil domain used in the polypeptide of the invention is preferably one which forms a trimer, such that the polypeptide of the invention can also assemble into a trimer. Preferred coiled-coil domains are those taken from bacterial transmembrane proteins. A preferred subset of transmembrane proteins is the adhesins (i.e., cell-surface proteins that mediate adhesion to other cells or to surfaces), and particularly non-fimbrial adhesins (e.g., in the oligomerization coiled-coil adhesins, or 'Oca', family). Specific sequences for use with the invention include those disclosed in reference 24 from *Yersinia enterocolitica* adhesin YadA, *Neisseria meningitidis* adhesin NadA, *Moraxella catarrhalis* surface protein UspA2, and other adhesins, such as the HadA adhesin from *Haemophilus influenzae* biogroup *aegyptius* etc (SEQ ID NOs 28-31 & 42-58 of ref. 24). In addition, the eukaryotic heat-shock transcription factor has a coiled-coil trimerization domain that can be separately expressed and therefore used with the invention.

Within the amino acid sequence of a polypeptide having a coiled-coil region, the heptad-repeat nature of the α-helices means that the boundary of the coiled-coil domain can be determined with some precision, but the precise residue where a coiled-coil arrangement can be said to end may not be known with absolute accuracy. This lack of absolute precision is not a problem for practicing the invention, however, as routine testing can reveal whether the coiled-coil requires any particular amino acid residue for which there might be doubt. Even so, the invention does not require the boundaries to be known with absolute precision, as the only basic requirement for the invention is that the coiled-coil domain should function in a way that allows the polypeptide to oligomerize with other coiled-coil domains without destroying the function of the other domains within the polypeptide.

Another class of oligomerization domain that can be used with the invention is found in the left-handed triple helix known as the collagen helix (25). These triple helix-forming sequences involve a basic tripeptide repeat sequence of $^1$Gly-$^2$Xaa-$^3$Xaa, where $^2$Xaa is often Pro, and $^3$Xaa is often 4-hydroxyproline. Although this motif is known as the "collagen" helix, it is found in many proteins beyond just collagen. The oligomerization domain may thus be a sequence comprising multiple repeats of the sequence motif $^1$Gly-$^2$Xaa-$^3$Xaa, which motif folds to form a helical structure that can oligomerize with corresponding helical structures in other polypeptide chains.

Collagen also provides another class of oligomerization domain. Reference 26 describes a motif found in the non-collagenous domain 1 (NC1) of type X collagen, and this motif can be used for trimer and higher order multimer formation without a triple helix. This trimeric association is highly thermostable without intermolecular disulfide bonds. The oligomerization domain may thus comprise an NC1 sequence.

Other oligomerization domains may be derived from the transmembrane domains of oligomeric TM proteins. As these are usually lipophilic, hydrophobic residues positioned on the outside of their TM regions may be substituted with charged residues, to provide a soluble domain. Such methods of solubilizing transmembrane domains by protein engineering are known in the art, for example from reference 27. This method has also been used for GCN4, where the "a" and "d" heptad repeat positions were replaced with isoleucine (11): KQIEDKIEEILSKIYHIENEIARIKKLIGEA (SEQ ID NO: 20). Suitable coiled coil sequences for use within the oligomerization domain will usually be between 20 and 35 amino acids long, e.g., 23 to 30 amino acid residues long.

Oligomerization domains used with the invention can generally maintain an oligomeric structure without the need for the formation of inter-monomer disulfide bridges, but oligomers containing disulfide-linked monomers are not excluded from the invention.

As an alternative, or in addition, to using an oligomerization domain to stabilize an F protein in its pre-fusion conformation, mutation can be used. For instance, reference 28 reports that mutation in a conserved region of the F2 subunit of the F proteins in simian virus 5 or hendra virus can influence the stability of the pre-fusion conformation.

In some circumstances a low pH may also be used to favor the pre-fusion conformation.

Stabilization of the HRB Domain Trimer

In another preferred aspect of the present invention, the post-fusion conformation of the F protein may be disfavored by stabilization of the HRB domain trimer. The HRB domain forms a triple stranded coiled coil in the pre-fusion and likely the intermediate forms. As discussed in the preceding section, due to their simplicity, coiled-coils have been extensively studied as model systems for intermolecular interactions between proteins and as model systems for longer range intra-molecular interactions (i.e., tertiary folding interactions). These studies are useful in teaching methods that may be used to stabilize the HRB domain in the trimeric coiled-coil form. By way of example, one or more residues at the a and/or d positions of the heptad repeat may be replaced with residues that favor formation of stable trimeric coiled-coils such as Ile residues. In addition, though less preferred, disfavorable ionic interactions at the e and g positions may be deleted or favorable ionic interactions at the e and g positions may be added.

The preferred region of the HRB domain for manipulation is the heptad repeat between P484-N517. Preferred examples of a and d residues to target for mutations are F488, I492, V495, I499, S502, I506, S509, L512, and V516. The serine residues are especially preferred as replacement of the hydrophilic residues with hydrophobic residues would stabilize the hydrophobic core of the coiled-coil. Another preferred target would be the phenylalanine with a smaller hydrophobic residue that would pack better in the core such as an isoleucine.

Destabilization of the HRA Domain Trimer

In another preferred aspect of the present invention, the post-fusion conformation of the F protein may be disfavored by destabilization of the HRA domain trimer. The HRA domain forms a triple stranded coiled coil in the post-fusion and possibly one or more intermediate forms. By way of example, one or more residues at the a and/or d positions of the heptad repeat may be replaced with residues that disfavor formation of stable trimeric coiled-coils. In addition, though less preferred, favorable ionic interactions at the e and g positions may be deleted or disfavorable ionic interactions at the e and g positions may be added. Preferably such mutations will be selected that have minimal impact on the stability of the HRA domain in the pre-fusion conformation as may be modeled based upon the available crystal structures of the PIV5 F protein in the pre-fusion and post fusion forms.

Other Modifications

In addition to the foregoing modifications, modifications can further be designed based upon molecular modeling of the hRSV F proteins based upon the available crystal structures of the PIV5 F protein in the pre-fusion and post fusion forms. Mutations may be made that destabilize the post-fusion conformation such as the 6HB fold of the HRA and HRB domains or that stabilize the pre-fusion conformation such as the HRA fold in the pre-fusion conformation. In addition, the energy barrier of the transitions leading to the post-fusion conformation may be increased. While one of skill in the art will appreciate that stabilizing the starting conformation or destabilizing the end conformation can have the effect of increasing the energy barrier, other modifications that affect the transition state itself may be introduced.

As an additional example, the amino acids N-terminal to the HRB domain (approximately a.a. 449-482, preferably V459-F483) act as a "tether" that allows the HRB domain to shift from one side of the F protein trimer to the other side so that the HRB domain can participate in the 6HB of the post-fusion conformation. Deletion of one or more of these amino acids will impair or outright prevent the HRB domain from participating in the 6HB fold of the post-fusion conformation of the F protein (see FIG. 3). In addition, the interaction between the tether and the F protein in the pre-fusion conformation can be stabilized to prevent the tether from pulling away to allow the HRB domain to participate in the 6HB fold. Examples of stabilizing mutations that could be made are cysteine bridges between the tether and the portion of the F protein which the tether contacts in the pre-fusion conformation.

Yet another example is stabilization of the HRA in the pre-fusion conformation (residues T50-Y306). Again, based upon the crystal structures of homologous F proteins, the hydrophobic core may be stabilized by replacing buried hydrophilic or ionic residues with similarly sized hydrophobic residues. Also, cysteine bridges may be introduced at the surface or within the core. In addition, as was demonstrated with extensive crystal structure analysis of lysozyme mutants, the hydrophobic cores or proteins are relatively rigid and therefore introducing holes predictably destabilized the lysozyme mutants. Similarly, repacking the core of the F protein in the pre-fusion conformation to eliminate any natural holes can stabilize the F protein in the pre-fusion or intermediate forms, thus disfavoring the post-fusion conformation.

Methods for Preparing Compositions

The invention relates to methods for preparing compositions and to compositions that contain RSV F protein, in particular soluble RSV F ecto-domain polypeptides, including immunogenic compositions. Preferably, the RSV F ecto-domain polypeptides are in a single form, such as uncleaved monomers, uncleaved trimers, cleaved trimers, rosettes of cleaved trimers, or in a dynamic equilibrium between a subset of such forms (e.g., equilibrium between uncleaved monomers and uncleaved trimers). The invention provides several advantages. For example, as described herein, the invention provides methods for producing compositions that contain a predominate desired form of RSV F protein, or a single desired form of RSV F protein, such as uncleaved monomers, uncleaved trimers, cleaved trimers, rosettes of cleaved trimers, a dynamic equilibrium between a subset of such forms (e.g., equilibrium between uncleaved monomers and uncleaved trimers), or a mixture of desired form of RSV F protein. These types of compositions can be used for a variety of purposes, such as, in the production of immunogenic compositions that can be used to produce vaccines. The presence of a single desired form of RSV F, or a dynamic equilibrium between known forms, in an immunogenic composition, provides for more predictable formulation, solubility and stability, and for a more predictable immune response when the composition is administered to a subject.

When RSV F protein ecto-domain polypeptides are produced by conventional recombinant expression in host cells, the polypeptides are cleaved at the furin cleavage sites at about position 109/110 and at about position 136/137 during production in the host cell before they are secreted into the culture media. Cleavage of the polypeptides by the host cells is permissive for RSV F protein ecto-domain polypeptide refolding, which results in exposure of the hydrophobic fusion peptide. Accordingly, the cleaved RSV F protein ecto-domain polypeptides, due to the presence of an exposed fusion peptide, form rosettes and associate with lipids and lipoproteins that are derived from the host cells and culture media. In fact, electron microscopy of cleaved RSV F ectodomain that are poduced in insect cells and purified by virtue of a HIS6-tag showed that the polypeptides had a crutch shape consistent with a post-fusion form and were bound to what appeared to residual cell debris. Accordingly, high purity preparations of rosettes and other forms and confirmations of RSV F protein ecto-domain polypeptides cannot be readily obtained by conventional recombinant expression in host cells.

Methods for Producing Cleaved RSV F Protein Ecto-Domain Polypeptides

In one aspect, the invention is a method for preparing a composition that contains cleaved RSV F protein ecto-domain polypeptides. In general, the method involves providing uncleaved RSV F protein ecto-domain polypeptides and then cleaving them to produce a $F_1$ subunit and a $F_2$ subunit. As described herein, uncleaved RSV F protein ecto-domain polypeptides can be readily purified and separated from contaminating lipids and lipoproteins using suitable methods, such as size exclusion chromatography. Without wishing to be bound by any particular theory, it is believed that the hydrophobic fusion peptide is not exposed in the uncleaved RSV F protein ecto-domain polypeptides and, therefore, the uncleaved polypeptides do not associate with lipid and lipoprotein contaminants. As further described herein, uncleaved RSV F protein ecto-domains can be cleaved to produce $F_1$ and $F_2$ subunits, which can be purified as trimers, rosettes of trimers, or a mixture of trimers and rosettes of trimers.

Uncleaved RSV F protein ecto-domain polypeptides can be produced using any suitable method. For example, by recombinant production in host cells that do not contain active furin or furin-like proteases at the time the RSV F protein ecto-domain polypeptides are being produced. A variety of methods can be used to achieve this method of production, such as, production in recombinant host cells that are mutated to prevent expression of furin or furin-like protease (conditionally or complete "knock-out"), and various methods that reduce or prevent expression of furin or furin-like proteases in the host cells, for example, using RNA interference or other similar methods, or inhibiting furin or furin-like protease activity in host cells using inhibitors of the proteases.

Uncleaved RSV F protein ecto-domain polypeptides are preferably produced by recombinant expression of constructs that encode a RSV F protein ecto-domain in which the amino acid sequence of the furin cleavage sites are altered, so that the RSV F protein ecto-domain polypeptides are secreted by a host cell that produces the polypeptides uncleaved. The uncleaved RSV F protein ecto-domain polypeptides can be produced using any suitable host cell, such as insect cells (e.g., *Aedes aegypti, Autographa californica, Bombyx mori, Drosophila melanogaster, Spodoptera frugiperda*, and *Trichoplusia ni*), mammalian cells (e.g., human, non-human primate, horse, cow, sheep, dog, cat, and rodent (e.g., hamster), avian cells (e.g., chicken, duck, and geese, bacteria (e.g., *E. coli, Bacillus subtilis*, and *Streptococcus* spp.), yeast cells (e.g., *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*), *Tetrahymena* cells (e.g., *Tetrahymena thermophila*) or combinations thereof. Many suitable insect cells and mammalian cells are well-known in the art. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in *Vaccine* 27:4975-4982 (2009) and WO2005/042728), EB66 cells, and the like.

Suitable insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insert cell expression systems are commercially available in kit form from, inter alia, Invitrogen, San Diego CA Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Similarly, bacterial and mammalian cell expression systems are also known in the art and described in, e.g., *Yeast Genetic Engineering* (Barr et al., eds., 1989) Butterworths, London.

Generally, the amino acid sequence of an uncleaved RSV F protein ecto-domain is altered to prevent cleavage at the furin cleavage sites at about position 109/110 and about position 136/137, but contains a naturally occurring or introduced protease cleavage site, that when cleaved produce a $F_1$ subunit and a $F_2$ subunit. For example, the uncleaved RSV F protein ecto-domain polypeptide can have an amino acid sequence that is altered to prevent cleavage at the furin cleavage sites at about position 109/110 and about position 136/137, but contain one or more naturally occurring or introduced protease cleavage sites from about position 101 to about position 161.

A variety of particular amino acid sequences that will allow uncleaved RSV F protein ecto-domain polypeptides to be produced and expressed by host cells, including amino acid sequences that are not cleaved at the furin cleavage sites at about position 109/110 and about position 136/137 can be readily designed and envisioned by a person of ordinary skill in the art. In general, one or more amino acids that are part of, or are located near by, the furin cleavage sites at about position 109/110 and about position 136/137 are independently replaced or deleted. Some amino acid substitutions and deletions that are suitable to prevent cleavage of RSV F protein ecto-domain polypeptides are known. For example, the substitutions R108N, R109N, R108N/R109N, which inhibit cleavage at 109/110, and the substitution K131Q or the deletion of the amino acids at positions 131-134, which inhibit cleavage at 136/137, have been described Gonzalez-Reyes et al., *Proc. Natl. Acad. Sci. USA,* 98:9859-9864 (2001). An uncleaved RSV F ecto-domain polypeptide that contains the amino acid substitutions R108N/R109N/K131Q/R133Q/R135Q/R136Q has been described. Ruiz-Arguello et al., *J. Gen. Virol.* 85:3677687 (2004). As described in detail herein, additional RSV F protein amino acid sequences that result in the RSV F ecto-domain polypeptide being secreted from a host cell uncleaved contain altered furin cleavage sites, e.g., alter amino acid sequences at about positions 106-109 and at about positions 133-136. The altered furin cleavage sites contain at least one amino acid substitution or deletion at about positions 106-109, and at least one amino acid substitution or deletion at about positions 133-136.

Similarly, a variety of particular amino acid sequences of uncleaved RSV F protein ecto-domain polypeptides that contain a protease cleavage site (e.g., naturally occurring or introduced) that when cleaved produce a first subunit that comprises an $F_1$ and a second subunit that comprises $F_2$, are possible and can be readily designed and envisioned. For example, the amino acid sequence of RSV F protein from about position 101 to about position 161 contains trypsin cleavage sites, and one or more of the trypsin cleavage sites can be cleaved by trypsin to generate $F_1$ and $F_2$ subunits. If desired, one or more suitable protease recognition sites can be introduced into the uncleaved RSV F protein ecto-domain polypeptide, for example, between about positions 101 to about position 161. The introduced protease recognition sites can be cleaved using the appropriate protease to generate $F_1$ and $F_2$ subunits. When a protease recognition site is introduced into the amino acid sequence of an uncleaved RSV F protein ecto-domain polypeptide, it is preferred that the site is recognized by a protease that does not cleave the ecto-domain of naturally occurring RSV F protein.

The method of this aspect of the invention includes: a) providing uncleaved RSV F protein ecto-domain polypeptides containing a protease cleavage site that, when cleaved, produces $F_1$ and $F_2$ subunits, and b) cleaving the uncleaved RSV F protein ecto-domain polypeptides with a protease that recognizes the protease cleavage site. In general, the amino acid sequence of the uncleaved RSV F protein ecto-domain polypeptides contains altered furin cleavage sites, and the RSV F protein ecto-domain polypeptides are secreted from a host cell that produces them uncleaved at the furin cleavage sites at about positions 106-109 and about positions 131-136.

The provided uncleaved RSV F protein ecto-domain polypeptides can be purified to the desired degree. For example, the provided uncleaved RSV F protein ecto-domain polypeptides can be provided as a cell lysate, cell homogenate or cell culture conditioned media that is substantially unprocessed (e.g., unprocessed, or clarified only), or in partially or substantially purified form. In particular examples, the provided uncleaved RSV F protein ecto-domain polypeptides are provided in cell culture conditioned media selected from the group consisting of insect cell conditioned media, mammalian cell conditioned media, avian cell conditioned media, yeast cell conditioned media, Tetrahymena cell conditioned media, and combinations thereof.

It is generally preferred that the provided uncleaved RSV F protein ecto-domain polypeptides are purified, for example, purified to be at least about 80%, at least about 85%, at least about 90%, at least about 95% or substantially homogenous. As described herein, uncleaved RSV F protein ecto-domain polypeptides can be readily purified from lipids and lipoproteins, while conventionally produced cleaved forms of RSV F protein co-purify with lipid and lipoprotein contaminants. Accordingly, when purified uncleaved RSV F protein ecto-domain polypeptides are provided, the method can be used to readily produce a composition containing cleaved RSV F protein ecto-domains that are substantially free of lipids or lipoproteins.

Suitable methods for cleaving polypeptides using a protease are well-known and conventional in the art. Generally, the polypeptides to be cleaved are combined with a sufficient amount of protease under conditions (e.g., pH, polypeptide and protease concentration, temperature) suitable for cleavage of the polypeptide. Many suitable proteases are commercially available, and suitable conditions for performing polypeptide cleavage are well-known for many proteases. If desired, the cleaved RSV F protein ecto-domain polypeptides can be purified following cleavage with protease.

In one example of the method, uncleaved RSV F protein ecto-domain polypeptides are provided that contain an intact fusion peptide, such as an uncleaved RSV F protein ecto-domain polypeptide in which none of the amino acids from positions 137-154 are substituted or deleted. In some embodiments, the provided uncleaved RSV F protein ecto-domain polypeptides are purified. The provided uncleaved RSV F protein ecto-domain polypeptides that contain an intact fusion peptide are cleaved, and cleavage results in the formation of rosettes of cleaved RSV F protein ecto-domain polypeptide trimers. If desired, the rosettes can be purified further using any suitable methods, such as size exclusion chromatography.

In another example of the method, uncleaved RSV F protein ecto-domain polypeptides are provided that contain an altered fusion peptide, such as an uncleaved RSV F protein ecto-domain polypeptide in which about amino 137-152, about amino acids 137-153, about amino acids 137-145 or about amino acids 137-142 are deleted. Other suitable fusion peptide deletions have also been described, such as the deletion of the amino acids at positions 137-146. Ruiz Arguello et al., *J. Gen. Virol.*, 85:3677-3687 (2004).

In some embodiments, the provided uncleaved RSV F protein ecto-domain polypeptides are purified. The provided uncleaved RSV F protein ecto-domain polypeptides are cleaved, and cleavage results in the formation of trimers of cleaved RSV F protein ecto-domain polypeptides. If desired, the trimers can be purified further using any suitable methods, such as size exclusion chromatography.

In particular examples of the method, the provided uncleaved RSV F protein ecto-domain polypeptides contain at least one polypeptide selected from the group consisting of furdel and delp23 furdel (e.g., homogenous trypsin-cleavable furdel, homogenous trypsin-cleavable delp23 furdel, or a mixture of trypsin-cleavable furdel and trypsin-cleavable delp23 furdel). The provided uncleaved RSV F protein ecto-domain polypeptides are cleaved, for example with trypsin, and cleavage results in the formation of cleaved trimers, rosettes of cleaved trimers, or a combination of cleaved trimers and rosettes of cleaved trimers of RSV F protein ecto-domain polypeptides. If desired, the cleaved trimers and/or rosettes of cleaved trimers can be purified further using any suitable methods, such as size exclusion chromatography.

Methods for Producing Uncleaved RSV F Protein Ecto-Domain Polypeptides

In another aspect, the invention is a method for preparing a composition that contains uncleaved RSV F protein ecto-domain polypeptides. In general, the method involves providing a biological material that contains uncleaved RSV F protein ecto-domain polypeptides, such as a cell lysate, cell homogenate or cell culture conditioned medium, and then purifying the uncleaved RSV F protein ecto-domain polypeptides. As described herein, it has been discovered that purified uncleaved RSV F protein ecto-domain polypeptide monomers can self associate to form uncleaved trimers, and that there is a mixture of uncleaved monomers and uncleaved trimers or an equilibrium between the uncleaved monomers and uncleaved trimers. Without wishing to be bound by any particular theory, it is believed that the equilibrium favors the monomer, but that the equilibrium will shift toward the trimer in concentrated solutions.

The method of this aspect of the invention includes: a) providing a biological material that contains uncleaved RSV F protein ecto-domain polypeptides, such as a cell lysate, cell homogenate or cell culture conditioned medium; and b) purifying uncleaved RSV F protein ecto-domain polypeptide monomers, trimers or a combination of monomers and trimers from the biological material. In some embodiments, uncleaved RSV F protein ecto-domain polypeptide monomers are purified, or uncleaved RSV F protein ecto-domain polypeptide trimers are purified, or monomers and trimers are purified.

In general, the amino acid sequence of the uncleaved RSV F protein ecto-domain polypeptides contains altered furin cleavage sites, and the RSV F protein ecto-domain polypeptides are secreted from a host cell that produces them uncleaved between about position 101 to about position 161 (including at the furin cleavage sites at positions 106-109 and 131-136). In more particular examples, the biological material that contains uncleaved RSV F protein ecto-domain polypeptides; includes at least one polypeptide selected from the group consisting of furmt, furdel, delp21 furx, delp23 furx, delp21 furdel, delp23 furdel, and the factor Xa construct, which can be cleaved using factor Xa.

In some embodiments, the amino acid sequence of the RSV F protein ecto-domain polypeptide contains altered furin cleavage sites, and other protease cleavage sites (e.g., trypsin cleavage sites) between about position 101 and about position 161 are altered or deleted to prevent protease (e.g., trypsin) cleavage. For example, trypsin is well-known to cleave after lysine and arginine residues. In certain preferred embodiments, the amino acid sequence of the uncleaved RSV F protein ecto-domain polypeptide contains altered furin cleavage sites, one or more lysine and/or arginine residues (e.g., all lysine and arginine residues) present between about position 101 and about position 161 are deleted or replaced with an amino acid that is not lysine or arginine, the RSV F protein ecto-domain polypeptides are secreted from a host cell that produces them uncleaved between about position 101 and about position 161, and the RSV F protein ecto-domain polypeptides are not cleaved by trypsin between about position 101 and about position 161. Preferably, the RSV F protein ecto-domain polypeptides are not cleaved by trypsin when a 1 mg/ml solution of RSV F protein ecto-domain polypeptide (diluted in 25 mM Tris pH 7.5, 300 mM NaCl) is treated with one-one thousandth volume of trypsin solution (trypsin from bovine plasma diluted to a 1 mg/ml concentration in 25 mM Tris pH 7.5, 300 mM NaCl; final mass ratio in digestion reaction is 0.001:1 trypsin:RSV F ecto-domain; trypsin used at 10-15 BAEE units per mg protein) for 1 hour at 37° C.

If desired, the uncleaved RSV F protein ecto-domain polypeptides (e.g., the polypeptides that contain alter furin cleavage sites, and polypeptide that contain altered furin cleavage sites and altered trypsin cleavage sites) can further contain an altered fusion peptide, such as an uncleaved RSV F protein ecto-domain polypeptide in which, for example, about amino acids 137-152 are deleted, about amino acids 137-154 are deleted, about amino acids 137-145 are deleted or about amino acids 137-142 are deleted. Other suitable fusion peptide deletions have also been described, such as the deletion of the amino acids at positions 137-146. Ruiz-Arguello et al., *J. Gen. Virol.*, 85:3677-3687 (2004).

In particular embodiments, the method includes: a) providing a biological material that contains uncleaved RSV F protein ecto-domain polypeptides, such as a cell lysate, cell homogenate or cell culture conditioned medium, wherein the amino acid sequence of the uncleaved RSV F protein ecto-domain polypeptide contains altered furin cleavage sites, the lysine and arginine residues present between about position 101 and about position 161 are deleted or replaced with an amino acid that is not lysine or arginine, the RSV F protein ecto-domain polypeptides are secreted from a host cell that produces them uncleaved between about position 101 and about position 161, and the RSV F protein ecto-domain polypeptides are not cleaved by trypsin between about position 101 and about position 161; and b) purifying uncleaved RSV F protein ecto-domain polypeptide monomers, trimers or a combination of monomers and trimers from the biological material.

In more particular examples, the biological material that contains uncleaved RSV F protein ecto-domain polypeptides; includes at least one polypeptide selected from the group consisting of Furx, Furx R113Q K123N K124N, delp21 furx and delp23 furx.

In other particular embodiments, the method includes: a) providing a biological material that contains uncleaved RSV F protein ecto-domain polypeptides in which the fusion peptide is mutated (e.g., at least a portion of the fusion peptide is deleted), such as a cell lysate, cell homogenate or cell culture conditioned medium; and b) purifying uncleaved RSV F protein ecto-domain polypeptides from the biological material. The uncleaved RSV F protein ecto-domain polypeptide can contain altered furin cleavage sites, and the RSV F protein ecto-domain polypeptides are secreted from a host cell that produces them uncleaved between about position 101 to about position 161 (including at the furin cleavage sites at positions 106-109 and 131-136). If desired, the uncleaved RSV F protein ecto-domain polypeptide with altered furin cleavage sites further contains altered or deleted sites for other proteases (e.g., trypsin cleavage sites) between about position 101 and about position 161 to prevent protease (e.g., trypsin) cleavage. For example, one or more lysine and/or arginine residues (e.g., all lysing and arginine residues) present between about position 101 and about position 161 are deleted or replaced with an amino acid that is not lysine or arginine, and the RSV F protein ecto-domain polypeptides are not cleaved by trypsin between about position 101 and about position 161.

The uncleaved RSV F protein ecto-domain polypeptide monomers, trimers and combinations of monomers and trimers can be purified to the desired degree. It is generally preferred that the uncleaved RSV F protein ecto-domain polypeptide monomers or trimers are purified, for example, to be at least about 75%, at least about 80%, at least about 85%, at least about 90%, at least about 95% or substantially homogenous. As described herein, uncleaved RSV F protein ecto-domain polypeptides can be readily purified from lipids and lipoproteins, for example, by size exclusion chromatography. Accordingly, the method can be used to readily produce a composition containing cleaved RSV F protein ecto-domain polypeptide monomers, trimers, or a combination of monomers and trimers that are substantially free of lipids and lipoproteins.

In one example, the method includes providing insect cell culture conditioned medium, mammalian cell culture conditioned medium, avian cell conditioned medium, yeast cell conditioned medium, Tetrahymena cell conditioned medium, or a combination thereof. In some embodiments, uncleaved RSV F protein ecto-domain polypeptide trimers are purified. In other embodiments, uncleaved RSV F protein ecto-domain polypeptide monomers are purified. In other embodiments, uncleaved RSV F protein ecto-domain polypeptide monomers and trimers are purified.

Methods for Producing Cleaved RSV F Protein Ecto-Domain Polypeptides with Altered Fusion Peptides In one aspect, the invention is a method for preparing a composition that contains cleaved RSV F protein ecto-domain polypeptides that contain an altered fusion peptide. When RSV F protein ecto-domain polypeptides that do not contain altered furin cleavage sites are expressed in host cells, the host cells process the polypeptides, in part by cleaving the polypeptide at the furin sites at about positions 109/110 and about positions 136/137 to produce $F_1$ and $F_2$ subunits. The processed polypeptides are secreted into the culture and can be recovered as associated $F_1$-$F_2$ subunits (e.g., disulphide bonding $F_1$ and $F_2$ subunits), which can form rosettes of trimers through aggregation of exposed fusion peptides. RSV F protein ecto-domain polypeptides that contain altered fusion peptides can be produced in and secreted from host cells as associated $F_1$-$F_2$ subunits, and preferably do not aggregate into rosettes or with lipids or lipoprotein contaminants. Without wishing to be bound by any particular theory, it is believed that the polypeptides do not form rosettes or associate with lipid and lipoprotein contaminants because the altered fusion peptide does not mediate aggregation.

The method of this aspect of the invention includes: a) providing a biological material that contains cleaved RSV F protein ecto-domain polypeptides that contain an altered fusion peptide (e.g., at least a portion of the fusion peptide is deleted), such as a cell lysate, cell homogenate or cell culture conditioned medium; and b) purifying cleaved RSV F protein ecto-domain polypeptides from the biological material. The purified cleaved RSV F protein ecto-domain polypeptides can be purified as cleaved trimers, rosettes of cleaved trimers, or a mixture of cleaved trimers and rosettes of cleaved trimers. Suitable RSV F protein ecto-domain polypeptides that contain altered fusion peptides contain cleavable furin cleavage sites at about 109/110 and about 136/137 and further contain an altered fusion peptide as described herein. For example, an RSV F protein ecto-domain polypeptide in which about amino acids 137-152 are deleted, about amino acids 137-153 are deleted, about amino acids 137-145 are deleted, about amino acids 137-146 are deleted or about amino acids 137-142 are deleted, can be used in the method. In particular examples, the biological material that contains uncleaved RSV F protein ecto-domain polypeptides; includes at least the fusion peptide deletion 1.

The cleaved RSV F protein ecto-domain polypeptides (e.g., cleaved trimers or a mixture of cleaved trimers and rosettes of cleaved trimers) can be purified to the desired degree. It is generally preferred that the cleaved RSV F protein ecto-domain polypeptides are purified, for example, to be at least about 75%, at least about 80%, at least about 85%, at least about 90%, at least about 95% or substantially homogenous. As described herein, cleaved RSV F protein ecto-domain polypeptides that contain an altered fusion peptide can be readily purified from lipids and lipoproteins, for example, by size exclusion chromatography. Accordingly, the method can be used to readily produce a composition containing cleaved RSV F protein ecto-domain polypeptide trimers, rosettes of cleaved trimers, or a combination of cleaved trimers and rosettes of cleaved trimers that are substantially free of lipids and lipoproteins.

Methods for Producing RSV F Protein Ecto-Domain Polypeptides with C-Terminal Furin Mutations In another aspect, the invention is a method for preparing a composition that contains C-terminal uncleaved RSV F ecto-domain polypeptides and a method for preparing cleaved RSV F protein ecto-domain polypeptides. Without wishing to be bound by any particular theory, it is believed that C-terminal uncleaved RSV F protein ecto-domain polypeptides are cleaved by cells that produce the proteins at the furin cleavage site at about postion 109/110, but not at the furin cleavage site at about position 136/137, and are secreted into the media as an $F_1$ subunit that is associated with an $F_2$ subunit. It is further believed that the hydrophobic fusion peptide is not exposed in the C-terminal uncleaved RSV F protein ecto-domain polypeptides and, therefore, the C-terminal uncleaved polypeptides do not associate with lipid and lipoprotein contaminants. As further described herein, C-terminal uncleaved RSV F protein ecto-domains can be cleaved further to produce a $F_1$ subunit, in which the amino terminus is from position 110 to about position 161, that is associated with a $F_2$ subunit. Such $F_1$ and $F_2$ subunits, which can be purified as trimers, rosettes of trimers, or a mixture of trimers and rosettes of trimers.

Generally, the amino acid sequence of a C-terminal uncleaved RSV F protein ecto-domain is altered to prevent cleavage at the furin cleavage site at about position 136/137, but contains a naturally occurring or introduced protease cleavage site, that when cleaved produces a $F_1$ subunit, in which the amino terminus is from position 110 to about position 161, and a $F_2$ subunit. For example, the C-terminal uncleaved RSV F protein ecto-domain polypeptide can have an amino acid sequence that is altered to prevent cleavage at the furin cleavage sites at about position 136/137, but contain one or more naturally occurring or introduced protease cleavage sites from about position 101 to about position 161. In a particular example, the amino acid sequence of a C-terminal uncleaved RSV F protein ecto-domain is altered to prevent cleavage at the furin cleavage site at about position 136/137, but contains a naturally occurring furin cleavage site at about position 109/110.

A variety of particular amino acid sequences that will allow C-terminal uncleaved RSV F protein ecto-domain polypeptides to be produced and expressed by host cells, including amino acid sequences that are not cleaved at the furin cleavage sites at about position 136/137, can be readily designed and envisioned by a person of ordinary skill in the art. In general, one or more amino acids that are part of, or are located near by, the furin cleavage sites at about position 136/137 are independently replaced or deleted. Suitable amino acid substitutions and deletions that prevent cleavage at about position 136/137 are described herein. For example, the substitution K131Q, the deletion of the amino acids at positions 131-134, or the substitutions K131Q/R133Q/R135Q/R136Q, each of which inhibit cleavage at 136/137, can be used. In certain embodiments, C-terminal uncleaved RSV F protein ecto-domain polypeptides comprise at least one amino acid substitution or deletion at about positions 133-136.

Similarly, a variety of particular amino acid sequences of C-terminal uncleaved RSV F protein ecto-domain polypeptides that contain a protease cleavage site (e.g., naturally occurring or introduced) that when cleaved produce a first subunit that comprises an $F_1$ and a second subunit that comprises $F_2$, are possible and can be readily designed and envisioned. For example, the amino acid sequence of RSV F protein from about position 101 to about position 161 contains trypsin cleavage sites, and one or more of the trypsin cleavage sites can be cleaved by trypsin to generate $F_1$ and $F_2$ subunits. If desired, one or more suitable protease recognition sites can be introduced into the C-terminal uncleaved RSV F protein ecto-domain polypeptide, for example, between about positions 101 to about position 161. The introduced protease recognition sites can be cleaved using the appropriate protease to generate $F_1$ and $F_2$ subunits. When a protease recognition site is introduced into the amino acid sequence of a C-terminal uncleaved RSV F protein ecto-domain polypeptide, it is preferred that the site is recognized by a protease that does not cleave the ecto-domain of naturally occurring RSV F protein.

C-terminal uncleaved RSV F protein ecto-domain polypeptides can be produced using any suitable method. A preferred method is by recombinant expression of constructs that encode a RSV F protein ecto-domain in which that amino acid sequence of the furin cleavage site at about positions 136/137 is altered, so that the C-terminal uncleaved RSV F protein ecto-domain polypeptides are secreted by a host cell that produces the polypeptides uncleaved at the furin cleavage site at about position 136/137. Preferably, the C-terminal uncleaved RSV F protein ecto-domain polypeptide is secreted by a host cell that produces it as an $F_1$ subunit that is associated with an $F_2$ subunit, wherein the amino terminus of the $F_1$ subunit is from position 132 to about position 161, but not position 137. The C-terminal uncleaved RSV F protein ecto-domain polypeptides can be produced using any suitable host cell, as described herein.

One method of this aspect of the invention includes: a) providing C-terminal uncleaved RSV F protein ecto-domain polypeptides that comprise an altered furin cleavage site at position 136/137, and said C-terminal uncleaved RSV F protein ecto-domain polypeptides are secreted from a cell that produces them in the form of an $F_2$ fragment that is associated with a subunit that comprises $F_1$ but is uncleaved at position 136/137, and b) cleaving the provided C-terminal uncleaved RSV F protein ecto-domain polypeptides with a protease that cleaves RSV F protein ecto-domain at a site between positions 101 and 161, thereby producing said composition. In particular embodiments, step b) comprises cleaving the provided C-terminal uncleaved RSV F protein ecto-domain polypeptides with a protease that cleaves RSV F protein ecto-domain at a site between about positions 101 and 132, or about positions 132 and 161, or about positions 110 and 132. Alternatively or in addition, in some embodiments, the C-terminal uncleaved RSV F protein ecto-domain polypeptides comprise an altered furin cleavage site at position 136/137, with the proviso that the altered furin cleavage site is not deletion of amino acids 131-134. In particular examples, the biological material that contains C-terminal uncleaved RSV F protein ecto-domain polypeptides; includes at least the N-term Furin polypeptide.

The provided C-terminal uncleaved RSV F protein ecto-domain polypeptides can be purified to the desired degree. For example, the provided C-terminal uncleaved RSV F protein ecto-domain polypeptides can be provided in a cell lysate, cell homogenate, or cell culture conditioned media that is substantially unprocessed (e.g., unprocessed, or clarified only), or in partially or substantially purified form. In particular examples, the provided C-terminal uncleaved RSV F protein ecto-domain polypeptides are provided in cell culture conditioned media selected from the group consisting of insect cell conditioned media, mammalian cell conditioned media, avian cell conditioned media, yeast cell conditioned media, Tetrahymena cell conditioned media, and combinations thereof.

It is generally preferred that the provided C-terminal uncleaved RSV F protein ecto-domain polypeptides are purified, for example, purified to be at least about 80%, at least about 85%, at least about 90%, at least about 95% or substantially homogenous. As described herein, C-terminal uncleaved RSV F protein ecto-domain polypeptides can be readily purified from lipids and lipoproteins, while conventionally produced cleaved forms of RSV F protein co-purify with lipid and lipoprotein contaminants. Accordingly, when purified C-terminal uncleaved RSV F protein ecto-domain polypeptides are provided, the method can be used to readily produce a composition containing cleaved RSV F protein ecto-domains that are substantially free of lipids or phospholipids.

Suitable methods for cleaving polypeptides using a protease are well-known and conventional in the art. Generally, the polypeptides to be cleaved are combined with a sufficient amount of protease under conditions (e.g., pH, polypeptide and protease concentration, temperature) suitable for cleavage of the polypeptide. Many suitable proteases are commercially available, and suitable conditions for performing polypeptide cleavage are well-known for many proteases. If desired, the RSV F protein ecto-domain polypeptides can be purified following cleavage with protease.

In one example of the method, C-terminal uncleaved RSV F protein ecto-domain polypeptides are provided that contain an intact fusion peptide, such as a C-terminal uncleaved RSV F protein ecto-domain polypeptide in which none of the amino acids from positions 137-154 are substituted or deleted. In another example of the method, C-terminal uncleaved RSV F protein ecto-domain polypeptides are provided that contain an altered fusion peptide, such as a C-terminal uncleaved RSV F protein ecto-domain polypeptide in which about amino 137-152, about amino acids 137-153, about amino acids 137-145 or about amino acids 137-142 are deleted. Other suitable fusion peptide deletions have also been described, such as the deletion of the amino acids at positions 137-146. Ruiz Arguello et al., *J. Gen. Virol.*, 85:3677-3687 (2004).

In some embodiments, the provided C-terminal uncleaved RSV F protein ecto-domain polypeptides are purified. The provided uncleaved RSV F protein ecto-domain polypeptides are cleaved, and cleavage results in the formation of trimers of cleaved RSV F protein ecto-domain polypeptides. If desired, the trimers can be purified further using any suitable methods, such as size exclusion chromatography.

In particular examples of the method, the provided C-terminal uncleaved RSV F protein ecto-domain polypeptides contain at least the N-terminal Furin polypeptide (FIGS. 1A-1C). The provided C-terminal uncleaved RSV F protein ecto-domain polypeptides are cleaved, for example with trypsin, and cleavage results in the formation of cleaved trimers, rosettes of cleaved trimers, or a combination of cleaved trimers and rosettes of cleaved trimers of RSV F protein ecto-domain polypeptides. If desired, the cleaved trimers and/or rosettes of cleaved trimers can be purified further using any suitable methods, such as size exclusion chromatography.

Another method of this aspect of the invention includes: a) providing a biological material, such as a cell lysate, cell homogenate or cell culture conditioned medium, that contains a C-terminal uncleaved RSV F protein ecto-domain polypeptides that comprise an altered furin cleavage site at position 136/137, and said soluble RSV F protein ecto-domain polypeptides are secreted from a cell that produces them in the form of an $F_2$ fragment that is associated with a subunit that comprises $F_1$ but is uncleaved at position 136/137, with the proviso that the altered furin cleavage site is not deletion of amino acids 131-134; and b) purifying the C-terminal uncleaved RSV F protein ecto-domain polypeptides from the biological material, thereby producing the composition. Preferably, the amino terminus of the $F_1$ subunit is from about position 110 to about position 132. More preferably, the amino terminus of the $F_1$ subunit is about position 110. It is particulary preferred that the amino terminus of the $F_1$ subunit is not position 137. In particular examples, the biological material that contains C-terminal uncleaved RSV F protein ecto-domain polypeptides; includes at least the N-term Furin polypeptide.

If desired, the C-terminal uncleaved RSV F protein ecto-domain polypeptide further contains altered or deleted sites for other proteases (e.g., trypsin cleavage sites) between about position 101 and about position 161 to prevent protease (e.g., trypsin) cleavage. For example, one or more lysine and/or arginine residues (e.g., all lysine and arginine residues) present between about position 101 and about position 161 are deleted or replaced with an amino acid that is not lysine or arginine, and the C-terminal uncleaved RSV F protein ecto-domain polypeptides are not cleaved by trypsin between about position 101 and about position 161. The C-terminal uncleaved RSV F protein ecto-domain polypeptides can contain an intact fusion peptide or an altered fusion peptide, as described herein.

The C-terminal uncleaved RSV F protein ecto-domain polypeptides, e.g., monomers, trimers and combinations of monomers and trimers can be purified to the desired degree. It is generally preferred that the C-terminal uncleaved RSV F protein ecto-domain polypeptide monomers or trimers are purified, for example, to be at least about 75%, at least about 80%, at least about 85%, at least about 90%, at least about 95% or substantially homogenous. As described herein, C-terminal uncleaved RSV F protein ecto-domain polypeptides can be readily purified from lipids and lipoproteins, for example, by size exclusion chromatography. Accordingly, the method can be used to readily produce a composition containing C-terminal uncleaved RSV F protein ecto-domain polypeptides, e.g., monomers, trimers, or a combination of monomers and trimers, that are substantially free of lipids and lipoproteins. In particular examples of the method, the C-terminal uncleaved RSV F protein ecto-domain polypeptides contain at least the N-terminal Furin polypeptide (FIGS. 1A-1C).

In one example, the method includes providing insect cell culture conditioned medium, mammalian cell culture conditioned medium, avian cell conditioned media, yeast cell conditioned media, Tetrahymena cell conditioned media or a combination thereof. In some embodiments, C-terminal uncleaved RSV F protean ecto-domain polypeptide trimers are purified. In other embodiments, C-terminal uncleaved RSV F protein ecto-domain polypeptide monomers are purified. In other embodiments, C-terminal uncleaved RSV F protein ecto-domain polypeptide monomers and trimers are purified.

Self-Replicating RNA

The RSV-F polypeptides described herein can be produced by expression of recombinant nucleic acids that encode the polypeptides in the cells of a subject. Prefereed nucleic acids that can be administered to a subject to cause the production of RSV-F polypeptides are self-replicating RNA molecules. The self-replicating RNA molecules of the invention are based on the genomic RNA of RNA viruses, but lack the genes encoding one or more structural proteins. The self-replicating RNA molecules are capable of being translated to produce non-structural proteins of the RNA virus and heterologous proteins encoded by the self-replicating RNA.

The self-replicating RNA generally contains at least one or more genes selected from the group consisting of viral replicase, viral proteases, viral helicases and other nonstructural viral proteins, and also comprise 5'- and 3'-end cis-active replication sequences, and if desired, a heterologous sequences that encode a desired amino acid sequences (e.g., a protein, an antigen). A subgenomic promoter that directs expression of the heterologous sequence can be included in the self-replicating RNA. If desired, the heterologous sequence may be fused in frame to other coding regions in the self-replicating RNA and/or may be under the control of an internal ribosome entry site (IRES).

Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinebis virus (SIN), Semliki forest virus and Venezuelan equine encephalitis virus (VEE), one or more genes encoding viral structural proteins, such as capsid and/or envelope glycoproteins, can be omitted. If desired, self-replicating RNA molecules of the invention can be designed to induce production of infectious viral particles that are attenuated or virulent, or to produce viral particles that are capable of a single round of subsequent infection.

A self-replicating RNA molecule can, when delivered to a vertebrate cell even without any proteins, lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus the delivered RNA leads to the production of multiple daughter RNAs. These transcripts are antisense relative to the delivered RNA and may be translated themselves to provide in situ expression of a gene product, or may be transcribed to provide further transcripts with the same sense as the delivered RNA which are translated to provide in situ expression of the encoded RSV-F polypeptide.

One suitable system for achieving self-replication is to use an alphavirus-based RNA replicon. These + stranded replicons are translated after delivery to a cell to give of a replicase (or replicase-transcriptase). The replicase is translated as a polyprotein which auto cleaves to provide a replication complex which creates genomic – strand copies of the + strand delivered RNA. These – strand transcripts can themselves be transcribed to give further copies of the + stranded parent RNA and also to give a subgenomic transcript which encodes the RSV-F polypeptide. Translation of the subgenomic transcript thus leads to in situ expression of the RSV-F polypeptide by the infected cell. Suitable alphavirus replicons can use a replicase from a sindbis virus, a semliki forest virus, an eastern equine encephalitis virus, a venezuelan equine encephalitis virus, etc.

A preferred self-replicating RNA molecule thus encodes (i) a RNA-dependent RNA polymerase which can transcribe RNA from the self-replicating RNA molecule and (ii) an RSV-F polypeptide. The polymerase can be an alphavirus replicase e.g. comprising alphavirus protein nsP4.

Whereas natural alphavirus genomes encode structural virion proteins in addition to the non structural replicase polyprotein, it is preferred that an alphavirus based self-replicating RNA molecule of the invention does not encode alphavirus structural proteins. Thus the self replicating RNA can lead to the production of genomic RNA copies of itself in a cell, but not to the production of RNA-containing alphavirus virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self replicating RNAs of the invention and their place is taken by gene(s) encoding the desired gene product, such that the subgenomic transcript encodes the desired gene product rather than the structural alphavirus virion proteins.

Thus a self-replicating RNA molecule useful with the invention may have two open reading frames. The first (5') open reading frame encodes a replicase; the second (3') open reading frame encodes an RSV-F polypeptide. In some embodiments the RNA may have additional (downstream) open reading frames e.g. that encode further desired gene products. A self-replicating RNA molecule can have a 5' sequence which is compatible with the encoded replicase.

In one aspect, the self-replicating RNA molecule is derived from or based on an alphavirus. In other aspects, the self-replicating RNA molecule is derived from or based on a virus other than an alphavirus, preferably, a positive-stranded RNA viruses, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA may be associated with a delivery system. The self-replicating RNA may be administered with or without an adjuvant.

RNA Delivery Systems

The self-replicating RNA of the invention are suitable for delivery in a variety of modalities, such as naked RNA delivery or in combination with lipids, polymers or other compounds that facilitate entry into the cells. Self-replicating RNA molecules of the present invention can be introduced into target cells or subjects using any suitable technique, e.g., by direct injection, microinjection, electroporation, lipofection, biolystics, and the like. The self-replicating RNA molecule may also be introduced into cells by way of receptor-mediated endocytosis. See e.g., U.S. Pat. No. 6,090,619; Wu and Wu, J. Biol. Chem., 263:14621 (1988); and Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues), which is itself coupled to an integrin receptor-binding moiety (e.g., a cyclic peptide having the sequence Arg-Gly-Asp).

The self-replicating RNA molecule of the present invention can be delivered into cells via amphiphiles. See e.g., U.S. Pat. No. 6,071,890. Typically, a nucleic acid molecule may form a complex with the cationic amphiphile. Mammalian cells contacted with the complex can readily take it up.

The self-replicating RNA can be delivered as naked RNA (e.g. merely as an aqueous solution of RNA) but, to enhance entry into cells and also subsequent intercellular effects, the self-replicating RNA is preferably administered in combination with a delivery system, such as a particulate or emulsion delivery system. A large number of delivery systems are well known to those of skill in the art. Such delivery systems include, for example liposome-based delivery (Debs and Zhu (1993) WO 93/24640; Mannino and Gould-Fogerite (1988) BioTechniques 6(7): 682-691; Rose U.S. Pat. No. 5,279,833; Brigham (1991) WO 91/06309; and Felgner et al. (1987) Proc. Natl. Acad. Sci. USA 84: 7413-7414), as well as use of viral vectors (e.g., adenoviral (see, e.g., Berns et al. (1995) Ann. NY Acad. Sci. 772: 95-104; Ali et al. (1994) Gene Ther. 1: 367-384; and Haddada et al. (1995) Curr. Top. Microbiol. Immunol. 199 (Pt 3): 297-306 for review), papillomaviral, retroviral (see, e.g., Buchscher et al. (1992) J. Virol. 66(5) 2731-2739; Johann et al. (1992) J. Virol. 66 (5): 1635-1640 (1992); Sommerfelt et al., (1990) Virol. 176:58-59; Wilson et al. (1989) J. Virol. 63:2374-2378; Miller et al., J. Virol. 65:2220-2224 (1991); Wong-Staal et al., PCT/US94/05700, and Rosenburg and Fauci (1993) in Fundamental Immunology, Third Edition Paul (ed) Raven Press, Ltd., New York and the references therein, and Yu et al., Gene Therapy (1994) supra.), and adeno-associated viral vectors (see, West et al. (1987) Virology 160:38-47; Carter et al. (1989) U.S. Pat. No. 4,797,368; Carter et al. WO 93/24641 (1993); Kotin (1994) Human Gene Therapy 5:793-801; Muzyczka (1994) J. Clin. Invst. 94:1351 and Samulski (supra) for an overview of AAV vectors; see also, Lebkowski, U.S. Pat. No. 5,173,414; Tratschin et al. (1985) Mol. Cell. Biol. 5(11):3251-3260; Tratschin, et al. (1984) Mol. Cell. Biol., 4:2072-2081; Hermonat and Muzyczka (1984) Proc. Natl. Acad. Sci. USA, 81:6466-6470; McLaughlin et al. (1988) and Samulski et al. (1989) J. Virol., 63:03822-3828), and the like.

Three particularly useful delivery systems are (i) liposomes (ii) non-toxic and biodegradable polymer microparticles (iii) cationic submicron oil-in-water emulsions.

Liposomes

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic. Suitable classes of phospholipid include, but are not limited to, phosphatidylethanolamines, phosphatidylcholines, phosphatidylserines, and phosphatidylglycerols, and some useful phospholipids are listed in Table 20. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. The lipids can be saturated or unsaturated.

Liposomes can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMPG (anionic, saturated). Where a mixture of lipids is used, not all of the component lipids in the mixture need to be amphiphilic e.g. one or more amphiphilic lipids can be mixed with cholesterol.

The hydrophilic portion of a lipid can be PEGylated (i.e. modified by covalent attachment of a polyethylene glycol). This modification can increase stability and prevent non-specific adsorption of the liposomes. For instance, lipids can be conjugated to PEG using techniques such as those disclosed in Heyes et al. (2005) *J Controlled Release* 107: 276-287.

A mixture of DSPC, DlinDMA, PEG-DMPG and cholesterol is used in the examples. A separate aspect of the invention is a liposome comprising DSPC, DlinDMA, PEG-DMG and cholesterol. This liposome preferably encapsulates RNA, such as a self-replicating RNA e.g. encoding an immunogen.

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomes useful with of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index <0.2.

Techniques for preparing suitable liposomes are well known in the art e.g. see Liposomes: Methods and Protocols, Volume 1: Pharmaceutical Nanocarriers: Methods and Protocols. (ed. Weissig). Humana Press, 2009. ISBN 160327359X; Liposome Technology, volumes I, II & III. (ed. Gregoriadis). Informa Healthcare, 2006; and Functional Polymer Colloids and Microparticles volume 4 (Microspheres, microcapsules & liposomes). (eds. Arshady & Guyot). Citus Books, 2002. One useful method involves mixing (i) an ethanolic solution of the lipids (ii) an aqueous solution of the nucleic acid and (iii) buffer, followed by mixing, equilibration, dilution and purification (Heyes et al. (2005) *J Controlled Release* 107:276-87.).

RNA is preferably encapsulated within the liposomes, and so the liposome forms a outer layer around an aqueous RNA-containing core. This encapsulation has been found to protect RNA from RNase digestion. The liposomes can include some external RNA (e.g. on the surface of the liposomes), but at least half of the RNA (and ideally all of it) is encapsulated.

Polymeric Microparticles

Various polymers can form microparticles to encapsulate or adsorb RNA. The use of a substantially non-toxic polymer means that a recipient can safely receive the particles, and the use of a biodegradable polymer means that the particles can be metabolised after delivery to avoid long-term persistence. Useful polymers are also sterilisable, to assist in preparing pharmaceutical grade formulations.

Suitable non-toxic and biodegradable polymers include, but are not limited to, poly(α-hydroxy acids), polyhydroxy butyric acids, polylactones (including polycaprolactones), polydioxanones, polyvalerolactone, polyorthoesters, polyanhydrides, polycyanoacrylates, tyrosine-derived polycarbonates, polyvinyl-pyrrolidinones or polyester-amides, and combinations thereof.

In some embodiments, the microparticles are formed from poly(α-hydroxy acids), such as a poly(lactides) ("PLA"), copolymers of lactide and glycolide such as a poly(D,L-lactide-co-glycolide) ("PLG"), and copolymers of D,L-lactide and caprolactone. Useful PLG polymers include those having a lactide/glycolide molar ratio ranging, for example, from 20:80 to 80:20 e.g. 25:75, 40:60, 45:55, 55:45, 60:40, 75:25. Useful PLG polymers include those having a molecular weight between, for example, 5,000-200,000 Da e.g. between 10,000-100,000, 20,000-70,000, 40,000-50,000 Da.

The microparticles ideally have a diameter in the range of 0.02 μm to 8 μm. For a composition comprising a population of microparticles with different diameters at least 80% by number should have diameters in the range of 0.03-7 μm.

Techniques for preparing suitable microparticles are well known in the art e.g. see Functional Polymer Colloids and Microparticles volume 4 (Microspheres, microcapsules & liposomes). (eds. Arshady & Guyot). Citus Books, 2002; *Polymers in Drug Delivery*. (eds. Uchegbu & Schatzlein). CRC Press, 2006. (in particular chapter 7) and *Microparticulate Systems for the Delivery of Proteins and Vaccines*. (eds. Cohen & Bernstein). CRC Press, 1996. To facilitate adsorption of RNA, a microparticle may include a cationic surfactant and/or lipid e.g. as disclosed in O'Hagan et al. (2001) *J Virology* 75:9037-9043; and Singh et al. (2003) *Pharmaceutical Research* 20: 247-251. An alternative way of making polymeric microparticles is by molding and curing e.g. as disclosed in WO2009/132206.

Microparticles of the invention can have a zeta potential of between 40-100 mV.

RNA can be adsorbed to the microparticles, and adsorption is facilitated by including cationic materials (e.g. cationic lipids) in the microparticle.

Oil-in-Water Cationic Emulsions

Oil-in-water emulsions are known for adjuvanting influenza vaccines e.g. the MF59™ adjuvant in the FLUAD™ product, and the AS03 adjuvant in the PREPANDRIX™ product. RNA delivery according to the present invention can utilise an oil-in-water emulsion, provided that the emulsion includes one or more cationic molecules. For instance, a cationic lipid can be included in the emulsion to provide a positive droplet surface to which negatively-charged RNA can attach.

The emulsion comprises one or more oils. Suitable oil(s) include those from, for example, an animal (such as fish) or a vegetable source. The oil is ideally biodegradable (metabolisable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α, β, γ, δ, ε or ξ tocopherols can be used, but α-tocopherols are preferred. D-α-tocopherol and DL-α-tocopherol can both be used. A preferred α-tocopherol is DL-α-tocopherol. An oil combination comprising squalene and a tocopherol (e.g. DL-α-tocopherol) can be used.

Preferred emulsions comprise squalene, a shark liver oil which is a branched, unsaturated terpenoid ($C_{30}H_{50}$; [($CH_3$)$_2$C[=$CHCH_2CH_2C(CH_3)$]$_2$=$CHCH_2$—]$_2$; 2,6,10,15,19,23-hexamethyl-2,6,10,14,18,22-tetracosahexaene; CAS RN 7683-64-9).

The oil in the emulsion may comprise a combination of oils e.g. squalene and at least one further oil.

The aqueous component of the emulsion can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

The emulsion also includes a cationic lipid. Preferably this lipid is a surfactant so that it can facilitate formation and stabilisation of the emulsion. Useful cationic lipids generally contains a nitrogen atom that is positively charged under physiological conditions e.g. as a tertiary or quaternary amine. This nitrogen can be in the hydrophilic head group of an amphiphilic surfactant. Useful cationic lipids include, but are not limited to: 1,2-dioleoyloxy-3-(trimethylammonio) propane (DOTAP), 3'-[N—(N',N'-Dimethylaminoethane)-carbamoyl]Cholesterol (DC Cholesterol), dimethyldioctadecyl-ammonium (DDA e.g. the bromide), 1,2-Dimyristoyl-3-Trimethyl-AmmoniumPropane (DMTAP), dipalmitoyl (C16:0)trimethyl ammonium propane (DPTAP), distearoyltrimethylammonium propane (DSTAP). Other useful cationic lipids are: benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC), cetyl trimethylammonium chloride (CTAC), N,N',N'-polyoxyethylene (10)-N-tallow-1,3-diaminopropane, dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimetylammonium salts, [1-(2,3-dioleyloxy)-propyl]-N,N,N,trimethylammonium chloride, 1,2-diacyl-3-(trimethylammonio) propane (acyl group=dimyristoyl, dipalmitoyl, distearoyl, dioleoyl), 1,2-diacyl-3 (dimethylammonio)propane (acyl group=dimyristoyl, dipalmitoyl, distearoyl, dioleoyl), 1,2-dioleoyl-3-(4'-trimethyl-ammonio)butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes (C12Me6; C12BU6), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group (C^GluPhCnN), ditetradecyl glutamate ester with pendant amino group (Cl4GluCnN+), cationic derivatives of cholesterol, including but not limited to cholesteryl-3 β-oxysuccinamidoethylenetrimethylammonium salt, cholesteryl-3 β-oxysuccinamidoethylene-dimethylamine, cholesteryl-3 β-carboxyamidoethylenetrimethylammonium salt, and cholesteryl-3 β-carboxyamido ethylenedimethylamine. Other useful cationic lipids are described in US 2008/0085870 and US 2008/0057080, which are incorporated herein by reference.

The cationic lipid is preferably biodegradable (metabolisable) and biocompatible.

In addition to the oil and cationic lipid, an emulsion can include a non-ionic surfactant and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of these surfactants can be included in the emulsion e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8).

Preferred amounts of oil (% by volume) in the final emulsion are between 2-20% e.g. 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil).

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm e.g. less than 200 nm, less than 150 nm. The average droplet size is usefully in the range of 80-180 nm. Ideally, at least 80% (by number) of the emulsion's oil droplets are less than 250 nm in diameter, and preferably at least 90%. Apparatuses for determining the average droplet size in an emulsion, and the size distribution, are commercially available. These these typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan).

Ideally, the distribution of droplet sizes (by number) has only one maximum i.e. there is a single population of droplets distributed around an average (mode), rather than having two maxima. Preferred emulsions have a polydispersity of <0.4 e.g. 0.3, 0.2, or less.

Suitable emulsions with submicron droplets and a narrow size distribution can be obtained by the use of microfluidisation. This technique reduces average oil droplet size by propelling streams of input components through geometrically fixed channels at high pressure and high velocity. These streams contact channel walls, chamber walls and each other. The results shear, impact and cavitation forces cause a reduction in droplet size. Repeated steps of microfluidisation can be performed until an emulsion with a desired droplet size average and distribution are achieved.

As an alternative to microfluidisation, thermal methods can be used to cause phase inversion. These methods can also provide a submicron emulsion with a tight particle size distribution.

Preferred emulsions can be filter sterilised i.e. their droplets can pass through a 220 nm filter. As well as providing a sterilisation, this procedure also removes any large droplets in the emulsion.

In certain embodiments, the cationic lipid in the emulsion is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc. In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc. In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml. In an exemplary embodiment, the cationic oil-in-water emulsion comprises from about 0.73 mg/ml to about 1.45 mg/ml DDA, such as 1.45 mg/ml.

Catheters or like devices may be used to deliver the self-replicating RNA molecules of the invention, as naked RNA or in combination with a delivery system, into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

The present invention includes the use of suitable delivery systems, such as liposomes, polymer microparticles or submicron emulsion microparticles with encapsulated or adsorbed self-replicating RNA, to deliver a self-replicating RNA molecule that encodes an RSV-F polypeptide, for example, to elicit an immune response alone, or in combination with another macromolecule. The invention includes liposomes, microparticles and submicron emulsions with adsorbed and/or encapsulated self-replicating RNA molecules, and combinations thereof.

As demonstrated further in the Examples, the self-replicating RNA molecules associated with liposomes and submicron emulsion microparticles can be effectively delivered to the host cell, and can induce an immune response to the protein encoded by the self-replicating RNA.

The Immunogenic Composition

The invention provides immunogenic compositions. The immunogenic compositions may include a single active immunogenic agent, or several immunogenic agents. For example, the immunogenic composition can comprise RSV F polypeptides that are in a single form (e.g., monomer, trimer, or rosettes) or in two or more forms (e.g., a mixture of monomer and trimer or a dynamic equilibrium between monomer and trimer). The immunogenic composition can comprise a self-replicating RNA encoding an RSV-F polypeptide, and preferably also comprises a suitable delivery system, such as liposomes, polymeric microparticles, an oil-in-water emulsion and combinations thereof.

Immunogenic compositions of the invention may also comprise one or more immunoregulatory agents. Preferably, one or more of the immunoregulatory agents include one or more adjuvants, for example two, three, four or more adjuvants. The adjuvants may include a TH1 adjuvant and/or a TH2 adjuvant, further discussed below.

In another embodiment, an immunogenic composition of the invention comprises a polypeptide that displays an epitope present in a pre-fusion or an intermediate conformation of RSV-F glycoprotein, but does not display the glycoprotein's post-fusion conformation.

In another embodiment, an immunogenic composition of the invention comprises a first polypeptide and a second polypeptide, wherein the first polypeptide comprises an RSV F protein, in whole or in part, and the second polypeptide comprises a heterologous oligomerization domain. The first polypeptide can comprise an RSV F protein ectodomain. The second polypeptide can be a trimerization domain from influenza hemagglutinin, a trimerization domain from SARS spike, a trimerization domain from HIV gp41, NadA, modified GCN4, or ATCase.

In one aspect, the invention is a composition comprising cleaved RSV F protein ecto-domain polypeptides produced by providing uncleaved RSV F protein ecto-domain polypeptides, or C-terminal uncleaved RSV F protein ecto-domain polypeptides, and cleaving them to produce $F_1$ and $F_2$ subunits, as described herein.

In another aspect, the invention is a composition comprising uncleaved RSV F protein ecto-domain polypeptide trimers and/or monomers produced by providing a biological material that contains uncleaved RSV F protein ecto-domain polypeptides, and purifying uncleaved RSV F protein ecto-domain polypeptides monomers, uncleaved trimers, or a combination of uncleaved monomers and uncleaved trimers (e.g., a mixture or a dynamic equilibrium) from the biological material, as described herein. In some embodiments, the RSV F protein ecto-domain polypeptide contains altered furin cleavage sites at about positions 106-109 and at about positions 133-136, and if desired can further contain an altered fusion peptide. In other embodiments, the RSV F protein ecto-domain contains altered furin cleavage sites about positions 106-109 and at about positions 133-136, and altered trypsin cleavage sites between about position 101 and about position 161, and if desired can further contain an altered fusion peptide.

In another aspect, the invention is a composition comprising C-terminal uncleaved RSV F protein ecto-domain polypeptide trimers and/or monomers produced by providing a biological material that contains C-terminal uncleaved RSV F protein ecto-domain polypeptides, and purifying uncleaved RSV F protein ecto-domain polypeptides monomers, uncleaved trimers, or a combination of uncleaved monomers and uncleaved trimers (e.g., a mixture or a dynamic equilibrium) from the biological material, as described herein.

In another aspect, the invention is a composition comprising cleaved RSV F protein ecto-domain polypeptides produced by providing a biological material that contains cleaved RSV F protein ecto-domain polypeptides that contain an altered fusion peptide (e.g., at least a portion of the fusion peptide is deleted) and purifying cleaved RSV F protein ecto-domain polypeptide trimers from the biological material, as described herein.

In another aspect, the invention is a composition comprising uncleaved RSV F protein ecto-domain polypeptides produced by providing a biological material that contains uncleaved RSV F protein ecto-domain polypeptides that contain an altered fusion peptide (e.g., at least a portion of the fusion peptide is deleted) and purifying uncleaved RSV F protein ecto-domain polypeptide monomers from the biological material, as described herein.

The compositions of the invention are preferably suitable for administration to a mammalian subject, such as a human, and include one or more pharmaceutically acceptable carrier(s) and/or excipient(s), including adjuvants. A thorough discussion of such components is available in reference 29. Compositions will generally be in aqueous form. When the composition is an immunogenic composition, it will elicit an immune response when administered to a mammal, such as a human. The immunogenic composition can be used to prepare a vaccine formulation for immunizing a mammal.

The immunogenic compositions may include a single active immunogenic agent, or several immunogenic agents. For example, the RSV F protein ecto-domain polypeptide can be in a single form (e.g., uncleaved monomer, cleaved monomer, uncleaved trimer, cleaved trimer, or rosettes of cleaved trimers) or in two or more forms (e.g., a mixture of uncleaved monomer and uncleaved trimer or a dynamic equilibrium between uncleaved monomer and uncleaved trimer). In addition, the compositions can contain an RSV F protein ecto-domain polypeptide and one or more other RSV proteins (e.g., a G protein and/or an M protein) and/or it may be combined with immunogens from other pathogens.

The composition may include preservatives such as thiomersal or 2-phenoxyethanol. It is preferred, however, that the vaccine should be substantially free from (i.e., less than 5 µg/ml) mercurial material, e.g., thiomersal-free. Immunogenic compositions containing no mercury are more preferred. Preservative-free immunogenic compositions are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, and the like.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range. The pH of a composition will generally be between 5.0 and 8.1, and more typically between 6.0 and 8.0, e.g., between 6.5 and 7.5, or between 7.0 and 7.8. A process of the invention may therefore include a step of adjusting the pH of the bulk vaccine prior to packaging.

The composition is preferably sterile. The composition is preferably non-pyrogenic, e.g., containing <1 EU (endotoxin unit, a standard measure) per dose, and preferably <0.1 EU per dose. The composition is preferably gluten free. Human vaccines are typically administered in a dosage volume of about 0.5 ml, although a half dose (i.e., about 0.25 ml) may be administered to children.

Adjuvants

Compositions of the invention, that contain RSV-F polypeptids, or nucleic acids that encode RSV-F polypeptids, may also include one or more adjuvants, for example two, three, four or more adjuvants, which can function to enhance the immune responses (humoral and/or cellular) elicited in a patient who receives the composition. The adjuvants may include a TH1 adjuvant and/or a TH2 adjuvant. Adjuvants which may be used in compositions of the invention include, but are not limited to:

Mineral-containing compositions. Mineral-containing compositions suitable for use as adjuvants in the invention include mineral salts, such as calcium salts and aluminum salts (or mixtures thereof). The invention includes mineral salts such as hydroxides (e.g. oxyhydroxides), phosphates (e.g. hydroxyphosphates, orthophosphates), sulphates, etc., or mixtures of different mineral compounds, with the compounds taking any suitable form (e.g. gel, crystalline, amorphous, etc.), and with adsorption being preferred. Calcium salts include calcium phosphate (e.g., the "CAP" particles disclosed in ref. 38). Aluminum salts include hydroxides, phosphates, sulfates, and the like. The mineral containing compositions may also be formulated as a particle of metal salt (39). Aluminum salt adjuvants are described in more detail below.

Oil emulsion compositions (see in more detail below). Oil emulsion compositions suitable for use as adjuvants in the invention include squalene-water emulsions, such as MF59 (5% Squalene, 0.5% Tween 80 and 0.5% Span, formulated into submicron particles using a microfluidizer).

Cytokine-inducing agents (see in more detail below). Cytokine-inducing agents suitable for use in the invention include toll-like receptor 7 (TLR7) agonists (e.g. benzonaphthyridine compounds disclosed in WO 2009/111337.

Saponins (chapter 22 of ref. 74), which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as STIMULON™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref 40. Saponin formulations may also comprise a sterol, such as cholesterol (41). Combinations of saponins and cholesterols can be used to form unique particles called immunostimulating complexes (ISCOMs) (chapter 23 of ref. 74). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 41-43. Optionally, the ISCOMS may be devoid of additional detergent (44). A review of the development of saponin based adjuvants can be found in refs. 45 & 46.

Fatty adjuvants (see in more detail below), including oil-in-water emulsions, modified natural lipid As derived from enterobacterial lipopolysaccharides, phospholipid compounds (such as the synthetic phospholipid dimer, E6020) and the like.

Bacterial ADP-ribosylating toxins (e.g., the *E. coli* heat labile enterotoxin "LT", cholera toxin "CT", or pertussis toxin "PT") and detoxified derivatives thereof, such as the mutant toxins known as LT-K63 and LT-R72 (47). The use of detoxified ADP-ribosylating toxins as mucosal adjuvants is described in ref. 48 and as parenteral adjuvants in ref. 49.

Bioadhesives and mucoadhesives, such as esterified hyaluronic acid microspheres (50) or chitosan and its derivatives (51).

Microparticles (i.e., a particle of ~100 nm to ~150 μm in diameter, more preferably ~200 nm to ~30 μm in diameter, or ~500 nm to ~10 μm in diameter) formed from materials that are biodegradable and non-toxic (e.g., a poly(α-hydroxy acid), a polyhydroxybutyric acid, a polyorthoester, a polyanhydride, a polycaprolactone, and the like), with poly(lactide-co-glycolide) being preferred, optionally treated to have a negatively-charged surface (e.g., with SDS) or a positively-charged surface (e.g., with a cationic detergent, such as CTAB).

Liposomes (Chapters 13 & 14 of ref. 74). Examples of liposome formulations suitable for use as adjuvants are described in refs. 52-54.

Polyoxyethylene ethers and polyoxyethylene esters (55). Such formulations further include polyoxyethylene sorbitan ester surfactants in combination with an octoxynol (56) as well as polyoxyethylene alkyl ethers or ester surfactants in combination with at least one additional non-ionic surfactant such as an octoxynol (57). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

An outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides.

A polyoxidonium polymer (58, 59) or other N-oxidized polyethylene-piperazine derivative.

Methyl inosine 5'-monophosphate ("MIMP") (60).

A polyhydroxlated pyrrolizidine compound (61), such as one having formula:

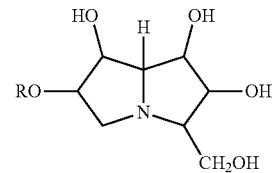

where R is selected from the group comprising hydrogen, straight or branched, unsubstituted or substituted, saturated or unsaturated acyl, alkyl (e.g., cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, and the like A CD1d ligand, such as an α-glycosylceramide (62-69) (e.g., α-galactosylceramide), phytosphingosine-containing α-glycosylceramides, OCH, KRN7000 [(2S,3S, 4R)-1-O-(α-D-galactopyranosyl)-2-(N-hexacosanoy-lamino)-1,3,4-octadecanetriol], CRONY-101, 3"-O-sulfo-galactosylceramide, etc.

A gamma inulin (70) or derivative thereof, such as algammulin.

Virosomes and virus-like particles (VLPs). These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1).

These and other adjuvant-active substances are discussed in more detail in references 74 & 75.

Compositions may include two, three, four or more adjuvants. For example, compositions of the invention may advantageously include both an oil-in-water emulsion and a cytokine-inducing agent, or both a mineral-containing composition and a cytokine-inducing agent, or two oil-in-water emulsion adjuvants, or two benzonaphthyridine compounds, etc.

Antigens and adjuvants in a composition will typically be in admixture.

Oil Emulsion Adjuvants

Oil emulsion compositions suitable for use as adjuvants in the invention include squalene-water emulsions, such as MF59 (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various oil-in-water emulsions are known, and they typically include at least one oil and at least one surfactant, with the oil(s) and surfactant(s) being biodegradable (metabolizable) and biocompatible. The oil droplets in the emulsion are generally less than 5 μm in diameter, and may even have a sub-micron diameter, with these small sizes being achieved with a microfluidizer to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used, e.g., obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene, which is particularly preferred herein. Squalane, the saturated analog to squalene, is also preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the TERGITOL™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are TWEEN 80™ (polyoxyethylene sorbitan monooleate), Span 85 (sorbitan trioleate), lecithin and Triton X-100.

Mixtures of surfactants can be used e.g., TWEEN 80™/Span 85 mixtures. A combination of a polyoxyethylene sorbitan ester such as polyoxyethylene sorbitan monooleate (TWEEN 80™) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as TWEEN 80™) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

A submicron emulsion of squalene, TWEEN 80™, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' (71-73), as described in more detail in Chapter 10 of ref. 74 and chapter 12 of ref. 75. The MF59 emulsion advantageously includes citrate ions, e.g., 10 mM sodium citrate buffer.

An emulsion of squalene, a tocopherol, and TWEEN 80™. The emulsion may include phosphate buffered saline. It may also include Span 85 (e.g., at 1%) and/or lecithin. These emulsions may have from 2 to 10% squalene, from 2 to 10% tocopherol and from 0.3 to 3% TWEEN 80™, and the weight ratio of squalene:tocopherol is preferably <1 as this provides a more stable emulsion. Squalene and TWEEN 80™ may be present volume ratio of about 5:2. One such emulsion can be made by dissolving TWEEN 80™ in PBS to give a 2% solution, then mixing 90 ml of this solution with a mixture of (5 g of DL-α-tocopherol and 5 ml squalene), then microfluidizing the mixture. The resulting emulsion may have submicron oil droplets, e.g., with an average diameter of between 100 and 250 nm, preferably about 180 nm.

An emulsion of squalene, a tocopherol, and a Triton detergent (e.g., Triton X-100). The emulsion may also include a 3d-MPL (see below). The emulsion may contain a phosphate buffer.

An emulsion comprising a polysorbate (e.g., polysorbate 80), a Triton detergent (e.g., Triton X-100) and a tocopherol (e.g., an α-tocopherol succinate). The emulsion may include these three components at a mass ratio of about 75:11:10 (e.g., 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("PLURONIC™ L121"). The emulsion can be formulated in phosphate buffered saline, pH 7.4. This emulsion is a useful delivery vehicle for muramyl dipeptides, and has been used with threonyl-MDP in the "SAF-1" adjuvant (76) (0.05-1% Thr-MDP, 5% squalane, 2.5% Pluronic L121 and 0.2% polysorbate 80). It can also be used without the Thr-MDP, as in the "AF" adjuvant (77) (5% squalane, 1.25% Pluronic L121 and 0.2% polysorbate 80). Microfluidization is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm. The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. As described in reference 78, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolizable oil (such as light mineral oil) and at least one surfactant (such as lecithin, TWEEN 80™ or Span 80). Additives may be included, such as QuilA saponin, cholesterol, a saponin-lipophile conjugate (such as GPI-0100, described in reference 79, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer).

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer).

An emulsion in which a saponin (e.g., QuilA or QS21) and a sterol (e.g., a cholesterol) are associated as helical micelles (80).

The emulsions may be mixed with antigen extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g., between 5:1 and 1:5) but is generally about 1:1.

Cytokine-Inducing Agents

Cytokine-inducing agents for inclusion in compositions of the invention are able, when administered to a patient, to elicit the immune system to release cytokines, including interferons and interleukins. Preferred agents can elicit the release of one or more of: interferon-γ; interleukin-1; interleukin-2; interleukin-12; TNF-α; TNF-β; and GM-CSF. Preferred agents elicit the release of cytokines associated with a Th1-type immune response, e.g., interferon-γ, TNF-α, interleukin-2. Stimulation of both interferon-γ and interleukin-2 is preferred.

As a result of receiving a composition of the invention, therefore, a patient will have T cells that, when stimulated with a RSV F protein, will release the desired cytokine(s) in an antigen-specific manner. For example, T cells purified from their blood will release γ-interferon when exposed in vitro to F protein. Methods for measuring such responses in peripheral blood mononuclear cells (PBMC) are known in the art, and include ELISA, ELISPOT, flow-cytometry and real-time PCR. For example, reference 81 reports a study in which antigen-specific T cell-mediated immune responses against tetanus toxoid, specifically γ-interferon responses, were monitored, and found that ELISPOT was the most sensitive method to discriminate antigen-specific TT-induced responses from spontaneous responses, but that intracytoplasmic cytokine detection by flow cytometry was the most efficient method to detect re-stimulating effects.

Suitable cytokine-inducing agents include, but are not limited to:

An immunostimulatory oligonucleotide, such as one containing a CpG motif (a dinucleotide sequence containing an unmethylated cytosine linked by a phosphate bond to a guanosine), or a double-stranded RNA, or an oligonucleotide containing a palindromic sequence, or an oligonucleotide containing a poly(dG) sequence.

3-O-deacylated monophosphoryl lipid A ('3dMPL', also known as 'MPL™') (82-85).

An imidazoquinoline compound, such as IMIQUIMOD™ ("R-837") (86, 87), RESIQUIMOD™ ("R-848") (88), and their analogs; and salts thereof (e.g., the hydrochloride salts). Further details about immunostimulatory imidazoquinolines can be found in references 89 to 93.

A benzonaphthyridine compound, such as: (a) a compound having the formula:

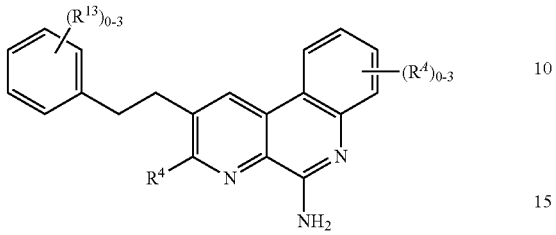

wherein:
R$^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)$_n$R$^7$, -LR$^8$, -LR$^{10}$, —OLR$^8$, —OLR$^{10}$, C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl groups of R$^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;
each L is independently selected from a bond, —(O(CH$_2$)$_m$)$_t$—, C$_1$-C$_6$alkyl, C$_2$-C$_6$alkenylene and C$_2$-C$_6$alkynylene, wherein the C$_1$-C$_6$alkyl, C$_2$-C$_6$alkenylene and C$_2$-C$_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;
R$^7$ is selected from H, C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl, wherein the C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl groups of R$^7$ are each optionally substituted with 1 to 3 R$^{13}$ groups;
each R$^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of R$^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —OR$^{10}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;
each R$^9$ is independently selected from H, —C(O)R$^8$, —C(O)OR$^8$, —C(O)R$^{10}$, —C(O)OR$^{10}$, —S(O)$_2$R$^{10}$, —C$_1$-C$_6$ alkyl, C$_1$-C$_6$ heteroalkyl and C$_3$-C$_6$ cycloalkyl, or each R$^9$ is independently a C$_1$-C$_6$alkyl that together with N they are attached to form a C$_3$-C$_8$heterocycloalkyl, wherein the C$_3$-C$_8$heterocycloalkyl ring optionally contains an additional heteroatom selected from N, O and S, and wherein the C$_1$-C$_6$ alkyl, C$_1$-C$_6$ heteroalkyl, C$_3$-C$_6$ cycloalkyl, or C$_3$-C$_8$heterocycloalkyl groups of R$^9$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)OR$^{11}$, —NR$^{11}$R$^{12}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —P(O)(OR$^{11}$)$_2$, and —OP(O)(OR$^{11}$)$_2$;
each R$^{10}$ is independently selected from aryl, C$_3$-C$_8$cycloalkyl, C$_3$-C$_8$heterocycloalkyl and heteroaryl, wherein the aryl, C$_3$-C$_8$cycloalkyl, C$_3$-C$_8$heterocycloalkyl and heteroaryl groups are optionally substituted with 1 to 3 substituents selected from halogen, —R$^8$, —OR$^8$, -LR$^9$, -LOR$^9$, —N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;
R$^{11}$ and R$^{12}$ are independently selected from H, C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl groups of R$^{11}$ and R$^{12}$ are each optionally substituted with 1 to 3 substituents independently selected from halogen, —CN, R$^8$, —OR$^8$, —C(O)R$^8$, ⁻OC(O)R$^8$, —C(O)OR$^8$, —N(R$^9$)$_2$, —NR$^8$C(O)R$^8$, —NR$^8$C(O)OR$^8$, —C(O)N(R$^9$)$_2$, C$_3$-C$_8$heterocycloalkyl, —S(O)$_2$R$^8$, —S(O)$_2$N(R$^9$)$_2$, —NR$^9$S(O)$_2$R$^8$, C$_1$-C$_6$haloalkyl and C$_1$-C$_6$haloalkoxy;
or R$^{11}$ and R$^{12}$ are each independently C$_1$-C$_6$alkyl and taken together with the N atom to which they are attached form an optionally substituted C$_3$-C$_8$heterocycloalkyl ring optionally containing an additional heteroatom selected from N, O and S;
each R$^{13}$ is independently selected from halogen, —CN, -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^8$, -LSR$^{10}$, -LC(O)R$^8$, —OLC(O)R$^8$, -LC(O)OR$^8$, -LC(O)R$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR$^9$C(O)OR$^8$, -LS(O)$_2$N(R$^9$)$_2$, —OLS(O)$_2$N(R$^9$)$_2$, -LNR$^9$S(O)$_2$R$^8$, -LC(O)NR$^9$LN(R$^9$)$_2$, -LP(O)(OR$^8$)$_2$, -LOP(O)(OR$^8$)$_2$, -LP(O)(OR$^{10}$)$_2$ and —OLP(O)(OR$^{10}$)$_2$;
each R$^A$ is independently selected from —R$^8$, —R$^7$, —OR$^7$, —OR$^8$, —R$^{10}$, —OR$^{10}$, —SR$^8$, —NO$_2$, —CN, —N(R$^9$)$_2$, —NR$^9$C(O)R$^8$, —NR$^9$C(S)R$^8$, —NR$^9$C(O)N(R$^9$)$_2$, —NR$^9$C(S)N(R$^9$)$_2$, —NR$^9$CO$_2$R$^8$, —NR$^9$NR$^9$C(O)R$^8$, —NR$^9$NR$^9$C(O)N(R$^9$)$_2$, —NR$^9$NR$^9$CO$_2$R$^8$, —C(O)C(O)R$^8$, —C(O)CH$_2$C(O)R$^8$, —CO$_2$R$^8$, —(CH$_2$)$_n$CO$_2$R$^8$, —C(O)R$^8$, —C(S)R$^8$, —C(O)N(R$^9$)$_2$, —C(S)N(R$^9$)$_2$, —OC (O)N(R$^9$)$_2$, —OC(O)R$^8$, —C(O)N(OR$^8$)R$^8$, —C(NOR$^8$)R$^8$, —S(O)$_2$R$^8$, —S(O)$_3$R$^8$, —SO$_2$N(R$^9$)$_2$, —S(O)R$^8$, —NR$^9$SO$_2$N(R$^9$)$_2$, —NR$^9$SO$_2$R$^8$, —P(O)(OR$^8$)$_2$, —OP(O)(OR$^8$)$_2$, —P(O)(OR$^{10}$)$_2$, —OP(O)(OR$^{10}$)$_2$, —N(OR$^8$)R$^8$, —CH=CHCO$_2$R$^8$, —C(=NH)—N(R$^9$)$_2$, and —(CH$_2$)$_n$NHC(O)R$^8$; or two adjacent R$^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8; (b) a compound having the formula:

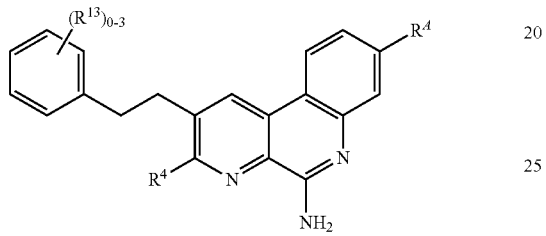

wherein:

R$^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)$_n$R$^7$, -LR$^8$, -LR$^{10}$, —OLR$^8$, —OLR$^{10}$, C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, aryl, heteroaryl, C$_3$-C$_8$cycloalkyl, and C$_3$-C$_8$heterocycloalkyl groups of R$^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;

each L is independently selected from a bond, —(O(CH$_2$)$_m$)$_t$—, C$_1$-C$_6$alkyl, C$_2$-C$_6$alkenylene and C$_2$-C$_6$alkynylene, wherein the C$_1$-C$_6$alkyl, C$_2$-C$_6$alkenylene and C$_2$-C$_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;

R$^7$ is selected from H, C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl, wherein the C$_1$-C$_6$alkyl, aryl, heteroaryl, C$_3$-C$_8$cycloalkyl, C$_1$-C$_6$heteroalkyl, C$_1$-C$_6$haloalkyl, C$_2$-C$_8$alkene, C$_2$-C$_8$alkyne, C$_1$-C$_6$alkoxy, C$_1$-C$_6$haloalkoxy, and C$_3$-C$_8$heterocycloalkyl groups of R$^7$ are each optionally substituted with 1 to 3 R$^{13}$ groups;

each R$^8$ is independently selected from H, —CH(R$^{10}$)$_2$, C$_1$-C$_8$alkyl, C$_2$-C$_8$alkene, C$_2$-C$_8$alkyne, C$_1$-C$_6$haloalkyl, C$_1$-C$_6$alkoxy, C$_1$-C$_6$heteroalkyl, C$_3$-C$_8$cycloalkyl, C$_2$-C$_8$heterocycloalkyl, C$_1$-C$_6$hydroxyalkyl and C$_1$-C$_6$haloalkoxy, wherein the C$_1$-C$_8$alkyl, C$_2$-C$_8$alkene, C$_2$-C$_8$alkyne, C$_1$-C$_6$heteroalkyl, C$_1$-C$_6$haloalkyl, C$_1$-C$_6$alkoxy, C$_3$-C$_8$cycloalkyl, C$_2$-C$_8$heterocycloalkyl, C$_1$-C$_6$hydroxyalkyl and C$_1$-C$_6$haloalkoxy groups of R$^8$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)N(R$^9$)$_2$, —C(O)OR$^{11}$, —NR$^9$C(O)R$^{11}$, —NR$^9$R$^{10}$, —NR$^{11}$R$^{12}$, —N(R$^9$)$_2$, —OR$^9$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^9$ is independently selected from H, —C(O)R$^8$, —C(O)OR$^8$, —C(O)R$^{10}$, —C(O)OR$^{10}$, —S(O)$_2$R$^{10}$, —C$_1$-C$_6$ alkyl, C$_1$-C$_6$ heteroalkyl and C$_3$-C$_6$ cycloalkyl, or each R$^9$ is independently a C$_1$-C$_6$alkyl that together with N they are attached to form a C$_3$-C$_8$heterocycloalkyl, wherein the C$_3$-C$_8$heterocycloalkyl ring optionally contains an additional heteroatom selected from N, O and S, and wherein the C$_1$-C$_6$ alkyl, C$_1$-C$_6$ heteroalkyl, C$_3$-C$_6$cycloalkyl, or C$_3$-C$_8$heterocycloalkyl groups of R$^9$ are each optionally substituted with 1 to 3 substituents independently selected from —CN, R$^{11}$, —OR$^{11}$, —SR$^{11}$, —C(O)R$^{11}$, —OC(O)R$^{11}$, —C(O)OR$^{11}$, —NR$^{11}$R$^{12}$, —C(O)NR$^{11}$R$^{12}$, —C(O)NR$^{11}$OH, —S(O)$_2$R$^{11}$, —S(O)R$^{11}$, —S(O)$_2$NR$^{11}$R$^{12}$, —NR$^{11}$S(O)$_2$R$^{11}$, —P(O)(OR$^{11}$)$_2$, and —OP(O)(OR$^{11}$)$_2$;

each R$^{10}$ is independently selected from aryl, C$_3$-C$_8$cycloalkyl, C$_3$-C$_8$heterocycloalkyl and heteroaryl, wherein the aryl, C$_3$-C$_8$cycloalkyl, C$_3$-C$_8$heterocycloalkyl and heteroaryl groups are optionally substituted with 1 to 3 substituents selected from halogen, —R$^8$, —OR$^8$, -LR$^9$, -LOR$^9$, —N(R$^9$)$_2$, —NR$^9$C(O)R$^8$, —NR$^9$CO$_2$R$^8$, —CO$_2$R$^8$, —C(O)R$^8$ and —C(O)N(R$^9$)$_2$;

R$^{11}$ and R$^{12}$ are independently selected from H, C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl, wherein the C$_1$-C$_6$alkyl, C$_1$-C$_6$heteroalkyl, C$_1$-C$_6$haloalkyl, aryl, heteroaryl, C$_3$-C$_8$cycloalkyl, and C$_3$-C$_8$heterocycloalkyl groups of R$^{11}$ and R$^{12}$ are each optionally substituted with 1 to 3 substituents independently selected from halogen, —CN, R$^8$, —OR$^8$, —C(O)R$^8$, ⁻OC(O)R$^8$, —C(O)OR$^8$, —N(R$^9$)$_2$, —NR$^8$C(O)R$^8$, —NR$^8$C(O)OR$^8$, —C(O)N(R$^9$)$_2$, C$_3$-C$_8$heterocycloalkyl, —S(O)$_2$R$^8$, —S(O)$_2$N(R$^9$)$_2$, —NR$^9$S(O)$_2$R$^8$, C$_1$-C$_6$haloalkyl and C$_1$-C$_6$haloalkoxy;

or R$^{11}$ and R$^{12}$ are each independently C$_1$-C$_6$alkyl and taken together with the N atom to which they are attached form an optionally substituted C$_3$-C$_8$heterocycloalkyl ring optionally containing an additional heteroatom selected from N, O and S;

each R$^{13}$ is independently selected from halogen, —CN, -LR$^9$, -LOR$^9$, —OLR$^9$, -LR$^{10}$, -LOR$^{10}$, —OLR$^{10}$, -LR$^8$, -LOR$^8$, —OLR$^8$, -LSR$^8$, -LSR$^{10}$, -LC(O)R$^8$, —OLC(O)R$^8$, -LC(O)OR$^8$, -LC(O)N$^{10}$, -LOC(O)OR$^8$, -LC(O)NR$^9$R$^{11}$, -LC(O)NR$^9$R$^8$, -LN(R$^9$)$_2$, -LNR$^9$R$^8$, -LNR$^9$R$^{10}$, -LC(O)N(R$^9$)$_2$, -LS(O)$_2$R$^8$, -LS(O)R$^8$, -LC(O)NR$^8$OH, -LNR$^9$C(O)R$^8$, -LNR⁹C(O)OR⁸, -LS(O)₂N(R⁹)₂, —OLS(O)₂N(R⁹)₂, -LNR⁹S(O)₂R⁸, -LC(O)NR⁹LN(R⁹)₂, -LP(O)(OR⁸)₂, -LOP(O)(OR⁸)₂, -LP(O)(OR¹⁰)₂ and —OLP(O)(OR¹⁰)₂;

each $R^A$ is independently selected from —R⁸, —R⁷, —OR⁷, —OR⁸, —R¹⁰, —OR¹⁰, —SR⁸, —NO₂, —CN, —N(R⁹)₂, —NR⁹C(O)R⁸, —NR⁹C(S)R⁸, —NR⁹C(O)N(R⁹)₂, —NR⁹C(S)N(R⁹)₂, —NR⁹CO₂R⁸, —NR⁹NR⁹C(O)R⁸, —NR⁹NR⁹C(O)N(R⁹)₂, —NR⁹NR⁹CO₂R⁸, —C(O)C(O)R⁸, —C(O)CH₂C(O)R⁸, —CO₂R⁸, —(CH₂)ₙCO₂R⁸, —C(O)R⁸, —C(S)R⁸, —C(O)N(R⁹)₂, —C(S)N(R⁹)₂, —OC(O)N(R⁹)₂, —OC(O)R⁸, —C(O)N(OR⁸)R⁸, —C(NOR⁸)R⁸, —S(O)₂R⁸, —S(O)₃R⁸, —SO₂N(R⁹)₂, —S(O)R⁸, —NR⁹SO₂N(R⁹)₂, —NR⁹SO₂R⁸, —P(O)(OR⁸)₂, —OP(O)(OR⁸)₂, —P(O)(OR¹⁰)₂, —OP(O)(OR¹⁰)₂, —N(OR⁸)R⁸, —CH=CHCO₂R⁸, —C(=NH)—N(R⁹)₂, and —(CH₂)ₙNHC(O)R⁸;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8; or (c) a pharmaceutically acceptable salt of any of (a) or (b). Other benzonaphthyridine compounds, and methods of making benzonaphthyridine compounds, are described in WO 2009/111337. A benzonaphthyridine compound, or a salt thereof, can be used on its own, or in combination with one or more further compounds. For example, a benzonaphthyridine compound can be used in combination with an oil-in-water emulsion or a mineral-containing composition. In a particular embodiment, a benzonaphthyridine compound is used in combination with an oil-in-water emulsion (e.g. a squalene-water emulsion, such as MF59) or a mineral-containing composition (e.g., a mineral sald such as an aluminum salt or a calcium salt).

A thiosemicarbazone compound, such as those disclosed in reference 94. Methods of formulating, manufacturing, and screening for active compounds are also described in reference 94. The thiosemicarbazones are particularly effective in the stimulation of human peripheral blood mononuclear cells for the production of cytokines, such as TNF-α.

A tryptanthrin compound, such as those disclosed in reference 95. Methods of formulating, manufacturing, and screening for active compounds are also described in reference 95. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

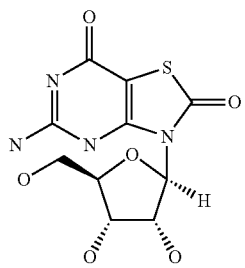 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 96 to 98; (f) a compound having the formula:

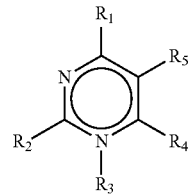

wherein:
$R_1$ and $R_2$ are each independently H, halo, —NR_aR_b, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;

$R_4$ and $R_5$ are each independently H, halo, heterocyclyl, substituted heterocyclyl, —C(O)—R_d, $C_{1-6}$ alkyl, substituted $C_{1-6}$ alkyl, or bound together to form a 5 membered ring as in $R_{4-5}$:

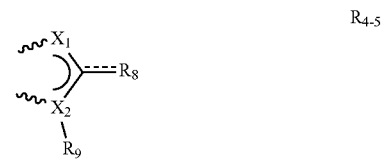

the binding being achieved at the bonds indicated by a ⁓

$X_1$ and $X_2$ are each independently N, C, O, or S;

$R_8$ is H, halo, —OH, $C_{1-6}$ alkyl, $C_{2-6}$ alkenyl, $C_{2-6}$ alkynyl, —OH, —NR_aR_b, —(CH₂)ₙ—O—R_c, —O—($C_{1-6}$ alkyl), —S(O)_pR_e, or —C(O)—R_d;

$R_9$ is H, $C_{1-6}$ alkyl, substituted $C_{1-6}$ alkyl, heterocyclyl, substituted heterocyclyl or $R_{9a}$, wherein $R_{9a}$ is:

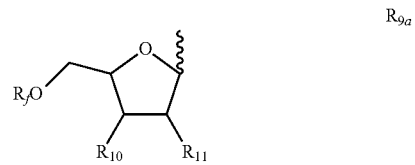

the binding being achieved at the bond indicated by a ⁓

$R_{10}$ and $R_{11}$ are each independently H, halo, $C_{1-6}$ alkoxy, substituted $C_{1-6}$ alkoxy, —NR_aR_b, or —OH;

each $R_a$ and $R_b$ is independently H, $C_{1-6}$ alkyl, substituted $C_{1-6}$ alkyl, —C(O)R_d, $C_{6-10}$ aryl;

each $R_c$ is independently H, phosphate, diphosphate, triphosphate, $C_{1-6}$ alkyl, or substituted $C_{1-6}$ alkyl;

each $R_d$ is independently H, halo, $C_{1-6}$ alkyl, substituted $C_{1-6}$ alkyl, $C_{1-6}$ alkoxy, substituted $C_{1-6}$ alkoxy, —NH₂, —NH($C_{1-6}$ alkyl), —NH(substituted $C_{1-6}$ alkyl), —N($C_{1-6}$ alkyl)$_2$, —N(substituted $C_{1-6}$ alkyl)$_2$, $C_{6-10}$ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, —C(O)$R_d$, phosphate, diphosphate, or triphosphate;

each n is independently 0, 1, 2, or 3;

each p is independently 0, 1, or 2; or or (g) a pharmaceutically acceptable salt of any of (a) to (f), a tautomer of any of (a) to (f), or a pharmaceutically acceptable salt of the tautomer.

Loxoribine (7-allyl-8-oxoguanosine) (99).

Compounds disclosed in reference 100, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (101, 102), Hydrapthalamide compounds, Benzophenone compounds, Isoxazole compounds, Sterol compounds, Quinazilinone compounds, Pyrrole compounds (103), Anthraquinone compounds, Quinoxaline compounds, Triazine compounds, Pyrazalopyrimidine compounds, and Benzazole compounds (104).

Compounds disclosed in reference 105.

An aminoalkyl glucosaminide phosphate derivative, such as RC-529 (106, 107).

A phosphazene, such as poly[di(carboxylatophenoxy) phosphazene] ("PCPP") as described, for example, in references 108 and 109.

Small molecule immunopotentiators (SMIPs) such as:
N2-methyl-1-(2-methylpropyl)-1H-imidazo[4,5-c]quinoline-2,4-diamine
N2,N2-dimethyl-1-(2-methylpropyl)-1H-imidazo[4,5-c]quinoline-2,4-diamine
N2-ethyl-N2-methyl-1-(2-methylpropyl)-1H-imidazo[4,5-c]quinoline-2,4-diamine
N2-methyl-1-(2-methylpropyl)-N2-propyl-1H-imidazo[4,5-c]quinoline-2,4-diamine
1-(2-methylpropyl)-N2-propyl-1H-imidazo[4,5-c]quinoline-2,4-diamine
N2-butyl-1-(2-methylpropyl)-1H-imidazo[4,5-c]quinoline-2,4-diamine
N2-butyl-N2-methyl-1-(2-methylpropyl)-1H-imidazo[4,5-c]quinoline-2,4-diamine
N2-methyl-1-(2-methylpropyl)-N2-pentyl-1H-imidazo[4,5-c]quinoline-2,4-diamine
N2-methyl-1-(2-methylpropyl)-N2-prop-2-enyl-1H-imidazo[4,5-c]quinoline-2,4-diamine
1-(2-methylpropyl)-2-[(phenylmethyl)thio]-1H-imidazo[4,5-c]quinolin-4-amine
1-(2-methylpropyl)-2-(propylthio)-1H-imidazo[4,5-c]quinolin-4-amine
2-[[4-amino-1-(2-methylpropyl)-1H-imidazo[4,5-c]quinolin-2-yl](methyl)amino]ethanol
2-[[4-amino-1-(2-methylpropyl)-1H-imidazo[4,5-c]quinolin-2-yl](methyl)amino]ethyl acetate
4-amino-1-(2-methylpropyl)-1,3-dihydro-2H-imidazo[4,5-c]quinolin-2-one
N2-butyl-1-(2-methylpropyl)-N4,N4-bis(phenylmethyl)-1H-imidazo[4,5-c]quinoline-2,4-diamine
N2-butyl-N2-methyl-1-(2-methylpropyl)-N4,N4-bis(phenylmethyl)-1H-imidazo[4,5-c]quinoline-2,4-diamine
N2-methyl-1-(2-methylpropyl)-N4,N4-bis(phenylmethyl)-1H-imidazo[4,5-c]quinoline-2,4-diamine
N2,N2-dimethyl-1-(2-methylpropyl)-N4,N4-bis(phenylmethyl)-1H-imidazo[4,5-c]quinoline-2,4-diamine
1-[4-amino-2-[methyl(propyl)amino]-1H-imidazo[4,5-c]quinolin-1-yl]-2-methylpropan-2-ol
1-[4-amino-2-(propylamino)-1H-imidazo[4,5-c]quinolin-1-yl]-2-methylpropan-2-ol
N4,N4-dibenzyl-1-(2-methoxy-2-methylpropyl)-N2-propyl-1H-imidazo[4,5-c]quinoline-2,4-diamine.

The cytokine-inducing agents for use in the present invention may be modulators and/or agonists of Toll-Like Receptors (TLR). For example, they may be agonists of one or more of the human TLR1, TLR2, TLR3, TLR4, TLR7, TLR8, and/or TLR9 proteins. Preferred agents are agonists of TLR4 (e.g., modified natural lipid As derived from enterobacterial lipopolysaccharides, phospholipid compounds, such as the synthetic phospholipid dimer, E6020), TLR7 (e.g., benzonaphthyridines, imidazoquinolines) and/or TLR9 (e.g., CpG oligonucleotides). These agents are useful for activating innate immunity pathways.

The cytokine-inducing agent can be added to the composition at various stages during its production. For example, it may be within an antigen composition, and this mixture can then be added to an oil-in-water emulsion. As an alternative, it may be within an oil-in-water emulsion, in which case the agent can either be added to the emulsion components before emulsification, or it can be added to the emulsion after emulsification. Similarly, the agent may be coacervated within the emulsion droplets. The location and distribution of the cytokine-inducing agent within the final composition will depend on its hydrophilic/lipophilic properties, e.g., the agent can be located in the aqueous phase, in the oil phase, and/or at the oil-water interface.

The cytokine-inducing agent can be conjugated to a separate agent, such as an antigen (e.g., CRM197). A general review of conjugation techniques for small molecules is provided in ref. 110. As an alternative, the adjuvants may be non-covalently associated with additional agents, such as by way of hydrophobic or ionic interactions.

Preferred cytokine-inducing agents are (a) benzonapthridine compounds; (b) immunostimulatory oligonucleotides and (c) 3dMPL.

Immunostimulatory oligonucleotides can include nucleotide modifications/analogs such as phosphorothioate modifications and can be double-stranded or (except for RNA) single-stranded. References 111, 112, and 113disclose possible analog substitutions, e.g., replacement of guanosine with 2'-deoxy-7-deazaguanosine. The adjuvant effect of CpG oligonucleotides is further discussed in refs. 114 to 119. A CpG sequence may be directed to TLR9, such as the motif GTCGTT or TTCGTT (120). The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 121-123. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 120 & 124-126. A useful CpG adjuvant is CpG7909, also known as PROMUNE (TM) (Coley Pharmaceutical Group, Inc.).

As an alternative, or in addition, to using CpG sequences, TpG sequences can be used (127). These oligonucleotides may be free from unmethylated CpG motifs.

The immunostimulatory oligonucleotide may be pyrimidine-rich. For example, it may comprise more than one consecutive thymidine nucleotide (e.g., TTTT, as disclosed in ref. 127), and/or it may have a nucleotide composition with >25% thymidine (e.g., >35%, >40%, >50%, >60%, >80%, etc.). For example, it may comprise more than one consecutive cytosine nucleotide (e.g., CCCC, as disclosed in ref. 127), and/or it may have a nucleotide composition with >25% cytosine (e.g., >35%, >40%, >50%, >60%, >80%, etc.). These oligonucleotides may be free from unmethylated CpG motifs.

Immunostimulatory oligonucleotides will typically comprise at least 20 nucleotides. They may comprise fewer than 100 nucleotides.

3dMPL (also known as 3 de-O-acylated monophosphoryl lipid A or 3-O-desacyl-4'-monophosphoryl lipid A) is an adjuvant in which position 3 of the reducing end glucosamine in monophosphoryl lipid A has been de-acylated. 3dMPL has been prepared from a heptoseless mutant of *Salmonella minnesota*, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF (see also ref. 128). Preparation of 3dMPL was originally described in reference 129.

3dMPL can take the form of a mixture of related molecules, varying by their acylation (e.g., having 3, 4, 5 or 6 acyl chains, which may be of different lengths). The two glucosamine (also known as 2-deoxy-2-amino-glucose) monosaccharides are N-acylated at their 2-position carbons (i.e., at positions 2 and 2'), and there is also 0-acylation at the 3' position. The group attached to carbon 2 has formula —NH—CO—CH$_2$—CR$^1$R$^{1'}$. The group attached to carbon 2' has formula —NH—CO—CH$_2$—CR$^2$R$^{2'}$. The group attached to carbon 3' has formula —O—CO—CH$_2$—CR$^3$R$^{3'}$. A representative structure is:

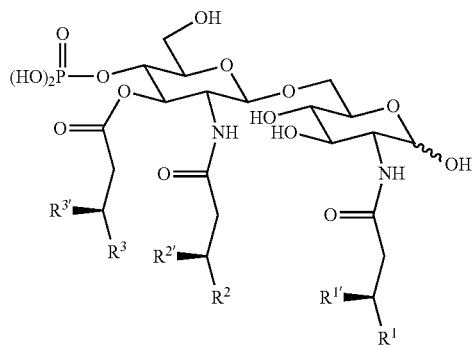

Groups R$^1$, R$^2$ and R$^3$ are each independently —(CH$_2$)$_n$—CH$_3$. The value of n is preferably between 8 and 16, more preferably between 9 and 12, and is most preferably 10.

Groups R$^{1'}$, R$^{2'}$ and R$^{3'}$ can each independently be: (a) —H; (b) —OH; or (c) —O—CO—R$^4$, where R$^4$ is either —H or —(CH$_2$)$_m$—CH$_3$, wherein the value of m is preferably between 8 and 16, and is more preferably 10, 12 or 14. At the 2 position, m is preferably 14. At the 2' position, m is preferably 10. At the 3' position, m is preferably 12. Groups R$^{1'}$, R$^{2'}$ and R$^{3'}$ are thus preferably —O-acyl groups from dodecanoic acid, tetradecanoic acid or hexadecanoic acid.

When all of R$^{1'}$, R$^{2'}$ and R$^{3'}$ are —H then the 3dMPL has only 3 acyl chains (one on each of positions 2, 2' and 3'). When only two of R$^{1'}$, R$^{2'}$ and R$^{3'}$ are —H then the 3dMPL can have 4 acyl chains. When only one of R$^{1'}$, R$^{2'}$ and R$^{3'}$ is —H then the 3dMPL can have 5 acyl chains. When none of R$^{1'}$, R$^{2'}$ and R$^{3'}$ is —H then the 3dMPL can have 6 acyl chains. The 3dMPL adjuvant used according to the invention can be a mixture of these forms, with from 3 to 6 acyl chains, but it is preferred to include 3dMPL with 6 acyl chains in the mixture, and in particular to ensure that the hexaacyl chain form makes up at least 10% by weight of the total 3dMPL e.g., >20%, >30%, >40%, >50% or more. 3dMPL with 6 acyl chains has been found to be the most adjuvant-active form.

Thus the most preferred form of 3dMPL for inclusion in compositions of the invention has formula (IV), shown below.

Where 3dMPL is used in the form of a mixture then references to amounts or concentrations of 3dMPL in compositions of the invention refer to the combined 3dMPL species in the mixture.

In aqueous conditions, 3dMPL can form micellar aggregates or particles with different sizes e.g., with a diameter <150 nm or >500 nm. Either or both of these can be used with the invention, and the better particles can be selected by routine assay. Smaller particles (e.g., small enough to give a clear aqueous suspension of 3dMPL) are preferred for use according to the invention because of their superior activity (130). Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm. These particles are small enough to be suitable for filter sterilization. Particle diameter can be assessed by the routine technique of dynamic light scattering, which reveals a mean particle diameter. Where a particle is said to have a diameter of x nm, there will generally be a distribution of particles about this mean, but at least 50% by number (e.g., >60%, >70%, >80%, >90%, or more) of the particles will have a diameter within the range x±25%.

3dMPL can advantageously be used in combination with an oil-in-water emulsion. Substantially all of the 3dMPL may be located in the aqueous phase of the emulsion.

The 3dMPL can be used on its own, or in combination with one or more further compounds. For example, it is known to use 3dMPL in combination with the QS21 saponin (131) (including in an oil-in-water emulsion (132)), with an immunostimulatory oligonucleotide, with both QS21 and an immunostimulatory oligonucleotide, with aluminum phosphate (133), with aluminum hydroxide (134), or with both aluminum phosphate and aluminum hydroxide.

Formula (IV)
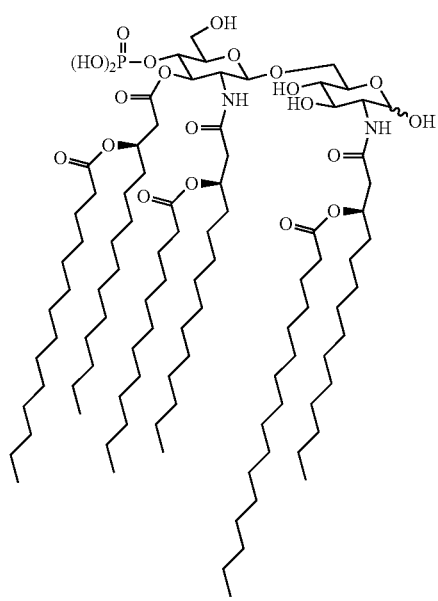
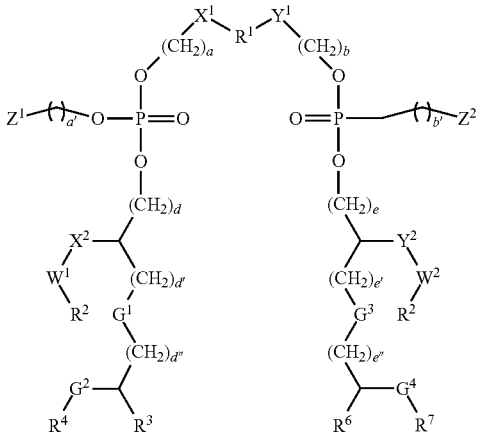
Fatty Adjuvants
Fatty adjuvants that can be used with the invention include the oil-in-water emulsions described above, and also include, for example:
A phospholipid compound of formula I, II or III, or a salt thereof:
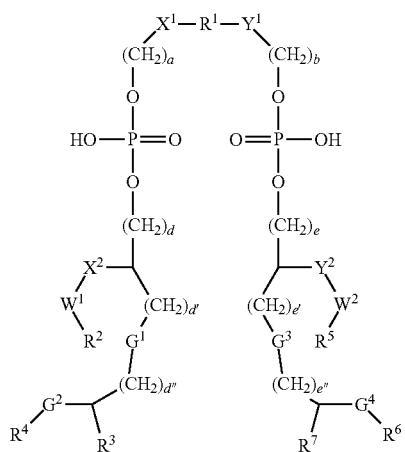
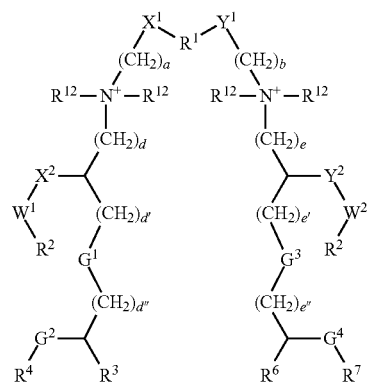
as defined in reference 135, such as 'ER 803058', 'ER 803732', 'ER 804053', ER 804058', 'ER 804059', 'ER 804442', 'ER 804680', 'ER 804764', ER 803022 or 'ER 804057' e.g.:

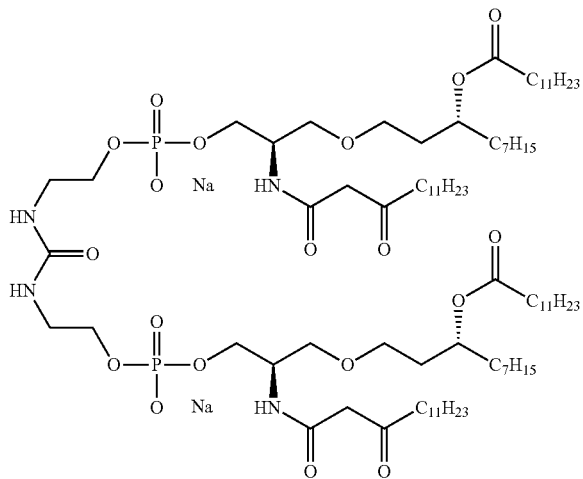

ER804057

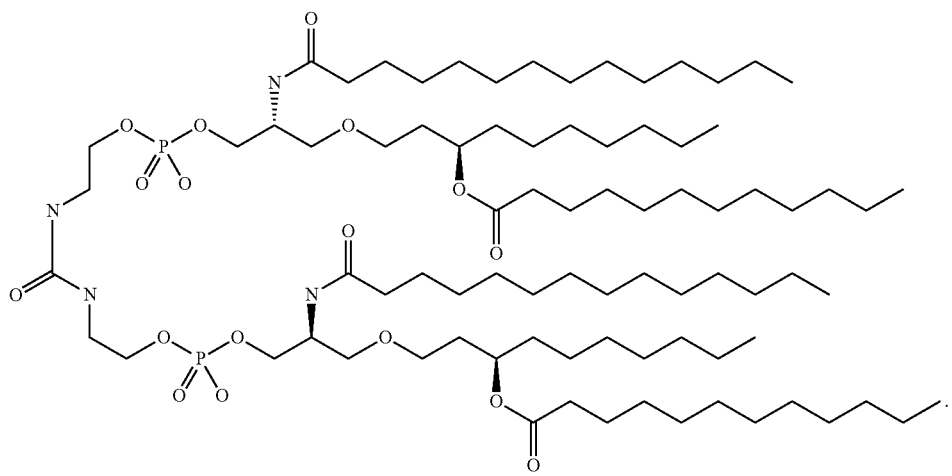

ER-803022

ER804057 is also called E6020. A phospholipid compound of formula I, II or III, or a salt thereof, can be used on its own, or in combination with one or more further compounds. For example, a compound of formula I, II or III, can be used in combination with an oil-in-water emulsion or a mineral-containing composition. In a particular embodiment, E6020 is used in combination with an oil-in-water emulsion (e.g. a squalene-water emulsion, such as MF59) or a mineral-containing composition (e.g., a mineral salt such as an aluminum salt or a calcium salt).

Derivatives of lipid A from *Escherichia coli* such as OM-174 (described in refs. 136 & 137).

A formulation of a cationic lipid and a (usually neutral) co-lipid, such as aminopropyl-dimethyl-myristoleyloxy-propanaminium bromide-diphytanoylphosphatidyl-ethanolamine ("VAXFECTIN™") or aminopropyl-dimethyl-bis-dodecyloxy-propanaminium bromide-dioleoylphosphatidyl-ethanolamine ("GAP-DLRIE: DOPE"). Formulations containing (+)-N-(3-aminopropyl)-N,N-dimethyl-2,3-bis(syn-9-tetradeceneyloxy)-1-propanaminium salts are preferred (138).

3-O-deacylated monophosphoryl lipid A (see above).

Compounds containing lipids linked to a phosphate-containing acyclic backbone, such as the TLR4 antagonist E5564 (139, 140):

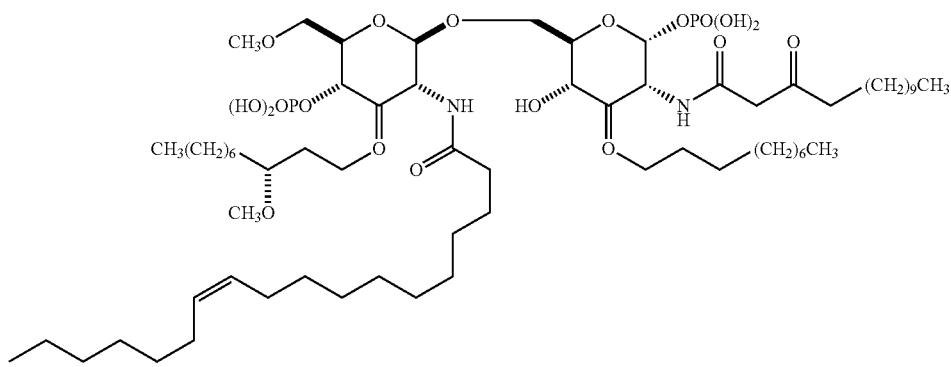

Lipopeptides (i.e., compounds comprising one or more fatty acid residues and two or more amino acid residues), such as lipopeptides based on glycerylcysteine. Specific examples of such peptides include compounds of the following formula

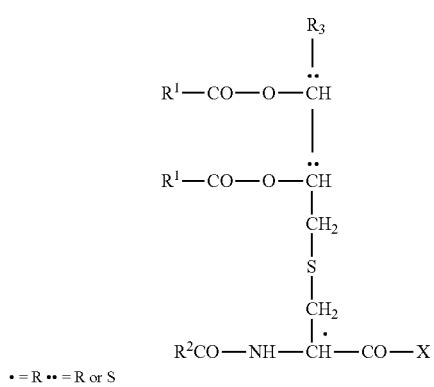

• = R •• = R or S in which each of $R^1$ and $R^2$ represents a saturated or unsaturated, aliphatic or mixed aliphatic-cycloaliphatic hydrocarbon radical having from 8 to 30, preferably 11 to 21, carbon atoms that is optionally also substituted by oxygen functions, $R^3$ represents hydrogen or the radical $R_1$—CO—O—CH$_2$— in which $R^1$ has the same meaning as above, and X represents an amino acid bonded by a peptide linkage and having a free, esterified or amidated carboxy group, or an amino acid sequence of from 2 to 10 amino acids of which the terminal carboxy group is in free, esterified or amidated form. In certain embodiments, the amino acid sequence comprises a D-amino acid, for example, D-glutamic acid (D-Glu) or D-gamma-carboxy-glutamic acid (D-Gla).

Bacterial lipopeptides generally recognize TLR2, without requiring TLR6 to participate. (TLRs operate cooperatively to provide specific recognition of various triggers, and TLR2 plus TLR6 together recognize peptidoglycans, while TLR2 recognizes lipopeptides without TLR6.) These are sometimes classified as natural lipopeptides and synthetic lipopeptides. Synthetic lipopeptides tend to behave similarly, and are primarily recognized by TLR2.

Lipopeptides suitable for use as adjuvants include compounds have the formula:

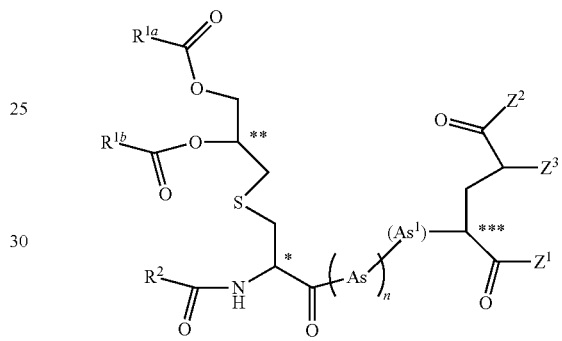

where the chiral center labeled * and the one labeled * are both in the R configuration; the chiral center labeled  is either in the R or S configuration;
each $R^{1a}$ and $R^{1b}$ is independently an aliphatic or cycloaliphatic-aliphatic hydrocarbon group having 7-21 carbon atoms, optionally substituted by oxygen functions, or one of $R^{1a}$ and $R^{1b}$, but not both, is H;
$R^2$ is an aliphatic or cycloaliphatic hydrocarbon group having 1-21 carbon atoms and optionally substituted by oxygen functions;
n is 0 or 1;
As represents either —O-Kw-CO— or —NH-Kw-CO—, where Kw is an aliphatic hydrocarbon group having 1-12 carbon atoms;
$As^1$ is a D- or L-alpha-amino acid;
$Z^1$ and $Z^2$ each independently represent —OH or the N-terminal radical of a D- or L-alpha amino acid of an amino-(lower alkane)-sulfonic acid or of a peptide having up to 6 amino acids selected from the D- and L-alpha aminocarboxylic acids and amino-lower alkyl-sulfonic acids; and
$Z^3$ is H or —CO—$Z^4$, wher $Z^4$ is —OH or the N-terminal radical of a D- or L-alpha amino acid of an amino-(lower alkane)-sulfonic acid or of a peptide having up to 6 amino acids selected from the D and L-alpha aminocarboxylic acids and amino-lower alkyl-sulfonic acids; or an ester or amide formed from the carboxylic acid of such compounds. Suitable amides include —NH$_2$ and NH(lower alkyl), and suitable esters include C1-C4 alkyl esters. (lower alkyl or lower alkane, as used herein, refers to $C_1$-$C_6$ straight chain or branched alkyls).

Such compounds are described in more detail in U.S. Pat. No. 4,666,886. In one particular embodiment, the lipopeptide has the formula:

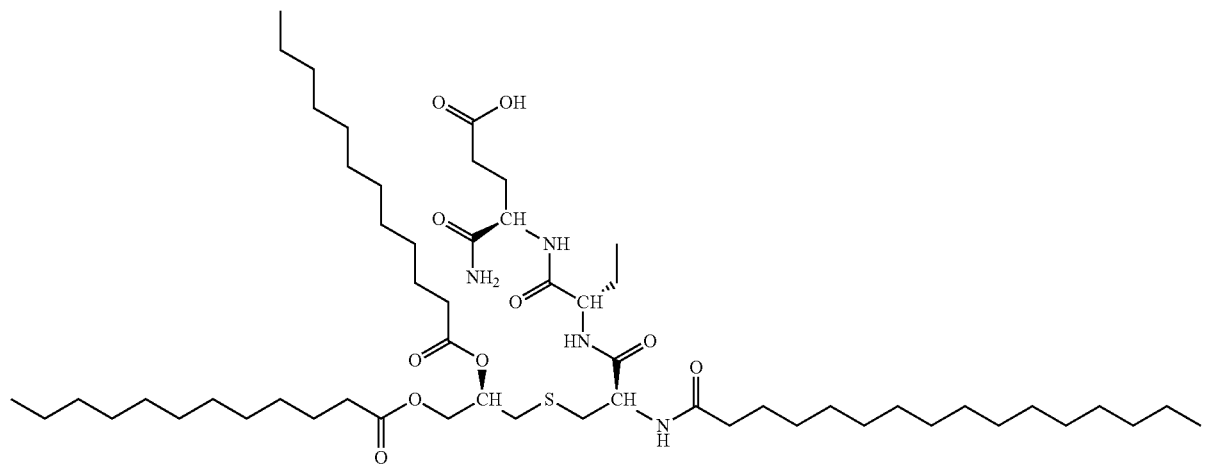 [SMILES: CCCCCCCCCCCCCCCC(=O)N[C@@H](CSC[C@@H](COC(=O)CCCCCCCCCCC)OC(=O)CCCCCCCCCCC)C(=O)N[C@@H](CC)C(=O)N[C@H](CCC(=O)O)C(N)=O]

Another example of a lipopeptide species is called LP40, and is an agonist of TLR2. Akdis, et al., *Eur. J. Immunology*, 33: 2717-26 (2003).

These are related to a known class of lipopeptides from *E. coli*, referred to as murein lipoproteins. Certain partial degradation products of those proteins called murein lipopetides are described in Hantke, et al., *Eur. J. Biochem.*, 34: 284-296 (1973). These comprise a peptide linked to N-acetyl muramic acid and are thus related to Muramyl peptides, which are described in Baschang, et al., *Tetrahedron*, 45(20): 6331-6360 (1989).

Aluminum Salt Adjuvants

The adjuvants known as "aluminum hydroxide" and "aluminum phosphate" may be used. These names are conventional, but are used for convenience only, as neither is a precise description of the actual chemical compound which is present (e.g., see chapter 9 of reference 74). The invention can use any of the "hydroxide" or "phosphate" adjuvants that are in general use as adjuvants.

The adjuvants known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as aluminum hydroxide $Al(OH)_3$, by infrared (IR) spectroscopy, in particular by the presence of an adsorption band at 1070 $cm^{-1}$ and a strong shoulder at 3090-3100 $cm^{-1}$ (chapter 9 of ref. 74). The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g., as seen in transmission electron micrographs) is typical for aluminum hydroxide adjuvants. The pI of aluminum hydroxide adjuvants is typically about 11, i.e., the adjuvant itself has a positive surface charge at physiological pH. Adsorptive capacities of between 1.8-2.6 mg protein per mg $Al^{+++}$ at pH 7.4 have been reported for aluminum hydroxide adjuvants.

The adjuvants known as "aluminum phosphate" are typically aluminum hydroxyphosphates, often also containing a small amount of sulfate (i.e., aluminum hydroxyphosphate sulfate). They may be obtained by precipitation, and the reaction conditions and concentrations during precipitation influence the degree of substitution of phosphate for hydroxyl in the salt. Hydroxyphosphates generally have a $PO_4/Al$ molar ratio between 0.3 and 1.2. Hydroxyphosphates can be distinguished from strict $AlPO_4$ by the presence of hydroxyl groups. For example, an IR spectrum band at 3164 $cm^{-1}$ (e.g., when heated to 200° C.) indicates the presence of structural hydroxyls (ch. 9 of ref. 74)

The $PO_4/Al^{3+}$ molar ratio of an aluminum phosphate adjuvant will generally be between 0.3 and 1.2, preferably between 0.8 and 1.2, and more preferably 0.95+0.1. The aluminum phosphate will generally be amorphous, particularly for hydroxyphosphate salts. A typical adjuvant is amorphous aluminum hydroxyphosphate with $PO_4/Al$ molar ratio between 0.84 and 0.92, included at 0.6 mg $Al^{3+}$/ml. The aluminum phosphate will generally be particulate (e.g., plate-like morphology as seen in transmission electron micrographs). Typical diameters of the particles are in the range 0.5-20 μm (e.g., about 5-10 μm) after any antigen adsorption. Adsorptive capacities of between 0.7-1.5 mg protein per mg $Al^{+++}$ at pH 7.4 have been reported for aluminum phosphate adjuvants.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5, e.g., about 5.7.

Suspensions of aluminum salts used to prepare compositions of the invention may contain a buffer (e.g., a phosphate or a histidine or a Tris buffer), but this is not always necessary. The suspensions are preferably sterile and pyrogen-free. A suspension may include free aqueous phosphate ions e.g., present at a concentration between 1.0 and 20 mM, preferably between 5 and 15 mM, and more preferably about 10 mM. The suspensions may also comprise sodium chloride.

The invention can use a mixture of both an aluminum hydroxide and an aluminum phosphate. In this case there may be more aluminum phosphate than hydroxide e.g., a weight ratio of at least 2:1 e.g., >5:1, >6:1, >7:1, >8:1, >9:1, etc.

The concentration of $Al^{+++}$ in a composition for administration to a patient is preferably less than 10 mg/ml e.g., <5 mg/ml, <4 mg/ml, <3 mg/ml, <2 mg/ml, <1 mg/ml, etc. A preferred range is between 0.3 and 1 mg/ml. A maximum of 0.85 mg/dose is preferred.

As well as including one or more aluminum salt adjuvants, the adjuvant component may include one or more further adjuvant or immunostimulating agents. Such additional components include, but are not limited to: a benzonaphthyridine compound, a 3-O-deacylated monophosphoryl lipid A adjuvant ('3d-MPL'); and/or an oil-in-water emulsion. 3d-MPL has also been referred to as 3 de-O-acylated monophosphoryl lipid A or as 3-O-desacyl-4'-monophosphoryl lipid A. The name indicates that position 3 of the reducing end glucosamine in monophosphoryl lipid A is de-acylated. It has been prepared from a heptoseless mutant of S. minnesota, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF. Preparation of 3d-MPL was originally described in reference 129, and the product has been manufactured and sold by Corixa Corporation under the name MPL™. Further details can be found in refs 82 to 85.

The use of an aluminum hydroxide and/or aluminum phosphate adjuvant is useful, particularly in children, and antigens are generally adsorbed to these salts. Squalene-in-water emulsions are also preferred, particularly in the elderly. Useful adjuvant combinations include combinations of Th1 and Th2 adjuvants such as CpG and alum, or resiquimod and alum. A combination of aluminum phosphate and 3dMPL may be used. Other combinations that may be used include: alum and a benzonapthridine compound or a SMIP, a squalene-in-water emulsion (such as MF59) and a benzonapthridine compound or a SMIP, and E6020 and a squalene-in-water emulsion, such as MF59) or alum.

The compositions of the invention may elicit both a cell mediated immune response as well as a humoral immune response.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

A composition may include a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Methods of Treatment, and Administration

Compositions of the invention are suitable for administration to mammals, and the invention provides a method of inducing an immune response in a mammal, comprising the step of administering a composition (e.g., an immunogenic composition) of the invention to the mammal. The compositions (e.g., an immunogenic composition) can be used to produce a vaccine formulation for immunizing a mammal. The mammal is typically a human, and the RSV F protein ecto-domain is typically a human RSV F protein ecto-domain. However, the mammal can be any other mammal that is susceptible to infection with RSV, such as a cow that can be infected with bovine RSV. For example, the immune response may be raised following administration of a purified RSV F protein, an alphavirus particle, or self-replicating RNA.

The invention also provides a composition of the invention for use as a medicament, e.g., for use in immunizing a patient against RSV infection.

The invention also provides the use of a polypeptide as described above in the manufacture of a medicament for raising an immune response in a patient.

The immune response raised by these methods and uses will generally include an antibody response, preferably a protective antibody response. Methods for assessing antibody responses after RSV vaccination are well known in the art.

Compositions of the invention can be administered in a number of suitable ways, such as intramuscular injection (e.g., into the arm or leg), subcutaneous injection, intranasal administration, oral administration, intradermal administration, transcutaneous administration, transdermal administration, and the like. The appropriate route of administration will be dependent upon the age, health and other characteristics of the mammal. A clinician will be able to determine an appropriate route of administration based on these and other factors.

Immunogenic compositions, and vaccine formulations, may be used to treat both children and adults, including pregnant women. Thus a subject may be less than 1 year old, 1-5 years old, 5-15 years old, 15-55 years old, or at least 55 years old. Preferred subjects for receiving the vaccines are the elderly (e.g., >50 years old, >60 years old, and preferably >65 years), the young (e.g., <6 years old, such as 4-6 years old, <5 years old), and pregnant women. The vaccines are not suitable solely for these groups, however, and may be used more generally in a population.

Treatment can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, and the like.).P Vaccine formulations produced using a composition of the invention may be administered to patients at substantially the same time as (e.g., during the same medical consultation or visit to a healthcare professional or vaccination centre) other vaccines.

Further Aspects of the Invention

The invention also provides a polypeptide (e.g., recombinant polypeptide) comprising a first domain and a second domain, wherein (i) the first domain comprises a RSV F glycoprotein ectodomain, in whole or part, and (ii) the second domain comprises a heterologous oligomerization domain. Further details are provided above. If the oligomerization domain comprises a heptad sequence (e.g., the sequence from GCN described above) then it is preferably in heptad repeat phase with the HR2 sequence (if present) of the ectodomain.

The invention also provides nucleic acid (e.g., DNA) encoding this polypeptide. It also provides vectors including such nucleic acids, and host cells including such vectors. The vectors may be used for, e.g., recombinant expression purposes, nucleic acid immunization, etc.

The invention also provides a composition comprising molecules comprising RSV F glycoprotein ectodomains, wherein the ectodomains of at least 50% (e.g., 50%, 60%, 70%, 80%, 85%, 90%, 95% or 100%) of the molecules are present in a pre-fusion conformation.

Other Viruses

As well as being used with human RSV, the invention may be used with other members of the Pneumoviridae and Paramyxoviridae, including, but not limited to, bovine respiratory syncytial virus, parainfluenzavirus 1, parainfluenzavirus 2, parainfluenzavirus 3, and parainfluenzavirus 5.

Thus the invention provides an immunogenic composition comprising a F glycoprotein from a Pneumoviridae or Paramyxoviridae, wherein the F glycoprotein is in pre-fusion conformation.

The invention also provides an immunogenic composition comprising a polypeptide that displays an epitope present in a pre-fusion conformation of the F glycoprotein of a Pneumoviridae or Paramyxoviridae, but absent the glycoprotein's post fusion conformation.

The invention also provides a polypeptide comprising a first domain and a second domain, wherein (i) the first domain comprises an ectodomain of the F glycoprotein of a Pneumoviridae or Paramyxoviridae, in whole or part, and (ii) the second domain comprises a heterologous oligomerization domain.

The invention also provides these polypeptides and compositions for use in immunization, etc.

The invention also provides a composition comprising molecules comprising RSV F glycoprotein ectodomains, wherein the ectodomains of at least 50% (e.g., 50%, 60%, 70%, 80%, 85%, 90%, 95% or 100%) of the molecules are present in a pre-fusion conformation or an intermediate conformation.

RSV F Protein Ecto-Domain Polypeptides

Particular RSV F protein ecto-domain polypeptides are used or included in some embodiments of the invention. Some of the particular RSV F protein ecto-domain polypeptides contain altered amino acid sequences from about position 100 to about position 161. The amino acid sequences from position 100 to position 150 for several particular RSV F protein ecto-domain polypeptides are shown in FIG. 1C. Amino acid sequences of several particular RSV F protein ecto-domain polypeptides are presented herein, e.g., in Example 1.

General

The term "comprising" encompasses "including" as well as "consisting" and "consisting essentially of" e.g., a composition "comprising" X may consist exclusively of X or may include something additional e.g., X+Y.

The word "substantially" does not exclude "completely" e.g., a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g., as in Ph Eur general chapter 5.2.3.

Identity between polypeptide sequences is preferably determined by the Smith-Waterman homology search algorithm as implemented in the MPSRCH program (Oxford Molecular), using an affine gap search with parameters gap open penalty=12 and gap extension penalty=1.

TABLE 1

| | Phospholipids |
|---|---|
| DDPC | 1,2-Didecanoyl-sn-Glycero-3-phosphatidylcholine |
| DEPA | 1,2-Dierucoyl-sn-Glycero-3-Phosphate |
| DEPC | 1,2-Erucoyl-sn-Glycero-3-phosphatidylcholine |
| DEPE | 1,2-Dierucoyl-sn-Glycero-3-phosphatidylethanolamine |
| DEPG | 1,2-Dierucoyl-sn-Glycero-3[Phosphatidyl-rac-(1-glycerol . . . ) |
| DLOPC | 1,2-Linoleoyl-sn-Glycero-3-phosphatidylcholine |
| DLPA | 1,2-Dilauroyl-sn-Glycero-3-Phosphate |
| DLPC | 1,2-Dilauroyl-sn-Glycero-3-phosphatidylcholine |
| DLPE | 1,2-Dilauroyl-sn-Glycero-3-phosphatidylethanolamine |
| DLPG | 1,2-Dilauroyl-sn-Glycero-3[Phosphatidyl-rac-(1-glycerol . . . ) |
| DLPS | 1,2-Dilauroyl-sn-Glycero-3-phosphatidylserine |
| DMG | 1,2-Dimyristoyl-sn-glycero-3-phosphoethanolamine |
| DMPA | 1,2-Dimyristoyl-sn-Glycero-3-Phosphate |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG | 1,2-Myristoyl-sn-Glycero-3[Phosphatidyl-rac-(1-glycerol . . . ) |
| DMPS | 1,2-Dimyristoyl-sn-Glycero-3-phosphatidylserine |
| DOPA | 1,2-Dioleoyl-sn-Glycero-3-Phosphate |
| DOPC | 1,2-Dioleoyl-sn-Glycero-3-phosphatidylcholine |
| DOPE | 1,2-Dioleoyl-sn-Glycero-3-phosphatidylethanolamine |
| DOPG | 1,2-Dioleoyl-sn-Glycero-3[Phosphatidyl-rac-(1-glycerol . . . ) |
| DOPS | 1,2-Dioleoyl-sn-Glycero-3-phosphatidylserine |
| DPPA | 1,2-Dipalmitoyl-sn-Glycero-3-Phosphate |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG | 1,2-Dipalmitoyl-sn-Glycero-3[Phosphatidyl-rac-(1-glycerol . . . ) |
| DPPS | 1,2-Dipalmitoyl-sn-Glycero-3-phosphatidylserine |
| DPyPE | 1,2-diphytanoyl-sn-glycero-3-phosphoethanolamine |
| DSPA | 1,2-Distearoyl-sn-Glycero-3-Phosphate |
| DSPC | 1,2-Distearoyl-sn-Glycero-3-phosphatidylcholine |
| DSPE | 1,2-Diostearpyl-sn-Glycero-3-phosphatidylethanolamine |
| DSPG | 1,2-Distearoyl-sn-Glycero-3[Phosphatidyl-rac-(1-glycerol . . . ) |
| DSPS | 1,2-Distearoyl-sn-Glycero-3-phosphatidylserine |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG | 1,2-Dioleoyl-sn-Glycero-3[Phosphatidyl-rac-(1-glycerol) . . . ] |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

EXEMPLIFICATION

Example 1

RSV F Polypeptides

This example provides sequences of a number of examples of polypeptides (e.g., that contain signal sequences) and nucleic acid sequences that may be used to express RSV F polypeptides of the present invention. The presented amino acid sequences include the signal peptide and contain an optional C-terminal linker and His tag (GGSAGSGHHHHHH (SEQ ID NO:90)). When these polypeptides are produced in host cells, the polypeptide will usually be processed by the cell to remove the signal peptide and, as described herein, some of the polypeptides will be cleaved, for example at unmodified furin cleavage sites. The invention includes compositions that contain, all forms of the particular RSV F protein ecto-domain polypeptides disclosed herein, including mature forms, which lack the signal peptide, forms that may be cleaved into subunits that comprise $F_1$ and $F_2$, and forms that lack the optional C-terminal His tag. The following examples are merely illustrative of the scope of the present invention and therefore are not intended to limit the scope in any way.

An example of wild-type furin cleavage is RSV F wild type Truncated HIS (SEQ ID NO:84).

Examples of polypeptides that can be produced as monomers include: RSV F Furx (SEQ ID NO:45); RSV F old furx Truncated HIS (SEQ ID NO:88); RSV F Furx R113Q K123N K124N Truncated HIS (SEQ ID NO:89); RSV F delP21 furx Truncated HIS (SEQ ID NO:47); and RSV F delP23 furx Truncated HIS (SEQ ID NO:48).

Examples of polypeptides that can be produced as trimers include: RSV F N-term Furin Truncated HIS (SEQ ID NO:85); RSV F Fusion Deletion Truncated HIS (SEQ ID NO:67); and RSV F Fusion Deletion 2 Truncated HIS (SEQ ID NO:68).

Examples of polypeptides that can be produced as monomers or rosettes of trimers include: RSV F furmt Truncated HIS (SEQ ID NO:50); RSV F furdel Truncated HIS (SEQ ID NO:51); RSV F delP21 furdel Truncated HIS (SEQ ID NO:86); and RSV F delP23 furdel Truncated HIS (SEQ ID NO:49), and RSV F Factor Xa Truncated HIS (SEQ ID NO:52).

An example of a wild-type cleavage that likely produces a rosette formation is RSV F C-term Furin Truncated HIS (SEQ ID NO:87).

Full

The following polypeptide is a full-length RSV F polypeptide.

```
                                                                    (SEQ ID NO: 21)
  1 MELLILKANA ITTILTAVTF CFASGQNITE EFYQSTCSAV SKGYLSALRT GWYTSVITIE

61 LSNIKENKCN GTDAKVKLIK QELDKYKNAV TELQLLMQST PATNNRARRE LPRFMNYTLN

121 NAKKTNVTLS KKRKRRFLGF LLGVGSAIAS GVAVSKVLHL EGEVNKIKSA LLSTNKAVVS

181 LSNGVSVLTS KVLDLKNYID KQLLPIVNKQ SCSISNIETV IEFQQKNNRL LEITREFSVN

241 AGVTTPVSTY MLTNSELLSL INDMPITNDQ KKLMSNNVQI VRQQSYSIMS IIKEEVLAYV

301 VQLPLYGVID TPCWKLHTSP LCTTNTKEGS NICLTRTDRG WYCDNAGSVS FFPQAETCKV

361 QSNRVFCDTM NSLTLPSEVN LCNVDIFNPK YDCKIMTSKT DVSSSVITSL GAIVSCYGKT

421 KCTASNKNRG IIKTFSNGCD YVSNKGVDTV SVGNTLYYVN KQEGKSLYVK GEPIINFYDP

481 LVFPSDEFDA SISQVNEKIN QSLAFIRKSD ELLHNVNAGK STTNIMITTI IIVIIVILLS

541 LIAVGLLLYC KARSTPVTLS KDQLSGINNI AFSN
```

The following nucleic acid sequence is the optimized coding sequence for the foregoing polypeptide sequence.

```
                                                                    (SEQ ID NO: 22)
  1 ATGGAACTGC TGATCCTGAA GGCCAACGCC ATCACCACCA TCCTGACCGC CGTGACCTTC

61 TGCTTCGCCA GCGGCCAGAA CATCACCGAG GAATTCTACC AGAGCACCTG CAGCGCCGTG

121 AGCAAGGGCT ACCTGAGCGC CCTGCGGACC GGCTGGTACA CCAGCGTGAT CACCATCGAG

181 CTGTCCAACA TCAAAGAAAA CAAGTGCAAC GGCACCGACG CCAAGGTGAA ACTGATCAAG

241 CAGGAACTGG ACAAGTACAA GAACGCCGTG ACCGAGCTGC AGCTGCTGAT GCAGAGCACC

301 CCCGCCACCA ACAACCGGGC CAGAAGAGAG CTGCCCCGGT TCATGAACTA CACCCTGAAC

361 AACGCCAAGA AAACCAACGT GACCCTGAGC AAGAAGCGGA AGCGGCGGTT CCTGGGCTTC

421 CTGCTGGGCG TGGGCAGCGC CATCGCCAGC GGGGTGGCCG TGTCCAAGGT GCTGCACCTG

481 GAAGGCGAGG TGAACAAGAT CAAGTCCGCC CTGCTGTCCA CCAACAAGGC CGTGGTGTCC

541 CTGAGCAACG GCGTGAGCGT GCTGACCAGC AAGGTGCTGG ATCTGAAGAA CTACATCGAC

601 AAGCAGCTGC TGCCCATCGT GAACAAGCAG AGCTGCAGCA TCAGCAACAT CGAGACCGTG
```

```
 661 ATCGAGTTCC AGCAGAAGAA CAACCGGCTG CTGGAAATCA CCCGGGAGTT CAGCGTGAAC

721 GCCGGCGTGA CCACCCCCGT GAGCACCTAC ATGCTGACCA ACAGCGAGCT GCTGTCCCTG

781 ATCAATGACA TGCCCATCAC CAACGACCAG AAAAAGCTGA TGAGCAACAA CGTGCAGATC

841 GTGCGGCAGC AGAGCTACTC CATCATGAGC ATCATCAAAG AAGAGGTGCT GGCCTACGTG

901 GTGCAGCTGC CCCTGTACGG CGTGATCGAC ACCCCCTGCT GGAAGCTGCA CACCAGCCCC

961 CTGTGCACCA CCAACACCAA AGAGGGCAGC AACATCTGCC TGACCCGGAC CGACCGGGGC

1021 TGGTACTGCG ACAACGCCGG CAGCGTGAGC TTCTTCCCCC AAGCCGAGAC CTGCAAGGTG

1081 CAGAGCAACC GGGTGTTCTG CGACACCATG AACAGCCTGA CCCTGCCCTC CGAGGTGAAC

1141 CTGTGCAACG TGGACATCTT CAACCCCAAG TACGACTGCA AGATCATGAC CTCCAAGACC

1201 GACGTGAGCA GCTCCGTGAT CACCTCCCTG GGCGCCATCG TGAGCTGCTA CGGCAAGACC

1261 AAGTGCACCG CCAGCAACAA GAACCGGGGC ATCATCAAGA CCTTCAGCAA CGGCTGCGAC

1321 TACGTGAGCA ACAAGGGCGT GGACACCGTG AGCGTGGGCA ACACACTGTA CTACGTGAAT

1381 AAGCAGGAAG GCAAGAGCCT GTACGTGAAG GGCGAGCCCA TCATCAACTT CTACGACCCC

1441 CTGGTGTTCC CCAGCGACGA GTTCGACGCC AGCATCAGCC AGGTCAACGA GAAGATCAAC

1501 CAGAGCCTGG CCTTCATCCG GAAGAGCGAC GAGCTGCTGC ACAATGTGAA TGCCGGCAAG

1561 AGCACCACCA ATATCATGAT CACCACAATC ATCATCGTGA TCATTGTGAT CCTGCTGTCT

1621 CTGATTGCCG TGGGCCTGCT GCTGTACTGC AAGGCCCGCA GCACCCCTGT GACCCTGTCC

1681 AAGGACCAGC TGTCCGGCAT CAACAATATC GCCTTCTCCA ACTGAAG
```

Full HIS

The following polypeptide includes the full-length RSV F polypeptide followed by a hexa-histidine tag.

```
                                                    (SEQ ID NO: 23)
  1 MELLILKANA ITTILTAVTF CFASGQNITE EFYQSTCSAV SKGYLSALRT GWYTSVITIE

61 LSNIKENKCN GTDAKVKLIK QELDKYKNAV TELQLLMQST PATNNRARRE LPRFMNYTLN

121 NAKKTNVTLS KKRKRRFLGF LLGVGSAIAS GVAVSKVLHL EGEVNKIKSA LLSTNKAVVS

181 LSNGVSVLTS KVLDLKNYID KQLLPIVNKQ SCSISNIETV IEFQQKNNRL LEITREFSVN

241 AGVTTPVSTY MLTNSELLSL INDMPITNDQ KKLMSNNVQI VRQQSYSIMS IIKEEVLAYV

301 VQLPLYGVID TPCWKLHTSP LCTTNTKEGS NICLTRTDRG WYCDNAGSVS FFPQAETCKV

361 QSNRVFCDTM NSLTLPSEVN LCNVDIFNPK YDCKIMTSKT DVSSSVITSL GAIVSCYGKT

421 KCTASNKNRG IIKTFSNGCD YVSNKGVDTV SVGNTLYYVN KQEGKSLYVK GEPIINFYDP

481 LVFPSDEFDA SISQVNEKIN QSLAFIRKSD ELLHNVNAGK STTNIMITTI IIVIIVILLS

541 LIAVGLLLYC KARSTPVTLS KDQLSGINNI AFSNSGGSAG SGHHHHHH
```

The following nucleic acid sequence is the optimized coding sequence for the foregoing polypeptide sequence.

```
                                                    (SEQ ID NO: 24)
  1 ATGGAACTGC TGATCCTGAA GGCCAACGCC ATCACCACCA TCCTGACCGC CGTGACCTTC

61 TGCTTCGCCA GCGGCCAGAA CATCACCGAG GAATTCTACC AGAGCACCTG CAGCGCCGTG

121 AGCAAGGGCT ACCTGAGCGC CCTGCGGACC GGCTGGTACA CCAGCGTGAT CACCATCGAG

181 CTGTCCAACA TCAAAGAAAA CAAGTGCAAC GGCACCGACG CCAAGGTGAA ACTGATCAAG

241 CAGGAACTGG ACAAGTACAA GAACGCCGTG ACCGAGCTGC AGCTGCTGAT GCAGAGCACC
```

-continued
```
 301 CCCGCCACCA ACAACCGGGC CAGAAGAGAG CTGCCCCGGT TCATGAACTA CACCCTGAAC

361 AACGCCAAGA AAACCAACGT GACCCTGAGC AAGAAGCGGA AGCGGCGGTT CCTGGGCTTC

421 CTGCTGGGCG TGGGCAGCGC CATCGCCAGC GGGGTGGCCG TGTCCAAGGT GCTGCACCTG

481 GAAGGCGAGG TGAACAAGAT CAAGTCCGCC CTGCTGTCCA CCAACAAGGC CGTGGTGTCC

541 CTGAGCAACG GCGTGAGCGT GCTGACCAGC AAGGTGCTGG ATCTGAAGAA CTACATCGAC

601 AAGCAGCTGC TGCCCATCGT GAACAAGCAG AGCTGCAGCA TCAGCAACAT CGAGACCGTG

661 ATCGAGTTCC AGCAGAAGAA CAACCGGCTG CTGGAAATCA CCCGGGAGTT CAGCGTGAAC

721 GCCGGCGTGA CCACCCCCGT GAGCACCTAC ATGCTGACCA ACAGCGAGCT GCTGTCCCTG

781 ATCAATGACA TGCCCATCAC CAACGACCAG AAAAAGCTGA TGAGCAACAA CGTGCAGATC

841 GTGCGGCAGC AGAGCTACTC CATCATGAGC ATCATCAAAG AAGAGGTGCT GGCCTACGTG

901 GTGCAGCTGC CCCTGTACGG CGTGATCGAC ACCCCCTGCT GGAAGCTGCA CACCAGCCCC

961 CTGTGCACCA CCAACACCAA AGAGGGCAGC AACATCTGCC TGACCCGGAC CGACCGGGGC

1021 TGGTACTGCG ACAACGCCGG CAGCGTGAGC TTCTTCCCCC AAGCCGAGAC CTGCAAGGTG

1081 CAGAGCAACC GGGTGTTCTG CGACACCATG AACAGCCTGA CCCTGCCCTC CGAGGTGAAC

1141 CTGTGCAACG TGGACATCTT CAACCCCAAG TACGACTGCA AGATCATGAC CTCCAAGACC

1201 GACGTGAGCA GCTCCGTGAT CACCTCCCTG GGCGCCATCG TGAGCTGCTA CGGCAAGACC

1261 AAGTGCACCG CCAGCAACAA GAACCGGGGC ATCATCAAGA CCTTCAGCAA CGGCTGCGAC

1321 TACGTGAGCA ACAAGGGCGT GGACACCGTG AGCGTGGGCA ACACACTGTA CTACGTGAAT

1381 AAGCAGGAAG GCAAGAGCCT GTACGTGAAG GGCGAGCCCA TCATCAACTT CTACGACCCC

1441 CTGGTGTTCC CCAGCGACGA GTTCGACGCC AGCATCAGCC AGGTCAACGA GAAGATCAAC

1501 CAGAGCCTGG CCTTCATCCG GAAGAGCGAC GAGCTGCTGC ACAATGTGAA TGCCGGCAAG

1561 AGCACCACCA ATATCATGAT CACCACAATC ATCATCGTGA TCATTGTGAT CCTGCTGTCT

1621 CTGATTGCCG TGGGCCTGCT GCTGTACTGC AAGGCCCGCA GCACCCCTGT GACCCTGTCC

1681 AAGGACCAGC TGTCCGGCAT CAACAATATC GCCTTCTCCA ACAGCGGCGG CAGCGCCGGC

1741 TCTGGCCACC ACCACCATCA CCACTGAAG
```

Full Pre HIS

The following polypeptide includes the full-length RSV F polypeptide with the trimerization domain of GCN4 (underlined) attached at the C-terminus of the RSV F polypeptide followed by a hexa-histidine tag.

```
                                                      (SEQ ID NO: 25)
  1 MELLILKANA ITTILTAVTF CFASGQNITE EFYQSTCSAV SKGYLSALRT GWYTSVITIE

61 LSNIKENKCN GTDAKVKLIK QELDKYKNAV TELQLLMQST PATNNRARRE LPRFMNYTLN

121 NAKKTNVTLS KKRKRRFLGF LLGVGSAIAS GVAVSKVLHL EGEVNKIKSA LLSTNKAVVS

181 LSNGVSVLTS KVLDLKNYID KQLLPIVNKQ SCSISNIETV IEFQQKNNRL LEITREFSVN

241 AGVTTPVSTY MLTNSELLSL INDMPITNDQ KKLMSNNVQI VRQQSYSIMS IIKEEVLAYV

301 VQLPLYGVID TPCWKLHTSP LCTTNTKEGS NICLTRTDRG WYCDNAGSVS FFPQAETCKV

361 QSNRVFCDTM NSLTLPSEVN LCNVDIFNPK YDCKIMTSKT DVSSSVITSL GAIVSCYGKT

421 KCTASNKNRG IIKTFSNGCD YVSNKGVDTV SVGNTLYYVN KQEGKSLYVK GEPIINFYDP

481 LVFPSDEFDA SISQVNEKIN QSLAFIRKSD ELLHNVNAGK STTNIMITTI IVIIIVILLS
```

```
541 LIAVGLLLYC KARSTPVTLS KDQLSGINNI AFSNGSSGRM KQIEDKIEEI LSKIYHIENE

601 IARIKKLIGE SGGSAGSGHH HHHH
```

The following nucleic acid sequence is the optimized coding sequence for the foregoing polypeptide sequence.

```
                                                                 (SEQ ID NO: 26)
   1 ATGGAACTGC TGATCCTGAA GGCCAACGCC ATCACCACCA TCCTGACCGC CGTGACCTTC

61 TGCTTCGCCA GCGGCCAGAA CATCACCGAG GAATTCTACC AGAGCACCTG CAGCGCCGTG

121 AGCAAGGGCT ACCTGAGCGC CCTGCGGACC GGCTGGTACA CCAGCGTGAT CACCATCGAG

181 CTGTCCAACA TCAAAGAAAA CAAGTGCAAC GGCACCGACG CCAAGGTGAA ACTGATCAAG

241 CAGGAACTGG ACAAGTACAA GAACGCCGTG ACCGAGCTGC AGCTGCTGAT GCAGAGCACC

301 CCCGCCACCA ACAACCGGGC CAGAAGAGAG CTGCCCCGGT TCATGAACTA CACCCTGAAC

361 AACGCCAAGA AAACCAACGT GACCCTGAGC AAGAAGCGGA AGCGGCGGTT CCTGGGCTTC

421 CTGCTGGGCG TGGGCAGCGC CATCGCCAGC GGGGTGGCCG TGTCCAAGGT GCTGCACCTG

481 GAAGGCGAGG TGAACAAGAT CAAGTCCGCC CTGCTGTCCA CCAACAAGGC CGTGGTGTCC

541 CTGAGCAACG GCGTGAGCGT GCTGACCAGC AAGGTGCTGG ATCTGAAGAA CTACATCGAC

601 AAGCAGCTGC TGCCCATCGT GAACAAGCAG AGCTGCAGCA TCAGCAACAT CGAGACCGTG

661 ATCGAGTTCC AGCAGAAGAA CAACCGGCTG CTGGAAATCA CCCGGGAGTT CAGCGTGAAC

721 GCCGGCGTGA CCACCCCCGT GAGCACCTAC ATGCTGACCA ACAGCGAGCT GCTGTCCCTG

781 ATCAATGACA TGCCCATCAC CAACGACCAG AAAAAGCTGA TGAGCAACAA CGTGCAGATC

841 GTGCGGCAGC AGAGCTACTC CATCATGAGC ATCATCAAAG AAGAGGTGCT GGCCTACGTG

901 GTGCAGCTGC CCCTGTACGG CGTGATCGAC ACCCCCTGCT GGAAGCTGCA CACCAGCCCC

961 CTGTGCACCA CCAACACCAA AGAGGGCAGC AACATCTGCC TGACCCGGAC CGACCGGGGC

1021 TGGTACTGCG ACAACGCCGG CAGCGTGAGC TTCTTCCCCC AAGCCGAGAC CTGCAAGGTG

1081 CAGAGCAACC GGGTGTTCTG CGACACCATG AACAGCCTGA CCCTGCCCTC CGAGGTGAAC

1141 CTGTGCAACG TGGACATCTT CAACCCCAAG TACGACTGCA AGATCATGAC CTCCAAGACC

1201 GACGTGAGCA GCTCCGTGAT CACCTCCCTG GGCGCCATCG TGAGCTGCTA CGGCAAGACC

1261 AAGTGCACCG CCAGCAACAA GAACCGGGGC ATCATCAAGA CCTTCAGCAA CGGCTGCGAC

1321 TACGTGAGCA ACAAGGGCGT GGACACCGTG AGCGTGGGCA ACACACTGTA CTACGTGAAT

1381 AAGCAGGAAG GCAAGAGCCT GTACGTGAAG GGCGAGCCCA TCATCAACTT CTACGACCCC

1441 CTGGTGTTCC CCAGCGACGA GTTCGACGCC AGCATCAGCC AGGTCAACGA GAAGATCAAC

1501 CAGAGCCTGG CCTTCATCCG GAAGAGCGAC GAGCTGCTGC ACAATGTGAA TGCCGGCAAG

1561 AGCACCACCA ATATCATGAT CACCACAATC ATCATCGTGA TCATTGTGAT CCTGCTGTCT

1621 CTGATTGCCG TGGGCCTGCT GCTGTACTGC AAGGCCCGCA GCACCCCTGT GACCCTGTCC

1681 AAGGACCAGC TGTCCGGCAT CAACAATATC GCCTTCTCCA ACGGCAGCAG CGGCCGGATG

1741 AAGCAGATCG AGGACAAGAT CGAGGAAATC CTGAGCAAGA TCTACCACAT CGAGAACGAG

1801 ATCGCCCGGA TCAAGAAGCT GATCGGCGAA AGCGGCGGCT CTGCCGGAAG CGGCCACCAC

1861 CACCATCACC ACTGAAG
```

Full Pre HIS 2

The following polypeptide includes the full-length RSV F polypeptide with the trimerization domain of GCN4 (underlined) attached at the C-terminus of the RSV F polypeptide followed by a hexa-histidine tag.

(SEQ ID NO: 27)

```
  1 MELLILKANA ITTILTAVTF CFASGQNITE EFYQSTCSAV SKGYLSALRT GWYTSVITIE

61 LSNIKENKCN GTDAKVKLIK QELDKYKNAV TELQLLMQST PATNNRARRE LPRFMNYTLN

121 NAKKTNVTLS KKRKRRFLGF LLGVGSAIAS GVAVSKVLHL EGEVNKIKSA LLSTNKAVVS

181 LSNGVSVLTS KVLDLKNYID KQLLPIVNKQ SCSISNIETV IEFQQKNNRL LEITREFSVN

241 AGVTTPVSTY MLTNSELLSL INDMPITNDQ KKLMSNNVQI VRQQSYSIMS IIKEEVLAYV

301 VQLPLYGVID TPCWKLHTSP LCTTNTKEGS NICLTRTDRG WYCDNAGSVS FFPQAETCKV

361 QSNRVFCDTM NSLTLPSEVN LCNVDIFNPK YDCKIMTSKT DVSSSVITSL GAIVSCYGKT

421 KCTASNKNRG IIKTFSNGCD YVSNKGVDTV SVGNTLYYVN KQEGKSLYVK GEPIINFYDP

481 LVFPSDEFDA SISQVNEKIN QSLAFIRKSD ELLHNVNAGK STTNIMITTI IIVIIVILLS

541 LIAVGLLLYC KARSTPVTLS KDQLSGINNI AFSNGSSGSG RMKQIEDKIE EILSKIYHIE

601 NEIARIKKLI GESGGSAGSG HHHHHH
```

25

The following nucleic acid sequence is the optimized coding sequence for the foregoing polypeptide sequence.

(SEQ ID NO: 28)

```
   1 ATGGAACTGC TGATCCTGAA GGCCAACGCC ATCACCACCA TCCTGACCGC CGTGACCTTC

61 TGCTTCGCCA GCGGCCAGAA CATCACCGAG GAATTCTACC AGAGCACCTG CAGCGCCGTG

121 AGCAAGGGCT ACCTGAGCGC CCTGCGGACC GGCTGGTACA CCAGCGTGAT CACCATCGAG

181 CTGTCCAACA TCAAAGAAAA CAAGTGCAAC GGCACCGACG CCAAGGTGAA ACTGATCAAG

241 CAGGAACTGG ACAAGTACAA GAACGCCGTG ACCGAGCTGC AGCTGCTGAT GCAGAGCACC

301 CCCGCCACCA ACAACCGGGC CAGAAGAGAG CTGCCCCGGT TCATGAACTA CACCCTGAAC

361 AACGCCAAGA AAACCAACGT GACCCTGAGC AAGAAGCGGA AGCGGCGGTT CCTGGGCTTC

421 CTGCTGGGCG TGGGCAGCGC CATCGCCAGC GGGGTGGCCG TGTCCAAGGT GCTGCACCTG

481 GAAGGCGAGG TGAACAAGAT CAAGTCCGCC CTGCTGTCCA CCAACAAGGC CGTGGTGTCC

541 CTGAGCAACG GCGTGAGCGT GCTGACCAGC AAGGTGCTGG ATCTGAAGAA CTACATCGAC

601 AAGCAGCTGC TGCCCATCGT GAACAAGCAG AGCTGCAGCA TCAGCAACAT CGAGACCGTG

661 ATCGAGTTCC AGCAGAAGAA CAACCGGCTG CTGGAAATCA CCCGGGAGTT CAGCGTGAAC

721 GCCGGCGTGA CCACCCCCGT GAGCACCTAC ATGCTGACCA ACAGCGAGCT GCTGTCCCTG

781 ATCAATGACA TGCCCATCAC CAACGACCAG AAAAAGCTGA TGAGCAACAA CGTGCAGATC

841 GTGCGGCAGC AGAGCTACTC CATCATGAGC ATCATCAAAG AAGAGGTGCT GGCCTACGTG

901 GTGCAGCTGC CCCTGTACGG CGTGATCGAC ACCCCCTGCT GGAAGCTGCA CACCAGCCCC

961 CTGTGCACCA CCAACACCAA AGAGGGCAGC AACATCTGCC TGACCCGGAC CGACCGGGGC

1021 TGGTACTGCG ACAACGCCGG CAGCGTGAGC TTCTTCCCCC AAGCCGAGAC CTGCAAGGTG

1081 CAGAGCAACC GGGTGTTCTG CGACACCATG AACAGCCTGA CCCTGCCCTC CGAGGTGAAC

1141 CTGTGCAACG TGGACATCTT CAACCCCAAG TACGACTGCA AGATCATGAC CTCCAAGACC

1201 GACGTGAGCA GCTCCGTGAT CACCTCCCTG GGCGCCATCG TGAGCTGCTA CGGCAAGACC

1261 AAGTGCACCG CCAGCAACAA GAACCGGGGC ATCATCAAGA CCTTCAGCAA CGGCTGCGAC

1321 TACGTGAGCA ACAAGGGCGT GGACACCGTG AGCGTGGGCA ACACACTGTA CTACGTGAAT
```

```
1381 AAGCAGGAAG GCAAGAGCCT GTACGTGAAG GGCGAGCCCA TCATCAACTT CTACGACCCC

1441 CTGGTGTTCC CCAGCGACGA GTTCGACGCC AGCATCAGCC AGGTCAACGA GAAGATCAAC

1501 CAGAGCCTGG CCTTCATCCG GAAGAGCGAC GAGCTGCTGC ACAATGTGAA TGCCGGCAAG

1561 AGCACCACCA ATATCATGAT CACCACAATC ATCATCGTGA TCATTGTGAT CCTGCTGTCT

1621 CTGATTGCCG TGGGCCTGCT GCTGTACTGC AAGGCCCGCA GCACCCCTGT GACCCTGTCC

1681 AAGGACCAGC TGTCCGGCAT CAACAATATC GCCTTCTCCA ACGGCAGCAG CGGCAGCGGC

1741 CGGATGAAGC AGATCGAGGA CAAGATCGAG GAAATCCTGA GCAAGATCTA CCACATCGAG

1801 AACGAGATCG CCCGGATCAA GAAGCTGATC GGCGAAAGCG GCGGCTCTGC CGGAAGCGGC

1861 CACCACCACC ATCACCACTG AAG
```

Ecto HIS

The following polypeptide includes the ecto domain of the RSV F polypeptide followed by a hexa-histidine tag.

```
                                              (SEQ ID NO: 29)
  1 MELLILKANA ITTILTAVTF CFASGQNITE EFYQSTCSAV
    SKGYLSALRT GWYTSVITIE

61 LSNIKENKCN GTDAKVKLIK QELDKYKNAV TELQLLMQST
    PATNNRARRE LPRFMNYTLN

121 NAKKTNVTLS KKRKRRFLGF LLGVGSAIAS GVAVSKVLHL
    EGEVNKIKSA LLSTNKAVVS

181 LSNGVSVLTS KVLDLKNYID KQLLPIVNKQ SCSISNIETV
    IEFQQKNNRL LEITREFSVN

241 AGVTTPVSTY MLTNSELLSL INDMPITNDQ KKLMSNNVQI
    VRQQSYSIMS IIKEEVLAYV

301 VQLPLYGVID TPCWKLHTSP LCTTNTKEGS NICLTRTDRG
    WYCDNAGSVS FFPQAETCKV

361 QSNRVFCDTM NSLTLPSEVN LCNVDIFNPK YDCKIMTSKT
    DVSSSVITSL GAIVSCYGKT

421 KCTASNKNRG IIKTFSNGCD YVSNKGVDTV SVGNTLYYVN
    KQEGKSLYVK GEPIINFYDP

481 LVFPSDEFDA SISQVNEKIN QSLAFIRKSD ELLHNVNSGG
    SAGSGHHHHH H
```

The following nucleic acid sequence is the optimized coding sequence for the foregoing polypeptide sequence.

```
                                              (SEQ ID NO: 30)
  1 ATGGAACTGC TGATCCTGAA GGCCAACGCC ATCACCACCA
    TCCTGACCGC CGTGACCTTC

61 TGCTTCGCCA GCGGCCAGAA CATCACCGAG GAATTCTACC
    AGAGCACCTG CAGCGCCGTG

121 AGCAAGGGCT ACCTGAGCGC CCTGCGGACC GGCTGGTACA
    CCAGCGTGAT CACCATCGAG

181 CTGTCCAACA TCAAAGAAAA CAAGTGCAAC GGCACCGACG
    CCAAGGTGAA ACTGATCAAG

241 CAGGAACTGG ACAAGTACAA GAACGCCGTG ACCGAGCTGC
    AGCTGCTGAT GCAGAGCACC

301 CCCGCCACCA ACAACCGGGC CAGAAGAGAG CTGCCCCGGT
    TCATGAACTA CACCCTGAAC

361 AACGCCAAGA AAACCAACGT GACCCTGAGC AAGAAGCGGA
    AGCGGCGGTT CCTGGGCTTC

421 CTGCTGGGCG TGGGCAGCGC CATCGCCAGC GGGGTGGCCG
    TGTCCAAGGT GCTGCACCTG

481 GAAGGCGAGG TGAACAAGAT CAAGTCCGCC CTGCTGTCCA
    CCAACAAGGC CGTGGTGTCC

541 CTGAGCAACG GCGTGAGCGT GCTGACCAGC AAGGTGCTGG
    ATCTGAAGAA CTACATCGAC

601 AAGCAGCTGC TGCCCATCGT GAACAAGCAG AGCTGCAGCA
    TCAGCAACAT CGAGACCGTG

661 ATCGAGTTCC AGCAGAAGAA CAACCGGCTG CTGGAAATCA
    CCCGGGAGTT CAGCGTGAAC

721 GCCGGCGTGA CCACCCCCGT GAGCACCTAC ATGCTGACCA
    ACAGCGAGCT GCTGTCCCTG

781 ATCAATGACA TGCCCATCAC CAACGACCAG AAAAAGCTGA
    TGAGCAACAA CGTGCAGATC

841 GTGCGGCAGC AGAGCTACTC CATCATGAGC ATCATCAAAG
    AAGAGGTGCT GGCCTACGTG

901 GTGCAGCTGC CCCTGTACGG CGTGATCGAC ACCCCCTGCT
    GGAAGCTGCA CACCAGCCCC

961 CTGTGCACCA CCAACACCAA AGAGGGCAGC AACATCTGCC
    TGACCCGGAC CGACCGGGGC

1021 TGGTACTGCG ACAACGCCGG CAGCGTGAGC TTCTTCCCCC
     AAGCCGAGAC CTGCAAGGTG
```

-continued

```
1081 CAGAGCAACC GGGTGTTCTG CGACACCATG AACAGCCTGA
     CCCTGCCCTC CGAGGTGAAC
1141 CTGTGCAACG TGGACATCTT CAACCCCAAG TACGACTGCA
     AGATCATGAC CTCCAAGACC
1201 GACGTGAGCA GCTCCGTGAT CACCTCCCTG GGCGCCATCG
     TGAGCTGCTA CGGCAAGACC
1261 AAGTGCACCG CCAGCAACAA GAACCGGGGC ATCATCAAGA
     CCTTCAGCAA CGGCTGCGAC
1321 TACGTGAGCA ACAAGGGCGT GGACACCGTG AGCGTGGGCA
     ACACACTGTA CTACGTGAAT
1381 AAGCAGGAAG GCAAGAGCCT GTACGTGAAG GGCGAGCCCA
     TCATCAACTT CTACGACCCC
1441 CTGGTGTTCC CCAGCGACGA GTTCGACGCC AGCATCAGCC
     AGGTCAACGA GAAGATCAAC
1501 CAGAGCCTGG CCTTCATCCG GAAGAGCGAC GAGCTGCTGC
     ACAATGTGAA TAGCGGCGGC
1561 AGCGCCGGCT CTGGCCACCA CCACCATCAC CACTGAAG
```

Ecto Pre HIS

The following polypeptide includes the ecto domain of the RSV F polypeptide with the trimerization domain of GCN4 (underlined) inserted into the RSV F polypeptide upstream of where the TM domain of the RSV protein would have been (beginning at a.a. 517) followed by a hexa-histidine tag.

```
                                        (SEQ ID NO: 31)
  1 MELLILKANA ITTILTAVTF CFASGQNITE EFYQSTCSAV
    SKGYLSALRT GWYTSVITIE
 61 LSNIKENKCN GTDAKVKLIK QELDKYKNAV TELQLLMQST
    PATNNRARRE LPRFMNYTLN
121 NAKKTNVTLS KKRKRRFLGF LLGVGSAIAS GVAVSKVLHL
    EGEVNKIKSA LLSTNKAVVS
181 LSNGVSVLTS KVLDLKNYID KQLLPIVNKQ SCSISNIETV
    IEFQQKNNRL LEITREFSVN
241 AGVTTPVSTY MLTNSELLSL INDMPITNDQ KKLMSNNVQI
    VRQQSYSIMS IIKEEVLAYV
301 VQLPLYGVID TPCWKLHTSP LCTTNTKEGS NICLTRTDRG
    WYCDNAGSVS FFPQAETCKV
361 QSNRVFCDTM NSLTLPSEVN LCNVDIFNPK YDCKIMTSKT
    DVSSSVITSL GAIVSCYGKT
421 KCTASNKNRG IIKTFSNGCD YVSNKGVDTV SVGNTLYYVN
    KQEGKSLYVK GEPIINFYDP
481 LVFPSDEFDA SISQVNEKIN QSLAFIRKSD ELLHNVNDKI
    EEILSKIYHI ENEIARIKKL
541 IGESGGSAGS GHHHHHH
```

The following nucleic acid sequence is the optimized coding sequence for the foregoing polypeptide sequence.

```
                                        (SEQ ID NO: 32)
  1 ATGGAACTGC TGATCCTGAA GGCCAACGCC ATCACCACCA
    TCCTGACCGC CGTGACCTTC
 61 TGCTTCGCCA GCGGCCAGAA CATCACCGAG GAATTCTACC
    AGAGCACCTG CAGCGCCGTG
121 AGCAAGGGCT ACCTGAGCGC CCTGCGGACC GGCTGGTACA
    CCAGCGTGAT CACCATCGAG
181 CTGTCCAACA TCAAAGAAAA CAAGTGCAAC GGCACCGACG
    CCAAGGTGAA ACTGATCAAG
241 CAGGAACTGG ACAAGTACAA GAACGCCGTG ACCGAGCTGC
    AGCTGCTGAT GCAGAGCACC
301 CCCGCCACCA ACAACCGGGC CAGAAGAGAG CTGCCCCGGT
    TCATGAACTA CACCCTGAAC
361 AACGCCAAGA AAACCAACGT GACCCTGAGC AAGAAGCGGA
    AGCGGCGGTT CCTGGGCTTC
421 CTGCTGGGCG TGGGCAGCGC CATCGCCAGC GGGGTGGCCG
    TGTCCAAGGT GCTGCACCTG
481 GAAGGCGAGG TGAACAAGAT CAAGTCCGCC CTGCTGTCCA
    CCAACAAGGC CGTGGTGTCC
541 CTGAGCAACG GCGTGAGCGT GCTGACCAGC AAGGTGCTGG
    ATCTGAAGAA CTACATCGAC
601 AAGCAGCTGC TGCCCATCGT GAACAAGCAG AGCTGCAGCA
    TCAGCAACAT CGAGACCGTG
661 ATCGAGTTCC AGCAGAAGAA CAACCGGCTG CTGGAAATCA
    CCCGGGAGTT CAGCGTGAAC
721 GCCGGCGTGA CCACCCCCGT GAGCACCTAC ATGCTGACCA
    ACAGCGAGCT GCTGTCCCTG
781 ATCAATGACA TGCCCATCAC CAACGACCAG AAAAAGCTGA
    TGAGCAACAA CGTGCAGATC
841 GTGCGGCAGC AGAGCTACTC CATCATGAGC ATCATCAAAG
    AAGAGGTGCT GGCCTACGTG
901 GTGCAGCTGC CCCTGTACGG CGTGATCGAC ACCCCCTGCT
    GGAAGCTGCA CACCAGCCCC
961 CTGTGCACCA CCAACACCAA AGAGGGCAGC AACATCTGCC
    TGACCCGGAC CGACCGGGGC
```

```
1021  TGGTACTGCG ACAACGCCGG CAGCGTGAGC TTCTTCCCCC
      AAGCCGAGAC CTGCAAGGTG

1081  CAGAGCAACC GGGTGTTCTG CGACACCATG AACAGCCTGA
      CCCTGCCCTC CGAGGTGAAC

1141  CTGTGCAACG TGGACATCTT CAACCCCAAG TACGACTGCA
      AGATCATGAC CTCCAAGACC

1201  GACGTGAGCA GCTCCGTGAT CACCTCCCTG GGCGCCATCG
      TGAGCTGCTA CGGCAAGACC

1261  AAGTGCACCG CCAGCAACAA GAACCGGGGC ATCATCAAGA
      CCTTCAGCAA CGGCTGCGAC

1321  TACGTGAGCA ACAAGGGCGT GGACACCGTG AGCGTGGGCA
      ACACACTGTA CTACGTGAAT

1381  AAGCAGGAAG GCAAGAGCCT GTACGTGAAG GGCGAGCCCA
      TCATCAACTT CTACGACCCC

1441  CTGGTGTTCC CCAGCGACGA GTTCGACGCC AGCATCAGCC
      AGGTCAACGA GAAGATCAAC

1501  CAGAGCCTGG CCTTCATCCG GAAGAGCGAC GAGCTGCTGC
      ACAATGTGAA TGACAAGATC

1561  GAGGAAATCC TGAGCAAGAT CTACCACATC GAGAACGAGA
      TCGCCCGGAT CAAGAAGCTG

1621  ATCGGCGAAA GCGGCGGCTC TGCCGGAAGC GGCCACCACC
      ACCATCACCA CTGAAG
```

Full Pre HA HIS

The following polypeptide includes the full-length RSV F polypeptide with the post-fusion trimerization domain of the influenza hemagglutinin polypeptide (underlined) attached at the C-terminus of the RSV F polypeptide followed by a hexa-histidine tag.

```
                                     (SEQ ID NO: 33)
  1  MELLILKANA ITTILTAVTF CFASGQNITE EFYQSTCSAV
     SKGYLSALRT GWYTSVITIE

61  LSNIKENKCN GTDAKVKLIK QELDKYKNAV TELQLLMQST
     PATNNRARRE LPRFMNYTLN

121  NAKKTNVTLS KKRKRRFLGF LLGVGSAIAS GVAVSKVLHL
     EGEVNKIKSA LLSTNKAVVS

181  LSNGVSVLTS KVLDLKNYID KQLLPIVNKQ SCSISNIETV
     IEFQQKNNRL LEITREFSVN

241  AGVTTPVSTY MLTNSELLSL INDMPITNDQ KKLMSNNVQI
     VRQQSYSIMS IIKEEVLAYV

301  VQLPLYGVID TPCWKLHTSP LCTTNTKEGS NICLTRTDRG
     WYCDNAGSVS FFPQAETCKV

361  QSNRVFCDTM NSLTLPSEVN LCNVDIFNPK YDCKIMTSKT
     DVSSSVITSL GAIVSCYGKT

421  KCTASNKNRG IIKTFSNGCD YVSNKGVDTV SVGNTLYYVN
     KQEGKSLYVK GEPIINFYDP

481  LVFPSDEFDA SISQVNEKIN QSLAFIRKSD ELLHNVNAGK
     STTNIMITTI IIVIIVILLS

541  LIAVGLLLYC KARSTPVTLS KDQLSGINNI AFSNGSSGNE
     KFHQIEKEFS EVEGRIQDLE

601  KSGGSAGSGH HHHHH
```

The following nucleic acid sequence is the optimized coding sequence for the foregoing polypeptide sequence.

```
                                     (SEQ ID NO: 34)
  1  ATGGAACTGC TGATCCTGAA GGCCAACGCC ATCACCACCA
     TCCTGACCGC CGTGACCTTC

61  TGCTTCGCCA GCGGCCAGAA CATCACCGAG GAATTCTACC
     AGAGCACCTG CAGCGCCGTG

121  AGCAAGGGCT ACCTGAGCGC CCTGCGGACC GGCTGGTACA
     CCAGCGTGAT CACCATCGAG

181  CTGTCCAACA TCAAAGAAAA CAAGTGCAAC GGCACCGACG
     CCAAGGTGAA ACTGATCAAG

241  CAGGAACTGG ACAAGTACAA GAACGCCGTG ACCGAGCTGC
     AGCTGCTGAT GCAGAGCACC

301  CCCGCCACCA ACAACCGGGC CAGAAGAGAG CTGCCCCGGT
     TCATGAACTA CACCCTGAAC

361  AACGCCAAGA AAACCAACGT GACCCTGAGC AAGAAGCGGA
     AGCGGCGGTT CCTGGGCTTC

421  CTGCTGGGCG TGGGCAGCGC CATCGCCAGC GGGGTGGCCG
     TGTCCAAGGT GCTGCACCTG

481  GAAGGCGAGG TGAACAAGAT CAAGTCCGCC CTGCTGTCCA
     CCAACAAGGC CGTGGTGTCC

541  CTGAGCAACG GCGTGAGCGT GCTGACCAGC AAGGTGCTGG
     ATCTGAAGAA CTACATCGAC

601  AAGCAGCTGC TGCCCATCGT GAACAAGCAG AGCTGCAGCA
     TCAGCAACAT CGAGACCGTG

661  ATCGAGTTCC AGCAGAAGAA CAACCGGCTG CTGGAAATCA
     CCCGGGAGTT CAGCGTGAAC

721  GCCGGCGTGA CCACCCCCGT GAGCACCTAC ATGCTGACCA
     ACAGCGAGCT GCTGTCCCTG

781  ATCAATGACA TGCCCATCAC CAACGACCAG AAAAAGCTGA
     TGAGCAACAA CGTGCAGATC
```

```
 841 GTGCGGCAGC AGAGCTACTC CATCATGAGC ATCATCAAAG
     AAGAGGTGCT GGCCTACGTG
 901 GTGCAGCTGC CCCTGTACGG CGTGATCGAC ACCCCCTGCT
     GGAAGCTGCA CACCAGCCCC
 961 CTGTGCACCA CCAACACCAA AGAGGGCAGC AACATCTGCC
     TGACCCGGAC CGACCGGGGC
1021 TGGTACTGCG ACAACGCCGG CAGCGTGAGC TTCTTCCCCC
     AAGCCGAGAC CTGCAAGGTG
1081 CAGAGCAACC GGGTGTTCTG CGACACCATG AACAGCCTGA
     CCCTGCCCTC CGAGGTGAAC
1141 CTGTGCAACG TGGACATCTT CAACCCCAAG TACGACTGCA
     AGATCATGAC CTCCAAGACC
1201 GACGTGAGCA GCTCCGTGAT CACCTCCCTG GGCGCCATCG
     TGAGCTGCTA CGGCAAGACC
1261 AAGTGCACCG CCAGCAACAA GAACCGGGGC ATCATCAAGA
     CCTTCAGCAA CGGCTGCGAC
1321 TACGTGAGCA ACAAGGGCGT GGACACCGTG AGCGTGGGCA
     ACACACTGTA CTACGTGAAT
1381 AAGCAGGAAG GCAAGAGCCT GTACGTGAAG GGCGAGCCCA
     TCATCAACTT CTACGACCCC
1441 CTGGTGTTCC CCAGCGACGA GTTCGACGCC AGCATCAGCC
     AGGTCAACGA GAAGATCAAC
1501 CAGAGCCTGG CCTTCATCCG GAAGAGCGAC GAGCTGCTGC
     ACAATGTGAA TGCCGGCAAG
1561 AGCACCACCA ATATCATGAT CACCACAATC ATCATCGTGA
     TCATTGTGAT CCTGCTGTCT
1621 CTGATTGCCG TGGGCCTGCT GCTGTACTGC AAGGCCCGCA
     GCACCCCTGT GACCCTGTCC
1681 AAGGACCAGC TGTCCGGCAT CAACAATATC GCCTTCTCCA
     ACGGCAGCAG CGGCAATGAG
1741 AAGTTCCACC AGATCGAGAA AGAATTCAGC GAGGTGGAGG
     GCCGGATCCA GGACCTGGAA
1801 AAGAGCGGCG GCTCTGCCGG AAGCGGCCAC CACCACCATC
     CCACTGAAG
```

Ecto Pre HA HIS

The following polypeptide includes the ecto domain of the RSV F polypeptide with the post-fusion trimerization domain of the influenza hemagglutinin polypeptide (underlined) inserted into the RSV F polypeptide up stream of where the TM domain of the RSV protein would have been (beginning at a.a. 517) followed by a hexa-histidine tag.

```
                                          (SEQ ID NO: 35)
  1 MELLILKANA ITTILTAVTF CFASGQNITE EFYQSTCSAV
    SKGYLSALRT GWYTSVITIE
 61 LSNIKENKCN GTDAKVKLIK QELDKYKNAV TELQLLMQST
    PATNNRARRE LPRFMNYTLN
121 NAKKTNVTLS KKRKRRFLGF LLGVGSAIAS GVAVSKVLHL
    EGEVNKIKSA LLSTNKAVVS
181 LSNGVSVLTS KVLDLKNYID KQLLPIVNKQ SCSISNIETV
    IEFQQKNNRL LEITREFSVN
241 AGVTTPVSTY MLTNSELLSL INDMPITNDQ KKLMSNNVQI
    VRQQSYSIMS IIKEEVLAYV
301 VQLPLYGVID TPCWKLHTSP LCTTNTKEGS NICLTRTDRG
    WYCDNAGSVS FFPQAETCKV
361 QSNRVFCDTM NSLTLPSEVN LCNVDIFNPK YDCKIMTSKT
    DVSSSVITSL GAIVSCYGKT
421 KCTASNKNRG IIKTFSNGCD YVSNKGVDTV SVGNTLYYVN
    KQEGKSLYVK GEPIINFYDP
481 LVFPSDEFDA SISQVNEKIN QSLAFIRKSD ELLHNVNEKF
    HQIEKEFSEV EGRIQDLEKS
541 GGSAGSGHHH HHH
```

The following nucleic acid sequence is the optimized coding sequence for the foregoing polypeptide sequence.

```
                                          (SEQ ID NO: 36)
  1 ATGGAACTGC TGATCCTGAA GGCCAACGCC ATCACCACCA
    TCCTGACCGC CGTGACCTTC
 61 TGCTTCGCCA GCGGCCAGAA CATCACCGAG GAATTCTACC
    AGAGCACCTG CAGCGCCGTG
121 AGCAAGGGCT ACCTGAGCGC CCTGCGGACC GGCTGGTACA
    CCAGCGTGAT CACCATCGAG
181 CTGTCCAACA TCAAAGAAAA CAAGTGCAAC GGCACCGACG
    CCAAGGTGAA ACTGATCAAG
241 CAGGAACTGG ACAAGTACAA GAACGCCGTG ACCGAGCTGC
    AGCTGCTGAT GCAGAGCACC
301 CCCGCCACCA ACAACCGGGC CAGAAGAGAG CTGCCCCGGT
    TCATGAACTA CACCCTGAAC
361 AACGCCAAGA AAACCAACGT GACCCTGAGC AAGAAGCGGA
    AGCGGCGGTT CCTGGGCTTC
421 CTGCTGGGCG TGGGCAGCGC CATCGCCAGC GGGGTGGCCG
    TGTCCAAGGT GCTGCACCTG
481 GAAGGCGAGG TGAACAAGAT CAAGTCCGCC CTGCTGTCCA
    CCAACAAGGC CGTGGTGTCC
```

```
541 CTGAGCAACG GCGTGAGCGT GCTGACCAGC AAGGTGCTGG
    ATCTGAAGAA CTACATCGAC
601 AAGCAGCTGC TGCCCATCGT GAACAAGCAG AGCTGCAGCA
    TCAGCAACAT CGAGACCGTG
661 ATCGAGTTCC AGCAGAAGAA CAACCGGCTG CTGGAAATCA
    CCCGGGAGTT CAGCGTGAAC
721 GCCGGCGTGA CCACCCCCGT GAGCACCTAC ATGCTGACCA
    ACAGCGAGCT GCTGTCCCTG
781 ATCAATGACA TGCCCATCAC CAACGACCAG AAAAAGCTGA
    TGAGCAACAA CGTGCAGATC
841 GTGCGGCAGC AGAGCTACTC CATCATGAGC ATCATCAAAG
    AAGAGGTGCT GGCCTACGTG
901 GTGCAGCTGC CCCTGTACGG CGTGATCGAC ACCCCCTGCT
    GGAAGCTGCA CACCAGCCCC
961 CTGTGCACCA CCAACACCAA AGAGGGCAGC AACATCTGCC
    TGACCCGGAC CGACCGGGGC
1021 TGGTACTGCG ACAACGCCGG CAGCGTGAGC TTCTTCCCCC
     AAGCCGAGAC CTGCAAGGTG
1081 CAGAGCAACC GGGTGTTCTG CGACACCATG AACAGCCTGA
     CCCTGCCCTC CGAGGTGAAC
1141 CTGTGCAACG TGGACATCTT CAACCCCAAG TACGACTGCA
     AGATCATGAC CTCCAAGACC
1201 GACGTGAGCA GCTCCGTGAT CACCTCCCTG GGCGCCATCG
     TGAGCTGCTA CGGCAAGACC
1261 AAGTGCACCG CCAGCAACAA GAACCGGGGC ATCATCAAGA
     CCTTCAGCAA CGGCTGCGAC
1321 TACGTGAGCA ACAAGGGCGT GGACACCGTG AGCGTGGGCA
     ACACACTGTA CTACGTGAAT
1381 AAGCAGGAAG GCAAGAGCCT GTACGTGAAG GGCGAGCCCA
     TCATCAACTT CTACGACCCC
1441 CTGGTGTTCC CCAGCGACGA GTTCGACGCC AGCATCAGCC
     AGGTCAACGA GAAGATCAAC
1501 CAGAGCCTGG CCTTCATCCG GAAGAGCGAC GAGCTGCTGC
     ACAATGTGAA TGAGAAGTTC
1561 CACCAGATCG AGAAAGAATT CAGCGAGGTG GAGGGCCGGA
     TCCAGGACCT GGAAAAGAGC
1621 GGCGGCTCTG CCGGAAGCGG CCACCACCAC CATCACCACT
     GAAG
```

Full∆HRB HIS

The following polypeptide includes the full-length RSV F polypeptide with the HRB domain deleted followed by a hexa-histidine tag.

```
                                      (SEQ ID NO: 37)
  1 MELLILKANA ITTILTAVTF CFASGQNITE EFYQSTCSAV
    SKGYLSALRT GWYTSVITIE
 61 LSNIKENKCN GTDAKVKLIK QELDKYKNAV TELQLLMQST
    PATNNRARRE LPRFMNYTLN
121 NAKKTNVTLS KKRKRRFLGF LLGVGSAIAS GVAVSKVLHL
    EGEVNKIKSA LLSTNKAVVS
181 LSNGVSVLTS KVLDLKNYID KQLLPIVNKQ SCSISNIETV
    IEFQQKNNRL LEITREFSVN
241 AGVTTPVSTY MLTNSELLSL INDMPITNDQ KKLMSNNVQI
    VRQQSYSIMS IIKEEVLAYV
301 VQLPLYGVID TPCWKLHTSP LCTTNTKEGS NICLTRTDRG
    WYCDNAGSVS FFPQAETCKV
361 QSNRVFCDTM NSLTLPSEVN LCNVDIFNPK YDCKIMTSKT
    DVSSSVITSL GAIVSCYGKT
421 KCTASNKNRG IIKTFSNGCD YVSNKGVDTV SVGNTLYYVN
    KQEGKSLYVK GEPNIMITTI
481 IIVIIVILLS LIAVGLLLYC KARSTPVTLS KDQLSGINNI
    AFSNMGGSHH HHHH
```

The following nucleic acid sequence is the optimized coding sequence for the foregoing polypeptide sequence.

```
                                      (SEQ ID NO: 38)
  1 ATGGAACTGC TGATCCTGAA GGCCAACGCC ATCACCACCA
    TCCTGACCGC CGTGACCTTC
 61 TGCTTCGCCA GCGGCCAGAA CATCACCGAG GAATTCTACC
    AGAGCACCTG CAGCGCCGTG
121 AGCAAGGGCT ACCTGAGCGC CCTGCGGACC GGCTGGTACA
    CCAGCGTGAT CACCATCGAG
181 CTGTCCAACA TCAAAGAAAA CAAGTGCAAC GGCACCGACG
    CCAAGGTGAA ACTGATCAAG
241 CAGGAACTGG ACAAGTACAA GAACGCCGTG ACCGAGCTGC
    AGCTGCTGAT GCAGAGCACC
301 CCCGCCACCA ACAACCGGGC CAGAAGAGAG CTGCCCCGGT
    TCATGAACTA CACCCTGAAC
361 AACGCCAAGA AAACCAACGT GACCCTGAGC AAGAAGCGGA
    AGCGGCGGTT CCTGGGCTTC
421 CTGCTGGGCG TGGGCAGCGC CATCGCCAGC GGGGTGGCCG
    TGTCCAAGGT GCTGCACCTG
481 GAAGGCGAGG TGAACAAGAT CAAGTCCGCC CTGCTGTCCA
    CCAACAAGGC CGTGGTGTCC
```

```
541 CTGAGCAACG GCGTGAGCGT GCTGACCAGC AAGGTGCTGG
    ATCTGAAGAA CTACATCGAC
601 AAGCAGCTGC TGCCCATCGT GAACAAGCAG AGCTGCAGCA
    TCAGCAACAT CGAGACCGTG
661 ATCGAGTTCC AGCAGAAGAA CAACCGGCTG CTGGAAATCA
    CCCGGGAGTT CAGCGTGAAC
721 GCCGGCGTGA CCACCCCCGT GAGCACCTAC ATGCTGACCA
    ACAGCGAGCT GCTGTCCCTG
781 ATCAATGACA TGCCCATCAC CAACGACCAG AAAAAGCTGA
    TGAGCAACAA CGTGCAGATC
841 GTGCGGCAGC AGAGCTACTC CATCATGAGC ATCATCAAAG
    AAGAGGTGCT GGCCTACGTG
901 GTGCAGCTGC CCCTGTACGG CGTGATCGAC ACCCCCTGCT
    GGAAGCTGCA CACCAGCCCC
961 CTGTGCACCA CCAACACCAA AGAGGGCAGC AACATCTGCC
    TGACCCGGAC CGACCGGGGC
1021 TGGTACTGCG ACAACGCCGG CAGCGTGAGC TTCTTCCCCC
     AAGCCGAGAC CTGCAAGGTG
1081 CAGAGCAACC GGGTGTTCTG CGACACCATG AACAGCCTGA
     CCCTGCCCTC CGAGGTGAAC
1141 CTGTGCAACG TGGACATCTT CAACCCCAAG TACGACTGCA
     AGATCATGAC CTCCAAGACC
1201 GACGTGAGCA GCTCCGTGAT CACCTCCCTG GGCGCCATCG
     TGAGCTGCTA CGGCAAGACC
1261 AAGTGCACCG CCAGCAACAA GAACCGGGGC ATCATCAAGA
     CCTTCAGCAA CGGCTGCGAC
1321 TACGTGAGCA ACAAGGGCGT GGACACCGTG AGCGTGGGCA
     ACACACTGTA CTACGTGAAT
```

```
1381 AAGCAGGAAG GCAAGAGCCT GTACGTGAAG GGCGAGCCCA
     ATATCATGAT CACCACAATC
1441 ATCATCGTGA TCATTGTGAT CCTGCTGTCT CTGATTGCCG
     TGGGCCTGCT GCTGTACTGC
1501 AAGGCCCGCA GCACCCCTGT GACCCTGTCC AAGGACCAGC
     TGTCCGGCAT CAACAATATC
1561 GCCTTCTCCA ACATGGGGGG TTCTCATCAT CATCATCATC
     ATTGAAG
```

Ecto

The following polypeptide includes just the ecto domain of the RSV F polypeptide.

```
                                        (SEQ ID NO: 39)
   1 MELLILKANA ITTILTAVTF CFASGQNITE EFYQSTCSAV
     SKGYLSALRT GWYTSVITIE
  61 LSNIKENKCN GTDAKVKLIK QELDKYKNAV TELQLLMQST
     PATNNRARRE LPRFMNYTLN
 121 NAKKTNVTLS KKRKRRFLGF LLGVGSAIAS GVAVSKVLHL
     EGEVNKIKSA LLSTNKAVVS
 181 LSNGVSVLTS KVLDLKNYID KQLLPIVNKQ SCSISNIETV
     IEFQQKNNRL LEITREFSVN
 241 AGVTTPVSTY MLTNSELLSL INDMPITNDQ KKLMSNNVQI
     VRQQSYSIMS IIKEEVLAYV
 301 VQLPLYGVID TPCWKLHTSP LCTTNTKEGS NICLTRTDRG
     WYCDNAGSVS FFPQAETCKV
 361 QSNRVFCDTM NSLTLPSEVN LCNVDIFNPK YDCKIMTSKT
     DVSSSVITSL GAIVSCYGKT
 421 KCTASNKNRG IIKTFSNGCD YVSNKGVDTV SVGNTLYYVN
     KQEGKSLYVK GEPIINFYDP
 481 LVFPSDEFDA SISQVNEKIN QSLAFIRKSD ELLHNVNAGK
     STTN
```

The following nucleic acid sequence is the optimized coding sequence for the foregoing polypeptide sequence.

```
                                        (SEQ ID NO: 40)
   1 ATGGAACTGC TGATCCTGAA GGCCAACGCC ATCACCACCA TCCTGACCGC CGTGACCTTC
  61 TGCTTCGCCA GCGGCCAGAA CATCACCGAG GAATTCTACC AGAGCACCTG CAGCGCCGTG
 121 AGCAAGGGCT ACCTGAGCGC CCTGCGGACC GGCTGGTACA CCAGCGTGAT CACCATCGAG
 181 CTGTCCAACA TCAAGAAAA CAAGTGCAAC GGCACCGACG CCAAGGTGAA ACTGATCAAG
 241 CAGGAACTGG ACAAGTACAA GAACGCCGTG ACCGAGCTGC AGCTGCTGAT GCAGAGCACC
 301 CCCGCCACCA ACAACCGGGC CAGAAGAGAG CTGCCCCGGT TCATGAACTA CACCCTGAAC
 361 AACGCCAAGA AAACCAACGT GACCCTGAGC AAGAAGCGGA AGCGGCGGTT CCTGGGCTTC
 421 CTGCTGGGCG TGGGCAGCGC CATCGCCAGC GGGGTGGCCG TGTCCAAGGT GCTGCACCTG
 481 GAAGGCGAGG TGAACAAGAT CAAGTCCGCC CTGCTGTCCA CCAACAAGGC CGTGGTGTCC
```

```
-continued
 541 CTGAGCAACG GCGTGAGCGT GCTGACCAGC AAGGTGCTGG ATCTGAAGAA CTACATCGAC

601 AAGCAGCTGC TGCCCATCGT GAACAAGCAG AGCTGCAGCA TCAGCAACAT CGAGACCGTG

661 ATCGAGTTCC AGCAGAAGAA CAACCGGCTG CTGGAAATCA CCCGGGAGTT CAGCGTGAAC

721 GCCGGCGTGA CCACCCCCGT GAGCACCTAC ATGCTGACCA ACAGCGAGCT GCTGTCCCTG

781 ATCAATGACA TGCCCATCAC CAACGACCAG AAAAAGCTGA TGAGCAACAA CGTGCAGATC

841 GTGCGGCAGC AGAGCTACTC CATCATGAGC ATCATCAAAG AAGAGGTGCT GGCCTACGTG

901 GTGCAGCTGC CCCTGTACGG CGTGATCGAC ACCCCCTGCT GGAAGCTGCA CACCAGCCCC

961 CTGTGCACCA CCAACACCAA AGAGGGCAGC AACATCTGCC TGACCCGGAC CGACCGGGGC

1021 TGGTACTGCG ACAACGCCGG CAGCGTGAGC TTCTTCCCCC AAGCCGAGAC CTGCAAGGTG

1081 CAGAGCAACC GGGTGTTCTG CGACACCATG AACAGCCTGA CCCTGCCCTC CGAGGTGAAC

1141 CTGTGCAACG TGGACATCTT CAACCCCAAG TACGACTGCA AGATCATGAC CTCCAAGACC

1201 GACGTGAGCA GCTCCGTGAT CACCTCCCTG GGCGCCATCG TGAGCTGCTA CGGCAAGACC

1261 AAGTGCACCG CCAGCAACAA GAACCGGGGC ATCATCAAGA CCTTCAGCAA CGGCTGCGAC

1321 TACGTGAGCA ACAAGGGCGT GGACACCGTG AGCGTGGGCA ACACACTGTA CTACGTGAAT

1381 AAGCAGGAAG GCAAGAGCCT GTACGTGAAG GGCGAGCCCA TCATCAACTT CTACGACCCC

1441 CTGGTGTTCC CCAGCGACGA GTTCGACGCC AGCATCAGCC AGGTCAACGA AGAGATCAAC

1501 CAGAGCCTGG CCTTCATCCG GAAGAGCGAC GAGCTGCTGC ACAATGTGAA TGCCGGCAAG

1561 AGCACCACCA ATTGAAG
```

RSV F Full Length (SEQ ID NO: 41)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVAGKSTTNI

MITTIIIVIIVILLSLIAVGLLLYCKARSTPVTLSKDQLSGINNIAFSN

RSV F Cleavage Enterokinase idealized (SEQ ID NO: 42)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQINEKINQILAFIRKIDELLHNINAGKSTTNG

SGSGDDDDDKGSGSGIMITTIIIVIIVILLSLIAVGLLLYCKARSTPVTLSKDQLSGINNIAFSN

RSV F Cleavage Thrombin idealized (SEQ ID NO: 43)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

-continued

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQINEKINQILAFIRKIDELLHNINAGKSTTNG

SGSGLVPRGSGSGIMITTIIIVIIVILLSLIAVGLLLYCKARSTPVTLSKDQLSGINNIAFSN

RSV F Cleavage FactorXa idealized
(SEQ ID NO: 44)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQINEKINQILAFIRKIDELLHNINAGKSTTNG

SGSGIEGRGSGSGIMITTIIIVIIVILLSLIAVGLLLYCKARSTPVTLSKDQLSGINNIAFSN

RSV F furx Truncated HIS (SEQ ID NO: 45)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELPRFMNYTLNNAKKTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F furx R113Q, K123N, K124N Truncated HIS (SEQ ID NO: 46)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELPQFMNYTLNNANNTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F furx R113Q, K123Q, K124Q Truncated HIS (SEQ ID NO: 93)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELPQFMNYTLNNAQQTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F delP21 furx Truncated HIS (SEQ ID NO: 47)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQN---------------------

QNQNQNFLGFLLGVGSAIASGVAVSKVLHLEGEVNKIKSALLSTNKAVVSLSNGVSVLTSKVLDLKNYIDKQLLP

IVNKQSCSISNIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDNAGSVSFFPQA

ETCKVQSNRVFCDTMNSLTLPSEVNLCNVDIFNPKYDCKIMTSKTDVSSSVITSLGAIVSCYGKTKCTASNKNRG

IIKTFSNGCDYVSNKGVDTVSVGNTLYYVNKQEGKSLYVKGEPIINFYDPLVFPSDEFDASISQVNEKINQSLAF

IRKSDELLHNVNAGKSTTNGGSAGSGHHHHHH (the symbol "-" idicates that the amino acid at this position is deleted)
RSV F delP23 furx Truncated HIS (SEQ ID NO: 48)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQN-----------------------

QNQNFLGFLLGVGSAIASGVAVSKVLHLEGEVNKIKSALLSTNKAVVSLSNGVSVLTSKVLDLKNYIDKQLLPIV

NKQSCSISNIETVIEFQQKNNRLLEITREFSVNAGVTTPVSTYMLTNSELLSLINDMPITNDQKKLMSNNVQIVR

QQSYSIMSIIKEEVLAYVVQLPLYGVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVITSLGAIVSCYGKTKCTASNKNRGII

KTFSNGCDYVSNKGVDTVSVGNTLYYVNKQEGKSLYVKGEPIINFYDPLVFPSDEFDASISQVNEKINQSLAFIR

KSDELLHNVNAGKSTTNGGSAGSGHHHHHH (the symbol "-" idicates that the amino acid at this position is deleted)
RSV F delP23 furdel Truncated HIS (SEQ ID NO: 49)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARQ-----------------------

QQQRFLGFLLGVGSAIASGVAVSKVLHLEGEVNKIKSALLSTNKAVVSLSNGVSVLTSKVLDLKNYIDKQLLPIV

NKQSCSISNIETVIEFQQKNNRLLEITREFSVNAGVTTPVSTYMLTNSELLSLINDMPITNDQKKLMSNNVQIVR

QQSYSIMSIIKEEVLAYVVQLPLYGVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVITSLGAIVSCYGKTKCTASNKNRGII

KTFSNGCDYVSNKGVDTVSVGNTLYYVNKQEGKSLYVKGEPIINFYDPLVFPSDEFDASISQVNEKINQSLAFIR

KSDELLHNVNAGKSTTNGGSAGSGHHHHHH (the symbol "-" idicates that the amino acid at this position is deleted)
RSV F furmt Truncated HIS (SEQ ID NO: 50)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARKELPRFMNYTLNNAKKTNVTLSKKRKKKFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

-continued

RSV F furdel Truncated HIS (SEQ ID NO: 51)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARQELPRFMNYTLNNAKKTNVTLSKK---

RFLGFLLGVGSAIASGVAVSKVLHLEGEVNKIKSALLSTNKAVVSLSNGVSVLTSKVLDLKNYIDKQLLPIVNKQ

SCSISNIETVIEFQQKNNRLLEITREFSVNAGVTTPVSTYMLTNSELLSLINDMPITNDQKKLMSNNVQIVRQQS

YSIMSIIKEEVLAYVVQLPLYGVIDTPCWKLHTSPLCTTNTKEGSNICLTRTDRGWYCDNAGSVSFFPQAETCKV

QSNRVFCDTMNSLTLPSEVNLCNVDIFNPKYDCKIMTSKTDVSSSVITSLGAIVSCYGKTKCTASNKNRGIIKTF

SNGCDYVSNKGVDTVSVGNTLYYVNKQEGKSLYVKGEPIINFYDPLVFPSDEFDASISQVNEKINQSLAFIRKSD

ELLHNVAGKSTTNGGSAGSGHHHHHH (the symbol "-" idicates that the amino acid at this position is deleted)

RSV F Factor Xa Truncated HIS (SEQ ID NO: 52)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNIEGRELPRFMNYTLNNAKKTNVTLSKKIEGRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVAGKSTTNG

GSAGSGHHHHHH

RSV F Short linker Foldon HIS (SEQ ID NO: 53)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVAGKSTTNG

SGYIPEAPRDGQAYVRKDGEWVLLSTFLGGSAGSGHHHHHH

RSV F Long linker Foldon HIS (SEQ ID NO:54)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVAGKSTTNN

KNDDKGSGYIPEAPRDGQAYVRKDGEWVLLSTFLGGSAGSGHHHHHH

RSV_F_ecto_pre_his (SEQ ID NO: 55)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

-continued

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNDKIEEILS

KIYHIENEIARIKKLIGESGGSAGSGHHHHHH

ECTO PRE HA HIS (SEQ ID NO: 56)

MELLILKANAITTILTAVTFCFASGQNITEEFYQSTCSAVSKGYLSALRTGWYTSVITIELSNIKENKCNGTDAK

VKLIQELDKYKNAVTELQLLMQSTPATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNEKFHQIEK

EFSEVEGRIQDLEKSGGSAGSGHHHHHH

RSV F ECTO Furx GCN HIS (SEQ ID NO: 57)

MELLILKANAITTILTAVTFCFASGQNITEEFYQSTCSAVSKGYLSALRTGWYTSVITIELSNIKENKCNGTDAK

VKLIQELDKYKNAVTELQLLMQSTPATNNQAQNELPQFMNYTLNNANNTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVN

DKIEEILSKIYHIENEIARIKKLIGESGGSAGSGHHHHHH

RSV F ECTO delp21 GCN HIS (SEQ ID NO: 58)

MELLILKANAITTILTAVTFCFASGQNITEEFYQSTCSAVSKGYLSALRTGWYTSVITIELSNIKENKCNGTDAK

VKLIQELDKYKNAVTELQLLMQSTPATNNQAQN---------------------

QNQNQNFLGFLLGVGSAIASGVAVSKVLHLEGEVNKIKSALLSTNKAVVSLSNGVSVLTSKVLDLKNYIDKQLLP

IVNKQSCSISNIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDNAGSVSFFPQA

ETCKVQSNRVFCDTMNSLTLPSEVNLCNVDIFNPKYDCKIMTSKTDVSSSVITSLGAIVSCYGKTKCTASNKNRG

IIKTFSNGCDYVSNKGVDTVSVGNTLYYVNKQEGKSLYVKGEPIINFYDPLVFPSDEFDASISQVNEKINQSLAF

IRKSDELLHNVN DKIEEILSKIYHIENEIARIKKLIGESGGSAGSGHHHHHH (the symbol "-" idicates that the amino acid at this position is deleted)
RSV F ECTO delp23 Furx GCN HIS (SEQ ID NO: 59)

MELLILKANAITTILTAVTFCFASGQNITEEFYQSTCSAVSKGYLSALRTGWYTSVITIELSNIKENKCNGTDAK

VKLIQELDKYKNAVTELQLLMQSTPATNNQAQN-----------------------

QNQNFLGFLLGVGSAIASGVAVSKVLHLEGEVNKIKSALLSTNKAVVSLSNGVSVLTSKVLDLKNYIDKQLLPIV

NKQSCSISNIETVIEFQQKNNRLLEITREFSVNAGVTTPVSTYMLTNSELLSLINDMPITNDQKKLMSNNVQIVR

QQSYSIMSIIKEEVLAYVVQLPLYGVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVITSLGAIVSCYGKTKCTASNKNRGII

-continued

KTFSNGCDYVSNKGVDTVSVGNTLYYVNKQEGKSLYVKGEPIINFYDPLVFPSDEFDASISQVNEKINQSLAFIR

KSDELLHNVN DKIEEILSKIYHIENEIARIKKLIGESGGSAGSGHHHHHH (the symbol "-" idicates that the amino acid at this position is deleted)
RSV F ECTO delp23 Furdel GCN HIS (SEQ ID NO: 60)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARQ----------------------

QQQRFLGFLLGVGSAIASGVAVSKVLHLEGEVNKIKSALLSTNKAVVSLSNGVSVLTSKVLDLKNYIDKQLLPIV

NKQSCSISNIETVIEFQQKNNRLLEITREFSVNAGVTTPVSTYMLTNSELLSLINDMPITNDQKKLMSNNVQIVR

QQSYSIMSIIKEEVLAYVVQLPLYGVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVITSLGAIVSCYGKTKCTASNKNRGII

KTFSNGCDYVSNKGVDTVSVGNTLYYVNKQEGKSLYVKGEPIINFYDPLVFPSDEFDASISQVNEKINQSLAFIR

KSDELLHNVN DKIEEILSKIYHIENEIARIKKLIGESGGSAGSGHHHHHH (the symbol "-" idicates that the amino acid at this position is deleted)
RSV F Full Length Furx (SEQ ID NO: 61)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELPQFMNYTLNNANNTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVN

AGKSTTNIMITTIIIVIIVILLSLIAVGLLLYCKARSTPVTLSKDQLSGINNIAFSN

RSV F Full Length delp21

(SEQ ID NO: 62)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQN---------------------

QNQNQNFLGFLLGVGSAIASGVAVSKVLHLEGEVNKIKSALLSTNKAVVSLSNGVSVLTSKVLDLKNYIDKQLLP

IVNKQSCSISNIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDNAGSVSFFPQA

ETCKVQSNRVFCDTMNSLTLPSEVNLCNVDIFNPKYDCKIMTSKTDVSSSVITSLGAIVSCYGKTKCTASNKNRG

IIKTFSNGCDYVSNKGVDTVSVGNTLYYVNKQEGKSLYVKGEPIINFYDPLVFPSDEFDASISQVNEKINQSLAF

IRKSDELLHNVN AGKSTTNIMITTIIIVIIVILLSLIAVGLLLYCKARSTPVTLSKDQLSGINNIAFSN (the symbol "-" idicates that the amino acid at this position is deleted)
RSV F Full Length p23 Furx GCN HIS (SEQ ID NO: 63)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQN----------------------

QNQNFLGFLLGVGSAIASGVAVSKVLHLEGEVNKIKSALLSTNKAVVSLSNGVSVLTSKVLDLKNYIDKQLLPIV

NKQSCSISNIETVIEFQQKNNRLLEITREFSVNAGVTTPVSTYMLTNSELLSLINDMPITNDQKKLMSNNVQIVR

QQSYSIMSIIKEEVLAYVVQLPLYGVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVITSLGAIVSCYGKTKCTASNKNRGII

KTFSNGCDYVSNKGVDTVSVGNTLYYVNKQEGKSLYVKGEPIINFYDPLVFPSDEFDASISQVNEKINQSLAFIR

KSDELLHNVN AGKSTTNIMITTIIIVIIVILLSLIAVGLLLYCKARSTPVTLSKDQLSGINNIAFSN

-continued (the symbol "-" idicates that the amino acid at this position is deleted)
RSV F Full Length p23 Furdel GCN HIS (SEQ ID NO: 64)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARQ----------------------

QQQRFLGFLLGVGSAIASGVAVSKVLHLEGEVNKIKSALLSTNKAVVSLSNGVSVLTSKVLDLKNYIDKQLLPIV

NKQSCSISNIETVIEFQQKNNRLLEITREFSVNAGVTTPVSTYMLTNSELLSLINDMPITNDQKKLMSNNVQIVR

QQSYSIMSIIKEEVLAYVVQLPLYGVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVITSLGAIVSCYGKTKCTASNKNRGII

KTFSNGCDYVSNKGVDTVSVGNTLYYVNKQEGKSLYVKGEPIINFYDPLVFPSDEFDASISQVNEKINQSLAFIR

KSDELLHNVN AGKSTTNIMITTIIIVIIVILLSLIAVGLLLYCKARSTPVTLSKDQLSGINNIAFSN (the symbol "-" idicates that the amino acid at this position is deleted)
RSV F N-term Furin Furx Truncated HIS (SEQ ID NO: 65)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELPQFMNYTLNNAQQTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F C-term Furin Furx Truncated HIS (SEQ ID NO: 66)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPQFMNYTLNNAQQTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F Fusion Deletion 1 Truncated HIS (SEQ ID NO: 67)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRSAIASGVAVSKVLH

LEGEVNKIKSALLSTNKAVVSLSNGVSVLTSKVLDLKNYIDKQLLPIVNKQSCSISNIETVIEFQQKNNRLLEIT

REFSVNAGVTTPVSTYMLTNSELLSLINDMPITNDQKKLMSNNVQIVRQQSYSIMSIIKEEVLAYVVQLPLYGVI

DTPCWKLHTSPLCTTNTKEGSNICLTRTDRGWYCDNAGSVSFFPQAETCKVQSNRVFCDTMNSLTLPSEVNLCNV

DIFNPKYDCKIMTSKTDVSSSVITSLGAIVSCYGKTKCTASNKNRGIIKTFSNGCDYVSNKGVDTVSVGNTLYYV

NKQEGKSLYVKGEPIINFYDPLVFPSDEFDASISQVNEKINQSLAFIRKSDELLHNVNAGKSTTNGGSAGSGHHH

HHH

-continued

RSV F Fusion Deletion 2 Truncated HIS (SEQ ID NO: 68)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRGVGSAIASGVAVSK

VLHLEGEVNKIKSALLSTNKAVVSLSNGVSVLTSKVLDLKNYIDKQLLPIVNKQSCSISNIETVIEFQQKNNRLL

EITREFSVNAGVTTPVSTYMLTNSELLSLINDMPITNDQKKLMSNNVQIRQQSYSIMSIIKEEVLAYVVQLPLY

GVIDTPCWKLHTSPLCTTNTKEGSNICLTRTDRGWYCDNAGSVSFFPQAETCKVQSNRVFCDTMNSLTLPSEVNL

CNVDIFNPKYDCKIMTSKTDVSSSVITSLGAIVSCYGKTKCTASNKNRGIIKTFSNGCDYVSNKGVDTVSVGNTL

YYVNKQEGKSLYVKGEPIINFYDPLVFPSDEFDASISQVNEKINQSLAFIRKSDELLHNVNAGKSTTNGGSAGSG

HHHHHH

RSV F Furx Truncated HIS (SEQ ID NO: 69)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELPQFMNYTLNNAQQTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F Furx Truncated (SEQ ID NO: 70)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELPQFMNYTLNNAQQTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTN

RSV F delP23 furdel Truncated No HIS (For CHO cells)

(SEQ ID NO: 71)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARQ-----------------------

QQQRFLGFLLGVGSAIASGVAVSKVLHLEGEVNKIKSALLSTNKAVVSLSNGVSVLTSKVLDLKNYIDKQLLPIV

NKQSCSISNIETVIEFQQKNNRLLEITREFSVNAGVTTPVSTYMLTNSELLSLINDMPITNDQKKLMSNNVQIR

QQSYSIMSIIKEEVLAYVVQLPLYGVIDTPCWKLHTSPLCTTNTKEGSNICLTRTDRGWYCDNAGSVSFFPQAET

CKVQSNRVFCDTMNSLTLPSEVNLCNVDIFNPKYDCKIMTSKTDVSSSVITSLGAIVSCYGKTKCTASNKNRGII

KTFSNGCDYVSNKGVDTVSVGNTLYYVNKQEGKSLYVKGEPIINFYDPLVFPSDEFDASISQVNEKINQSLAFIR

KSDELLHNVNAGKSTTN (the symbol "-" idicates that the amino acid at this position is deleted)

RSV F (Wt) Truncated HIS (SEQ ID NO: 84)
MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIRQQSYSIMSIIKEEVLAYV

-continued

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F old furx Truncated HIS (SEQ ID NO: 88)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELQRFMNYTLNNANNTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F Furx R113Q K123N K124N Truncated HIS (SEQ ID NO: 89)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELPQFMNYTLNNAQQTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F N-term Furin Truncated HIS (SEQ ID NO: 85)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARRELPQFMNYTLNNAQQTNVTLSQNQNQNFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

RSV F delP21 furdel Truncated HIS (SEQ ID NO: 86)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNRARQ---------------------

QNQQQRFLGFLLGVGSAIASGVAVSKVLHLEGEVNKIKSALLSTNKAVVSLSNGVSVLTSKVLDLKNYIDKQLLP

IVNKQSCSISNIETVIEFQQKNNRLLEITREFSVNAGVTTPVSTYMLTNSELLSLINDMPITNDQKKLMSNNVQI

VRQQSYSIMSIIKEEVLAYVVQLPLYGVIDTPCWKLHTSPLCTTNTKEGSNICLTRTDRGWYCDNAGSVSFFPQA

ETCKVQSNRVFCDTMNSLTLPSEVNLCNVDIFNPKYDCKIMTSKTDVSSSVITSLGAIVSCYGKTKCTASNKNRG

IIKTFSNGCDYVSNKGVDTVSVGNTLYYVNKQEGKSLYVKGEPIINFYDPLVFPSDEFDASISQVNEKINQSLAF

IRKSDELLHNVNAGKSTTNGGSAGSGHHHHHH

RSV F C-term Furin Truncated HIS
(SEQ ID NO: 87)

MELLILKANAITTILTAVTFCFASGQNITEEFYQSTCSAVSKGYLSALRTGWYTSVITIELSNIKENKCNGTDAK

VKLIKQELDKYKNAVTELQLLMQSTPATNNQAQNELPQFMNYTLNNAQQTNVTLSKKRKRRFLGFLLGVGSAIAS

GVAVSKVLHLEGEVNKIKSALLSTNKAVVSLSNGVSVLTSKVLDLKNYIDKQLLPIVNKQSCSISNIETVIEFQQ

KNNRLLEITREFSVNAGVTTPVSTYMLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVSFFPQAETCKVQSNRVFCDTMNSLTL

PSEVNLCNVDIFNPKYDCKIMTSKTDVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKINQSLAFIRKSDELLHNVNAGKSTTNG

GSAGSGHHHHHH

Example 2

Expression and Purification of RSV F Constructs

The RSV F ECTO and truncated constructs, lacking the transmembrane domain and cytoplasmic tail region with either wild-type furin cleavage sites or harboring knock-out mutations to the furin cleavage sites and with or without prefusion stabilization mutations, were cloned into a pFast-Bac baculovirus expression vector (Invitrogen). Several of these constructs contain a C-terminal flexible linker followed by a His6-tag sequence used for chelating purification. The production of high-titer baculovirus stocks were passaged in Sf9 insect cells. Proteins were expressed by infecting either Sf9, Tn5 or High Five insect cells with the required baculovirus and harvesting the media supernatant two or three days post infection, monitored by western blot using an anti-RSV F or anti-6HIS antibody.

Large scale expression media was concentrated/purified by one of two general strategies for eliminating the deleterious Effect of the ferritin present in insect cell media from corrupting the chelating resin. The first approach was to concentrate the approximately 10-20 liters of insect expression media down to approximately 300 mls using a GE Healthcare Hollotube fiber concentration column. Copper sulfate was added to this concentrated mixture to a final concentration of 500 µM and the resulting solution was loaded onto 5 ml HiTrap chelating columns. The bound HIS-tagged protein was then eluted from the column with 25 mM Tris pH 7.5, 300 mM NaCl and a gradient of imidazole.

In the second purification strategy, $CuCl_2$ was added to media supernatant to a final concentration of 500 µM. To each 1 liter of media, four milliliters of chelation resin (Chelating Resin, BioRad) was added and the slurry was rocked for at least thirty minutes at 4 degrees centigrade and the resin and media were separated by a gravity column. The resin was washed with ten-times column volume of equilibration buffer (25 mM Tris pH 7.5, 300 mM NaCl) and the F protein was eluted with ten-times column volume of elution buffer (equilibration buffer with 250 mM imidazole). The elution was dialyzed against 25 mM Tris buffer pH 7.5, and the resulting solution was loaded onto a 5 ml Hitrap chelation column charged with $NiSO_4$ and eluted with 25 mM Tris pH 7.5, 300 mM NaCl and a gradient of imidazole.

Elutions from the imidazole gradient in either case were evaluated using anti-6HIS western and coomassie gels. Fractions containing pure constructs were collected, dialyzed against different buffer/saline solutions and were concentrated for subsequent analysis using Millipore Centriprep Concentrators and/or Vivaspin concentration units. We have also developed a size-exclusion purification protocol capable of further purifying monodisperced RSV trimers from rosettes (below).

SEC Analysis of RSV F Proteins:

A documented feature of other paramyxovirus fusion proteins stabilized in their prefusion conformation is that, even when cleaved so that the fusion peptide is exposed, they do not form rosettes as is observed for the postfusion conformation. A simple size-exclusion chromatography analysis allows for identification of a protein and determination of whether a protein is forming rosettes. Two methods were developed, HPLC-SEC and FPLC-SEC, which also serves as an efficient purification step.

HPLC-SEC was performed using a Biorad SEC column (18 mm) with a 25 mM Tris pH 7.5, 300 mM NaCl mobile phase. Using Biorad HPLC-SEC standards to calibrate the system, we found that the RSV rosettes (representing cleaved-postfusion conformations) elute in the column void volume of the analysis, while RSV monodispersed trimers (presumed trimers from subsequent EM analysis) elute with an apparent molecular weight of approximately 100 kDa.

FPLC-SEC was performed on a GE Healtcare FPLC using a 16/60 Superdex 200 column with 25 mM Tris pH 7.5, 300 mM NaCl mobile phase. Using GE Healthcare High molecular weight standards to calibrate the system, we found that the RSV rosettes elute in the column void volume of the analysis, while RSV monodispersed trimers elute with an apparent molecular weight of approximately 100 kDa.

Electron Microscopy (EM) of RSV F proteins.

Protein solutions of approximately 50 micrograms per ml RSV F constructs were absorbed onto glow-discharged carbon coated grids and were negatively stained with 2% sodium phosphotungstate (pH 7.0) or 0.75% Urynal-formate (unquantified low pH). The grids were observed on a Technai Spirit or JOEL 1230 transmission electron microscope operating between 80-120 kV with a magnification between 20,000 to 150,000 depending on required resolution.

TABLE 2

| Construct | Conformation by EM |
| --- | --- |
| RSV F ECTO HIS | Predominately rosettes |
| RSV F Furdel ECTO (cleaved) | Predominately rosettes |
| RSV F Delp23 Furdel Truncated (uncleaved) | Trimers observed |
| RSV F Fusion Peptide Deletion 1 Truncated (uncleaved) | Timers |
| RSV F Delp23 Furdel Truncated (cleaved by Trypsin after purification) | Predominantly rosettes with some trimers |

TABLE 2-continued

| Construct | Conformation by EM |
|---|---|
| RSV F Delp23 Furdel Truncated (cleaved by Trypsin after purification in presence of nanolipid disk) | Asymmetric rosettes with apparent nanolipid disk at the center of rosette |

Example 3

Detection of Pre-Fusion and Post-Fusion RSV F

A number of methods are available to determine the conformation of the RSV F protein to assay whether a modification to the RSV F polypeptide or added molecule disfavors the post-fusion conformation. Examples include liposome association, conformation specific monoclonal antibodies (including as used in FACS, ELISA, etc.), electron microscopy, differential protease sensitivity between the conformations, gel filtration chromatography, analytical ultracentrifugation, dynamic light scattering, deuterium exchange NMR experiments, mass spectroscopy, circular dichroism spectroscopy, isothermal titration calorimetry, tryptophan spectroscopy, and X-ray crystallography.

Liposome Association

Liposome association may be used to assay the conformation of the RSV F protein. Soluble forms of the RSV F protein in the pre-fusion conformation will not associate with liposomes while the post-fusion conformation will associate with liposomes.

Liposomes may be prepared as follows: 1-palmitoyl-2-oleoyl-sn-glycero-3-phosphocholine, 1-palmitoyl-2-oleoyl-sn-glycero-3-phosphoethanolamine, and cholesterol in chloroform (available from Avanti Polar Lipids) are mixed at an 8:2:5 molar ratio. The chloroform is evaporated under argon. A lipid film will form that is dried under vacuum overnight and resuspended in PBS at 40 mM total lipid. After five freeze-thaw cycles, the lipids are vortexed and extruded 21 times through two 100-μm filters by using a miniextruder (available from Avanti Polar Lipids).

Once the liposomes have been prepared, the liposome association assay may be performed. For each sample to be tested, 2 μg of the RSV F polypeptide to test is cleaved with 25 milliunits of trypsin (available from Worthington Biochemical) in 100 mM phosphate buffer (pH 7.1) for 30 min at 25° C. After cleavage, 40 pg of soybean trypsin inhibitor (available from Worthington Biochemical) is added to each sample to end the reaction. The samples are pretreated at 60° C. for 30 min which would induce a conformational shift from the pre-fusion to the post-fusion forms in native isolated RSF F protein. Liposomes (40 μl per sample) and PBS are added (80 μl final volume), and the samples are incubated at 60° C. for 30 min. Sucrose is added to a final concentration of 50% (500 μl final volume). The samples are overlaid with 500 μl each of 40% sucrose, 25% sucrose, and PBS and are spun in a TLS55 rotor at 49,000 rpm for 3 h at 25° C. Fractions (500 μl) are collected from the top of the gradients. Proteins are solubilized in 0.5% Triton X-100 and precipitated by using 12.5% vol/vol trichloroacetic acid. Polypeptides are separated by SDS/PAGE and transferred to PVDF membranes. Blots are probed with anti-RSV F monoclonal antibodies.

Electron Microscopy

Electron microscopy was used to assay the conformational distribution of RSV F polypeptides. RSV F polypeptides in the pre-fusion form have a "ball and stem" shape with a length of ~12 nm. In contrast, RSV F polypeptides in the post-fusion form have a "golf tee" shape with a length of ~16 nm. In addition, the fusion peptides at the narrow end of the "golf tees" aggregate to form a rosette structures. Thus, electron microscopy may be used to assay the distribution of conformations in a sample of RSV F polypeptides owing to the readily distinguishable shapes.

Example 4

RSV F Ectodomain Trimers and Rosettes

The RSV F protein ecto-domain constructs, encoding polypeptides that lack the transmembrane domain and cytoplasmic tail region with either wild-type furin cleavage sites or harboring knock-out mutations to the furin cleavage sites and/or fusion peptide mutations mutations, were cloned into a pFastBac baculovirus expression vector (Invitrogen). Several of these constructs contain a C-terminal flexible linker followed by a HIS6-tag sequence used for chelating purification. The production of high-titer baculovirus stocks were obtained by passage in Sf9 insect cells. Proteins were expressed by infecting either Sf9, Tn5 or High Five insect cells with the required baculovirus and harvesting the conditioned media supernatant two or three days post infection. Protein production was monitored by western blot using an anti-RSV F or anti-HIS6 antibody.

Large scale expression media was concentrated/purified using one of two general strategies for eliminating the deleterious effect of the ferritin present in insect cell media, which can corrupt the chelating resin. The first approach was to concentrate the approximately 10-20 liters of insect expression media down to approximately 300 mls using a GE Healthcare Hollotube fiber concentration column. Copper sulfate was added to this concentrated mixture to a final concentration of 500 μM, and the resulting solution was loaded onto 5 ml HiTrap chelating columns. The bound HIS-tagged protein was then eluted from the column with 25 mM Tris pH 7.5, 300 mM NaCl and a gradient of imidazole.

In the second purification strategy, $CuCl_2$ was added to media supernatant to a final concentration of 500 μM. To each 1 liter of media, approximately four to ten milliliters of chelating resin (Chelating Resin, BioRad) was added, and the slurry was rocked for at least thirty minutes at 4 degrees centigrade, and the resin and media were separated using a gravity column. The resin was washed with approximately ten times the column volume of equilibration buffer (25 mM Tris pH 7.5, 300 mM NaCl), and the F protein ecto-domain was eluted with approximately ten-times the column volume of elution buffer (equilibration buffer with 250 mM imidazole). The elution was dialyzed against 25 mM Tris buffer pH 7.5, and the resulting solution was loaded onto a 5 ml Hitrap chelation column charged with $NiSO_4$. Bound protein was eluted with 25 mM Tris pH 7.5, 300 mM NaCl and a gradient of imidazole.

Elutions from the imidazole gradient in either case were evaluated using anti-$HIS_6$ western blots and/or Coomassie-stained SDS-PAGE gels. Fractions containing pure constructs were collected, dialyzed against different buffer/saline solutions and were concentrated for subsequent analysis using Millipore Centriprep concentrators and/or Vivaspin concentration units. In some instances, monomers, trimers or rosettes were further purified using size exclusion chromatography.

SEC Analysis and Purification of RSV F Ecto-Domains

Size exclusion chromatography was used to purify and analyze RSV F protein ecto-domain monomers, trimers and rosettes. This method also allowed uncleaved RSV F protein ecto-domains to be purified away from host cell or media derived lipid and lipoprotein contaminants. Two methods were developed, HPLC-SEC and FPLC-SEC, which may also serve as an efficient purification step.

HPLC-SEC was performed using a Biorad SEC column (18 mm) with a 25 mM Tris pH 7.5, 300 mM NaCl mobile phase. Using Biorad HPLC-SEC standards to calibrate the system, we found that the RSV rosettes (representing cleaved, postfusion conformations) elute in the column void volume of the analysis, while RSV F monomers elute with an apparent molecular weight of approximately 75-85 kDa.

FPLC-SEC was performed on a GE Healthcare FPLC using a 16/60 Superdex 200 column with 25 mM Tris pH 7.5, 300 mM NaCl as a mobile phase. Using GE Healthcare High molecular weight standards to calibrate the system, we found that the RSV rosettes elute in the column void volume of the analysis, while RSV monodispersed trimers elute with an apparent molecular weight of approximately 140-160 kDa and RSV F monomers elute with an apparent molecular weitght of approximately 75-85 kDa.

For purification, the FPLC-SEC method was used and 1 ml fractions were collected.

Typsin Cleavage of Furdel or Delp23 Furdel Constructs to Form Postfusion Rosettes In general, trypsin digestion of Delp23 Furdel monomers is done with 1:1000 trypsin:RSV F by weight, or 10-15 BAEE units of trypsin for 1 mg of RSV F antigen. In a typical reaction, trypsin from bovine plasma (Sigma Aldrich, T8802: 10,000-15,000 BAEE units/mg trypsin) was diluted to a 1 mg/ml concentration in 25 mM Tris pH 7.5, 300 mM NaCl. A 1 mg/ml solution of RSV F protein ecto-domain polypeptide (diluted in 25 mM Tris pH 7.5, 300 mM NaCl) was treated with one microliter of trypsin solution (final mass ratio 0.001:1 trypsin:RSV F or approximately 10-15 BAEE units of trypsin to each milligram of RSV F) for 1 hour at 37° C. Typically, progress of the cleavage reaction was monitored by SDS-PAGE gel. The cleavage reaction was stopped using a trypsin inhibitor. The cleaved RSV F protein was further purified by size exclusion chromatography.

On occasion, 1:100 volume of immobilized trypsin inhibitor (Sigma) or 1 microliter of 1 mM soybean trypsin inhibitor was added to the cleavage solution and the mixture was incubated at room temperature for approximately 15-30 minutes with gentle rocking to stop the trypsin reaction. The inhibitor resin was separated from the protein solution using microcentrifuge columns. The resulting solution was purified by SEC purification.

Electron Microscopy (EM) of RSV F Proteins.

RSV F protein ecto-domain polypeptides (approximately 50 micrograms per ml), were absorbed onto glow-discharged carbon-coated grids and were negatively stained with 2% sodium phosphotungstate (pH 7.0) or 0.75% uranyl-formate (unquantified low pH). The grids were observed on a Technai Spirit or JOEL 1230 transmission electron microscope operating between 80-120 kV with a magnification between 20,000 to 150,000 depending on required resolution.

Phospholipid Assay

This assay is based on the Wako Pure Chemical Industries, Ltd. assay Phospholipids C choline oxidase—DAOS method (Cat. No 433-36201). The assay protocol is modified only to reduce the amount of material used in the assay, and to decrease the sample dilution in the reaction relative to the general protocol from the vendor. To determine the lipid content of the RSV F sample, generate the color reagent by dissolving one bottle of Color Reagent with one bottle of Buffer (color reagent is stable for 1 week at 4° C.). Dilute the 300 mg/dL (3 mg/ml) phospholipid standard to 1.5, 1.0, 0.75, 0.5 and 0.25 mg/ml with distilled water. For each standard, a water blank and sample reaction, add to a microcentrifuge tube 10 μl of color reagent and 2 μl of either standard, distilled water (0 mg/ml standard) or sample. Centrifuge reactions briefly to ensure proper mixing and incubate the tubes for 15 min at 37° C. Record the absorbance at 595 nm for each standard point and generate a standard curve. Record the 595 nm absorbance for each sample and calculate the phospholipids concentration from the prepared calibration curve.

Immunogenicity in Cotton Rats

Immunogenicity of RSV F protein ectodomain polypeptides in the forms of monomers (uncleaved delp21 furx), rosettes of trimers (cleaved delp23 furdel), and trimers (fusion peptide deletion) were determined in cotton rats (*Sigmodon hispidus*) in two studies. In study 1 (FIGS. 8A and 8B), 10 cotton rats per group were vaccinated intramuscularly with 10 μg of monomers or rosettes (each adsorbed to aluminum hydroxide) on days 0 and 21. Serum anti-RSV F protein IgG and RSV neutralizing antibody titers were measured 2 weeks after the 1$^{st}$ vaccination (2wp1) and 2 weeks after the 2$^{nd}$ vaccination (2wp2), or 3 weeks after the 1$^{st}$ vaccination (3wp1) and 2 weeks after the 2$^{nd}$ vaccination (2wp2). Anti-RSV F protein IgG (FIG. 8A) was determined by ELISA using RSV F protein coated plates and horse radish peroxidase-conjugated chicken anti-cotton rat IgG detection antibody. Data are presented as $\log_{10}$ geometric mean titers (GMT)+standard deviations of individual cotton rats. RSV neutralization titers (FIG. 8B) were measured by plaque reduction neutralization test (PRNT). In brief, dilutions of heat-inactivated serum were preincubated with RSV Long, and then inoculated on HEp-2 cells in 12-well plates. After a 2 hour infection the inoculum was removed and cells were overlaid with agarose. Plaques were enumerated 5 days later by neutral red staining. The neutralization titer is defined as the reciprocal of the serum dilution producing at least a 60% reduction in number of plaques per well, relative to controls (no serum). Data are presented as $\log_{10}$ GMT+standard error of 2 pools of 5 cotton rats per group.

In study 2 (FIG. 8C), 9 cotton rats per group were immunized intramuscularly with the indicated doses of monomers, trimers, or rosettes (each adsorbed to aluminum hydroxide). Serum anti-RSV F protein IgG titers were measured 2wp1 as above.

Results

The soluble RSV F ecto-domain (with un-mutated furin cleavage sites) was expressed, but could not be purified from lipid and lipoprotein impurities derived from the host cells or culture media using size exclusion chromatography. These RSV F ecto-domain polypeptides elute in the SEC column void volume along with the lipid and lipoprotein contaminants.

Several constructs were prepared for making RSV F ecto-domain polypeptides that contain mutations to the furin cleavage sites, including the Furdel constructs. See, FIGS. 1A-1C. Polypeptides produced by expression of the Furdel constructs were secreted from the cells as an ~65 kDa uncleaved species. The Furdel mutation also prevents fusion peptide exposure, which in turn prevents rosette formation. As a result, soluble RSV F Furdel migrated in the included volume of a Superdex 200 preparatory column, resulting in separation from both the lipid debris, which eluted in the void volume, and insect protein impurity. These results show that RSV F ecto-domain polypeptides in which the furin cleavage sites have been mutated are produced as uncleaved polypeptide that can be purified by SEC. In addition, analysis of the uncleaved RSV F retention time was consistent with the polypeptides being monomers rather than trimers.

Whether the RSV F furdel polypeptides were monomers, trimers or a mixture of monomers and trimers was assessed further using analytical ultracentrifugation. Analytical ultracentrifugation studies were performed using protein purified from the monomer peak from the SEC purification. Sedimentation velocity data of the uncleaved RSV F showed a step pattern suggesting two species in solution. Analysis of the sedimentation velocity experiment showed that the uncleaved RSV F ecto-domain had a high population of monomer and a minor population of apparent trimer in the solution. Equilibrium run data was collected and attempts to fit the data to either an ideal monomer model or a monomer-trimer equilibrium model were performed. However, the residuals of the fits are poor, particularly toward the bottom of the cell where the protein concentration is higher. These observations suggested that the uncleaved RSV F ecto-domain polypeptides are predominantly a monomer with a smaller population which self associates (potentially as trimers) or aggregates at higher concentrations.

Further analysis of select RSV F protein ectodomain polypeptides was conducted using size exclusion (SEC) chromatography. FIGS. 6A-6D. The principle peaks containing monomers, trimers or rosettes of trimers are indicated by an asterisk in FIGS. 6A-6D, with the retention time of the Superdex P200 16/60 column (GE Healthcare) is indicated in milliliters. On a calibrated column, the approximate retention times of 47 mls, 65 mls and 77 mls correspond to the column void volume, the retention of F trimers and the retention of the monomers, respectively. In FIG. 6A, the uncleaved Delp23 Furdel (Δ23 Furdel) construct was purified from the monomer peak. When the uncleaved Delp23 Furdel RSV F antigen was treated with trypsin, the protein formed rosettes, which migrated on SEC in the void volume (FIG. 6B). The cleaved trimer species of RSV F fusion peptide deletion was purified from the trimer peak at approximately 65 mls retention time (FIG. 6C) while the uncleaved Delp21 Furx construct (Δp21 Furx) was purified from the monomer peak at approximately 77 mls (FIG. 6D).

Several RSV F protein ecto-domain polypeptides in uncleaved form or after trypsin cleavage were assessed by EM. The RSV F Furdel and delp23 Furdel constructs have arginine residues remaining in the furin cleavage site. These arginines are susceptible to trypsin cleavage. Upon cleavage, the uncleaved $F_0$ species was converted to the $F_1/F_2$ species, in which the fusion peptide is exposed. EM analysis confirmed that following trypsin cleavage the uncleaved RSV ecto-domains formed rosettes of trimers by virtue of their fusion peptides, as has been observed for related fusion proteins. The results are presented in the Table 3, and show that uncleaved RSV F protein ecto-domain polypeptides can be cleaved to form rosettes of trimers. The fusion peptide deleted construct, which is cleaved by furin, formed monodispersed trimers. See, also, FIGS. 7A-7D. Advantageously, producing rosettes of trimers in this way results in rosettes of trimers that are substantially free of lipid debris and lipoproteins.

The results of the immunogenicity studies showed that RSV F protein ectodomain polypeptides in the form of monomers (uncleaved delp21 furx), rosettes of trimers (cleaved delp23 furdel), and trimers (fusion peptide deletion) were immunogenic in cotton rats (*Sigmodon hispidus*), and induced neutralizing antibodies. FIG. 8A-8C.

TABLE 3

| Construct | Conformation by EM |
|---|---|
| RSV F wild type ecto-domain (cleaved in host cell during expression) | Rosettes of trimers associated with lipid debris |
| Trypsin-cleavable Furdel (purified monomer peak—uncleaved) | Variable. Some preparations show monodispersed trimers; others show little material visible by EM of negatively-stained material |
| Trypsin-cleavable Furdel (purified monomer peak—trypsin cleaved after purification) | Rosettes of trimers |
| Trypsin-cleavable delp23 furdel (purified monomer peak—uncleaved) | Variable. Some preparations show monodispersed trimers; others show little material visible by EM of negatively-stained material |
| Trypsin-cleavable delp23 Furdel (purified monomer peak—trypsin cleaved after purification) | Rosettes of trimers |
| Cleaved Fusion Peptide Deletion (purified monomer peak) | Monodispersed trimers |

Example 5

Methods for Making RSV F Subunit Antigens in Insect or CHO Cells

RSV F Antigen Purification from Insect Cells:

RSV F ectodomain subunits, including Delp21 Furx, Delp23 Furdel and Fusion Peptide Deletion constructs, were expressed in HiFive insect cells (Invitrogen) using the pFAST Bac baculovirus system. The RSV F subunit was purified from large scale expressions, 10-25 liters, via a two step chelating method that reduced the deleterious effect of the ferritin contaminent present in insect cell media, which can corrupt the chelating resin. $CuSO_4$ was added to media supernatant to a final concentration of 500 μM. Approximately ten to twenty milliliters of chelating resin (Chelating Resin, BioRad) was added to each 1 liter of media, the slurry was rocked for at least thirty minutes at 4° C., and the resin and media were separated using a gravity column. The resin was washed with approximately two-times the resin volume of equilibration buffer (25 mM Tris pH 7.5, 300 mM NaCl), and the F protein ecto-domain was eluted with approximately two-times the column volume of elution buffer (equilibration buffer with 250 mM imidazole). The elution was dialyzed against 25 mM Tris buffer pH 7.5, 300 mM NaCl and the resulting solution was loaded onto a 5 ml Hitrap chelation column charged with $NiSO_4$ (GE Healthcare). Bound protein was eluted with 25 mM Tris pH 7.5, 300 mM NaCl and a gradient of imidazole.

Elutions from the imidazole gradient in both cases were evaluated using anti-HIS6 western blots and/or Coomassie-stained SDS-PAGE gels. Fractions containing pure constructs were collected and concentrated to approximately 1 mg/ml using Millipore Centriprep concentrators and/or Vivaspin concentration units for subsequent analysis/purification by size exclusion chomatography.

SEC Analysis and Purification of RSV F Ectodomains

Size exclusion chromatography (SEC) was used to purify and analyze RSV F protein ectodomain uncleaved monomers and cleaved trimers. This method also allowed uncleaved RSV F protein ectodomains to be purified away from host cell or media derived lipid and lipoprotein contaminants. In the case of clean-rosette generation, the uncleaved Delp23 Furdel construct was initially purified as a monomer and subsequently protease treated and re-purified using SEC to purify homogeneous rosettes (see below). Two methods were developed for analysis of RSV F oligamerization, HPLC-SEC and FPLC-SEC, which may also serve as an efficient purification step.

HPLC-SEC was performed using a Biorad SEC column (18 mm) with a 25 mM Tris pH 7.5, 300 mM NaCl mobile phase. Using Biorad HPLC-SEC standards to calibrate the system, we found that the RSV rosettes (representing cleaved, postfusion conformations) elute in the column void volume of the analysis while RSV F monomers elute with an apparent molecular weight of approximately 75-85 kDa.

FPLC-SEC was performed on a GE Healthcare FPLC using a 16/60 Superdex 200 column with 25 mM Tris pH 7.5, 300 mM NaCl as a mobile phase. Using GE Healthcare High molecular weight standards to calibrate the system, we found that the RSV rosettes elute in the column void volume of the analysis, while RSV monodispersed trimers elute with an apparent molecular weight of approximately 140-160 kDa and RSV F monomers elute with an apparent molecular weight of approximately 75-85 kDa. For purification of RSV uncleaved Delp21 Furx or Delp23 Furdel (monomers) or Fusion Peptide Deletion (trimer) 0.5-2 mls of approximately 1 mg/ml chelation purified material was loaded on to an equilibrated Superdex P200 16/60 column with a flow rate between 0.5-2 mls/min and relevant fractions were collected.

Typsin Cleavage of Delp23 Furdel Constructs to Form Postfusion Rosettes

Trypsin from bovine plasma (Sigma Aldrich, T8802: 10,000-15,000 BAEE units/mg trypsin) was diluted to a 1 mg/ml concentration in 25 mM Tris pH 7.5, 300 mM NaCl. A 1 mg/ml solution of RSV F protein ecto-domain polypeptide (diluted in 25 mM Tris pH 7.5, 300 mM NaCl) was treated with one microliter of trypsin solution (final mass ratio 0.001:1 trypsin:RSV F or approximately 10-15 BAEE units of trypsin to each milligram of RSV F) for 1 hour at 37° C. Progress of the cleavage reaction was monitored by SDS-PAGE gel. The cleavage reaction was stopped using a trypsin inhibitor (Gibco Soy Bean Trypsin Inhibitor using equal mass of inhibitor to trypsin). It was found that an incubation period was required between the cleavage step and subsequent rosette purification to allow higher efficiency of monomer to rosette conversion. A one to 6 hour incubation period at 37° C. was given to provide higher rosette formation efficiency. The cleaved RSV F protein was further purified from unconverted monomer species using size exclusion chromatography (as described above) where homogeneous rosettes can be collected in the column void volume fractions.

RSV F Antigen Purification from CHO Cells:

RSV F Fusion Peptide Deletion constructs, which do not contain a HIS-tag, were purified by cation purification. CHO material containing expressed RSV F trimer antigen was concentrated to approximately one-tenth the original volume on a GE Healthcare hollow fiber cartridge concentration system (MWCO 10,000 kDa). The concentrated solution was then buffer exchanged four times with an equivalent volume of 25 mM Sodium Acetate pH 6.0, 25 mM NaCl. The resulting solution, containing concentrated RSV F trimer in the acetate/saline buffer, was loaded onto a precharged GE Healthcare HiTrap CM column which had been equilibrated with acetate/saline buffer. The protein was eluted from the column using a step gradient of 25 mM acetate buffer containing either 25, 150, 250, 500 or 1000 mM NaCl (the 250 mM and 500 mM NaCl fractions containing the bulk of the eluted material). This material could be further purified using a SEC purification similar to the protocol above.

Example 6

Immunogenicity of RSV F Subunits in Cotton Rats

The immunogenicity and protective capacity of RSV-F trimer (RSV-F-fusion-peptide-deletion-trun) and rosette (RSV-F-delp23-furdel-trunc,cleaved) subunits, each formulated with alum or MF59, was evaluated in the cotton rat model. The antigen used for ELISA in this study was RSV-F-fusion-peptide-deletion-trunc (Table 4). Neutralization was against infectious RSV, strain Long (Table 5). All combinations were immunogenic, eliciting high titer RSV-F-specific IgG and RSV neutralizing antibody responses that were boosted by a second vaccination, and afforded protection from nasal RSV challenge.

Methods

Vaccination and Challenge of Cotton Rats

Female cotton rats (*Sigmodon hispidis*) were obtained from Harlan Laboratories. Groups of animals were immunized intramuscularly (i.m., 100 µl) with the indicated vaccines on days 0 and 21. Serum samples were collected 3 weeks after the first immunization (3wp1) and 2 weeks after the second immunziation (2wp2). Immunized or unvaccinated control animals were challenged intranasally (i.n.) with $1\times10^5$ pfu RSV Long 4 weeks after the final immunization. Blood collection and RSV challenge were performed under anesthesia with 3% isoflurane using a precision vaporizer.

RSV F-Specific ELISA

Individual serum samples were assayed for the presence of RSV F-specific IgG by enzyme-linked immunosorbent assay (ELISA). ELISA plates (MaxiSorp 96-well, Nunc) were coated overnight at 4° C. with 1 µg/ml purified RSV F (fusion-peptide deletion-trunc) in PBS. After washing (PBS with 0.1% Tween-20), plates were blocked with Superblock Blocking Buffer in PBS (Thermo Scientific) for at least 1.5 hours at 37° C. The plates were then washed, serial dilutions of serum in assay diluent (PBS with 0.1% Tween-20 and 5% goat serum) from experimental or control cotton rats were added, and plates were incubated for 2 hours at 37° C. After washing, plates were incubated with horse radish peroxidase (HRP)-conjugated chicken anti-cotton rat IgG (Immunology Consultants Laboratory, Inc, diluted 1:5,000 in assay diluent) for 1 hour at 37° C. Finally, plates were washed and 100 µl of TMB peroxidase substrate solution (Kirkegaard & Perry Laboratories, Inc) was added to each well. Reactions were stopped by addition of 100 µl of 1M $H_3PO_4$, and absorbance was read at 450 nm using a plate reader. For each serum sample, a plot of optical density (OD) versus logarithm of the reciprocal serum dilution was generated by nonlinear regression (GraphPad Prism). Titers were defined as the reciprocal serum dilution at an OD of approximately 0.5 (normalized to a standard, pooled sera from RSV-infected cotton rats with a defined titer of 1:2500, that was included on every plate).

Micro Neutralization Assay

Serum samples were tested for the presence of neutralizing antibodies by microneutralization assay. Two-fold serial dilutions of heat inactivated (HI)-serum (in PBS with 5% HI-fetal bovine serum(FBS)) were added to an equal volume of RSV, strain Long previously titered to give approximately 115 PFU/25 Serum/virus mixtures were incubated for 2 hours at 37° C. and 5% CO2, to allow virus neutralization to occur, and then 25 µl of this mixture (containing approximately 115 PFU) was inoculated on duplicate wells of HEp-2 cells in 96 well plates. After 2 hours at 37° and 5% CO2, the cells were overlayed with 0.75% Methyl Cellulose/EMEM 5% HI-FBS and incubated for 42 hours. The number of infectious virus particles was determined by detection of syncytia formation by immunostaining followed by automated counting. The neutralization titer is defined as the reciprocal of the serum dilution producing at least a 60% reduction in number of synctia per well, relative to controls (no serum).

Viral Load

Viral load in the lung was determined by plaque assay. Specifically, lungs were harvested 5 days post RSV infection and one right lobe was placed into 2.5 ml Dulbecco's Modified Eagle Medium (DMEM, Invitrogen) with 25% sucrose and disrupted with a tissue homogenizer. Cell-free supernatants from these samples were stored at −80° C. To assay for infectious virus, dilutions of clarified lung homogenate (in PBS with 5% HI-FBS) were inoculated on confluent HEp-2 cell monolayers in a volume of 200 µl/well of a 12-well plate. After 2 hours with periodic gentle rocking (37° C., 5% $CO_2$), the inoculum was removed, and cells were overlaid with 1.5 ml of 1.25% SeaPlaque agarose (Lonza) in Eagle's Minimal Essential Medium (EMEM, Lonza) supplemented with 5% HI-FBS, glutamine, and antibiotics. After 3-4 days of incubation, cells were again overlaid with 1 ml of 1.25% agarose in EMEM (Sigma) containing 0.1% neutral red (Sigma). Plaques were counted one day later with the aid of a light box.

An alternative method for determining viral load is quantitative real-time PCR (qRT-PCR). Viral load can be determined by qRT-PCR using oligonucleotide primers specific for the RSV-F gene as described (I. Borg et al, Eur Respir J 2003; 21:944-51) with some modifications. Briefly, RNA is isolated from 140 µl of clarified lung homogenate, or from a known number of plaque forming units (PFU) of RSV (determined by plaque assay, and diluted in lung homogenate from uninfected animals), using the RNeasy kit (Qiagen) with a final elution volume of 100 µl $H_2O$. cDNA synthesis and PCR is performed in a single tube using the SuperScript III Platinum One-Step Quantitative RT-PCR kit (Invitrogen) with 5 µL of eluted RNA, 10 µM of each primer, and 50 µM of the probe (primers and probes from Integrated DNA Technologies). Forward primer: TTGGATCTG CAATCGCCA (SEQ ID NO:72). Reverse primer: CTTTT-GATCTTGTTCACTTCTCCTTCT (SEQ ID NO:73). Probe: 5'-carboxyfluorescein (FAM)-TGGCACTGCTG TATCTAAGGTCCTGCACT-tetramethylcarboxyrhodam ine(TAMRA)-3' (SEQ ID NO:74). Amplification and detection is performed with an ABI Prism 7900HT or 7500 (Applied Biosystems). A threshold cycle value (Ct) is defined for each sample as the cycle number at which the fluorescent signal first becomes detectable above a set threshold. PFU equivalents for each sample is then determined based on a standard curve of Ct verses the logarithm of defined copy number of viral RNA.

Results

The cotton rat as a model has been used extensively in the study of RSV pathogenesis and immunity because of the many similarities between RSV-induced disease in cotton rats and humans. Two important parallels are the efficacy of neutralizing antibodies and the enhanced lung histopathology associated with formalin-inactivated RSV vaccination. Cotton rats are also more susceptible to RSV infection than other small animals such as mice.

To evaluate the immunogenicity of our RSV-F subunit vaccines, groups of female cotton rats were vaccinated intramuscularly with various doses of trimers (RSV-F-fusion-peptide-deletion-trunc) or rosettes (RSV-F-delp23-furdel-trunc, cleaved), each formulated with either alum or MF59. In all cases, a single immunization was sufficient to induce both F-specific and neutralizing antibody in the serum when measured three weeks after the first vaccination (3wp1). All cotton rats were given a homologous booster immunization three weeks after the first, and this resulted in a significant increase in F-specific IgG and neutralizing antibody when measured two weeks later (2wp2). Generally, the immunogenicity of rosettes was equal to or greater than that of trimers, MF59 formulation enhanced titers more than alum formulation, and higher protein doses yielded higher titers, although there were some exceptions.

To determine the protective capacity of the subunit vaccines, all cotton rats were infected four weeks after the second vaccination with RSV by the nasal route and the viral load in the lung was measured five days later by plaque assay. In all cases, subunit vaccination conferred protection from challenge, as pulmonary viral loads in vaccinated cotton rats were greater than three orders of magnitude lower than unimmunized, but challenged control animals.

TABLE 4

F-specific serum IgG titer

| Serum collected | Protein dose (µg) | F-specific serum IgG titer[a] | | | |
|---|---|---|---|---|---|
| | | alum | | MF59 | |
| | | trimer | rosette | trimer | rosette |
| 3wp1 | 10 | 20276 | 36841 | 10251 | 22415 |
| | 1 | 18341 | 20802 | 3712 | 28610 |
| | 0.1 | 2698 | 6896 | 1065 | 8293 |
| 2wp2 | 10 | 103670 | 97174 | 130016 | 156144 |
| | 1 | 142331 | 102405 | 177441 | 299501 |
| | 0.1 | 11581 | 34354 | 50238 | 111099 |

[a]geometric mean titer for individual cotton rats (7-8 per group)
trimer immunogen was RSV-F-fusion-peptide-deletion-trunc
rosette immonogen was RSV-F-delp23-furdel-trun, cleaved.

TABLE 4A

Lung viral titer 5 days post RSV challenge[a]

| vaccination | Protein dose (µg) | viral titer[b] |
|---|---|---|
| none | — | 822760 |
| trimer/alum | 10 | 546 |
| | 1 | 636 |
| | 0.1 | 903 |
| rosette/alum | 10 | 305 |
| | 1 | 341 |
| | 0.1 | 548 |
| trimer/MF59 | 10 | 360 |
| | 1 | 301 |
| | 0.1 | 456 |
| rosette/MF59 | 10 | 244 |
| | 1 | 257 |
| | 0.1 | 716 |

[a]intranasal challenge with 1 x $10^5$ plaque-forming units (pfu) of RSV Long
[b]pfu/gram lung 5 days post challenge
Geometric mean titers of 7-8 individual cotton rats/group.
If an individual animal had a titer of <203 (limit of detection) it was assigned a titer of 100

TABLE 5

RSV serum neutralization titer

| Serum collected | Protein dose (μg) | RSV serum neutralization titer[a] | | | |
|---|---|---|---|---|---|
| | | alum | | MF59 | |
| | | trimer | rosette | trimer | rosette |
| 3wp1 | 10 | 628 | 1050 | 578 | 229 |
| | 1 | 208 | 633 | 165 | 205 |
| | 0.1 | 57 | 200 | 51 | 65 |
| 2wp2 | 10 | 3669 | 4015 | 3983 | 3436 |
| | 1 | 3369 | 2844 | 5728 | 3940 |
| | 0.1 | 744 | 1902 | 2414 | 2093 |

[a] 60% synctia reduction neutralization titers
geometric mean titer for two pools of 3-4 cotton rats per group Example 7

RSV RNA Vaccine

RNA Synthesis

Plasmid DNA encoding alphavirus replicon (FIGS. 4A-4F, SEQ ID NO:77) served as a template for synthesis of RNA in vitro. For these experiments the full length surface fusion glycoprotein of RSV (RSV-F) was used (FIGS. 4A-4F). Upon delivery of the replicons to eukaryotic cells, the positive-stranded RNA was translated to produce four non-structural proteins, which together replicated the genomic RNA and transcribed abundant subgenomic mRNAs encoding the heterologous gene product. Due to the lack of expression of the alphavirus structural proteins, replicons are incapable of inducing the generation of infectious particles. A bacteriophage (T7 or SP6) promoter upstream of the alphavirus cDNA facilitates the synthesis of the replicon RNA in vitro and the hepatitis delta virus (HDV) ribozyme immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion, Austin, TX). Following transcription, the template DNA was digested with TURBO DNase (Ambion, Austin, TX). The replicon RNA was precipitated with LiCl and reconstituted in nuclease-free water. Uncapped RNA was capped post-transcripionally with Vaccinia Capping Enzyme (VCE) using the ScriptCap m$^7$G Capping System (Epicentre Biotechnologies, Madison, WI) as outlined in the user manual. Post-transcriptionally capped RNA was precipitated with LiCl and reconstituted in nuclease-free water. The concentration of the RNA samples was determined by measuring the optical density at 260 nm. Integrity of the in vitro transcripts was confirmed by denaturing agarose gel electrophoresis.

Lipid Nanoparticle (Liposome) Formulation RV01(01)

1,2-dilinoleyloxy-N,N-dimethyl-3-aminopropane (DlinDMA) was synthesized using a previously published procedure [Heyes, J., Palmer, L., Bremner, K., MacLachlan, I. Cationic lipid saturation influences intracellular delivery of encapsulated nucleic acids. Journal of Controlled Release, 107: 276-287 (2005)]. 1, 2-Diastearoyl-sn-glycero-3-phosphocholine (DSPC) was purchased from Genzyme. Cholesterol was obtained from Sigma-Aldrich (St. Lois, MO). 1, 2-dimyristoyl-sn-glycero-3-phosphoethanolamine-N-[methoxy(polyethylene glycol)-2000] (ammonium salt) (PEG DMG 2000), 1, 2-dimyristoyl-sn-glycero-3-phosphoethanolamine-N-[methoxy(polyethylene glycol)-2000] (ammonium salt) was obtained from Avanti Polar Lipids (Alabaster, AL).

Fresh lipid stock solutions in ethanol were prepared. 37 mg of DlinDMA, 11.8 mg of DSPC, 27.8 mg of Cholesterol and 8.07 mg of PEG DMG 2000 were weighed and dissolved in 7.55 mL of ethanol. The freshly prepared lipid stock solution was gently rocked at 37° C. for about 15 minutes to form a homogenous mixture. Then, 7554 of the stock was added to 1.245 mL ethanol to make a working lipid stock solution of 2 mL. This amount of lipid was used to form LNPs with 250 μg RNA at a 8:1 N:P (Nitrogen to Phosphate) ratio. The protonatable nitrogen on DlinDMA (the cationic lipid) and phosphates on the RNA are used for this calculation. Each μg of self-replicating RNA molecule was assumed to contain 3 nmoles of anionic phosphate, each μg of DlinDMA was assumed to contain 1.6 nmoles of cationic nitrogen. A 2 mL working solution of RNA was also prepared from a stock solution of ~1 μg/μL in 100 mM citrate buffer (pH 6) (Teknova, Hollister, CA)). Three 20 mL glass vials (with stir bars) were rinsed with RNase Away solution (Molecular BioProducts, San Diego, CA) and washed with plenty of MilliQ water before use to decontaminate the vials of RNAses. One of the vials was used for the RNA working solution and the others for collecting the lipid and RNA mixes (as described below). The working lipid and RNA solutions were heated at 37° C. for 10 minutes before being loaded into 3 cc luer-lok syringes (BD Medical, Franklin Lakes, NJ). 2 mL of citrate buffer (pH 6) was loaded in another 3 cc syringe. Syringes containing RNA and the lipids were connected to a T mixer (PEEK™ 500 μm ID junction, Idex Health Science, Oak Harbor, WA) using FEP tubing([fluorinated ethylene-propylene] 2 mm ID×3 mm OD, Idex Health Science, Oak Harbor, WA). The outlet from the T mixer was also FEP tubing (2 mm ID×3 mm). The third syringe containing the citrate buffer was connected to a separate piece of tubing (2 mm ID×3 mm OD). All syringes were then driven at a flow rate of 7 mL/min using a syringe pump (kdScientific, model no. KDS-220, Holliston, MA). The tube outlets were positioned to collect the mixtures in a 20 mL glass vial (while stirring). The stir bar was taken out and the ethanol/aqueous solution was allowed to equilibrate to room temperature for 1 hour. 4 ml of the mixture was loaded into a 5 cc syringe (BD Medical), which was connected to a piece of FEP tubing (2 mm ID×3 mm OD, Idex Health Science, Oak Harbor, WA) and in another 5 cc syringe connected to an equal length of FEP tubing, an equal amount of 100 mM citrate buffer (pH 6) was loaded. The two syringes were driven at 7 mL/min flow rate using the syringe pump and the final mixture collected in a 20 mL glass vial (while stirring). Next, the mixture collected from the second mixing step (liposomes) were passed through a Mustang Q membrane (an anion-exchange support that binds and removes anionic molecules, obtained from Pall Corporation, AnnArbor, MI, USA). Before passing the liposomes, 4 mL of 1 M NaOH, 4 mL of 1 M NaCl and 10 mL of 100 mM citrate buffer (pH 6) were successively passed through the Mustang membrane. Liposomes were warmed for 10 minutes at 37° C. before passing through the mustang filter. Next, liposomes were concentrated to 2 mL and dialyzed against 10-15 volumes of 1×PBS (from Teknova) using the Tangential Flow Filtration (TFF)

system before recovering the final product. The TFF system and hollow fiber filtration membranes were purchased from Spectrum Labs (Rancho Dominguez, CA) and were used according to the manufacturer's guidelines. Polysulfone hollow fiber filtration membranes (part number P/N: X1AB-100-20P) with a 100 kD pore size cutoff and 8 cm² surface area were used. For in vitro and in vivo experiments, formulations were diluted to the required RNA concentration with 1×PBS (from Teknova).

Method of Preparing Cationic Emulsion 17 (CNE17)

Squalene, sorbitan trioleate (Span 85), and polyoxy-ethylene sorbitan monololeate (Tween 80) were obtained from Sigma (St. Louis, MO, USA). 1,2-Dioleoyl-3-trimethylammonium-propane (DOTAP) was purchased from Lipoid (Ludwigshafen Germany). Cationic nanoemulsions (CNEs) were prepared similarly to charged MF59 as previously described with minor modifications Ott, et al. Journal of Controlled Release, 79(1-3):1-5 (2002)). Briefly, oil soluble components (ie. Squalene, span 85, cationic lipids, lipid surfactants) were combined in a beaker, lipid components were dissolved in chloroform ($CHCl_3$) or dichloromethane (DCM). The resulting lipid solution was added directly to the oil plus span 85. The solvent was allowed to evaporate at room temperature for 2 hours in a fume hood prior to combining the aqueous phase and homogenizing the sample using an IKA T25 homogenizer at 24K RPM in order to provide a homogeneous feedstock. The primary emulsions were passed three to five times through a Microfluidezer M110S or M110PS homogenizer with an ice bath cooling coil at a homogenization pressure of approximately 15 k-20 k PSI (Microfluidics, Newton, MA). The 20 ml batch samples were removed from the unit and stored at 4° C. The table below describes the composition of CNE17.

TABLE 6

Composition of CNE17

| CNE | Cationic Lipid (+) | mg/ml + Lipid | Surfactant | Squalene | Buffer/water |
|---|---|---|---|---|---|
| CNE 17 | DOTAP (in DCM) | 1.40 | 0.5% SPAN 85 0.5% Tween 80 | 4.3% | 10 mM citrate buffer pH 6.5 |

RNA Complexation

The number of nitrogens in solution were calculated from the cationic lipid concentration, DOTAP for example has 1 nitrogen that can be protonated per molecule. The RNA concentration was used to calculate the amount of phosphate in solution using an estimate of 3 nmols of phosphate per microgram of RNA. By varying the amount of RNA:Lipid the N/P ratio can be modified. RNA was complexed to CNE17 at a nitrogen/phosphate ratios (N/P) of 10:1. Using these values the RNA was diluted to the appropriate concentration in RNase free water and added directly into an equal volume of emulsion while vortexing lightly. The solution was allowed to sit at room temperature for approximately 2 hours. Once complexed the resulting solution was diluted to the required concentration prior to administration.

Electroporation

Electroporation was a very effective method for the delivery of pDNA vaccines and this technique was used to deliver self-replicating RNA. Mice were anesthetized under isofluorane, both hind legs were closely shaven to expose the area on the limb to be treated. A dose of 30 ul of vaccine was injected to the calf muscle of the hind limb using a ½ cc insulin syringe. The muscle was electroporated using the Elgen® DNA Delivery System (Inovio, San Diego). The instrument parameters are as follows: 60V, 2 pulses each at 60 ms. Another dose was similarly delivered to the second limb, followed by electroporation.

Viral Replicon Particles (VRP)

To compare RNA vaccines to traditional RNA-vectored approaches for achieving in vivo expression of reporter genes or antigens, we utilized viral replicon particles (VRPs) produced in BHK cells by the methods described by Perri et al. In this system, the antigen (or reporter gene) replicons consisted of alphavirus chimeric replicons (VCR) derived from the genome of Venezuelan equine encephalitis virus (VEEV) engineered to contain the 3' terminal sequences (3' UTR) of Sindbis virus and a Sindbis virus packaging signal (PS) (see FIG. 2 of Perri et al). These replicons were packaged into VRPs by co-electroporating them into baby hamster kidney (BHK) cells along with defective helper RNAs encoding the Sindbis virus capsid and glycoprotein genes (see FIG. 2 of Perri et al). The VRPs were then harvested and titrated by standard methods and inoculated into animals in culture fluid or other isotonic buffers. Perri S, Greer C E, Thudium K, Doe B, Legg H, Liu H, Romero R E, Tang Z, Bin Q, Dubensky T W, Jr. et al (2003) An alphavirus replicon particle chimera derived from venezuelan equine encephalitis and sindbis viruses is a potent gene-based vaccine delivery vector. J Virol 77: 10394-10403

RSV F Trimer Subunit Vaccine

The RSV F trimer is a recombinant protein comprising the ectodomain of RSV F with a deletion of the fusion peptide region preventing association with other trimers. The resulting construct forms a homogeneous trimer, as observed by size exclusion chromatography, and has an expected phenotype consistent with a postfusion F conformation as observed by electron microscopy. The protein was expressed in insect cells and purified by virtue of a HIS-tagged in fusion with the construct's C-terminus followed by size exclusion chromatography using conventional techniques. The resulting protein sample exhibits greater than 95% purity. For the in vivo evaluation of the F-subunit vaccine, 100 µg/mL trimer protein was adsorbed on 2 mg/mL alum using 10 mM Histidine buffer, pH 6.3 and isotonicity adjusted with sodium chloride to 150 mM. F-subunit protein was adsorbed on alum overnight with gentle stirring at 2-8° C. The pH and osmolality of the final vaccine was targeted as 6.5-7.5 and 240-360 mOsm/kg. The vaccine was characterized for protein adsorption by SDS-PAGE (Invitrogen Corporation, USA) and for endotoxin content by LAL assay (Charles River Laboratories, USA). The vaccine was mixed by gentle inversion prior to immunization.

Murine Immunogenicity Studies

Groups of 10 female BALB/c mice aged 8-10 weeks and weighing about 20 grams were immunized at day 0 and day 21 with bleeds taken at days 14, 35 and 49. All animals were injected in the quadriceps in the two hind legs each getting an equivalent volume (50 µl per site) for a total of 100 µl of vaccine to deliver 10 µg antigen dose. When measurement of T cell responses was required, spleens were harvested at day 35 or 49.

Vaccination and Challenge of Cotton Rats

Female cotton rats (*Sigmodon hispidis*) were obtained from Harlan Laboratories. All experiments were approved and performed according to Novartis Animal Care and Use Committee. Groups of animals were immunized intramuscularly (i.m., 100 µl) with the indicated vaccines on days 0 and 21. Serum samples were collected 2 weeks after each immunization. Immunized or unvaccinated control animals were challenged intranasally (i.n.) with $1 \times 10^5$ PFU RSV 4 weeks after the final immunization. Blood collection and RSV challenge were performed under anesthesia with 3% isoflurane using a precision vaporizer.

Mouse T Cell Function Assays

Intracellular Cytokines Immunofluorescence Assay

Two to five spleens from identically vaccinated BALB/c mice were pooled and single cell suspensions were prepared for culture. Two antigen-stimulated cultures and two unstimulated cultures were established for each splenocyte pool. Antigen-stimulated cultures contained $1\times10^6$ splenocytes, RSV F peptide 85-93 ($1\times10^{-6}$M), RSV F peptide 249-258 ($1\times10^{-6}$M), RSV F peptide 51-66 ($1\times10^{-6}$ M), anti-CD28 mAb (1 mcg/mL), and Brefeldin A (1:1000). Unstimulated cultures did not contain RSV F peptides, and were otherwise identical to the stimulated cultures. After culturing for 6 hours at 37° C., cultures were processed for immunofluorescence. Cells were washed and then stained with fluorecently labeled anti-CD4 and anti-CD8 monoclonal antibodies (mAb). Cells were washed again and then fixed with Cytofix/cytoperm for 20 minutes. The fixed cells were then washed with Perm-wash buffer and then stained with fluorescently labeled mAbs specific for IFN-g, TNF-a, IL-2, and IL-5. Stained cells were washed and then analyzed on an LSR II flow cytometer. FlowJo software was used to analyze the acquired data. The CD4+8− and CD8+4− T cell subsets were analyzed separately. For each subset in a given sample the % cytokine-positive cells was determined. The % RSV F antigen-specific T cells was calculated as the difference between the % cytokine-positive cells in the antigen-stimulated cultures and the % cytokine-positive cells in the unstimulated cultures. The 95% confidence limits for the % antigen-specific cells were determined using standard methods (*Statistical Methods, 7th Edition*, G. W. Snedecor and W. G. Cochran).

Secreted Cytokines Assay

The cultures for the secreted cytokines assay were similar to those for the intracellular cytokines immunofluorescence assay except that Brefeldin A was omitted. Culture supernatants were collected after overnight culture at 37° C., and were analyzed for multiple cytokines using mouse Th1/Th2 cytokine kits from Meso Scale Discovery. The amount of each cytokine per culture was determined from standard curves produced using purified, recombinant cytokines supplied by the manufacturer.

RSV F-Specific ELISA

Individual serum samples were assayed for the presence of RSV F-specific IgG by enzyme-linked immunosorbent assay (ELISA). ELISA plates (MaxiSorp 96-well, Nunc) were coated overnight at 4° C. with 1 µg/ml purified RSV F (delp23-furdel-trunc uncleaved) in PBS. After washing (PBS with 0.1% Tween-20), plates were blocked with Superblock Blocking Buffer in PBS (Thermo Scientific) for at least 1.5 hours at 37° C. The plates were then washed, serial dilutions of serum in assay diluent (PBS with 0.1% Tween-20 and 5% goat serum) from experimental or control cotton rats were added, and plates were incubated for 2 hours at 37° C. After washing, plates were incubated with horse radish peroxidase (HRP)-conjugated chicken anti-cotton rat IgG (Immunology Consultants Laboratory, Inc, diluted 1:5,000 in assay diluent) for 1 hour at 37° C. Finally, plates were washed and 100 µl of TMB peroxidase substrate solution (Kirkegaard & Perry Laboratories, Inc) was added to each well. Reactions were stopped by addition of 100 µl of 1M $H_3PO_4$, and absorbance was read at 450 nm using a plate reader. For each serum sample, a plot of optical density (OD) versus logarithm of the reciprocal serum dilution was generated by nonlinear regression (GraphPad Prism). Titers were defined as the reciprocal serum dilution at an OD of approximately 0.5 (normalized to a standard, pooled sera from RSV-infected cotton rats with a defined titer of 1:2500, that was included on every plate).

Micro Neutralization Assay

Serum samples were tested for the presence of neutralizing antibodies by a plaque reduction neutralization test (PRNT). Two-fold serial dilutions of HI-serum (in PBS with 5% HI-FBS) were added to an equal volume of RSV Long previously titered to give approximately 115 PFU/25 µl. Serum/virus mixtures were incubated for 2 hours at 37° C. and 5% CO2, to allow virus neutralization to occur, and then 25 µl of this mixture (containing approximately 115 PFU) was inoculated on duplicate wells of HEp-2 cells in 96 well plates. After 2 hours at 37° C. and 5% CO2, the cells were overlayed with 0.75% Methyl Cellulose/EMEM 5% HI-FBS and incubated for 42 hours. The number of infectious virus particles was determined by detection of syncytia formation by immunostaining followed by automated counting. The neutralization titer is defined as the reciprocal of the serum dilution producing at least a 60% reduction in number of synctia per well, relative to controls (no serum).

Viral Load

Viral load in the lung was determined by plaque assay. Specifically, lungs were harvested 5 days post RSV infection and one right lobe was placed into 2.5 ml Dulbecco's Modified Eagle Medium (DMEM, Invitrogen) with 25% sucrose and disrupted with a tissue homogenizer. Cell-free supernatants from these samples were stored at −80° C. To assay for infectious virus, dilutions of clarified lung homogenate (in PBS with 5% heat-inactivated fetal bovine serum, HI-FBS) were inoculated on confluent HEp-2 cell monolayers in a volume of 200 µl/well of a 12-well plate. After 2 hours with periodic gentle rocking (37° C., 5% $CO_2$), the inoculum was removed, and cells were overlaid with 1.5 ml of 1.25% SeaPlaque agarose (Lonza) in Eagle's Minimal Essential Medium (EMEM, Lonza) supplemented with 5% HI-FBS, glutamine, and antibiotics. After 3-4 days of incubation, cells were again overlaid with 1 ml of 1.25% agarose in EMEM (Sigma) containing 0.1% neutral red (Sigma). Plaques were counted one day later with the aid of a light box.

Cotton Rat Lung Pathology

Five days after RSV challenge lungs were harvested and 4 lobes from each animal were collected and fixed with 10% neutral buffered formalin (NBF) by gentle intratracheal instillation followed by immersion fixation. Tissues were processed routinely to prepare hematoxylin & eosin-stained sections for microscopic examination. Findings were evaluated using a modification of previously published criteria [Prince G A, et al., 2001] for the following parameters: peribronchiolitis, alveolitis, bronchitis, perivascular cellular infiltrates, and interstitial pneumonitis. Lesions were graded on a 4-point semiquantitative scale. Minimal (+) change contained one or a few small foci; mild (++) change was composed of small- to medium-size foci; moderate (+++) change contained frequent and/or moderately-sized foci; and marked (++++) change showed extensive to confluent foci affecting most/all of the tissue.

Example 7

A—Cotton Rat RSV Challenge Study (CRIS14)

The A317 replicon, which expresses the surface fusion glycoprotein of RSV (RSV-F) was used for this experiment. Cotton rats (*Sigmodon hispidus*), 8 animals per group, were given bilateral intramuscular vaccinations (50 µL per leg) on days 0 and 21 with naked self-replicating RNA (A317, 1 µg or 10 µg), self-replicating RNA formulated in LNP [RV01 (01), A317, 0.1 µg or 1 µg), VRPs ($5\times10^6$ IU) expressing RSV-F, F-trimer/alum subunit (10 µg), or formalin inactivated RSV vaccine (5200 FI-pfu). Serum was collected for antibody analysis on days 14 (2wp1) and 35 (2wp2). All animals were challenged with $1\times10^5$ pfu RSV intranasally on day 49 and lungs were collected on day 54 (5dpc) for determination of viral load and lung pathology.

Results

TABLE 7

F-specific serum IgG titers on day 14 and 35

| vaccine | dose | F-specific IgG 2wp1 | F-specific IgG 2wp2 |
|---|---|---|---|
| A317 | 10 µg | 198 | 1599 |
| A317 | 1 µg | 78 | 526 |
| CNE17 | 1 µg | 408 | 4918 |
| CNE17 | 0.1 µg | 325 | 2512 |
| RV01(01) | 1 µg | 531 | 4351 |
| RV01(01) | 0.1 µg | 134 | 1033 |
| VRP | 5 × 106 IU | 961 | 5864 |
| F-trimer/alum | 10 µg | 3526 | 111893 |
| FI-RSV | 5200 FI-pfu | 17 | 2074 |
| none | | 5 | 5 |

F-specific serum IgG titers of cotton rats (Sigmodon hispidus), 8 animals per group, after intramuscular vaccinations on days 0 and 21. Serum was collected for antibody analysis on days 14 (2wp1) and 35 (2wp2), all animals were challenged with $1 \times 10^5$ pfu RSV intranasally on day 49. Lungs were collected on day 54 (5dpc) for determination of viral load and lung pathology. Data are represented as geometric mean titers of 8 individual cotton rats per group. If an individual animal had a titer of <25 (limit of detection) it was assigned a titer of 5.

TABLE 8

RSV serum neutralization titers on days 14 and 35

| vaccine | dose | PRNT60 2wp1 | PRNT60 2wp2 |
|---|---|---|---|
| A317 | 10 µg | 78 | 240 |
| A317 | 1 µg | 58 | 70 |
| CNE17 | 1 µg | 91 | 269 |
| CNE17 | 0.1 µg | 63 | 145 |
| RV01(01) | 1 µg | 103 | 667 |
| RV01(01) | 0.1 µg | 46 | 130 |
| VRP | 5 × 10⁶ IU | 149 | 683 |
| F-trimer/alum | 10 µg | 142 | >5120 |
| FI-RSV | 5200 FI-pfu | 28 | 38 |
| none | | 30 | <20 |

RSV serum neutralization titers of cotton rats (Sigmodon hispidus), 8 animals per group, after intramuscular vaccinations on days 0 and 21. Serum was collected for analysis on days 14 (2wp1) and 35 (2wp2). Data are represented as 60% plaque reduction neutralization titers. Geometric mean titer of 2 pools of 4 cotton rats per group. If an individual animal had a titer of <25 (limit of detection) it was assigned a titer of 5.

TABLE 9

Lung viral titers 5 days post RSV challenge

| vaccine | dose | pfu/g lung 5dpc |
|---|---|---|
| A317 | 10 µg | 397 |
| A317 | 1 µg | 659 |
| CNE17 | 1 µg | 414 |
| CNE17 | 0.1 µg | 572 |
| RV01(01) | 1 µg | 445 |
| RV01(01) | 0.1 µg | 716 |
| VRP | 5 × 10⁶ IU | 359 |
| F-trimer/alum | 10 µg | 190 |
| FI-RSV | 5200 FI-pfu | 5248 |
| none (challenged) | | 728618 |

Lung viral titers 5 days post RSV challenge of cotton rats (Sigmodon hispidus), 8 animals per group, after intramuscular vaccinations on days 0 and 21. All animals were challenged with $1 \times 10^5$ pfu RSV intranasally on day 49. Lungs were collected on day 54 (5dpc) for determination of viral load and lung pathology. Data are represented as plaque forming units per gram lung as determined by plaque assay. Geometric mean titers of 8 individual cotton rats per group. In an individual animal had a titer of <200 (limit of detection) it was assigned a titer of 100.

TABLE 10

Lung alveolitis scores 5 days post RSV challenge

| vaccine | dose | # of cotton rats with indicated alveolitis score | | | | |
|---|---|---|---|---|---|---|
| | | 0 | 1 | 2 | 3 | 4 |
| A3171 | 10 µg | 8 | | | | |
| A3171 | 1 µg | 8 | | | | |
| CNE17 | 1 µg | 8 | | | | |
| CNE17 | 0.1 µg | 7 | 1 | | | |
| RV01(01) | 1 µg | 6 | 2 | | | |
| RV01(01) | 0.1 µg | 8 | | | | |
| VRP | 5 × 10⁶ IU | 3 | 4 | 1 | | |
| F-trimer/alum | 10 µg | 7 | 1 | | | |
| FI-RSV | 5200 FI-pfu | | 1 | 4 | 3 | |
| none (challenged) | | 5 | 3 | | | |

Table 10. Lung alveolitis 5 days post RSV challenge of cotton rats (Sigmodon hispidus), 8 animals per group, after intramuscular vaccinations on days 0 and 21. All animals were challenged with $1 \times 10^5$ pfu RSV intranasally on day 49. Lungs were collected on day 54 (5 dpc) for determination of viral load and lung pathology. Lesions were graded on a 4-point semiquantitative scale. Minimal (1) change contained one or a few small foci; mild (2) change was composed of small- to medium-size foci; moderate (3) change contained frequent and/or moderately-sized foci; and marked (4) change showed extensive to confluent foci affecting most/all of the tissue.

Conclusions

One objective of this study was to determine the immunogenicity and protective capacity of replicon RNA in the cotton rat RSV model. Another objective was to evaluate the effect of Liposomes and CNE17 formulations on vaccine immunogenicity and efficacy. Unformulated replicon RNA induced serum F-specific IgG and RSV neutralizing antibodies after one vaccination, and this response was boosted by a second vaccination. Liposomes and CNE17 formulations were similarly effective in this model, boosting F-specific IgG titers to 1 µg replicon RNA approximately 8-fold and neutralization titers by 4-10-fold (CNE17 and Liposomes, respectively) after the second vaccination. All replicon RNA vaccines provided protection from a nasal RSV challenge, reducing the lung viral load great than 3 order of magnitude when measured 5 days later. The magnitude and protective capacity of the immune response generated by 1 µg replicon RNA formulated with Liposomes was within 2-fold the response elicited by 5×10⁶ VRPs. The alum adjuvanted trimer subunit elicited the highest total anti-F IgG ELISA titers, elicited the highest neutralization titers, and elicited the greatest degree of protection from RSV titers in the lung on challenge of any of the vaccine preparations tested in this study.

Example 7B

RSV-F Immunogenicity Study (10-1001)

The A317 replicon that expresses the surface fusion glycoprotein of RSV (RSV-F) was used for this experiment. BALB/c mice, 10 animals per group, were given bilateral intramuscular vaccinations (50 µL per leg) on days 0 and 21 with VRP's expressing RSV-F (1×10⁶ IU), naked self-replicating RNA (A317, 1 µg), self-replicating RNA delivered using electroporation (A317, 10 µg), self-replicating RNA formulated in liposomes [RV01(01), A317, 0.1 µg or 1 µg) and self-replicating RNA formulated with CNE17 (A317, 0.1 µg or 1 µg). Serum was collected for antibody analysis on days 14 (2wp1), 35 (2wp2) and 49 (4wp2). Spleens were harvested from 5 mice per group at day 49 (4wp2) for T cell analysis.

Results

TABLE 11

F-specific serum IgG titers on day 14

| 1 µg A317 | 0.1 µg RV01(01) | 1 µg RV01(01) | 0.1 µg CNE17 | 1 µg CNE17 | 10 µg A317 + EP | 1E6 IU VRP |
|---|---|---|---|---|---|---|
| 529 | 14385 | 19299 | 2429 | 3373 | 5 | 6041 |
| 1530 | 10713 | 19170 | 2060 | 4417 | 88 | 4912 |
| 2734 | 12756 | 13860 | 2012 | 1927 | 964 | 12923 |
| 2503 | 11546 | 17352 | 1887 | 3597 | 7235 | 7075 |
| 5539 | 15300 | 22094 | 3174 | 5731 | 2558 | 6829 |
| 1033 | 14072 | 21213 | 3904 | 2852 | 5105 | 4885 |
| 5110 | 18274 | 17915 | 1481 | 3739 | 9806 | 3680 |
| 1106 | 7873 | 15659 | 2345 | 4904 | 2787 | 9813 |
| 1493 | 17175 | 6669 | 3084 | 3824 | 2576 | 8631 |
| 3456 | 19730 | 13259 | 2497 | 3004 | 1858 | 6314 |
| GMT 1980 | 13731 | 15903 | 2398 | 3590 | 1180 | 6685 |

Table 11. (10-1001) F-specific serum IgG titers of mice, 10 animals per group, 14 days after intramuscular vaccination. Data are represented as titers for individual mice and the geometric mean titers of 10 individual mice per group. If an individual animal had a titer of <25 (limit of detection) it was assigned a titer of 5.

TABLE 12

F-specific serum IgG titers on day 35

| 1 µg A317 | 0.1 µg RV01(01) | 1 µg RV01(01) | 0.1 µg CNE17 | 1 µg CNE17 | 10 µg A317 + EP | 1E6 IU VRP |
|---|---|---|---|---|---|---|
| 958 | 128208 | 227021 | 48079 | 8473 | 14612 | 813045 |
| 12518 | 191729 | 212911 | 17589 | 58556 | 22805 | 365485 |
| 4839 | 315786 | 303987 | 8522 | 12053 | 32156 | 961601 |
| 10128 | 218147 | 335071 | 10985 | 20395 | 24090 | 349215 |
| 18451 | 225622 | 155976 | 30801 | 51514 | 31053 | 297526 |
| 9805 | 182693 | 519162 | 13372 | 26348 | 18105 | 207652 |
| 19154 | 185342 | 169332 | 5137 | 80686 | 23918 | 1580066 |
| 4490 | 82744 | 489441 | 47173 | 21014 | 9091 | 900889 |
| 14674 | 190010 | 131361 | 78232 | 61076 | 21006 | 822285 |
| 15223 | 553164 | 254500 | 24135 | 25499 | 9835 | 587121 |
| GMT 8532 | 201892 | 253687 | 20767 | 29111 | 19117 | 579033 |

Table 12. (10-1001) F-specific serum IgG titers of mice, 10 animals per group after intramuscular vaccinations on days 0 and 21. Serum was collected for antibody analysis on day 35 (2wp2). Data are represented as titers for individual mice and the geometric mean titers of 10 individual mice per group. If an individual animal had a titer of <25 (limit of detection) it was assigned a titer of 5.

TABLE 13

F-specific serum IgG titers on day 49

| 1 µg A317 | 0.1 µg RV01(01) | 1 µg RV01(01) | 0.1 µg CNE17 | 1 µg CNE17 | 10 µg A317 + EP | 1E6 IU VRP |
|---|---|---|---|---|---|---|
| 1248 | 140407 | 133787 | 52747 | 34245 | 30388 | 366771 |
| 12441 | 155669 | 182995 | 29352 | 128030 | 20768 | 209400 |
| 4967 | 203059 | 211020 | 10857 | 17016 | 53763 | 360615 |
| 14536 | 134253 | 488698 | 28800 | 57250 | 28373 | 191475 |
| 31556 | 370726 | 158816 | 44613 | 76576 | 34318 | 139148 |
| 13815 | 184738 | 185184 | 20314 | 42357 | 35736 | 63839 |
| 20495 | 141644 | 103026 | 4546 | 101445 | 34611 | 192101 |
| 4800 | 76711 | 312096 | 27476 | 47285 | 10138 | 177858 |
| 19159 | 143275 | 139811 | 68386 | 55865 | 23958 | 130218 |
| 26836 | 479594 | 230331 | 24360 | 52871 | 13624 | 174378 |
| GMT 10947 | 177168 | 194350 | 24891 | 53615 | 25888 | 180420 |

Table 13. (10-1001) F-specific serum IgG titers of mice, 10 animals per group, after intramuscular vaccinations on days 0 and 21. Serum was collected for antibody analysis on days 49 (4wp2). Data are represented as titers for individual mice and the geometric mean titers of 10 individual mice per group. If an individual animal had a titer of <25 (limit of detection) it was assigned a titer of 5.

TABLE 14

RSV serum neutralization titers on day 35

| A317, 1 µg 2wp2 | RV01(01) 0.1 µg 2wp2 | RV01(01) 1 µg 2wp2 | CNE17 0.1 µg 2wp2 | CNE17 1 µg 2wp2 | VRP 1E6 IU 2wp2 |
|---|---|---|---|---|---|
| NA | 143 | 106 | NA | NA | 265 |
| NA | 272 | 62 | NA | NA | 73 |
| NA | 294 | <40 | NA | NA | 77 |
| NA | 814 | 334 | NA | NA | 140 |
| NA | 67 | 86 | NA | NA | 290 |
| NA | 420 | 125 | NA | NA | 134 |
| NA | <40 | 566 | NA | NA | 466 |
| NA | 104 | 292 | NA | NA | 127 |
| NA | 241 | <40 | NA | NA | 75 |
| NA | 223 | 44 | NA | NA | 77 |
| GMT NA | 176 | 96 | NA | NA | 139 |

Table 14: (10-1001) RSV serum neutralization titers of mice, 10 animals per group, after intramuscular vaccinations on days 0 and 21. Serum was collected for analysis on day 35 (2wp2). Data are represented as 60% plaque reduction neutralization titers of individual mice and the geometric mean titer of 10 individual mice per group. If an individual animal had a titer of <40 (limit of detection) it was assigned a titer of 20. NA = not assayed.

TABLE 15

RSV serum neutralization titers on day 49

| A317, 1 µg 4wp2 | RV01(01) 0.1 µg 4wp2 | RV01(01) 1 µg 4wp2 | CNE17 0.1 µg 4wp2 | CNE17 1 µg 4wp2 | VRP 1E6 IU 4wp2 |
|---|---|---|---|---|---|
| <40 | 194 | 82 | <40 | <40 | 161 |
| <40 | 272 | 165 | <40 | 70 | 64 |
| <40 | 142 | <40 | <40 | <40 | 126 |
| <40 | 881 | 442 | <40 | 76 | 151 |
| <40 | 61 | 108 | 42 | 57 | 194 |
| <40 | 426 | 156 | 52 | <40 | 123 |
| <40 | 78 | 814 | <40 | <40 | 1033 |
| <40 | <40 | 291 | 173 | <40 | 174 |
| <40 | 246 | 103 | <40 | <40 | 122 |
| <40 | 574 | 396 | <40 | <40 | 76 |
| GMT <40 | 231 | 215 | 29 | 29 | 155 |

Table 15: (10-1001) RSV serum neutralization titers of mice, 10 animals per group, after intramuscular vaccinations on days 0 and 21. Serum was collected for analysis on day 49 (4wp2). Data are represented as 60% plaque reduction neutralization titers of individual mice and the geometric mean titer of 10 individual mice per group. If an individual animal had a titer of <40 (limit of detection) it was assigned a titer of 20. NA = not assayed.

TABLE 16

T cell responses at day 49

| 4wp2 splenic CD4 T cell responses | CD4+ CD8− splenic T cells: % cytokine-positive and specific for RSV F51-66 peptide | | | |
|---|---|---|---|---|
| | IFNg+ | IL2+ | IL5+ | TNFa+ |
| VRP 1E6 IU | 0.07 ± 0.06 | 0.04 ± 0.05 | 0.00 ± 0.02 | 0.10 ± 0.04 |
| 1 µg A317 | 0.00 ± 0.05 | 0.05 ± 0.04 | 0.00 ± 0.01 | 0.03 ± 0.02 |
| RV01(01) 1 µg | 0.04 ± 0.06 | 0.07 ± 0.05 | 0.00 ± 0.01 | 0.09 ± 0.03 |
| RV01(01) 0.1 µg | 0.06 ± 0.05 | 0.08 ± 0.04 | 0.00 ± 0.01 | 0.10 ± 0.03 |
| CNE17 1 µg | 0.00 ± 0.05 | 0.04 ± 0.04 | 0.00 ± 0.01 | 0.05 ± 0.02 |
| CNE17 0.1 µg | 0.00 ± 0.05 | 0.02 ± 0.04 | 0.00 ± 0.01 | 0.02 ± 0.02 |
| 10 µg vA317 + EP | 0.02 ± 0.06 | 0.04 ± 0.04 | 0.01 ± 0.01 | 0.05 ± 0.03 |
| none | 0.04 ± 0.06 | 0.00 ± 0.05 | 0.00 ± 0.02 | 0.00 ± 0.01 |

(10-1001) Frequencies of RSV F-specific CD4+ splenic T cells on day 49 (4wp2). Shown are net (antigen-specific) cytokine-positive frequency (%) ± 95% confidence half-interval. Net frequencies shown in bold indicate stimulated responses that were statistically significantly > 0.

TABLE 17

T cell responses at day 49

| 4wp2 splenic CD8 T cell responses | CD8+ CD4− splenic T cells: % cytokine-positive and specific for RSV F peptides F85-93 and F249-258 | | | |
|---|---|---|---|---|
| | IFNg+ | IL2+ | IL5+ | TNFa+ |
| VRP 1E6 IU | 3.48 ± 0.29 | 1.21 ± 0.18 | −0.03 ± 0.05 | 3.31 ± 0.28 |
| 1 µg A317 | 0.74 ± 0.15 | 0.46 ± 0.11 | −0.03 ± 0.04 | 0.70 ± 0.14 |
| RV01(01) 1 µg | 3.69 ± 0.28 | 1.43 ± 0.18 | −0.01 ± 0.04 | 3.44 ± 0.27 |
| RV01(01) 0.1 µg | 2.52 ± 0.23 | 1.10 ± 0.15 | 0.03 ± 0.03 | 2.31 ± 0.22 |
| CNE17 1 µg | 1.25 ± 0.17 | 0.60 ± 0.12 | 0.01 ± 0.03 | 1.15 ± 0.16 |
| CNE17 0.1 µg | 0.89 ± 0.15 | 0.49 ± 0.11 | −0.03 ± 0.04 | 0.83 ± 0.14 |
| 10 µg A317 + EP | 0.85 ± 0.15 | 0.53 ± 0.11 | 0.01 ± 0.04 | 0.72 ± 0.15 |
| none | 0.01 ± 0.07 | 0.00 ± 0.05 | −0.02 ± 0.05 | 0.02 ± 0.06 |

(10-1001) Frequencies of RSV F-specific CD8+ splenic T cells on day 49 (4wp2). Shown are net (antigen-specific) cytokine-positive frequency (%) ± 95% confidence half-interval. Net frequencies shown in bold indicate stimulated responses that were statistically significantly > 0.

Conclusions

Liposome formulation significantly enhanced immunogenicity, as determined by increased F-specific IgG titers (8-30-fold increase), neutralization titers, and CD4 and CD8 T cell responses, relative to the naked RNA control. Surprisingly, the F-specific IgG titers and neutralization titers for RV01(01) at both the 0.1 and 1.0 µg doses were equivalent to the VRP (1×10$^6$ IU). T cell responses for the LNP formulation were equivalent at the higher dose to the VRP (1×10$^6$ IU). Formulation of the self-replicating RNA with CNE17 significantly enhanced immunogenicity, as determined by increased F-specific IgG titers (2-5-fold increase), neutralization titers, and CD4 and CD8 T cell responses, relative to the naked RNA control. Electroporation of RNA enhanced immunogenicity relative to the naked RNA control, but was significantly lower than Liposome delivery.

Example 7C

RSV-F Immunogenicity Study (10-1018)

The A317 replicon that expresses the surface fusion glycoprotein of RSV (RSV-F) was used for this experiment. BALB/c mice, 8 animals per group, were given bilateral intramuscular vaccinations (50 µL per leg) on days 0 and 21 with VRP's expressing RSV-F (1×10$^6$ IU), naked self-replicating RNA (A306, 1, 0.1, 0.01 µg) and self-replicating RNA formulated in liposomes (RV01(01) using method 1 (A317, 10.0, 1.0, 0.1, 0.01 µg). Serum was collected for antibody analysis on days 14 (2wp1) and (2wp2). Spleens were harvested from 5 mice per group at day 49 (4wp2) for T cell analysis.

Results

RV01(01) liposome formulation had a Z average particle diameter of 158 nm with a polydispersity index of 0.14, the encapsulation efficiency was 96%. F-specific serum IgG titers on day 14 and 35 are shown in tables 18 and 19 and T cell responses at day 49 are shown in tables 20 and 21.

TABLE 18

F-specific serum IgG titers on day 14 and 35

| VRP | | A317 | | | | | |
|---|---|---|---|---|---|---|---|
| 1E6 IU | | 1 µg | | 0.1 µg | | 0.01 µg | |
| 2wp1 | 2wp2 | 2wp1 | 2wp2 | 2wp1 | 2wp2 | 2wp1 | 2wp2 |
| 6334 | 39539 | 772 | 4687 | 5 | 2334 | 143 | 1377 |
| 1500 | 14895 | 5 | 142 | 5 | 161 | 5 | 333 |
| 5450 | 38252 | 109 | 2972 | 5 | 145 | 5 | 5 |
| 1835 | 12831 | 5 | 3674 | 5 | 97 | 5 | 5 |

TABLE 18-continued

F-specific serum IgG titers on day 14 and 35

| VRP | | A317 | | | | | |
|---|---|---|---|---|---|---|---|
| 1E6 IU | | 1 µg | | 0.1 µg | | 0.01 µg | |
| 2wp1 | 2wp2 | 2wp1 | 2wp2 | 2wp1 | 2wp2 | 2wp1 | 2wp2 |
| 2277 | 30326 | 5 | 5003 | 5 | 1077 | 5 | 175 |
| 2818 | 33437 | 663 | 8258 | 221 | 457 | 5 | 5 |
| 2405 | 22551 | 257 | 845 | 5 | 1558 | 5 | 456 |
| 2137 | 19179 | 5 | 1765 | 5 | 5 | 5 | 180 |
| GMT 2735 | 24427 | 41 | 2144 | 8 | 259 | 8 | 73 |

Table 18: (10-1018) F-specific serum IgG titers of mice, 8 animals per group, after intramuscular vaccinations on days 0 and 21. Serum was collected for antibody analysis on days 14 (2wp1) and 35 (2wp2). Data are represented as individual mice and the geometric mean titers of 8 individual cotton rats per group. If an individual animal had a titer of <25 (limit of detection) it was assigned a titer of 5.

TABLE 19

F-specific serum IgG titers on day 14 and 35

| RV01(01) | | | | | | | |
|---|---|---|---|---|---|---|---|
| 10 µg | | 1 µg | | 0.1 µg | | 0.01 µg | |
| 2wp1 | 2wp2 | 2wp1 | 2wp2 | 2wp1 | 2wp2 | 2wp1 | 2wp2 |
| 5880 | 82689 | 7255 | 45018 | 4072 | 22174 | 619 | 2872 |
| 6126 | 42529 | 3009 | 22288 | 3974 | 27730 | 474 | 3603 |
| 8069 | 76263 | 5385 | 23561 | 3272 | 15328 | 914 | 2692 |
| 5966 | 108234 | 4148 | 53675 | 3968 | 24456 | 2011 | 11542 |
| 8590 | 57912 | 4210 | 37004 | 4950 | 13014 | 903 | 4684 |
| 7172 | 74162 | 2179 | 24179 | 2856 | 13694 | 1575 | 6720 |
| 8072 | 122796 | 1640 | 5994 | 4073 | 17849 | 438 | 16514 |
| 8706 | 83601 | 5725 | 28760 | 3797 | 17342 | 1058 | 13665 |
| GMT 7235 | 77338 | 3783 | 25790 | 3826 | 18325 | 879 | 6235 |

Table 19: Continued from 23A. (10-1018) F-specific serum IgG titers of mice, 8 animals per group, after intramuscular vaccinations on days 0 and 21. Serum was collected for antibody analysis on days 14 (2wp1) and 35 (2wp2). Data are represented as individual animals and the geometric mean titers (GMT) of 8 individual cotton rats per group. If an individual animal had a titer of <25 (limit of detection) it was assigned a titer of 5.

TABLE 20

T cell responses at day 49

| 4wp2 splenic T cell responses | CD4+ CD8− splenic T cells: % cytokine-positive and specific for RSV F51-66 peptide | | | |
|---|---|---|---|---|
| | IFNg+ | IL2+ | IL5+ | TNFa+ |
| VRP 1E6 IU | 0.00 ± 0.02 | 0.07 ± 0.02 | 0.00 ± 0.01 | 0.07 ± 0.03 |
| 1 µg A317 | 0.01 ± 0.01 | 0.03 ± 0.02 | 0.00 ± 0.01 | 0.03 ± 0.02 |
| 0.1 µg A317 | 0.00 ± 0.01 | 0.01 ± 0.01 | 0.00 ± 0.00 | 0.01 ± 0.01 |
| 0.01 µg A317 | 0.00 ± 0.00 | 0.01 ± 0.01 | 0.01 ± 0.01 | 0.00 ± 0.01 |
| RV01(01), 10 µg | 0.02 ± 0.01 | 0.05 ± 0.02 | 0.00 ± 0.00 | 0.06 ± 0.02 |
| RV01(01), 1 µg | 0.03 ± 0.02 | 0.08 ± 0.02 | 0.00 ± 0.01 | 0.09 ± 0.02 |
| RV01(01), 0.1 µg | 0.02 ± 0.01 | 0.03 ± 0.01 | 0.00 ± 0.01 | 0.03 ± 0.01 |
| RV01(01), 0.01 µg | 0.00 ± 0.00 | 0.02 ± 0.02 | 0.01 ± 0.01 | 0.02 ± 0.02 |
| none | 0.00 ± 0.01 | 0.00 ± 0.01 | 0.00 ± 0.01 | 0.01 ± 0.01 |

Frequencies of RSV F-specific CD4+ splenic T cells on day 49 (Expt. 10-1018, 4wp2). Shown are net (antigen-specific) cytokine-positive frequency (%) ± 95% confidence half-interval. Net frequencies shown in bold indicate stimulated responses that were statistically significantly > 0.

TABLE 21

T cell responses at day 49

| 4wp2 splenic T cell responses | CD8+ CD4− splenic T cells: % cytokine-positive and specific for RSV F peptides F85-93 and F249-258 | | | |
|---|---|---|---|---|
| | IFNg+ | IL2+ | IL5+ | TNFa+ |
| VRP 1E6 IU | 2.45 ± 0.21 | 0.58 ± 0.10 | 0.00 ± 0.01 | 2.64 ± 0.21 |
| 1 µg A317 | 1.68 ± 0.17 | 0.45 ± 0.09 | 0.00 ± 0.02 | 1.75 ± 0.18 |
| 0.1 µg A317 | 0.21 ± 0.07 | 0.08 ± 0.04 | 0.01 ± 0.02 | 0.30 ± 0.08 |
| 0.01 µg A317 | 0.06 ± 0.05 | 0.05 ± 0.03 | 0.01 ± 0.02 | 0.16 ± 0.06 |
| RV01(01), 10 µg | 3.32 ± 0.23 | 0.69 ± 0.11 | 0.00 ± 0.02 | 3.90 ± 0.25 |
| RV01(01), 1 µg | 1.81 ± 0.17 | 0.59 ± 0.10 | 0.00 ± 0.02 | 2.04 ± 0.20 |
| RV01(01), 0.1 µg | 0.91 ± 0.12 | 0.32 ± 0.07 | 0.00 ± 0.01 | 1.06 ± 0.14 |
| RV01(01), 0.01 µg | 0.58 ± 0.10 | 0.33 ± 0.08 | 0.00 ± 0.01 | 0.64 ± 0.11 |
| none | 0.01 ± 0.02 | 0.01 ± 0.01 | 0.00 ± 0.01 | 0.00 ± 0.05 |

F-specific splenic CD8+ T cell frequencies on day 49 (Expt. 10-1018, 4wp2). Shown are net (antigen-specific) cytokine-positive frequency (%) ± 95% confidence half-interval. Net frequencies shown in bold indicate stimulated responses that were statistically significantly > 0.

Conclusions

Liposome formulation significantly enhanced immunogenicity, as determined by increased F-specific IgG titers and T cell frequencies, relative to the naked RNA controls. The F-specific IgG titers and CD8 T cell frequencies for RV01 (01) at the 10 µg RNA dose were enhanced relative to the VRP group ($1 \times 10^6$ IU).

ADDITIONAL REFERENCES

The following references are hereby incorporated by reference for all that they teach.
1. *Fields Virology*. 4th edition, 2001.
2. Snell et al. (1997) *Virus Genes* 14:63-72.
3. Bembridge et al. (1999) *J Virol* 73: 10086-10094.
4. Li et al. (1998) *J Exp Med* 188:681-688
5. U.S. Pat. No. 6,060,308.
6. Yin et al. (2006) *Nature* 439:38-45.
7. Kim et al. (2007) *J Med Virol* 79: 820-828.
8. Yin et al. (2005) *Proc Natl Acad Sci USA*. 102(26):9288-93.
9. Chen et al. (2004) *J Virol* 78:4508-16.
10. Yang et at. (2002) *J Virol* 76:4634-42.
11. Harbury et al. (1993) *Science* 262:1401-1407.
12. Stevens et al. (2004) *Science* 303:1866-70.
13. Burkhard et al. (2001) *Trends Cell Biol* 11:82-88.
14. Section 5.5.2 of Proteins by Creighton (ISBN 0-7167-2317-4).
15. Yu (2002) *Adv Drug Deliv Rev* 54:1113-1129.
16. Muller et al. (2000) *Methods Enzymol* 328:261-282.
17. Beck & Brodsky (1998) *J Struct Biol* 122:17-29.
18. Lupas (1996) *Trends Biochem Sci* 21:375-382.
19. Adamson et al. (1993) *Curr Opin Biotechnol* 4:428-347.
20. Kammerer (1997) *Matrix Biol* 15:555-568.
21. Chao et al. (1998) *J Chromatog B Biomed Sci Appl* 715:307-329.
22. Arndt et al. (2002) *Structure* 10:1235-1248.
23. Liu & Lu (2002) *J Biol Chem* 277:48708-48713.
24. WO2006/011060.
25. Section 5.5.3 of Proteins by Creighton (ISBN 0-7167-2317-4).
26. Zhang & Chen (1999) *J Biol Chem* 274:22409-22413.
27. Slovic et al. (2003) *Protein Sci* 12:337-348
28. Gardner & Dutch (2007) *J Virol* 8 1:8303-14.
29. Gennaro (2000) *Remington: The Science and Practice of Pharmacy*. 20th edition, ISBN: 0683306472.
30. Nony et al. (2001) *Vaccine* 27:3645-51.
31. Greenbaum et al. (2004) *Vaccine* 22:2566-77.
32. Zurbriggen et al. (2003) *Expert Rev Vaccines* 2:295-304.
33. Piascik (2003) *J Am Pharm Assoc (Wash DC)*. 43:728-30.
34. Mann et al. (2004) *Vaccine* 22:2425-9.
35. Halperin et al. (1979) *Am J Public Health* 69:1247-50.
36. Herbert et al. (1979) *J Infect Dis* 140:234-8.
37. Chen et al. (2003) *Vaccine* 21:2830-6.
38. U.S. Pat. No. 6,355,271.
39. WO00/23105.
40. U.S. Pat. No. 5,057,540.
41. WO96/33739.
42. EP-A-0109942.
43. WO96/11711.
44. WO00/07621.
45. Barr et al. (1998) *Advanced Drug Delivery Reviews* 32:247-271.
46. Sjolanderet et al. (1998) *Advanced Drug Delivery Reviews* 32:321-338.
47. Pizza et al. (2000) *Int J Med Microbiol* 290:455-461.
48. WO95/17211.
49. WO98/42375.
50. Singh et al (2001) *J Cont Release* 70:267-276.
51. WO99/27960.
52. U.S. Pat. No. 6,090,406.
53. U.S. Pat. No. 5,916,588.
54. EP-A-0626169.
55. WO99/52549.
56. WO01/21207.
57. WO01/21152.
58. Dyakonova et al. (2004) *Int Immunopharmacol* 4(13): 1615-23.
59. FR-2859633.
60. Signorelli & Hadden (2003) *Int Immunopharmacol* 3(8):1177-86.
61. WO2004/064715.
62. De Libero et al, (2005) *Nature Reviews Immunology* 5:485-496
63. U.S. Pat. No. 5,936,076.
64. Old et al., *J Clin Investig,* 113:1631-1640
65. US2005/0192248
66. Yang et al. (2004) *Angew Chem Int Ed* 43:3818-3822
67. WO2005/102049.
68. Goffet et al (2004) *Am Chem Soc* 126:13602-13603
69. WO03/105769.
70. Cooper (1995) *Pharm Biotechnol* 6:559-80.
71. WO90/14837.
72. Podda & Del Giudice (2003) *Expert Rev Vaccines* 2:197-203.
73. Podda (2001) *Vaccine* 19: 2673-2680.
74. *Vaccine Design: The Subunit and Adjuvant Approach* (eds. Powell & Newman) Plenum Press 1995 (ISBN 0-306-44867-X).
75. *Vaccine Adjuvants: Preparation Methods and Research Protocols* (Volume 42 of *Methods in Molecular Medicine* series). ISBN: 1-59259-083-7. Ed. O'Hagan.
76. Allison & Byars (1992) *Res Immunol* 143:519-25.
77. Hariharan et al. (1995) *Cancer Res* 55:3486-9.
78. WO95/1 1700.
79. U.S. Pat. No.6,080,725.
80. WO2005/0971 81.
81. Tassignon et al. (2005) *J Immunol Meth* 305:188-98.
82. Myers et al. (1990) pages 145-156 of *Cellular and molecular aspects of endotoxin reactions.*
83. Ulrich (2000) Chapter 16 (pages 273-282) of reference 75.
84. Johnson et al. (1999) *J Med Chem* 42:4640-9.

85. Baldrick et al. (2002) *Regulatory Toxicol Pharmacol* 35:398-413.
86. U.S. Pat. No. 4,680,338.
87. U.S. Pat. No. 4,988,815.
88. WO92/15582.
89. Stanley (2002) *Clin Exp Dermatol* 27:57 1-577.
90. Wu et al. (2004) *Antiviral Res.* 64(2):79-83.
91. Vasilakos et al. (2000) *Cell Immunol.* 204(1):64-74.
92. U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,664,264, 6,664,265, 6,667,312, 6,677,347, 6,677,348, 6,677,349, 6,683,088, 6,703,402, 6,743,920, 6,800,624, 6,809,203, 6,888,000, and 6,924,293.
93. Jones (2003) *Curr Opin Investig Drugs* 4:214-218.
94. WO2004/060308.
95. WO2004/064759.
96. U.S. Pat. No. 6,924,271.
97. US2005/0070556.
98. U.S. Pat. No. 5,658,731.
99. U.S. Pat. No. 5,011,828.
100. WO2004/87 153.
101. U.S. Pat. No. 6,605,617.
102. WO02/18383.
103. WO2004/018455.
104. WO03/082272.
105. WO2006/002422.
106. Johnson et al. (1999) *Bioorg Med Chem Lett* 9:2273-2278.
107. Evans et al. (2003) *Expert Rev Vaccines* 2:219-229.
108. Andrianov et al. (1998) *Biomaterials* 19:109-115.
109. Payne et al. (1998) *Adv Drug Delivery Review* 31:185-196.
110. Thompson et al. (2003) *Methods in Molecular Medicine* 94:255-266.
111. Kandimalla et al. (2003) *Nucleic Acids Research* 31:2393-2400.
112. WO02/26757.
113. WO99/62923.
114. Krieg (2003) *Nature Medicine* 9:831-835.
115. McCluskie et al. (2002) *FEMS Immunology and Medical Microbiology* 32:179-185.
116. WO98/40100.
117. U.S. Pat. No. 6,207,646.
118. U.S. Pat. No. 6,239,116.
119. U.S. Pat. No. 6,429,199.
120. Kandimalla et al. (2003) *Biochemical Society Transactions* 31 (part 3): 654-658.
121. Blackwell et al. (2003) *J Immunol* 170:4061-4068.
122. Krieg (2002) *Trends Immunol* 23:64-65.
123. WO01/95935.
124. Kandimalla et al. (2003) *BBRC* 306:948-953.
125. Bhagat et al. (2003) *BBRC* 300:853-861.
126. WO03/035836.
127. WO01/22972.
128. Thompson et al. (2005) *J Leukoc Biol* 78: 'The low-toxicity versions of LPS, MPL® adjuvant and RC529, are efficient adjuvants for CD4+ T cells'.
129. UK patent application GB-A-22202 11.
130. WO94/21292.
131. WO94/00153.
132. WO95/17210.
133. WO96/26741.
134. WO93/19780.
135. WO03/011223.
136. Meraldi et al. (2003) *Vaccine* 21:2485-249 1.
137. Pajak et al. (2003) *Vaccine* 21:836-842.
138. U.S. Pat. No. 6,586,409.
139. Wong et al. (2003) *J Clin Pharmacol* 43(7):735-42.
140. US2005/0215517.

The entire teachings of all documents cited herein are hereby incorporated herein by reference.

---

The invention claimed is:

1. A respiratory syncytial virus (RSV)-F heterodimer comprising a F1 subunit, a F2 subunit, and an oligomerization domain, wherein:
   the F1 subunit comprises an amino acid sequence at least 95% identical to the F1 subunit of SEQ ID NO: 1;
   the F2 subunit comprises an amino acid sequence at least 95% identical to the F2 subunit of SEQ ID NO: 1; and
   the oligomerization domain is a trimerizing sequence from bacteriophage T4 fibritin comprising amino acid residues 3-29 of SEQ ID NO: 19.

2. The RSV-F heterodimer of claim 1, wherein the F1 subunit comprises an amino acid sequence at least 95% identical to amino acids 137-574 of SEQ ID NO: 1; and the F2 subunit comprises an amino acid sequence at least 95% identical to amino acids 22 to 109 of SEQ ID NO: 1.

3. The RSV-F heterodimer of claim 1, wherein the trimerizing sequence from bacteriophage T4 fibritin is attached to a C-terminus of the F1 subunit.

4. The RSV-F heterodimer of claim 3, wherein the trimerizing sequence is attached to the C-terminus of the F1 subunit with a linker sequence.

5. A RSV-F F1-F2 homotrimer comprising three RSV-F heterodimers of claim 1.

6. A nucleic acid encoding the RSV-F heterodimer of claim 1.

7. A vector comprising the nucleic acid of claim 6.

8. A host cell comprising the vector of claim 7.

9. A method of making a RSV-F heterodimer comprising a F1 subunit, a F2 subunit, and an oligomerization domain, wherein: the F1 subunit comprises an amino acid sequence at least 95% identical to the F1 subunit of SEQ ID NO: 1; the F2 subunit comprises an amino acid sequence at least 95% identical to the F2 subunit of SEQ ID NO: 1, and the oligomerization domain is a trimerizing sequence from bacteriophage T4 fibritin comprising amino acid residues 3-29 of SEQ ID NO: 19, the method comprising: culturing the host cell of claim 8 and recovering the heterodimer from a culture media.

10. An immunogenic composition comprising the RSV-F heterodimer of claim 1.

11. The immunogenic composition of claim 10, further comprising an adjuvant.

12. A method of inducing an immune response to RSV in a subject, the method comprising administering an effective amount of the immunogenic composition of claim 10 to the subject.

* * * * *

SEQUENCE LISTING

```
<160> NUMBER OF SEQ ID NOS: 112

<210> SEQ ID NO 1
<211> LENGTH: 574
<212> TYPE: PRT
<213> ORGANISM: Human respiratory syncytial virus

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125
```

```
Leu Ser Lys Lys Arg Lys Arg Arg Phe Leu Gly Phe Leu Leu Gly Val
            130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
530                 535                 540
```

```
Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 2
<211> LENGTH: 574
<212> TYPE: PRT
<213> ORGANISM: Human respiratory syncytial virus

<400> SEQUENCE: 2

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Arg Ala Arg Arg Glu Ala Pro
                100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Arg Leu Leu Pro Ile Val Asn
        195                 200                 205

Gln Gln Ser Cys Arg Ile Ser Asn Ile Glu Thr Val Ile Glu Phe Gln
    210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

```
Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
            565                 570

<210> SEQ ID NO 3
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Thr Pro Ala Thr Asn Asn Arg Ala Arg Lys Glu Leu Pro Arg Phe Met
1               5                   10                  15

Asn Tyr Thr Leu Asn Asn Ala Lys Lys Thr Asn Val Thr Leu Ser Lys
            20                  25                  30

Lys Arg Lys Lys Lys Phe Leu Gly Phe Leu Leu Gly Val Gly Ser Ala
        35                  40                  45

Ile Ala Ser
    50

<210> SEQ ID NO 4
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Thr Pro Ala Thr Asn Asn Arg Ala Arg Gln Glu Leu Pro Arg Phe Met
1               5                   10                  15
```

Asn Tyr Thr Leu Asn Asn Ala Lys Lys Thr Asn Val Thr Leu Ser Lys
            20                  25                  30

Lys Arg Phe Leu Gly Phe Leu Gly Val Gly Ser Ala Ile Ala Ser
        35                  40                  45

<210> SEQ ID NO 5
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Thr Pro Ala Thr Asn Asn Gln Ala Gln Asn Glu Leu Pro Gln Phe Met
1               5                   10                  15

Asn Tyr Thr Leu Asn Asn Ala Asn Asn Thr Asn Val Thr Leu Ser Gln
            20                  25                  30

Asn Gln Asn Gln Asn Phe Leu Gly Phe Leu Leu Gly Val Gly Ser Ala
        35                  40                  45

Ile Ala Ser
    50

<210> SEQ ID NO 6
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Thr Pro Ala Thr Asn Asn Gln Ala Gln Asn Glu Leu Pro Arg Phe Met
1               5                   10                  15

Asn Tyr Thr Leu Asn Asn Ala Lys Lys Thr Asn Val Thr Leu Ser Gln
            20                  25                  30

Asn Gln Asn Gln Asn Phe Leu Gly Phe Leu Leu Gly Val Gly Ser Ala
        35                  40                  45

Ile Ala Ser
    50

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Thr Pro Ala Thr Asn Asn Gln Ala Gln Asn Gln Asn Gln Asn Gln Asn
1               5                   10                  15

Phe Leu Gly Phe Leu Leu Gly Val Gly Ser Ala Ile Ala Ser
            20                  25                  30

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 8

Thr Pro Ala Thr Asn Asn Gln Ala Gln Asn Gln Asn Gln Asn Phe Leu
1               5                   10                  15

Gly Phe Leu Leu Gly Val Gly Ser Ala Ile Ala Ser
            20                  25

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Pro Ala Thr Asn Asn Arg Ala Arg Gln Gln Gln Gln Arg Phe Leu
1               5                   10                  15

Gly Phe Leu Leu Gly Val Gly Ser Ala Ile Ala Ser
            20                  25

<210> SEQ ID NO 10
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Thr Pro Ala Thr Asn Asn Arg Ala Arg Arg Glu Leu Pro Gln Phe Met
1               5                   10                  15

Asn Tyr Thr Leu Asn Asn Ala Gln Gln Thr Asn Val Thr Leu Ser Gln
            20                  25                  30

Asn Gln Asn Gln Asn Phe Leu Gly Phe Leu Leu Gly Val Gly Ser Ala
        35                  40                  45

Ile Ala Ser
    50

<210> SEQ ID NO 11
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Thr Pro Ala Thr Asn Asn Gln Ala Gln Asn Glu Leu Pro Gln Phe Met
1               5                   10                  15

Asn Tyr Thr Leu Asn Asn Ala Gln Gln Thr Asn Val Thr Leu Ser Lys
            20                  25                  30

Lys Arg Lys Arg Arg Phe Leu Gly Phe Leu Leu Gly Val Gly Ser Ala
        35                  40                  45

Ile Ala Ser
    50

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 12

Thr Pro Ala Thr Asn Asn Arg Ala Arg Arg Glu Leu Pro Arg Phe Met
1               5                   10                  15

Asn Tyr Thr Leu Asn Asn Ala Lys Lys Thr Asn Val Thr Leu Ser Lys
            20                  25                  30

Lys Arg Lys Arg Arg Ser Ala Ile Ala Ser
        35                  40

<210> SEQ ID NO 13
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Thr Pro Ala Thr Asn Asn Ile Glu Gly Arg Glu Leu Pro Arg Phe Met
1               5                   10                  15

Asn Tyr Thr Leu Asn Asn Ala Lys Lys Thr Asn Val Thr Leu Ser Lys
            20                  25                  30

Lys Ile Glu Gly Arg Phe Leu Gly Phe Leu Leu Gly Val Gly Ser Ala
        35                  40                  45

Ile Ala Ser
    50

<210> SEQ ID NO 14
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His Asn Val Asn Asp Lys Ile Glu Glu Ile Leu Ser Lys Ile
        35                  40                  45

Tyr His Ile Glu Asn Glu Ile Ala Arg Ile Lys Lys Leu Ile Gly Glu
    50                  55                  60

<210> SEQ ID NO 15
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His Asn Val Asn Glu Lys Phe His Gln Ile Glu Lys Glu Phe
        35                  40                  45

Ser Glu Val Glu Gly Arg Ile Gln Asp Leu Glu Lys

<210> SEQ ID NO 16
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Pro Leu Val Phe Pro Ser Asp Glu Phe Asp Ala Ser Ile Ser Gln Ile
1               5                   10                  15

Asn Glu Lys Ile Asn Gln Ile Leu Ala Phe Ile Arg Lys Ile Asp Glu
            20                  25                  30

Leu Leu His Asn Ile Asn
        35

<210> SEQ ID NO 17
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His Asn Val Asn Gly Ser Gly Tyr Ile Pro Glu Ala Pro Arg
        35                  40                  45

Asp Gly Gln Ala Tyr Val Arg Lys Asp Gly Glu Trp Val Leu Leu Ser
    50                  55                  60

Thr Phe Leu
65

<210> SEQ ID NO 18
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His Asn Val Asn Asn Lys Asn Asp Asp Lys Gly Ser Gly Tyr
        35                  40                  45

Ile Pro Glu Ala Pro Arg Asp Gly Gln Ala Tyr Val Arg Lys Asp Gly
    50                  55                  60

Glu Trp Val Leu Leu Ser Thr Phe Leu
65                  70

<210> SEQ ID NO 19
<211> LENGTH: 29
<212> TYPE: PRT
<213> ORGANISM: Unknown

```
<220> FEATURE:
<223> OTHER INFORMATION: Description of Unknown:
      Bacteriophage T4 fibritin sequence

<400> SEQUENCE: 19

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu
            20                  25

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Lys Gln Ile Glu Asp Lys Ile Glu Ile Leu Ser Lys Ile Tyr His
1               5                   10                  15

Ile Glu Asn Glu Ile Ala Arg Ile Lys Lys Leu Ile Gly Glu Ala
            20                  25                  30

<210> SEQ ID NO 21
<211> LENGTH: 574
<212> TYPE: PRT
<213> ORGANISM: Human respiratory syncytial virus

<400> SEQUENCE:

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Thr Asn Ile Met Ile Thr
    515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 22
<211> LENGTH: 1727
<212> TYPE: DNA
<213> ORGANISM: Human respiratory syncytial virus

<400> SEQUENCE: 22
atggaactgc tgatcctgaa ggccaacgcc atcaccacca tcctgaccgc cgtgaccttc     60
tgcttcgcca gcggcagaa catcaccgag gaattctacc agagcacctg cagcgccgtg    120
agcaagggct acctgagcgc cctgcggacc ggctggtaca ccagcgtgat caccatcgag    180
```

-continued

```
ctgtccaaca tcaaagaaaa caagtgcaac ggcaccgacg ccaaggtgaa actgatcaag      240
caggaactgg acaagtacaa gaacgccgtg accgagctgc agctgctgat gcagagcacc      300
cccgccacca caaccgggc cagaagagag ctgccccggt tcatgaacta cccctgaac        360 aacgccaaga aaaccaacgt gaccctgagc aagaagcgga gcggcggtt cctgggcttc       420 ctgctgggcg tgggcagcgc catcgccagc ggggtggccg tgtccaaggt gctgcacctg      480
gaaggcgagt gaacaagat caagtccgcc ctgctgtcca ccaacaaggc cgtggtgtcc       540
ctgagcaacg gcgtgagcgt gctgaccagc aaggtgctgg atctgaagaa ctacatcgac      600
aagcagctgc tgcccatcgt gaacaagcag agctgcagca tcagcaacat cgagaccgtg      660
atcgagttcc agcagaagaa caaccggctg ctggaaatca cccgggagtt cagcgtgaac      720
gccggcgtga ccacccccgt gagcacctac atgctgacca cagcgagct gctgtccctg       780 atcaatgaca tgcccatcac caacgaccag aaaaagctga tgagcaacaa cgtgcagatc      840
gtgcggcagc agagctactc catcatgagc atcatcaaag aagaggtgct ggcctacgtg      900
gtgcagctgc ccctgtacgg cgtgatcgac accccctgct ggaagctgca caccagcccc     960
ctgtgcacca ccaacaccaa agagggcagc aacatctgcc tgacccggac cgaccggggc     1020
tggtactgcg acaacgccgg cagcgtgagc ttcttccccc aagccgagac ctgcaaggtg     1080
cagagcaacc gggtgttctg cgacaccatg aacagcctga ccctgccctc cgaggtgaac     1140
ctgtgcaacg tggacatctt caaccccaag tacgactgca agatcatgac ctccaagacc     1200
gacgtgagca gctccgtgat cacctccctg ggcgccatcg tgagctgcta cggcaagacc     1260
aagtgcaccg ccagcaacaa gaaccgggc atcatcaaga ccttcagcaa cggctgcgac     1320
tacgtgagca acaagggcgt ggacaccgtg agcgtgggca cacactgta ctacgtgaat     1380 aagcaggaag caagagcct gtacgtgaag ggcgagccca tcatcaactt ctacgacccc     1440
ctggtgttcc ccagcgacga gttcgacgcc agcatcagcc aggtcaacga gaagatcaac     1500
cagagcctgg ccttcatccg gaagagcgac gagctgctgc acaatgtgaa tgccggcaag     1560
agcaccacca atatcatgat caccacaatc atcatcgtga tcattgtgat cctgctgtct     1620
ctgattgccg tgggcctgct gctgtactgc aaggcccgca gcaccctgt gaccctgtcc     1680 aaggaccagc tgtccggcat caacaatatc gccttctcca actgaag                  1727
```

<210> SEQ ID NO 23
<211> LENGTH: 588
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80
```

```
Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
```

```
                500             505             510
Leu His Asn Val Asn Ala Gly Lys Ser Thr Asn Ile Met Ile Thr
            515             520             525

Thr Ile Ile Ile Val Ile Ile Val Ile Leu Leu Ser Leu Ile Ala Val
                530             535             540

Gly Leu Leu Leu Tyr Cys Lys Ala Arg Ser Thr Pro Val Thr Leu Ser
545             550             555             560

Lys Asp Gln Leu Ser Gly Ile Asn Asn Ile Ala Phe Ser Asn Ser Gly
                565             570             575

Gly Ser Ala Gly Ser Gly His His His His His His
            580             585

<210> SEQ ID NO 24
<211> LENGTH: 1769
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atggaactgc tgatcctgaa ggccaacgcc atcaccacca tcctgaccgc cgtgaccttc      60
tgcttcgcca gcggccagaa catcaccgag gaattctacc agagcacctg cagcgccgtg     120
agcaagggct acctgagcgc cctgcggacc ggctggtaca ccagcgtgat caccatcgag     180
ctgtccaaca tcaaagaaaa caagtgcaac ggcaccgacg ccaaggtgaa actgatcaag     240
caggaactgg acaagtacaa gaacgccgtg accgagctgc agctgctgat gcagagcacc     300
cccgccacca caaccgggc cagaagagag ctgccccggt tcatgaacta cacctgaac     360 aacgccaaga aaaccaacgt gaccctgagc aagaagcgga agcggcggtt cctgggcttc     420
ctgctgggcg tgggcagcgc catcgccagc ggggtggccg tgtccaaggt gctgcacctg     480
gaaggcgagg tgaacaagat caagtccgcc ctgctgtcca ccaacaaggc cgtggtgtcc     540
ctgagcaacg gcgtgagcgt gctgaccagc aaggtgctgg atctgaagaa ctacatcgac     600
aagcagctgc tgcccatcgt gaacaagcag agctgcagca tcagcaacat cgagaccgtg     660
atcgagttcc agcagaagaa caaccggctg ctggaaatca cccgggagtt cagcgtgaac     720
gccggcgtga ccacccccgt gagcacctac atgctgacca cagcgagct gctgtccctg     780 atcaatgaca tgcccatcac caacgaccag aaaaagctga tgagcaacaa cgtgcagatc     840
gtgcggcagc agagctactc catcatgagc atcatcaaag aagaggtgct ggcctacgtg     900
gtgcagctgc ccctgtacgg cgtgatcgac accccctgct ggaagctgca ccagccccc     960 ctgtgcacca ccaacaccaa agagggcagc aacatctgcc tgacccggac cgaccggggc    1020
tggtactgcg acaacgccgg cagcgtgagc ttcttccccc aagccgagac tgcaaggtg    1080 cagagcaacc gggtgttctg cgacaccatg aacagcctga cctgccctc cgaggtgaac    1140 ctgtgcaacg tggacatctt caaccccaag tacgactgca gatcatgac ctccaagacc    1200 gacgtgagca gctccgtgat cacctccctg ggcgccatcg tgagctgcta cggcaagacc    1260
aagtgcaccg ccagcaacaa gaaccggggc atcatcaaga ccttcagcaa cggctgcgac    1320
tacgtgagca acaagggcgt ggacaccgtg agcgtgggca acacactgta ctacgtgaat    1380
aagcaggaag gcaagagcct gtacgtgaag ggcgagccca tcatcaactt ctacgacccc    1440
ctggtgttcc ccagcgacga gttcgacgcc agcatcagcc aggtcaacga gaagatcaac    1500
cagagcctgg ccttcatccg gaagagcgac gagctgctgc acaatgtgaa tgccggcaag    1560
```

```
agcaccacca atatcatgat caccacaatc atcatcgtga tcattgtgat cctgctgtct      1620
ctgattgccg tgggcctgct gctgtactgc aaggcccgca gcacccctgt gaccctgtcc      1680
aaggaccagc tgtccggcat caacaatatc gccttctcca acagcggcgg cagcgccggc      1740
tctggccacc accaccatca ccactgaag                                        1769
```

```
<210> SEQ ID NO 25
<211> LENGTH: 624
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25
```

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320
```

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn Gly Ser
            565                 570                 575

Ser Gly Arg Met Lys Gln Ile Glu Asp Lys Ile Glu Glu Ile Leu Ser
            580                 585                 590

Lys Ile Tyr His Ile Glu Asn Glu Ile Ala Arg Ile Lys Lys Leu Ile
            595                 600                 605

Gly Glu Ser Gly Gly Ser Ala Gly Ser Gly His His His His His His
            610                 615                 620

<210> SEQ ID NO 26
<211> LENGTH: 1877
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atggaactgc tgatcctgaa ggccaacgcc atcaccacca tcctgaccgc cgtgaccttc     60
tgcttcgcca gcggcagaa catcaccgag gaattctacc agagcacctg cagcgccgtg    120
agcaagggct acctgagcgc cctgcggacc ggctggtaca ccagcgtgat caccatcgag    180
ctgtccaaca tcaaagaaaa caagtgcaac ggcaccgacg ccaaggtgaa actgatcaag    240
caggaactgg acaagtacaa gaacgccgtg accgagctgc agctgctgat gcagagcacc    300

-continued

```
cccgccacca caaccgggc cagaagagag ctgccccggt tcatgaacta caccctgaac    360
aacgccaaga aaccaacgt gaccctgagc aagaagcgga agcggcggtt cctgggcttc    420
ctgctgggcg tgggcagcgc catcgccagc ggggtggccg tgtccaaggt gctgcacctg    480
gaaggcgagg tgaacaagat caagtccgcc ctgctgtcca ccaacaaggc cgtggtgtcc    540
ctgagcaacg gcgtgagcgt gctgaccagc aaggtgctgg atctgaagaa ctacatcgac    600
aagcagctgc tgcccatcgt gaacaagcag agctgcagca tcagcaacat cgagaccgtg    660
atcgagttcc agcagaagaa caaccggctg ctggaaatca cccgggagtt cagcgtgaac    720
gccggcgtga ccacccccgt gagcacctac atgctgacca cagcgagct gctgtccctg    780
atcaatgaca tgcccatcac caacgaccag aaaaagctga tgagcaacaa cgtgcagatc    840
gtgcggcagc agagctactc catcatgagc atcatcaaag aagaggtgct ggcctacgtg    900
gtgcagctgc ccctgtacgg cgtgatcgac acccctgct ggaagctgca caccagcccc    960
ctgtgcacca ccaacaccaa agagggcagc aacatctgcc tgacccggac cgaccggggc   1020
tggtactgcg acaacgccgg cagcgtgagc ttcttccccc aagccgagac ctgcaaggtg   1080
cagagcaacc gggtgttctg cgacaccatg aacagcctga ccctgcccctc cgaggtgaac   1140
ctgtgcaacg tggacatctt caaccccaag tacgactgca gatcatgac ctccaagacc    1200
gacgtgagca gctccgtgat cacctccctg ggcgccatcg tgagctgcta cggcaagacc   1260
aagtgcaccg ccagcaacaa gaaccggggc atcatcaaga ccttcagcaa cggctgcgac   1320
tacgtgagca caagggcgt ggacaccgtg agcgtgggca acacactgta ctacgtgaat    1380
aagcaggaag gcaagagcct gtacgtgaag ggcgagccca tcatcaactt ctacgacccc   1440
ctggtgttcc ccagcgacga gttcgacgcc agcatcagcc aggtcaacga aagatcaac    1500
cagagcctgg ccttcatccg gaagagcgac gagctgctgc acaatgtgaa tgccggcaag   1560
agcaccacca atatcatgat caccacaatc atcatcgtga tcattgtgat cctgctgtct   1620
ctgattgccg tgggcctgct gctgtactgc aaggcccgca gcaccctgt gaccctgtcc   1680
aaggaccagc tgtccggcat caacaatatc gccttctcca acggcagcag cggccggatg   1740
aagcagatcg aggacaagat cgaggaaatc ctgagcaaga tctaccacat cgagaacgag   1800
atcgcccgga tcaagaagct gatcggcgaa agcggcggct ctgccggaag cggccaccac   1860
caccatcacc actgaag                                                  1877
```

<210> SEQ ID NO 27
<211> LENGTH: 626
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80
```

```
Gln Glu Leu Asp Lys Tyr Lys Asn Ala Val Thr Leu Gln Leu Leu
                85                  90                  95

Met Gln Ser Thr Pro Ala Thr Asn Asn Arg Ala Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495
```

| | | | | | | | | | | | |
|---|---|---|---|---|---|---|---|---|---|---|---|
| Glu | Lys | Ile | Asn | Gln | Ser | Leu | Ala | Phe | Ile | Arg | Lys | Ser | Asp | Glu | Leu |
| | | | 500 | | | | 505 | | | | 510 | | | | |

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn Gly Ser
                565                 570                 575

Ser Gly Ser Gly Arg Met Lys Gln Ile Glu Asp Lys Ile Glu Glu Ile
            580                 585                 590

Leu Ser Lys Ile Tyr His Ile Glu Asn Glu Ile Ala Arg Ile Lys Lys
        595                 600                 605

Leu Ile Gly Glu Ser Gly Gly Ser Ala Gly Ser Gly His His His
    610                 615                 620

His His
625

<210> SEQ ID NO 28
<211> LENGTH: 1883
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
atggaactgc tgatcctgaa ggccaacgcc atcaccacca tcctgaccgc cgtgaccttc    60
tgcttcgcca gcggccagaa catcaccgag gaattctacc agagcacctg cagcgccgtg   120
agcaagggct acctgagcgc cctgcggacc ggctggtaca ccagcgtgat caccatcgag   180
ctgtccaaca tcaaagaaaa caagtgcaac ggcaccgacg ccaaggtgaa actgatcaag   240
caggaactgg acaagtacaa gaacgccgtg accgagctgc agctgctgat gcagagcacc   300
cccgccacca caaccgggc cagaagagag ctgccccggt tcatgaacta caccctgaac   360
aacgccaaga aaaccaacgt gaccctgagc aagaagcgga agcggcggtt cctgggcttc   420
ctgctgggcg tgggcagcgc catcgccagc ggggtggccg tgtccaaggt gctgcacctg   480
gaaggcgagg tgaacaagat caagtccgcc ctgctgtcca ccaacaaggc cgtggtgtcc   540
ctgagcaacg gcgtgagcgt gctgaccagc aaggtgctgg atctgaagaa ctacatcgac   600
aagcagctgc tgcccatcgt gaacaagcag agctgcagca tcagcaacat cgagaccgtg   660
atcgagttcc agcagaagaa caccggctg ctggaaatca cccgggagtt cagcgtgaac   720
gccggcgtga ccaccccccgt gagcacctac atgctgacca cagcgagct gctgtccctg   780
atcaatgaca tgcccatcac caacgaccag aaaaagctga tgagcaacaa cgtgcagatc   840
gtgcggcagc agagctactc catcatgagc atcatcaaag aagaggtgct ggcctacgtg   900
gtgcagctgc ccctgtacgg cgtgatcgac accccctgct ggaagctgca caccagcccc   960
ctgtgcacca ccaacaccaa agagggcagc aacatctgcc tgacccggac cgaccggggc  1020
tggtactgcg acaacgccgg cagcgtgagc ttcttccccc aagccgagac tgcaaggtg  1080
cagagcaacc gggtgttctg cgacaccatg aacagcctga cctgccctc cgaggtgaac  1140
ctgtgcaacg tggacatctt caaccccaag tacgactgca agatcatgac ctccaagacc  1200
gacgtgagca gctccgtgat cacctccctg ggcgccatcg tgagctgcta cggcaagacc  1260
```

```
aagtgcaccg ccagcaacaa gaaccggggc atcatcaaga ccttcagcaa cggctgcgac   1320
tacgtgagca acaagggcgt ggacaccgtg agcgtgggca acacactgta ctacgtgaat   1380
aagcaggaag gcaagagcct gtacgtgaag ggcgagccca tcatcaactt ctacgacccc   1440
ctggtgttcc ccagcgacga gttcgacgcc agcatcagcc aggtcaacga aagatcaac    1500 cagagcctgg ccttcatccg gaagagcgac gagctgctgc acaatgtgaa tgccggcaag   1560
agcaccacca atatcatgat caccacaatc atcatcgtga tcattgtgat cctgctgtct   1620
ctgattgccg tgggcctgct gctgtactgc aaggcccgca gcaccctgt gaccctgtcc    1680 aaggaccagc tgtccggcat caacaatatc gccttctcca acggcagcag cggcagcggc   1740
cggatgaagc agatcgagga caagatcgag gaaatcctga gcaagatcta ccacatcgag   1800
aacgagatcg cccggatcaa gaagctgatc ggcgaaagcg cggctctgc cggaagcggc    1860 caccaccacc atcaccactg aag                                           1883
```

<210> SEQ ID NO 29
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ser Gly Gly Ser Ala Gly Ser Gly His His His
        515                 520                 525

His His His
    530
```

<210> SEQ ID NO 30
<211> LENGTH: 1598
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
atggaactgc tgatcctgaa ggccaacgcc atcaccacca tcctgaccgc cgtgaccttc      60
tgcttcgcca gcggccagaa catcaccgag gaattctacc agagcacctg cagcgccgtg     120
agcaagggct acctgagcgc cctgcggacc ggctggtaca ccagcgtgat caccatcgag     180
ctgtccaaca tcaaagaaaa caagtgcaac ggcaccgacg ccaaggtgaa actgatcaag     240
caggaactgg acaagtacaa gaacgccgtg accgagctgc agctgctgat gcagagcacc     300
cccgccacca caaccgggc cagaagagag ctgccccggt tcatgaacta caccctgaac     360
```

```
aacgccaaga aaaccaacgt gaccctgagc aagaagcgga agcggcggtt cctgggcttc    420
ctgctgggcg tgggcagcgc catcgccagc ggggtggccg tgtccaaggt gctgcacctg    480
gaaggcgagg tgaacaagat caagtccgcc ctgctgtcca ccaacaaggc cgtggtgtcc    540
ctgagcaacg gcgtgagcgt gctgaccagc aaggtgctgg atctgaagaa ctacatcgac    600
aagcagctgc tgcccatcgt gaacaagcag agctgcagca tcagcaacat cgagaccgtg    660
atcgagttcc agcagaagaa caaccggctg ctggaaatca cccgggagtt cagcgtgaac    720
gccggcgtga ccaccccgt gagcacctac atgctgacca cagcgagct gctgtccctg    780 atcaatgaca tgcccatcac caacgaccag aaaaagctga tgagcaacaa cgtgcagatc    840
gtgcggcagc agagctactc catcatgagc atcatcaaag aagaggtgct ggcctacgtg    900
gtgcagctgc ccctgtacgg cgtgatcgac acccccctgct ggaagctgca caccagcccc    960
ctgtgcacca ccaacaccaa agagggcagc aacatctgcc tgacccggac cgaccggggc   1020
tggtactgcg acaacgccgg cagcgtgagc ttcttcccc aagccgagac ctgcaaggtg   1080
cagagcaacc gggtgttctg cgacaccatg aacagcctga ccctgcccctc cgaggtgaac   1140 ctgtgcaacg tggacatctt caaccccaag tacgactgca agatcatgac ctccaagacc   1200
gacgtgagca gctccgtgat cacctccctg ggcgccatcg tgagctgcta cggcaagacc   1260
aagtgcaccg ccagcaacaa gaaccggggc atcatcaaga ccttcagcaa cggctgcgac   1320
tacgtgagca acaagggcgt ggacaccgtg agcgtgggca acacactgta ctacgtgaat   1380
aagcaggaag gcaagagcct gtacgtgaag ggcgagccca tcatcaactt ctacgacccc   1440
ctggtgttcc ccagcgacga gttcgacgcc agcatcagcc aggtcaacga aagatcaac   1500 cagagcctgg ccttcatccg gaagagcgac gagctgctgc acaatgtgaa tagcggcggc   1560
agcgccggct ctggccacca ccaccatcac cactgaag                            1598
```

<210> SEQ ID NO 31
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
```

```
            130                 135                 140
Gly Ser Ala Ile Ala Ser Gly Val Ala Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Ser Asn Ile Glu Thr Val Ile Glu Phe Gln
                210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
                370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Asp Lys Ile Glu Glu Ile Leu Ser Lys Ile Tyr
                515                 520                 525

His Ile Glu Asn Glu Ile Ala Arg Ile Lys Lys Leu Ile Gly Glu Ser
                530                 535                 540

Gly Gly Ser Ala Gly Ser Gly His His His His His
545                 550                 555
```

<210> SEQ ID NO 32
<211> LENGTH: 1676
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
atggaactgc tgatcctgaa ggccaacgcc atcaccacca tcctgaccgc cgtgaccttc      60
tgcttcgcca gcggccagaa catcaccgag gaattctacc agagcacctg cagcgccgtg     120
agcaagggct acctgagcgc cctgcggacc ggctggtaca ccagcgtgat caccatcgag     180
ctgtccaaca tcaaagaaaa caagtgcaac ggcaccgacg ccaaggtgaa actgatcaag     240
caggaactgg acaagtacaa gaacgccgtg accgagctgc agctgctgat gcagagcacc     300
cccgccacca caaccgggc cagaagagag ctgccccggt tcatgaacta cacccctgaac   360
aacgccaaga aaccaacgt gaccctgagc aagaagcgga agcggcggtt cctgggcttc     420
ctgctgggcg tgggcagcgc catcgccagc ggggtggccg tgtccaaggt gctgcacctg     480
gaaggcgagg tgaacaagat caagtccgcc ctgctgtcca ccaacaaggc cgtggtgtcc     540
ctgagcaacg gcgtgagcgt gctgaccagc aaggtgctgg atctgaagaa ctacatcgac     600
aagcagctgc tgcccatcgt gaacaagcag agctgcagca tcagcaacat cgagaccgtg     660
atcgagttcc agcagaagaa caaccggctg ctggaaatca cccgggagtt cagcgtgaac     720
gccggcgtga ccacccccgt gagcacctac atgctgacca cagcgagct gctgtccctg     780
atcaatgaca tgcccatcac caacgaccag aaaaagctga tgagcaacaa cgtgcagatc     840
gtgcggcagc agagctactc catcatgagc atcatcaaag aagaggtgct ggcctacgtg     900
gtgcagctgc ccctgtacgg cgtgatcgac accccctgct ggaagctgca caccagcccc     960
ctgtgcacca ccaacaccaa agagggcagc aacatctgcc tgacccggac cgaccggggc    1020
tggtactgcg acaacgccgg cagcgtgagc ttcttccccc aagccgagac tgcaaggtg    1080
cagagcaacc gggtgttctg cgacaccatg aacagcctga cctgccctc cgaggtgaac   1140
ctgtgcaacg tggacatctt caaccccaag tacgactgca agatcatgac ctccaagacc    1200
gacgtgagca gctccgtgat cacctccctg ggcgccatcg tgagctgcta cggcaagacc    1260
aagtgcaccg ccagcaacaa gaaccggggc atcatcaaga ccttcagcaa cggctgcgac    1320
tacgtgagca acaagggcgt ggacaccgtg agcgtgggca acacactgta ctacgtgaat    1380
aagcaggaag gcaagagcct gtacgtgaag ggcgagccca tcatcaactt ctacgacccc    1440
ctggtgttcc ccagcgacga gttcgacgcc agcatcagcc aggtcaacga gaagatcaac    1500
cagagcctgg ccttcatccg gaagagcgac gagctgctgc acaatgtgaa tgacaagatc    1560
gaggaaatcc tgagcaagat ctaccacatc gagaacgaga tcgcccggat caagaagctg    1620
atcggcgaaa gcggcggctc tgccggaagc ggccaccacc accatcacca ctgaag        1676
```

<210> SEQ ID NO 33
<211> LENGTH: 615
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
    195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
```

```
                420             425             430
Lys Thr Phe Ser Asn Gly Cys Asp Tyr Val Ser Asn Lys Gly Val Asp
            435             440             445

Thr Val Ser Val Gly Asn Thr Leu Tyr Tyr Val Asn Lys Gln Glu Gly
        450             455             460

Lys Ser Leu Tyr Val Lys Gly Glu Pro Ile Ile Asn Phe Tyr Asp Pro
465             470             475             480

Leu Val Phe Pro Ser Asp Glu Phe Asp Ala Ser Ile Ser Gln Val Asn
                485             490             495

Glu Lys Ile Asn Gln Ser Leu Ala Phe Ile Arg Lys Ser Asp Glu Leu
            500             505             510

Leu His Asn Val Asn Ala Gly Lys Ser Thr Thr Asn Ile Met Ile Thr
        515             520             525

Thr Ile Ile Ile Val Ile Ile Val Ile Leu Leu Ser Leu Ile Ala Val
            530             535             540

Gly Leu Leu Leu Tyr Cys Lys Ala Arg Ser Thr Pro Val Thr Leu Ser
545             550             555             560

Lys Asp Gln Leu Ser Gly Ile Asn Asn Ile Ala Phe Ser Asn Gly Ser
                565             570             575

Ser Gly Asn Glu Lys Phe His Gln Ile Glu Lys Glu Phe Ser Glu Val
            580             585             590

Glu Gly Arg Ile Gln Asp Leu Glu Lys Ser Gly Gly Ser Ala Gly Ser
        595             600             605

Gly His His His His His His
    610             615

<210> SEQ ID NO 34
<211> LENGTH: 1850
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggaactgc tgatcctgaa ggccaacgcc atcaccacca tcctgaccgc cgtgaccttc     60
tgcttcgcca gcggccagaa catcaccgag gaattctacc agagcacctg cagcgccgtg    120
agcaagggct acctgagcgc cctgcggacc ggctggtaca ccagcgtgat caccatcgag    180
ctgtccaaca tcaaagaaaa caagtgcaac ggcaccgacg ccaaggtgaa actgatcaag    240
caggaactgg acaagtacaa gaacgccgtg accgagctgc agctgctgat gcagagcacc    300
cccgccacca caaccgggc agaagagag ctgccccggt tcatgaacta cacccctgaac    360 aacgccaaga aaaccaacgt gaccctgagc aagaagcgga gcggcggtt cctgggcttc    420 ctgctgggcg tgggcagcgc catcgccagc ggggtggccg tgtccaaggt gctgcacctg    480
gaaggcgagt gaacaagat caagtccgcc ctgctgtcca ccaacaaggc cgtggtgtcc    540
ctgagcaacg gcgtgagcgt gctgaccagc aaggtgctgg atctgaagaa ctacatcgac    600
aagcagctgc tgcccatcgt gaacaagcag agctgcagca tcagcaacat cgagaccgtg    660
atcgagttcc agcagaagaa caaccggctg ctggaaatca cccgggagtt cagcgtgaac    720
gccggcgtga ccaccccccgt gagcacctac atgctgacca cagcgagct gctgtccctg    780 atcaatgaca tgcccatcac caacgaccag aaaaagctga tgagcaacaa cgtgcagatc    840
gtgcggcagc agagctactc catcatgagc atcatcaaag aagaggtgct ggcctacgtg    900
```

```
gtgcagctgc ccctgtacgg cgtgatcgac accccctgct ggaagctgca caccagcccc    960
ctgtgcacca ccaacaccaa agagggcagc aacatctgcc tgacccggac cgaccggggc   1020
tggtactgcg acaacgccgg cagcgtgagc ttcttccccc aagccgagac ctgcaaggtg   1080
cagagcaacc gggtgttctg cgacaccatg aacagcctga ccctgccctc cgaggtgaac   1140
ctgtgcaacg tggacatctt caaccccaag tacgactgca agatcatgac ctccaagacc   1200
gacgtgagca gctccgtgat cacctccctg ggcgccatcg tgagctgcta cggcaagacc   1260
aagtgcaccg ccagcaacaa gaaccggggc atcatcaaga ccttcagcaa cggctgcgac   1320
tacgtgagca acaagggcgt ggacaccgtg agcgtgggca cacactgta ctacgtgaat   1380
aagcaggaag gcaagagcct gtacgtgaag ggcgagccca tcatcaactt ctacgacccc   1440
ctggtgttcc ccagcgacga gttcgacgcc agcatcagcc aggtcaacga aagatcaac    1500
cagagcctgg ccttcatccg gaagagcgac gagctgctgc acaatgtgaa tgccggcaag   1560
agcaccacca atatcatgat caccacaatc atcatcgtga tcattgtgat cctgctgtct   1620
ctgattgccg tgggcctgct gctgtactgc aaggcccgca gcacccctgt gaccctgtcc   1680
aaggaccagc tgtccggcat caacaatatc gccttctcca acggcagcag cggcaatgag   1740
aagttccacc agatcgagaa agaattcagc gaggtggagg gccggatcca ggacctggaa   1800
aagagcggcg gctctgccgg aagcggccac caccaccatc accactgaag              1850
```

```
<210> SEQ ID NO 35
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190
```

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Glu Lys Phe His Gln Ile Glu Lys Glu Phe Ser
        515                 520                 525

Glu Val Glu Gly Arg Ile Gln Asp Leu Glu Lys Ser Gly Gly Ser Ala
530                 535                 540

Gly Ser Gly His His His His His His
545                 550

<210> SEQ ID NO 36
<211> LENGTH: 1664
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
atggaactgc tgatcctgaa ggccaacgcc atcaccacca tcctgaccgc cgtgaccttc    60
tgcttcgcca gcggccagaa catcaccgag gaattctacc agagcacctg cagcgccgtg   120
agcaagggct acctgagcgc cctgcggacc ggctggtaca ccagcgtgat caccatcgag   180
ctgtccaaca tcaagaaaaa caagtgcaac ggcaccgacg ccaaggtgaa actgatcaag   240
caggaactgg acaagtacaa gaacgccgtg accgagctgc agctgctgat gcagagcacc   300
cccgccacca caaccgggc cagaagagag ctgccccggt tcatgaacta cacccctgaac  360
aacgccaaga aaccaacgt gaccctgagc aagaagcgga agcggcggtt cctgggcttc   420
ctgctgggcg tgggcagcgc catcgccagc ggggtggccg tgtccaaggt gctgcacctg   480
gaaggcgagg tgaacaagat caagtccgcc ctgctgtcca ccaacaaggc cgtggtgtcc   540
ctgagcaacg gcgtgagcgt gctgaccagc aaggtgctgg atctgaagaa ctacatcgac   600
aagcagctgc tgcccatcgt gaacaagcag agctgcagca tcagcaacat cgagaccgtg   660
atcgagttcc agcagaagaa caaccggctg ctggaaatca cccgggagtt cagcgtgaac   720
gccggcgtga ccacccccgt gagcacctac atgctgacca cagcgagct gctgtccctg   780
atcaatgaca tgcccatcac caacgaccag aaaaagctga tgagcaacaa cgtgcagatc   840
gtgcggcagc agagctactc catcatgagc atcatcaaag aagaggtgct ggcctacgtg   900
gtgcagctgc ccctgtacgg cgtgatcgac accccctgct ggaagctgca caccagcccc   960
ctgtgcacca ccaacaccaa agagggcagc aacatctgcc tgacccggac cgaccggggc  1020
tggtactgcg acaacgccgg cagcgtgagc ttcttccccc aagccgagac ctgcaaggtg  1080
cagagcaacc gggtgttctg cgacaccatg aacagcctga cctgccctc cgaggtgaac   1140
ctgtgcaacg tggacatctt caaccccaag tacgactgca agatcatgac ctccaagacc   1200
gacgtgagca gctccgtgat cacctccctg ggcgccatcg tgagctgcta cggcaagacc   1260
aagtgcaccg ccagcaacaa gaaccggggc atcatcaaga ccttcagcaa cggctgcgac   1320
tacgtgagca acaagggcgt ggacaccgtg agcgtgggca acacactgta ctacgtgaat   1380
aagcaggaag gcaagagcct gtacgtgaag ggcgagccca tcatcaactt ctacgacccc   1440
ctggtgttcc cagcgacga gttcgacgcc agcatcagcc aggtcaacga agatcaac    1500
cagagcctgg ccttcatccg gaagagcgac gagctgctgc acaatgtgaa tgagaagttc    1560
caccagatcg agaaagaatt cagcgaggtg gagggccgga tccaggacct ggaaaagagc  1620
ggcggctctg ccggaagcgg ccaccaccac catcaccact gaag                 1664
```

<210> SEQ ID NO 37
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Asn Ile Met Ile Thr Thr Ile
465                 470                 475                 480
```

```
Ile Ile Val Ile Ile Val Ile Leu Leu Ser Leu Ile Ala Val Gly Leu
            485                 490                 495

Leu Leu Tyr Cys Lys Ala Arg Ser Thr Pro Val Thr Leu Ser Lys Asp
        500                 505                 510

Gln Leu Ser Gly Ile Asn Asn Ile Ala Phe Ser Asn Met Gly Gly Ser
        515                 520                 525

His His His His His His
        530

<210> SEQ ID NO 38
<211> LENGTH: 1607
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atggaactgc tgatcctgaa ggccaacgcc atcaccacca tcctgaccgc cgtgaccttc      60
tgcttcgcca gcggccagaa catcaccgag gaattctacc agagcacctg cagcgccgtg     120
agcaagggct acctgagcgc cctgcggacc ggctggtaca ccagcgtgat caccatcgag     180
ctgtccaaca tcaaagaaaa caagtgcaac ggcaccgacg ccaaggtgaa actgatcaag     240
caggaactgg acaagtacaa gaacgccgtg accgagctgc agctgctgat gcagagcacc     300
cccgccacca caaccgggc cagaagagag ctgccccggt tcatgaacta cacctgaac     360 aacgccaaga aaaccaacgt gaccctgagc aagaagcgga agcggcggtt cctgggcttc     420
ctgctgggcg tgggcagcgc catcgccagc ggggtggccg tgtccaaggt gctgcacctg     480
gaaggcgagg tgaacaagat caagtccgcc ctgctgtcca ccaacaaggc cgtggtgtcc     540
ctgagcaacg gcgtgagcgt gctgaccagc aaggtgctgg atctgaagaa ctacatcgac     600
aagcagctgc tgcccatcgt gaacaagcag agctgcagca tcagcaacat cgagaccgtg     660
atcgagttcc agcagaagaa caaccggctg ctggaaatca cccgggagtt cagcgtgaac     720
gccggcgtga ccaccccgt gagcacctac atgctgacca cagcgagct gctgtccctg     780 atcaatgaca tgcccatcac caacgaccag aaaaagctga tgagcaacaa cgtgcagatc     840
gtgcggcagc agagctactc catcatgagc atcatcaaag aagaggtgct ggcctacgtg     900
gtgcagctgc ccctgtacgg cgtgatcgac acccctgct ggaagctgca caccagcccc     960
ctgtgcacca ccaacaccaa agagggcagc aacatctgcc tgacccggac cgaccggggc    1020
tggtactgcg acaacgccgg cagcgtgagc ttcttccccc aagccgagac ctgcaaggtg    1080
cagagcaacc gggtgttctg cgacaccatg aacagcctga cctgccctc cgaggtgaac    1140 ctgtgcaacg tggacatctt caaccccaag tacgactgca agatcatgac ctccaagacc    1200
gacgtgagca gctccgtgat cacctccctg ggcgccatcg tgagctgcta cggcaagacc    1260
aagtgcaccg ccagcaacaa gaaccggggc atcatcaaga ccttcagcaa cggctgcgac    1320
tacgtgagca acaagggcgt ggacaccgtg agcgtgggca acacactgta ctacgtgaat    1380
aagcaggaag gcaagagcct gtacgtgaag ggcgagccca atatcatgat caccacaatc    1440
atcatcgtga tcattgtgat cctgctgtct ctgattgccg tgggcctgct gctgtactgc    1500
aaggcccgca gcacccctgt gaccctgtcc aaggaccagc tgtccggcat caacaatatc    1560
gccttctccc acatgggggg ttctcatcat catcatcatc attgaag               1607

<210> SEQ ID NO 39
```

-continued

```
<211> LENGTH: 524
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
```

```
                    370                375                380
Asp Ile Phe Asn Pro Lys Tyr Asp Cys Lys Ile Met Thr Ser Lys Thr
385                 390                395                400

Asp Val Ser Ser Val Ile Thr Ser Leu Gly Ala Ile Val Ser Cys
            405                410                415

Tyr Gly Lys Thr Lys Cys Thr Ala Ser Asn Lys Asn Arg Gly Ile Ile
                420                425                430

Lys Thr Phe Ser Asn Gly Cys Asp Tyr Val Ser Asn Lys Gly Val Asp
            435                440                445

Thr Val Ser Val Gly Asn Thr Leu Tyr Val Asn Lys Gln Glu Gly
            450                455                460

Lys Ser Leu Tyr Val Lys Gly Glu Pro Ile Ile Asn Phe Tyr Asp Pro
465                 470                475                480

Leu Val Phe Pro Ser Asp Glu Phe Asp Ala Ser Ile Ser Gln Val Asn
                485                490                495

Glu Lys Ile Asn Gln Ser Leu Ala Phe Ile Arg Lys Ser Asp Glu Leu
                500                505                510

Leu His Asn Val Asn Ala Gly Lys Ser Thr Thr Asn
            515                520

<210> SEQ ID NO 40
<211> LENGTH: 1577
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atggaactgc tgatcctgaa ggccaacgcc atcaccacca tcctgaccgc cgtgaccttc      60
tgcttcgcca gcggccagaa catcaccgag gaattctacc agagcacctg cagcgccgtg     120
agcaagggct acctgagcgc cctgcggacc ggctggtaca ccagcgtgat caccatcgag     180
ctgtccaaca tcaaagaaaa caagtgcaac ggcaccgacg ccaaggtgaa actgatcaag     240
caggaactgg acaagtacaa gaacgccgtg accgagctgc agctgctgat gcagagcacc     300
cccgccacca caaccgggc cagaagagag ctgccccggt tcatgaacta caccctgaac     360
aacgccaaga aaccaacgt gaccctgagc aagaagcgga agcggcggtt cctgggcttc     420
ctgctgggcg tgggcagcgc catcgccagc ggggtggccg tgtccaaggt gctgcacctg     480
gaaggcgagg tgaacaagat caagtccgcc ctgctgtcca ccaacaaggc cgtggtgtcc     540
ctgagcaacg gcgtgagcgt gctgaccagc aaggtgctgg atctgaagaa ctacatcgac     600
aagcagctgc tgcccatcgt gaacaagcag agctgcagca tcagcaacat cgagaccgtg     660
atcgagttcc agcagaagaa caaccggctg ctggaaatca cccgggagtt cagcgtgaac     720
gccggcgtga ccaccccgt gagcacctac atgctgacca cagcgagct gctgtccctg     780 atcaatgaca tgcccatcac caacgaccag aaaaagctga tgagcaacaa cgtgcagatc     840
gtgcggcagc agagctactc catcatgagc atcatcaaag aagaggtgct ggcctacgtg     900
gtgcagctgc ccctgtacgg cgtgatcgac acccccctgct ggaagctgca caccagcccc     960
ctgtgcacca ccaacaccaa agagggcagc aacatctgcc tgacccggac cgaccggggc    1020
tggtactgcg acaacgccgg cagcgtgagc ttcttccccc aagccgagac ctgcaaggtg    1080
cagagcaacc gggtgttctg cgacaccatg aacagcctga cctgccctc cgaggtgaac    1140 ctgtgcaacg tggacatctt caaccccaag tacgactgca agatcatgac ctccaagacc    1200
```

```
gacgtgagca gctccgtgat cacctccctg ggcgccatcg tgagctgcta cggcaagacc    1260
aagtgcaccg ccagcaacaa gaaccggggc atcatcaaga ccttcagcaa cggctgcgac    1320
tacgtgagca acaagggcgt ggacaccgtg agcgtgggca acacactgta ctacgtgaat    1380
aagcaggaag gcaagagcct gtacgtgaag ggcgagccca tcatcaactt ctacgacccc    1440
ctggtgttcc ccagcgacga gttcgacgcc agcatcagcc aggtcaacga aagatcaac    1500 cagagcctgg ccttcatccg gaagagcgac gagctgctgc acaatgtgaa tgccggcaag    1560
agcaccacca attgaag                                                  1577

<210> SEQ ID NO 41
<211> LENGTH: 574
<212> TYPE: PRT
<213> ORGANISM: Human respiratory syncytial virus

<400> SEQUENCE: 41

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300
```

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 42
<211> LENGTH: 590
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu

```
            85              90              95
Met Gln Ser Thr Pro Ala Thr Asn Asn Arg Ala Arg Arg Glu Leu Pro
            100             105             110

Arg Phe Met Asn Tyr Thr Leu Asn Asn Ala Lys Lys Thr Asn Val Thr
            115             120             125

Leu Ser Lys Lys Arg Lys Arg Arg Phe Leu Gly Phe Leu Leu Gly Val
130             135             140

Gly Ser Ala Ile Ala Ser Gly Val Ala Val Ser Lys Val Leu His Leu
145             150             155             160

Glu Gly Glu Val Asn Lys Ile Lys Ser Ala Leu Leu Ser Thr Asn Lys
                165             170             175

Ala Val Val Ser Leu Ser Asn Gly Val Ser Val Leu Thr Ser Lys Val
            180             185             190

Leu Asp Leu Lys Asn Tyr Ile Asp Lys Gln Leu Leu Pro Ile Val Asn
            195             200             205

Lys Gln Ser Cys Ser Ile Ser Asn Ile Glu Thr Val Ile Glu Phe Gln
210             215             220

Gln Lys Asn Asn Arg Leu Leu Glu Ile Thr Arg Glu Phe Ser Val Asn
225             230             235             240

Ala Gly Val Thr Thr Pro Val Ser Thr Tyr Met Leu Thr Asn Ser Glu
                245             250             255

Leu Leu Ser Leu Ile Asn Asp Met Pro Ile Thr Asn Asp Gln Lys Lys
            260             265             270

Leu Met Ser Asn Asn Val Gln Ile Val Arg Gln Gln Ser Tyr Ser Ile
            275             280             285

Met Ser Ile Ile Lys Glu Glu Val Leu Ala Tyr Val Val Gln Leu Pro
290             295             300

Leu Tyr Gly Val Ile Asp Thr Pro Cys Trp Lys Leu His Thr Ser Pro
305             310             315             320

Leu Cys Thr Thr Asn Thr Lys Glu Gly Ser Asn Ile Cys Leu Thr Arg
                325             330             335

Thr Asp Arg Gly Trp Tyr Cys Asp Asn Ala Gly Ser Val Ser Phe Phe
            340             345             350

Pro Gln Ala Glu Thr Cys Lys Val Gln Ser Asn Arg Val Phe Cys Asp
            355             360             365

Thr Met Asn Ser Leu Thr Leu Pro Ser Glu Val Asn Leu Cys Asn Val
370             375             380

Asp Ile Phe Asn Pro Lys Tyr Asp Cys Lys Ile Met Thr Ser Lys Thr
385             390             395             400

Asp Val Ser Ser Ser Val Ile Thr Ser Leu Gly Ala Ile Val Ser Cys
                405             410             415

Tyr Gly Lys Thr Lys Cys Thr Ala Ser Asn Lys Asn Arg Gly Ile Ile
            420             425             430

Lys Thr Phe Ser Asn Gly Cys Asp Tyr Val Ser Asn Lys Gly Val Asp
            435             440             445

Thr Val Ser Val Gly Asn Thr Leu Tyr Tyr Val Asn Lys Gln Glu Gly
            450             455             460

Lys Ser Leu Tyr Val Lys Gly Glu Pro Ile Ile Asn Phe Tyr Asp Pro
465             470             475             480

Leu Val Phe Pro Ser Asp Glu Phe Asp Ala Ser Ile Ser Gln Ile Asn
                485             490             495

Glu Lys Ile Asn Gln Ile Leu Ala Phe Ile Arg Lys Ile Asp Glu Leu
            500             505             510
```

```
Leu His Asn Ile Asn Ala Gly Lys Ser Thr Thr Asn Gly Ser Gly Ser
        515                 520                 525

Gly Asp Asp Asp Asp Lys Gly Ser Gly Ser Gly Ile Met Ile Thr
530                 535                 540

Thr Ile Ile Ile Val Ile Ile Val Ile Leu Leu Ser Leu Ile Ala Val
545                 550                 555                 560

Gly Leu Leu Leu Tyr Cys Lys Ala Arg Ser Thr Pro Val Thr Leu Ser
                565                 570                 575

Lys Asp Gln Leu Ser Gly Ile Asn Asn Ile Ala Phe Ser Asn
                580                 585                 590

<210> SEQ ID NO 43
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
```

```
            275                 280                 285
Met Ser Ile Ile Lys Glu Glu Val Leu Ala Tyr Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Ile Asn
                485                 490                 495

Glu Lys Ile Asn Gln Ile Leu Ala Phe Ile Arg Lys Ile Asp Glu Leu
                500                 505                 510

Leu His Asn Ile Asn Ala Gly Lys Ser Thr Thr Asn Gly Ser Gly Ser
            515                 520                 525

Gly Leu Val Pro Arg Gly Ser Gly Ser Gly Ile Met Ile Thr Thr Ile
    530                 535                 540

Ile Ile Val Ile Ile Val Ile Leu Leu Ser Leu Ile Ala Val Gly Leu
545                 550                 555                 560

Leu Leu Tyr Cys Lys Ala Arg Ser Thr Pro Val Thr Leu Ser Lys Asp
                565                 570                 575

Gln Leu Ser Gly Ile Asn Asn Ile Ala Phe Ser Asn
            580                 585

<210> SEQ ID NO 44
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

-continued

```
Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Gln Glu Gly
450                 455                 460

Lys Ser Leu Tyr Val Lys Gly Glu Pro Ile Ile Asn Phe Tyr Asp Pro
```

```
                465                 470                 475                 480
Leu Val Phe Pro Ser Asp Glu Phe Asp Ala Ser Ile Ser Gln Ile Asn
                    485                 490                 495
Glu Lys Ile Asn Gln Ile Leu Ala Phe Ile Arg Lys Ile Asp Glu Leu
                500                 505                 510
Leu His Asn Ile Asn Ala Gly Lys Ser Thr Thr Asn Gly Ser Gly Ser
                515                 520                 525
Gly Ile Glu Gly Arg Gly Ser Gly Ser Gly Ile Met Ile Thr Thr Ile
                530                 535                 540
Ile Ile Val Ile Ile Val Ile Leu Leu Ser Leu Ile Ala Val Gly Leu
545                 550                 555                 560
Leu Leu Tyr Cys Lys Ala Arg Ser Thr Pro Val Thr Leu Ser Lys Asp
                565                 570                 575
Gln Leu Ser Gly Ile Asn Asn Ile Ala Phe Ser Asn
                580                 585

<210> SEQ ID NO 45
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
                20                  25                  30
Tyr Gln Ser Thr Cys Ser Ala Val Ser Lys Gly Tyr Leu Ser Ala Leu
                35                  40                  45
Arg Thr Gly Trp Tyr Thr Ser Val Ile Thr Ile Glu Leu Ser Asn Ile
                50                  55                  60
Lys Glu Asn Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Gln Ala Gln Asn Glu Leu Pro
                100                 105                 110
Arg Phe Met Asn Tyr Thr Leu Asn Asn Ala Lys Lys Thr Asn Val Thr
                115                 120                 125
Leu Ser Gln Asn Gln Asn Gln Asn Phe Leu Gly Phe Leu Leu Gly Val
                130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asp Lys Gln Leu Leu Pro Ile Val Asn
                195                 200                 205
Lys Gln Ser Cys Ser Ile Ser Asn Ile Glu Thr Val Ile Glu Phe Gln
                210                 215                 220
Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
            515                 520                 525

Gly Ser Gly His His His His His His
            530                 535

<210> SEQ ID NO 46
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
            50                  55                  60
```

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Gln Ala Gln Asn Glu Leu Pro
            100                 105                 110

Gln Phe Met Asn Tyr Thr Leu Asn Asn Ala Asn Asn Thr Asn Val Thr
            115                 120                 125

Leu Ser Gln Asn Gln Asn Gln Asn Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480
```

```
Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Thr Asn Gly Gly Ser Ala
        515                 520                 525

Gly Ser Gly His His His His His His
        530                 535

<210> SEQ ID NO 47
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Gln Asn Gln
            100                 105                 110

Asn Gln Asn Phe Leu Gly Phe Leu Leu Gly Val Gly Ser Ala Ile Ala
        115                 120                 125

Ser Gly Val Ala Val Ser Lys Val Leu His Leu Glu Gly Glu Val Asn
    130                 135                 140

Lys Ile Lys Ser Ala Leu Leu Ser Thr Asn Lys Ala Val Val Ser Leu
145                 150                 155                 160

Ser Asn Gly Val Ser Val Leu Thr Ser Lys Val Leu Asp Leu Lys Asn
                165                 170                 175

Tyr Ile Asp Lys Gln Leu Leu Pro Ile Val Asn Lys Gln Ser Cys Ser
            180                 185                 190

Ile Ser Asn Ile Glu Thr Val Ile Glu Phe Gln Gln Lys Asn Asn Arg
        195                 200                 205

Leu Leu Glu Ile Thr Arg Glu Phe Ser Val Asn Ala Gly Val Thr Thr
    210                 215                 220

Pro Val Ser Thr Tyr Met Leu Thr Asn Ser Glu Leu Leu Ser Leu Ile
225                 230                 235                 240

Asn Asp Met Pro Ile Thr Asn Asp Gln Lys Lys Leu Met Ser Asn Asn
                245                 250                 255

Val Gln Ile Val Arg Gln Gln Ser Tyr Ser Ile Met Ser Ile Ile Lys
            260                 265                 270

Glu Glu Val Leu Ala Tyr Val Val Gln Leu Pro Leu Tyr Gly Val Ile
        275                 280                 285

Asp Thr Pro Cys Trp Lys Leu His Thr Ser Pro Leu Cys Thr Thr Asn
    290                 295                 300
```

```
Thr Lys Glu Gly Ser Asn Ile Cys Leu Thr Arg Thr Asp Arg Gly Trp
305                 310                 315                 320

Tyr Cys Asp Asn Ala Gly Ser Val Ser Phe Pro Gln Ala Glu Thr
                325                 330                 335

Cys Lys Val Gln Ser Asn Arg Val Phe Cys Asp Thr Met Asn Ser Leu
            340                 345                 350

Thr Leu Pro Ser Glu Val Asn Leu Cys Asn Val Asp Ile Phe Asn Pro
        355                 360                 365

Lys Tyr Asp Cys Lys Ile Met Thr Ser Lys Thr Asp Val Ser Ser Ser
370                 375                 380

Val Ile Thr Ser Leu Gly Ala Ile Val Ser Cys Tyr Gly Lys Thr Lys
385                 390                 395                 400

Cys Thr Ala Ser Asn Lys Asn Arg Gly Ile Ile Lys Thr Phe Ser Asn
                405                 410                 415

Gly Cys Asp Tyr Val Ser Asn Lys Gly Val Asp Thr Val Ser Val Gly
            420                 425                 430

Asn Thr Leu Tyr Tyr Val Asn Lys Gln Glu Gly Lys Ser Leu Tyr Val
        435                 440                 445

Lys Gly Glu Pro Ile Ile Asn Phe Tyr Asp Pro Leu Val Phe Pro Ser
450                 455                 460

Asp Glu Phe Asp Ala Ser Ile Ser Gln Val Asn Glu Lys Ile Asn Gln
465                 470                 475                 480

Ser Leu Ala Phe Ile Arg Lys Ser Asp Glu Leu Leu His Asn Val Asn
                485                 490                 495

Ala Gly Lys Ser Thr Thr Asn Gly Gly Ser Ala Gly Ser Gly His His
            500                 505                 510

His His His His
        515

<210> SEQ ID NO 48
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Gln Asn Gln
            100                 105                 110

Asn Phe Leu Gly Phe Leu Leu Gly Val Gly Ser Ala Ile Ala Ser Gly
        115                 120                 125

Val Ala Val Ser Lys Val Leu His Leu Glu Gly Glu Val Asn Lys Ile
```

```
            130                 135                 140
Lys Ser Ala Leu Leu Ser Thr Asn Lys Ala Val Val Ser Leu Ser Asn
145                 150                 155                 160

Gly Val Ser Val Leu Thr Ser Lys Val Leu Asp Leu Lys Asn Tyr Ile
                165                 170                 175

Asp Lys Gln Leu Leu Pro Ile Val Asn Lys Gln Ser Cys Ser Ile Ser
                180                 185                 190

Asn Ile Glu Thr Val Ile Glu Phe Gln Gln Lys Asn Asn Arg Leu Leu
            195                 200                 205

Glu Ile Thr Arg Glu Phe Ser Val Asn Ala Gly Val Thr Thr Pro Val
        210                 215                 220

Ser Thr Tyr Met Leu Thr Asn Ser Glu Leu Leu Ser Leu Ile Asn Asp
225                 230                 235                 240

Met Pro Ile Thr Asn Asp Gln Lys Lys Leu Met Ser Asn Asn Val Gln
                245                 250                 255

Ile Val Arg Gln Gln Ser Tyr Ser Ile Met Ser Ile Ile Lys Glu Glu
                260                 265                 270

Val Leu Ala Tyr Val Val Gln Leu Pro Leu Tyr Gly Val Ile Asp Thr
            275                 280                 285

Pro Cys Trp Lys Leu His Thr Ser Pro Leu Cys Thr Thr Asn Thr Lys
        290                 295                 300

Glu Gly Ser Asn Ile Cys Leu Thr Arg Thr Asp Arg Gly Trp Tyr Cys
305                 310                 315                 320

Asp Asn Ala Gly Ser Val Ser Phe Phe Pro Gln Ala Glu Thr Cys Lys
                325                 330                 335

Val Gln Ser Asn Arg Val Phe Cys Asp Thr Met Asn Ser Leu Thr Leu
                340                 345                 350

Pro Ser Glu Val Asn Leu Cys Asn Val Asp Ile Phe Asn Pro Lys Tyr
            355                 360                 365

Asp Cys Lys Ile Met Thr Ser Lys Thr Asp Val Ser Ser Ser Val Ile
        370                 375                 380

Thr Ser Leu Gly Ala Ile Val Ser Cys Tyr Gly Lys Thr Lys Cys Thr
385                 390                 395                 400

Ala Ser Asn Lys Asn Arg Gly Ile Ile Lys Thr Phe Ser Asn Gly Cys
                405                 410                 415

Asp Tyr Val Ser Asn Lys Gly Val Asp Thr Val Ser Val Gly Asn Thr
                420                 425                 430

Leu Tyr Tyr Val Asn Lys Gln Glu Gly Lys Ser Leu Tyr Val Lys Gly
            435                 440                 445

Glu Pro Ile Ile Asn Phe Tyr Asp Pro Leu Val Phe Pro Ser Asp Glu
        450                 455                 460

Phe Asp Ala Ser Ile Ser Gln Val Asn Glu Lys Ile Asn Gln Ser Leu
465                 470                 475                 480

Ala Phe Ile Arg Lys Ser Asp Glu Leu Leu His Asn Val Asn Ala Gly
                485                 490                 495

Lys Ser Thr Thr Asn Gly Gly Ser Ala Gly Ser Gly His His His
                500                 505                 510

His His

<210> SEQ ID NO 49
<211> LENGTH: 514
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 49

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Gln Gln Gln Gln
            100                 105                 110

Arg Phe Leu Gly Phe Leu Leu Gly Val Gly Ser Ala Ile Ala Ser Gly
        115                 120                 125

Val Ala Val Ser Lys Val Leu His Leu Glu Gly Glu Val Asn Lys Ile
    130                 135                 140

Lys Ser Ala Leu Leu Ser Thr Asn Lys Ala Val Val Ser Leu Ser Asn
145                 150                 155                 160

Gly Val Ser Val Leu Thr Ser Lys Val Leu Asp Leu Lys Asn Tyr Ile
                165                 170                 175

Asp Lys Gln Leu Leu Pro Ile Val Asn Lys Gln Ser Cys Ser Ile Ser
            180                 185                 190

Asn Ile Glu Thr Val Ile Glu Phe Gln Gln Lys Asn Asn Arg Leu Leu
        195                 200                 205

Glu Ile Thr Arg Glu Phe Ser Val Asn Ala Gly Val Thr Thr Pro Val
    210                 215                 220

Ser Thr Tyr Met Leu Thr Asn Ser Glu Leu Leu Ser Leu Ile Asn Asp
225                 230                 235                 240

Met Pro Ile Thr Asn Asp Gln Lys Lys Leu Met Ser Asn Asn Val Gln
                245                 250                 255

Ile Val Arg Gln Gln Ser Tyr Ser Ile Met Ser Ile Ile Lys Glu Glu
            260                 265                 270

Val Leu Ala Tyr Val Val Gln Leu Pro Leu Tyr Gly Val Ile Asp Thr
    275                 280                 285

Pro Cys Trp Lys Leu His Thr Ser Pro Leu Cys Thr Thr Asn Thr Lys
290                 295                 300

Glu Gly Ser Asn Ile Cys Leu Thr Arg Thr Asp Arg Gly Trp Tyr Cys
305                 310                 315                 320

Asp Asn Ala Gly Ser Val Ser Phe Phe Pro Gln Ala Glu Thr Cys Lys
                325                 330                 335

Val Gln Ser Asn Arg Val Phe Cys Asp Thr Met Asn Ser Leu Thr Leu
            340                 345                 350

Pro Ser Glu Val Asn Leu Cys Asn Val Asp Ile Phe Asn Pro Lys Tyr
        355                 360                 365

Asp Cys Lys Ile Met Thr Ser Lys Thr Asp Val Ser Ser Ser Val Ile
    370                 375                 380

Thr Ser Leu Gly Ala Ile Val Ser Cys Tyr Gly Lys Thr Lys Cys Thr
385                 390                 395                 400
```

```
Ala Ser Asn Lys Asn Arg Gly Ile Ile Lys Thr Phe Ser Asn Gly Cys
            405                 410                 415

Asp Tyr Val Ser Asn Lys Gly Val Asp Thr Val Ser Val Gly Asn Thr
            420                 425                 430

Leu Tyr Tyr Val Asn Lys Gln Glu Gly Lys Ser Leu Tyr Val Lys Gly
            435                 440                 445

Glu Pro Ile Ile Asn Phe Tyr Asp Pro Leu Val Phe Pro Ser Asp Glu
        450                 455                 460

Phe Asp Ala Ser Ile Ser Gln Val Asn Glu Lys Ile Asn Gln Ser Leu
465                 470                 475                 480

Ala Phe Ile Arg Lys Ser Asp Glu Leu Leu His Asn Val Asn Ala Gly
            485                 490                 495

Lys Ser Thr Thr Asn Gly Gly Ser Ala Gly Ser Gly His His His His
            500                 505                 510

His His
```

```
<210> SEQ ID NO 50
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Lys Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Lys Lys Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
        515                 520                 525

Gly Ser Gly His His His His His His
    530                 535

<210> SEQ ID NO 51
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile

```
                50                  55                  60
Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Gln Glu Leu Pro
                100                 105                 110

Arg Phe Met Asn Tyr Thr Leu Asn Asn Ala Lys Lys Thr Asn Val Thr
                115                 120                 125

Leu Ser Lys Lys Arg Phe Leu Gly Phe Leu Leu Gly Val Gly Ser Ala
                130                 135                 140

Ile Ala Ser Gly Val Ala Val Ser Lys Val Leu His Leu Glu Gly Glu
145                 150                 155                 160

Val Asn Lys Ile Lys Ser Ala Leu Leu Ser Thr Asn Lys Ala Val Val
                165                 170                 175

Ser Leu Ser Asn Gly Val Ser Val Leu Thr Ser Lys Val Leu Asp Leu
                180                 185                 190

Lys Asn Tyr Ile Asp Lys Gln Leu Leu Pro Ile Val Asn Lys Gln Ser
                195                 200                 205

Cys Ser Ile Ser Asn Ile Glu Thr Val Ile Glu Phe Gln Gln Lys Asn
210                 215                 220

Asn Arg Leu Leu Glu Ile Thr Arg Glu Phe Ser Val Asn Ala Gly Val
225                 230                 235                 240

Thr Thr Pro Val Ser Thr Tyr Met Leu Thr Asn Ser Glu Leu Leu Ser
                245                 250                 255

Leu Ile Asn Asp Met Pro Ile Thr Asn Asp Gln Lys Lys Leu Met Ser
                260                 265                 270

Asn Asn Val Gln Ile Val Arg Gln Gln Ser Tyr Ser Ile Met Ser Ile
                275                 280                 285

Ile Lys Glu Glu Val Leu Ala Tyr Val Val Gln Leu Pro Leu Tyr Gly
                290                 295                 300

Val Ile Asp Thr Pro Cys Trp Lys Leu His Thr Ser Pro Leu Cys Thr
305                 310                 315                 320

Thr Asn Thr Lys Glu Gly Ser Asn Ile Cys Leu Thr Arg Thr Asp Arg
                325                 330                 335

Gly Trp Tyr Cys Asp Asn Ala Gly Ser Val Ser Phe Phe Pro Gln Ala
                340                 345                 350

Glu Thr Cys Lys Val Gln Ser Asn Arg Val Phe Cys Asp Thr Met Asn
                355                 360                 365

Ser Leu Thr Leu Pro Ser Glu Val Asn Leu Cys Asn Val Asp Ile Phe
370                 375                 380

Asn Pro Lys Tyr Asp Cys Lys Ile Met Thr Ser Lys Thr Asp Val Ser
385                 390                 395                 400

Ser Ser Val Ile Thr Ser Leu Gly Ala Ile Val Ser Cys Tyr Gly Lys
                405                 410                 415

Thr Lys Cys Thr Ala Ser Asn Lys Asn Arg Gly Ile Ile Lys Thr Phe
                420                 425                 430

Ser Asn Gly Cys Asp Tyr Val Ser Asn Lys Gly Val Asp Thr Val Ser
                435                 440                 445

Val Gly Asn Thr Leu Tyr Tyr Val Asn Lys Gln Glu Gly Lys Ser Leu
450                 455                 460

Tyr Val Lys Gly Glu Pro Ile Ile Asn Phe Tyr Asp Pro Leu Val Phe
465                 470                 475                 480
```

Pro Ser Asp Glu Phe Asp Ala Ser Ile Ser Gln Val Asn Glu Lys Ile
            485                 490                 495

Asn Gln Ser Leu Ala Phe Ile Arg Lys Ser Asp Glu Leu Leu His Asn
        500                 505                 510

Val Asn Ala Gly Lys Ser Thr Thr Asn Gly Gly Ser Ala Gly Ser Gly
        515                 520                 525

His His His His His His
        530

<210> SEQ ID NO 52
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Ile Glu Gly Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Ile Glu Gly Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro

```
                290                 295                 300
Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
        515                 520                 525

Gly Ser Gly His His His His His His
    530                 535

<210> SEQ ID NO 53
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110
```

```
Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Ser Gly Tyr
        515                 520                 525

Ile Pro Glu Ala Pro Arg Asp Gly Gln Ala Tyr Val Arg Lys Asp Gly
```

```
            530                 535                 540
Glu Trp Val Leu Leu Ser Thr Phe Leu Gly Gly Ser Ala Gly Ser Gly
545                 550                 555                 560

His His His His His His
            565

<210> SEQ ID NO 54
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320
```

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Asn Lys Asn Asp
            515                 520                 525

Asp Lys Gly Ser Gly Tyr Ile Pro Glu Ala Pro Arg Asp Gly Gln Ala
    530                 535                 540

Tyr Val Arg Lys Asp Gly Glu Trp Val Leu Leu Ser Thr Phe Leu Gly
545                 550                 555                 560

Gly Ser Ala Gly Ser Gly His His His His His
            565                 570

<210> SEQ ID NO 55
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

```
Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Asp Lys Ile Glu Glu Ile Leu Ser Lys Ile Tyr
        515                 520                 525
```

His Ile Glu Asn Glu Ile Ala Arg Ile Lys Lys Leu Ile Gly Glu Ser
                530                 535                 540

Gly Gly Ser Ala Gly Ser Gly His His His His His His
545                 550                 555

<210> SEQ ID NO 56
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

```
Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Glu Lys Phe His Gln Ile Glu Lys Glu Phe Ser
            515                 520                 525

Glu Val Glu Gly Arg Ile Gln Asp Leu Glu Lys Ser Gly Gly Ser Ala
            530                 535                 540

Gly Ser Gly His His His His His His
545                 550
```

<210> SEQ ID NO 57
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
            50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Ser Thr Pro Ala Thr Asn Asn Gln Ala Gln Asn Glu Leu Pro
            100                 105                 110

Gln Phe Met Asn Tyr Thr Leu Asn Asn Ala Asn Asn Thr Asn Val Thr
            115                 120                 125

Leu Ser Gln Asn Gln Asn Gln Asn Phe Leu Gly Phe Leu Leu Gly Val
```

```
            130                 135                 140
Gly Ser Ala Ile Ala Ser Gly Val Ala Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Ser Asn Ile Glu Thr Val Ile Glu Phe Gln
                210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
                290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
                370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Asp Lys Ile Glu Glu Ile Leu Ser Lys Ile Tyr
                515                 520                 525

His Ile Glu Asn Glu Ile Ala Arg Ile Lys Lys Leu Ile Gly Glu Ser
                530                 535                 540

Gly Gly Ser Ala Gly Ser Gly His His His His His
545                 550                 555
```

-continued

<210> SEQ ID NO 58
<211> LENGTH: 536
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Gln Asn Gln
            100                 105                 110

Asn Gln Asn Phe Leu Gly Phe Leu Leu Gly Val Gly Ser Ala Ile Ala
        115                 120                 125

Ser Gly Val Ala Val Ser Lys Val Leu His Leu Glu Gly Glu Val Asn
    130                 135                 140

Lys Ile Lys Ser Ala Leu Leu Ser Thr Asn Lys Ala Val Val Ser Leu
145                 150                 155                 160

Ser Asn Gly Val Ser Val Leu Thr Ser Lys Val Leu Asp Leu Lys Asn
                165                 170                 175

Tyr Ile Asp Lys Gln Leu Leu Pro Ile Val Asn Lys Gln Ser Cys Ser
            180                 185                 190

Ile Ser Asn Ile Glu Thr Val Ile Glu Phe Gln Gln Lys Asn Asn Arg
        195                 200                 205

Leu Leu Glu Ile Thr Arg Glu Phe Ser Val Asn Ala Gly Val Thr Thr
    210                 215                 220

Pro Val Ser Thr Tyr Met Leu Thr Asn Ser Glu Leu Leu Ser Leu Ile
225                 230                 235                 240

Asn Asp Met Pro Ile Thr Asn Asp Gln Lys Lys Leu Met Ser Asn Asn
                245                 250                 255

Val Gln Ile Val Arg Gln Gln Ser Tyr Ser Ile Met Ser Ile Ile Lys
            260                 265                 270

Glu Glu Val Leu Ala Tyr Val Val Gln Leu Pro Leu Tyr Gly Val Ile
        275                 280                 285

Asp Thr Pro Cys Trp Lys Leu His Thr Ser Pro Leu Cys Thr Thr Asn
    290                 295                 300

Thr Lys Glu Gly Ser Asn Ile Cys Leu Thr Arg Thr Asp Arg Gly Trp
305                 310                 315                 320

Tyr Cys Asp Asn Ala Gly Ser Val Ser Phe Phe Pro Gln Ala Glu Thr
                325                 330                 335

Cys Lys Val Gln Ser Asn Arg Val Phe Cys Asp Thr Met Asn Ser Leu
            340                 345                 350

Thr Leu Pro Ser Glu Val Asn Leu Cys Asn Val Asp Ile Phe Asn Pro
```

355                 360                 365
Lys Tyr Asp Cys Lys Ile Met Thr Ser Lys Thr Asp Val Ser Ser Ser
    370                 375                 380

Val Ile Thr Ser Leu Gly Ala Ile Val Ser Cys Tyr Gly Lys Thr Lys
385                 390                 395                 400

Cys Thr Ala Ser Asn Lys Asn Arg Gly Ile Ile Lys Thr Phe Ser Asn
                405                 410                 415

Gly Cys Asp Tyr Val Ser Asn Lys Gly Val Asp Thr Val Ser Val Gly
            420                 425                 430

Asn Thr Leu Tyr Tyr Val Asn Lys Gln Glu Gly Lys Ser Leu Tyr Val
        435                 440                 445

Lys Gly Glu Pro Ile Ile Asn Phe Tyr Asp Pro Leu Val Phe Pro Ser
    450                 455                 460

Asp Glu Phe Asp Ala Ser Ile Ser Gln Val Asn Glu Lys Ile Asn Gln
465                 470                 475                 480

Ser Leu Ala Phe Ile Arg Lys Ser Asp Glu Leu Leu His Asn Val Asn
                485                 490                 495

Asp Lys Ile Glu Glu Ile Leu Ser Lys Ile Tyr His Ile Glu Asn Glu
            500                 505                 510

Ile Ala Arg Ile Lys Lys Leu Ile Gly Glu Ser Gly Gly Ser Ala Gly
        515                 520                 525

Ser Gly His His His His His His
    530                 535

<210> SEQ ID NO 59
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Gln Asn Gln
            100                 105                 110

Asn Phe Leu Gly Phe Leu Leu Gly Val Gly Ser Ala Ile Ala Ser Gly
        115                 120                 125

Val Ala Val Ser Lys Val Leu His Leu Glu Gly Glu Val Asn Lys Ile
    130                 135                 140

Lys Ser Ala Leu Leu Ser Thr Asn Lys Ala Val Val Ser Leu Ser Asn
145                 150                 155                 160

Gly Val Ser Val Leu Thr Ser Lys Val Leu Asp Leu Lys Asn Tyr Ile
                165                 170                 175

```
Asp Lys Gln Leu Leu Pro Ile Val Asn Lys Gln Ser Cys Ser Ile Ser
            180                 185                 190

Asn Ile Glu Thr Val Ile Glu Phe Gln Gln Lys Asn Asn Arg Leu Leu
            195                 200                 205

Glu Ile Thr Arg Glu Phe Ser Val Asn Ala Gly Val Thr Thr Pro Val
            210                 215                 220

Ser Thr Tyr Met Leu Thr Asn Ser Glu Leu Leu Ser Leu Ile Asn Asp
225                 230                 235                 240

Met Pro Ile Thr Asn Asp Gln Lys Lys Leu Met Ser Asn Asn Val Gln
            245                 250                 255

Ile Val Arg Gln Gln Ser Tyr Ser Ile Met Ser Ile Ile Lys Glu Glu
            260                 265                 270

Val Leu Ala Tyr Val Val Gln Leu Pro Leu Tyr Gly Val Ile Asp Thr
            275                 280                 285

Pro Cys Trp Lys Leu His Thr Ser Pro Leu Cys Thr Thr Asn Thr Lys
            290                 295                 300

Glu Gly Ser Asn Ile Cys Leu Thr Arg Thr Asp Arg Gly Trp Tyr Cys
305                 310                 315                 320

Asp Asn Ala Gly Ser Val Ser Phe Phe Pro Gln Ala Glu Thr Cys Lys
            325                 330                 335

Val Gln Ser Asn Arg Val Phe Cys Asp Thr Met Asn Ser Leu Thr Leu
            340                 345                 350

Pro Ser Glu Val Asn Leu Cys Asn Val Asp Ile Phe Asn Pro Lys Tyr
            355                 360                 365

Asp Cys Lys Ile Met Thr Ser Lys Thr Asp Val Ser Ser Ser Val Ile
            370                 375                 380

Thr Ser Leu Gly Ala Ile Val Ser Cys Tyr Gly Lys Thr Lys Cys Thr
385                 390                 395                 400

Ala Ser Asn Lys Asn Arg Gly Ile Ile Lys Thr Phe Ser Asn Gly Cys
            405                 410                 415

Asp Tyr Val Ser Asn Lys Gly Val Asp Thr Val Ser Val Gly Asn Thr
            420                 425                 430

Leu Tyr Tyr Val Asn Lys Gln Glu Gly Lys Ser Leu Tyr Val Lys Gly
            435                 440                 445

Glu Pro Ile Ile Asn Phe Tyr Asp Pro Leu Val Phe Pro Ser Asp Glu
450                 455                 460

Phe Asp Ala Ser Ile Ser Gln Val Asn Glu Lys Ile Asn Gln Ser Leu
465                 470                 475                 480

Ala Phe Ile Arg Lys Ser Asp Glu Leu Leu His Asn Val Asn Asp Lys
            485                 490                 495

Ile Glu Glu Ile Leu Ser Lys Ile Tyr His Ile Glu Asn Glu Ile Ala
            500                 505                 510

Arg Ile Lys Lys Leu Ile Gly Glu Ser Gly Ser Ala Gly Ser Gly
            515                 520                 525

His His His His His His
    530

<210> SEQ ID NO 60
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60
```

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Gln Gln Gln Gln
                100                 105                 110

Arg Phe Leu Gly Phe Leu Leu Gly Val Gly Ser Ala Ile Ala Ser Gly
    115                 120                 125

Val Ala Val Ser Lys Val Leu His Leu Glu Gly Glu Val Asn Lys Ile
    130                 135                 140

Lys Ser Ala Leu Leu Ser Thr Asn Lys Ala Val Val Ser Leu Ser Asn
145                 150                 155                 160

Gly Val Ser Val Leu Thr Ser Lys Val Leu Asp Leu Lys Asn Tyr Ile
                165                 170                 175

Asp Lys Gln Leu Leu Pro Ile Val Asn Lys Gln Ser Cys Ser Ile Ser
                180                 185                 190

Asn Ile Glu Thr Val Ile Glu Phe Gln Gln Lys Asn Asn Arg Leu Leu
            195                 200                 205

Glu Ile Thr Arg Glu Phe Ser Val Asn Ala Gly Val Thr Thr Pro Val
    210                 215                 220

Ser Thr Tyr Met Leu Thr Asn Ser Glu Leu Leu Ser Leu Ile Asn Asp
225                 230                 235                 240

Met Pro Ile Thr Asn Asp Gln Lys Lys Leu Met Ser Asn Asn Val Gln
                245                 250                 255

Ile Val Arg Gln Gln Ser Tyr Ser Ile Met Ser Ile Ile Lys Glu Glu
            260                 265                 270

Val Leu Ala Tyr Val Val Gln Leu Pro Leu Tyr Gly Val Ile Asp Thr
    275                 280                 285

Pro Cys Trp Lys Leu His Thr Ser Pro Leu Cys Thr Thr Asn Thr Lys
    290                 295                 300

Glu Gly Ser Asn Ile Cys Leu Thr Arg Thr Asp Arg Gly Trp Tyr Cys
305                 310                 315                 320

Asp Asn Ala Gly Ser Val Ser Phe Phe Pro Gln Ala Glu Thr Cys Lys
                325                 330                 335

Val Gln Ser Asn Arg Val Phe Cys Asp Thr Met Asn Ser Leu Thr Leu
            340                 345                 350

Pro Ser Glu Val Asn Leu Cys Asn Val Asp Ile Phe Asn Pro Lys Tyr
    355                 360                 365

Asp Cys Lys Ile Met Thr Ser Lys Thr Asp Val Ser Ser Ser Val Ile
    370                 375                 380

Thr Ser Leu Gly Ala Ile Val Ser Cys Tyr Gly Lys Thr Lys Cys Thr
385                 390                 395                 400

Ala Ser Asn Lys Asn Arg Gly Ile Ile Lys Thr Phe Ser Asn Gly Cys
                405                 410                 415

Asp Tyr Val Ser Asn Lys Gly Val Asp Thr Val Ser Val Gly Asn Thr
                420                 425                 430

Leu Tyr Tyr Val Asn Lys Gln Glu Gly Lys Ser Leu Tyr Val Lys Gly
        435                 440                 445

Glu Pro Ile Ile Asn Phe Tyr Asp Pro Leu Val Phe Pro Ser Asp Glu
    450                 455                 460

Phe Asp Ala Ser Ile Ser Gln Val Asn Glu Lys Ile Asn Gln Ser Leu
465                 470                 475                 480

Ala Phe Ile Arg Lys Ser Asp Glu Leu Leu His Asn Val Asn Asp Lys
                485                 490                 495

Ile Glu Glu Ile Leu Ser Lys Ile Tyr His Ile Glu Asn Glu Ile Ala
            500                 505                 510

Arg Ile Lys Lys Leu Ile Gly Glu Ser Gly Gly Ser Ala Gly Ser Gly
        515                 520                 525

His His His His His His
    530

<210> SEQ ID NO 61
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Glu Leu Pro
            100                 105                 110

Gln Phe Met Asn Tyr Thr Leu Asn Asn Ala Asn Asn Thr Asn Val Thr
        115                 120                 125

Leu Ser Gln Asn Gln Asn Gln Asn Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

```
Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 62
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
```

```
                20                  25                  30
Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Gln Asn Gln
            100                 105                 110

Asn Gln Asn Phe Leu Gly Phe Leu Leu Gly Val Gly Ser Ala Ile Ala
        115                 120                 125

Ser Gly Val Ala Val Ser Lys Val Leu His Leu Glu Gly Glu Val Asn
        130                 135                 140

Lys Ile Lys Ser Ala Leu Leu Ser Thr Asn Lys Ala Val Val Ser Leu
145                 150                 155                 160

Ser Asn Gly Val Ser Val Leu Thr Ser Lys Val Leu Asp Leu Lys Asn
                165                 170                 175

Tyr Ile Asp Lys Gln Leu Leu Pro Ile Val Asn Lys Gln Ser Cys Ser
            180                 185                 190

Ile Ser Asn Ile Glu Thr Val Ile Glu Phe Gln Gln Lys Asn Asn Arg
        195                 200                 205

Leu Leu Glu Ile Thr Arg Glu Phe Ser Val Asn Ala Gly Val Thr Thr
210                 215                 220

Pro Val Ser Thr Tyr Met Leu Thr Asn Ser Glu Leu Leu Ser Leu Ile
225                 230                 235                 240

Asn Asp Met Pro Ile Thr Asn Asp Gln Lys Lys Leu Met Ser Asn Asn
                245                 250                 255

Val Gln Ile Val Arg Gln Gln Ser Tyr Ser Ile Met Ser Ile Ile Lys
            260                 265                 270

Glu Glu Val Leu Ala Tyr Val Val Gln Leu Pro Leu Tyr Gly Val Ile
        275                 280                 285

Asp Thr Pro Cys Trp Lys Leu His Thr Ser Pro Leu Cys Thr Thr Asn
        290                 295                 300

Thr Lys Glu Gly Ser Asn Ile Cys Leu Thr Arg Thr Asp Arg Gly Trp
305                 310                 315                 320

Tyr Cys Asp Asn Ala Gly Ser Val Ser Phe Phe Pro Gln Ala Glu Thr
                325                 330                 335

Cys Lys Val Gln Ser Asn Arg Val Phe Cys Asp Thr Met Asn Ser Leu
            340                 345                 350

Thr Leu Pro Ser Glu Val Asn Leu Cys Asn Val Asp Ile Phe Asn Pro
        355                 360                 365

Lys Tyr Asp Cys Lys Ile Met Thr Ser Lys Thr Asp Val Ser Ser Ser
        370                 375                 380

Val Ile Thr Ser Leu Gly Ala Ile Val Ser Cys Tyr Gly Lys Thr Lys
385                 390                 395                 400

Cys Thr Ala Ser Asn Lys Asn Arg Gly Ile Ile Lys Thr Phe Ser Asn
                405                 410                 415

Gly Cys Asp Tyr Val Ser Asn Lys Gly Val Asp Thr Val Ser Val Gly
            420                 425                 430

Asn Thr Leu Tyr Tyr Val Asn Lys Gln Glu Gly Lys Ser Leu Tyr Val
        435                 440                 445
```

```
Lys Gly Glu Pro Ile Ile Asn Phe Tyr Asp Pro Leu Val Phe Pro Ser
            450                 455                 460

Asp Glu Phe Asp Ala Ser Ile Ser Gln Val Asn Glu Lys Ile Asn Gln
465                 470                 475                 480

Ser Leu Ala Phe Ile Arg Lys Ser Asp Glu Leu Leu His Asn Val Asn
                485                 490                 495

Ala Gly Lys Ser Thr Thr Asn Ile Met Ile Thr Thr Ile Ile Ile Val
            500                 505                 510

Ile Ile Val Ile Leu Leu Ser Leu Ile Ala Val Gly Leu Leu Leu Tyr
            515                 520                 525

Cys Lys Ala Arg Ser Thr Pro Val Thr Leu Ser Lys Asp Gln Leu Ser
530                 535                 540

Gly Ile Asn Asn Ile Ala Phe Ser Asn
545                 550
```

<210> SEQ ID NO 63
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Gln Asn Gln
            100                 105                 110

Asn Phe Leu Gly Phe Leu Leu Gly Val Gly Ser Ala Ile Ala Ser Gly
        115                 120                 125

Val Ala Val Ser Lys Val Leu His Leu Glu Gly Glu Val Asn Lys Ile
    130                 135                 140

Lys Ser Ala Leu Leu Ser Thr Asn Lys Ala Val Val Ser Leu Ser Asn
145                 150                 155                 160

Gly Val Ser Val Leu Thr Ser Lys Val Leu Asp Leu Lys Asn Tyr Ile
                165                 170                 175

Asp Lys Gln Leu Leu Pro Ile Val Asn Lys Gln Ser Cys Ser Ile Ser
            180                 185                 190

Asn Ile Glu Thr Val Ile Glu Phe Gln Gln Lys Asn Asn Arg Leu Leu
        195                 200                 205

Glu Ile Thr Arg Glu Phe Ser Val Asn Ala Gly Val Thr Thr Pro Val
    210                 215                 220

Ser Thr Tyr Met Leu Thr Asn Ser Glu Leu Leu Ser Leu Ile Asn Asp
225                 230                 235                 240

Met Pro Ile Thr Asn Asp Gln Lys Lys Leu Met Ser Asn Asn Val Gln
```

245                 250                 255
Ile Val Arg Gln Gln Ser Tyr Ser Ile Met Ser Ile Ile Lys Glu Glu
            260                 265                 270

Val Leu Ala Tyr Val Val Gln Leu Pro Leu Tyr Gly Val Ile Asp Thr
        275                 280                 285

Pro Cys Trp Lys Leu His Thr Ser Pro Leu Cys Thr Thr Asn Thr Lys
    290                 295                 300

Glu Gly Ser Asn Ile Cys Leu Thr Arg Thr Asp Arg Gly Trp Tyr Cys
305                 310                 315                 320

Asp Asn Ala Gly Ser Val Ser Phe Phe Pro Gln Ala Glu Thr Cys Lys
                325                 330                 335

Val Gln Ser Asn Arg Val Phe Cys Asp Thr Met Asn Ser Leu Thr Leu
            340                 345                 350

Pro Ser Glu Val Asn Leu Cys Asn Val Asp Ile Phe Asn Pro Lys Tyr
        355                 360                 365

Asp Cys Lys Ile Met Thr Ser Lys Thr Asp Val Ser Ser Ser Val Ile
    370                 375                 380

Thr Ser Leu Gly Ala Ile Val Ser Cys Tyr Gly Lys Thr Lys Cys Thr
385                 390                 395                 400

Ala Ser Asn Lys Asn Arg Gly Ile Ile Lys Thr Phe Ser Asn Gly Cys
                405                 410                 415

Asp Tyr Val Ser Asn Lys Gly Val Asp Thr Val Ser Val Gly Asn Thr
            420                 425                 430

Leu Tyr Tyr Val Asn Lys Gln Glu Gly Lys Ser Leu Tyr Val Lys Gly
        435                 440                 445

Glu Pro Ile Ile Asn Phe Tyr Asp Pro Leu Val Phe Pro Ser Asp Glu
    450                 455                 460

Phe Asp Ala Ser Ile Ser Gln Val Asn Glu Lys Ile Asn Gln Ser Leu
465                 470                 475                 480

Ala Phe Ile Arg Lys Ser Asp Glu Leu Leu His Asn Val Asn Ala Gly
                485                 490                 495

Lys Ser Thr Thr Asn Ile Met Ile Thr Thr Ile Ile Val Ile Ile
            500                 505                 510

Val Ile Leu Leu Ser Leu Ile Ala Val Gly Leu Leu Leu Tyr Cys Lys
        515                 520                 525

Ala Arg Ser Thr Pro Val Thr Leu Ser Lys Asp Gln Leu Ser Gly Ile
    530                 535                 540

Asn Asn Ile Ala Phe Ser Asn
545                 550

<210> SEQ ID NO 64
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

```
Arg Thr Gly Trp Tyr Thr Ser Val Ile Thr Ile Glu Leu Ser Asn Ile
    50              55                  60

Lys Glu Asn Lys Cys Asn Gly Thr Asp Ala Lys Val Lys Leu Ile Lys
 65              70              75                      80

Gln Glu Leu Asp Lys Tyr Lys Asn Ala Val Thr Glu Leu Gln Leu Leu
                 85              90                  95

Met Gln Ser Thr Pro Ala Thr Asn Asn Arg Ala Arg Gln Gln Gln Gln
            100             105             110

Arg Phe Leu Gly Phe Leu Leu Gly Val Gly Ser Ala Ile Ala Ser Gly
        115             120             125

Val Ala Val Ser Lys Val Leu His Leu Glu Gly Glu Val Asn Lys Ile
    130             135             140

Lys Ser Ala Leu Leu Ser Thr Asn Lys Ala Val Val Ser Leu Ser Asn
145             150             155             160

Gly Val Ser Val Leu Thr Ser Lys Val Leu Asp Leu Lys Asn Tyr Ile
                165             170             175

Asp Lys Gln Leu Leu Pro Ile Val Asn Lys Gln Ser Cys Ser Ile Ser
            180             185             190

Asn Ile Glu Thr Val Ile Glu Phe Gln Gln Lys Asn Asn Arg Leu Leu
            195             200             205

Glu Ile Thr Arg Glu Phe Ser Val Asn Ala Gly Val Thr Thr Pro Val
            210             215             220

Ser Thr Tyr Met Leu Thr Asn Ser Glu Leu Leu Ser Leu Ile Asn Asp
225             230             235             240

Met Pro Ile Thr Asn Asp Gln Lys Lys Leu Met Ser Asn Asn Val Gln
                245             250             255

Ile Val Arg Gln Gln Ser Tyr Ser Ile Met Ser Ile Ile Lys Glu Glu
            260             265             270

Val Leu Ala Tyr Val Val Gln Leu Pro Leu Tyr Gly Val Ile Asp Thr
            275             280             285

Pro Cys Trp Lys Leu His Thr Ser Pro Leu Cys Thr Thr Asn Thr Lys
            290             295             300

Glu Gly Ser Asn Ile Cys Leu Thr Arg Thr Asp Arg Gly Trp Tyr Cys
305             310             315             320

Asp Asn Ala Gly Ser Val Ser Phe Phe Pro Gln Ala Glu Thr Cys Lys
                325             330             335

Val Gln Ser Asn Arg Val Phe Cys Asp Thr Met Asn Ser Leu Thr Leu
            340             345             350

Pro Ser Glu Val Asn Leu Cys Asn Val Asp Ile Phe Asn Pro Lys Tyr
            355             360             365

Asp Cys Lys Ile Met Thr Ser Lys Thr Asp Val Ser Ser Ser Val Ile
    370             375             380

Thr Ser Leu Gly Ala Ile Val Ser Cys Tyr Gly Lys Thr Lys Cys Thr
385             390             395             400

Ala Ser Asn Lys Asn Arg Gly Ile Ile Lys Thr Phe Ser Asn Gly Cys
                405             410             415

Asp Tyr Val Ser Asn Lys Gly Val Asp Thr Val Ser Val Gly Asn Thr
            420             425             430

Leu Tyr Tyr Val Asn Lys Gln Glu Gly Lys Ser Leu Tyr Val Lys Gly
            435             440             445

Glu Pro Ile Ile Asn Phe Tyr Asp Pro Leu Val Phe Pro Ser Asp Glu
450             455             460

Phe Asp Ala Ser Ile Ser Gln Val Asn Glu Lys Ile Asn Gln Ser Leu
```

```
                             465                 470                 475                 480
Ala Phe Ile Arg Lys Ser Asp Glu Leu Leu His Asn Val Asn Ala Gly
                485                 490                 495

Lys Ser Thr Thr Asn Ile Met Ile Thr Thr Ile Ile Val Ile Ile
                500                 505                 510

Val Ile Leu Leu Ser Leu Ile Ala Val Gly Leu Leu Tyr Cys Lys
                515                 520                 525

Ala Arg Ser Thr Pro Val Thr Leu Ser Lys Asp Gln Leu Ser Gly Ile
530                 535                 540

Asn Asn Ile Ala Phe Ser Asn
545                 550

<210> SEQ ID NO 65
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Glu Leu Pro
            100                 105                 110

Gln Phe Met Asn Tyr Thr Leu Asn Asn Ala Gln Gln Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

Leu Met Ser Asn Asn Val Gln Ile Val Arg Gln Ser Tyr Ser Ile
            275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
        515                 520                 525

Gly Ser Gly His His His His His His
    530                 535

<210> SEQ ID NO 66
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

```
Met Gln Ser Thr Pro Ala Thr Asn Asn Arg Ala Arg Glu Leu Pro
                100                 105                 110

Gln Phe Met Asn Tyr Thr Leu Asn Ala Gln Gln Thr Asn Val Thr
            115                 120                 125

Leu Ser Gln Asn Gln Asn Gln Asn Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510
```

```
Leu His Asn Val Asn Ala Gly Lys Ser Thr Thr Asn Gly Gly Ser Ala
            515                 520                 525

Gly Ser Gly His His His His His
        530                 535

<210> SEQ ID NO 67
<211> LENGTH: 528
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Ser Ala Ile Ala Ser Gly Val Ala
    130                 135                 140

Val Ser Lys Val Leu His Leu Glu Gly Glu Val Asn Lys Ile Lys Ser
145                 150                 155                 160

Ala Leu Leu Ser Thr Asn Lys Ala Val Val Ser Leu Ser Asn Gly Val
                165                 170                 175

Ser Val Leu Thr Ser Lys Val Leu Asp Leu Lys Asn Tyr Ile Asp Lys
            180                 185                 190

Gln Leu Leu Pro Ile Val Asn Lys Gln Ser Cys Ser Ile Ser Asn Ile
        195                 200                 205

Glu Thr Val Ile Glu Phe Gln Gln Lys Asn Asn Arg Leu Leu Glu Ile
    210                 215                 220

Thr Arg Glu Phe Ser Val Asn Ala Gly Val Thr Thr Pro Val Ser Thr
225                 230                 235                 240

Tyr Met Leu Thr Asn Ser Glu Leu Leu Ser Leu Ile Asn Asp Met Pro
                245                 250                 255

Ile Thr Asn Asp Gln Lys Lys Leu Met Ser Asn Asn Val Gln Ile Val
            260                 265                 270

Arg Gln Gln Ser Tyr Ser Ile Met Ser Ile Ile Lys Glu Glu Val Leu
        275                 280                 285

Ala Tyr Val Val Gln Leu Pro Leu Tyr Gly Val Ile Asp Thr Pro Cys
    290                 295                 300

Trp Lys Leu His Thr Ser Pro Leu Cys Thr Thr Asn Thr Lys Glu Gly
305                 310                 315                 320

Ser Asn Ile Cys Leu Thr Arg Thr Asp Arg Gly Trp Tyr Cys Asp Asn
                325                 330                 335
```

```
Ala Gly Ser Val Ser Phe Phe Pro Gln Ala Glu Thr Cys Lys Val Gln
            340                 345                 350

Ser Asn Arg Val Phe Cys Asp Thr Met Asn Ser Leu Thr Leu Pro Ser
            355                 360                 365

Glu Val Asn Leu Cys Asn Val Asp Ile Phe Asn Pro Lys Tyr Asp Cys
370                 375                 380

Lys Ile Met Thr Ser Lys Thr Asp Val Ser Ser Val Ile Thr Ser
385                 390                 395                 400

Leu Gly Ala Ile Val Ser Cys Tyr Gly Lys Thr Lys Cys Thr Ala Ser
            405                 410                 415

Asn Lys Asn Arg Gly Ile Ile Lys Thr Phe Ser Asn Gly Cys Asp Tyr
            420                 425                 430

Val Ser Asn Lys Gly Val Asp Thr Val Ser Val Gly Asn Thr Leu Tyr
            435                 440                 445

Tyr Val Asn Lys Gln Glu Gly Lys Ser Leu Tyr Val Lys Gly Glu Pro
            450                 455                 460

Ile Ile Asn Phe Tyr Asp Pro Leu Val Phe Pro Ser Asp Glu Phe Asp
465                 470                 475                 480

Ala Ser Ile Ser Gln Val Asn Glu Lys Ile Asn Gln Ser Leu Ala Phe
            485                 490                 495

Ile Arg Lys Ser Asp Glu Leu Leu His Asn Val Asn Ala Gly Lys Ser
            500                 505                 510

Thr Thr Asn Gly Gly Ser Ala Gly Ser Gly His His His His His His
            515                 520                 525

<210> SEQ ID NO 68
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Gly Val Gly Ser Ala Ile Ala Ser
        130                 135                 140

Gly Val Ala Val Ser Lys Val Leu His Leu Glu Gly Glu Val Asn Lys
145                 150                 155                 160

Ile Lys Ser Ala Leu Leu Ser Thr Asn Lys Ala Val Val Ser Leu Ser
```

```
            165                 170                 175
Asn Gly Val Ser Val Leu Thr Ser Lys Val Leu Asp Leu Lys Asn Tyr
            180                 185                 190

Ile Asp Lys Gln Leu Leu Pro Ile Val Asn Lys Gln Ser Cys Ser Ile
        195                 200                 205

Ser Asn Ile Glu Thr Val Ile Glu Phe Gln Gln Lys Asn Asn Arg Leu
    210                 215                 220

Leu Glu Ile Thr Arg Glu Phe Ser Val Asn Ala Gly Val Thr Thr Pro
225                 230                 235                 240

Val Ser Thr Tyr Met Leu Thr Asn Ser Glu Leu Leu Ser Leu Ile Asn
                245                 250                 255

Asp Met Pro Ile Thr Asn Asp Gln Lys Lys Leu Met Ser Asn Asn Val
            260                 265                 270

Gln Ile Val Arg Gln Gln Ser Tyr Ser Ile Met Ser Ile Ile Lys Glu
        275                 280                 285

Glu Val Leu Ala Tyr Val Val Gln Leu Pro Leu Tyr Gly Val Ile Asp
    290                 295                 300

Thr Pro Cys Trp Lys Leu His Thr Ser Pro Leu Cys Thr Thr Asn Thr
305                 310                 315                 320

Lys Glu Gly Ser Asn Ile Cys Leu Thr Arg Thr Asp Arg Gly Trp Tyr
                325                 330                 335

Cys Asp Asn Ala Gly Ser Val Ser Phe Phe Pro Gln Ala Glu Thr Cys
            340                 345                 350

Lys Val Gln Ser Asn Arg Val Phe Cys Asp Thr Met Asn Ser Leu Thr
        355                 360                 365

Leu Pro Ser Glu Val Asn Leu Cys Asn Val Asp Ile Phe Asn Pro Lys
    370                 375                 380

Tyr Asp Cys Lys Ile Met Thr Ser Lys Thr Asp Val Ser Ser Ser Val
385                 390                 395                 400

Ile Thr Ser Leu Gly Ala Ile Val Ser Cys Tyr Gly Lys Thr Lys Cys
                405                 410                 415

Thr Ala Ser Asn Lys Asn Arg Gly Ile Ile Lys Thr Phe Ser Asn Gly
            420                 425                 430

Cys Asp Tyr Val Ser Asn Lys Gly Val Asp Thr Val Ser Val Gly Asn
        435                 440                 445

Thr Leu Tyr Tyr Val Asn Lys Gln Glu Gly Lys Ser Leu Tyr Val Lys
    450                 455                 460

Gly Glu Pro Ile Ile Asn Phe Tyr Asp Pro Leu Val Phe Pro Ser Asp
465                 470                 475                 480

Glu Phe Asp Ala Ser Ile Ser Gln Val Asn Glu Lys Ile Asn Gln Ser
                485                 490                 495

Leu Ala Phe Ile Arg Lys Ser Asp Glu Leu Leu His Asn Val Asn Ala
            500                 505                 510

Gly Lys Ser Thr Thr Asn Gly Gly Ser Ala Gly Ser Gly His His His
        515                 520                 525

His His His
        530

<210> SEQ ID NO 69
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 69

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Glu Leu Pro
            100                 105                 110

Gln Phe Met Asn Tyr Thr Leu Asn Asn Ala Gln Gln Thr Asn Val Thr
        115                 120                 125

Leu Ser Gln Asn Gln Asn Gln Asn Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
```

```
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
            515                 520                 525

Gly Ser Gly His His His His His His
            530                 535

<210> SEQ ID NO 70
<211> LENGTH: 524
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Glu Leu Pro
            100                 105                 110

Gln Phe Met Asn Tyr Thr Leu Asn Asn Ala Gln Gln Thr Asn Val Thr
            115                 120                 125

Leu Ser Gln Asn Gln Asn Gln Asn Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220
```

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn
        515                 520

<210> SEQ ID NO 71
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60
```

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Gln Gln Gln Gln
            100                 105                 110

Arg Phe Leu Gly Phe Leu Leu Gly Val Gly Ser Ala Ile Ala Ser Gly
        115                 120                 125

Val Ala Val Ser Lys Val Leu His Leu Glu Gly Glu Val Asn Lys Ile
    130                 135                 140

Lys Ser Ala Leu Leu Ser Thr Asn Lys Ala Val Val Ser Leu Ser Asn
145                 150                 155                 160

Gly Val Ser Val Leu Thr Ser Lys Val Leu Asp Leu Lys Asn Tyr Ile
                165                 170                 175

Asp Lys Gln Leu Leu Pro Ile Val Asn Lys Gln Ser Cys Ser Ile Ser
            180                 185                 190

Asn Ile Glu Thr Val Ile Glu Phe Gln Gln Lys Asn Asn Arg Leu Leu
        195                 200                 205

Glu Ile Thr Arg Glu Phe Ser Val Asn Ala Gly Val Thr Thr Pro Val
    210                 215                 220

Ser Thr Tyr Met Leu Thr Asn Ser Glu Leu Leu Ser Leu Ile Asn Asp
225                 230                 235                 240

Met Pro Ile Thr Asn Asp Gln Lys Lys Leu Met Ser Asn Asn Val Gln
                245                 250                 255

Ile Val Arg Gln Gln Ser Tyr Ser Ile Met Ser Ile Ile Lys Glu Glu
            260                 265                 270

Val Leu Ala Tyr Val Val Gln Leu Pro Leu Tyr Gly Val Ile Asp Thr
        275                 280                 285

Pro Cys Trp Lys Leu His Thr Ser Pro Leu Cys Thr Thr Asn Thr Lys
    290                 295                 300

Glu Gly Ser Asn Ile Cys Leu Thr Arg Thr Asp Arg Gly Trp Tyr Cys
305                 310                 315                 320

Asp Asn Ala Gly Ser Val Ser Phe Phe Pro Gln Ala Glu Thr Cys Lys
                325                 330                 335

Val Gln Ser Asn Arg Val Phe Cys Asp Thr Met Asn Ser Leu Thr Leu
            340                 345                 350

Pro Ser Glu Val Asn Leu Cys Asn Val Asp Ile Phe Asn Pro Lys Tyr
        355                 360                 365

Asp Cys Lys Ile Met Thr Ser Lys Thr Asp Val Ser Ser Ser Val Ile
    370                 375                 380

Thr Ser Leu Gly Ala Ile Val Ser Cys Tyr Gly Lys Thr Lys Cys Thr
385                 390                 395                 400

Ala Ser Asn Lys Asn Arg Gly Ile Ile Lys Thr Phe Ser Asn Gly Cys
                405                 410                 415

Asp Tyr Val Ser Asn Lys Gly Val Asp Thr Val Ser Val Gly Asn Thr
            420                 425                 430

Leu Tyr Tyr Val Asn Lys Gln Glu Gly Lys Ser Leu Tyr Val Lys Gly
        435                 440                 445

Glu Pro Ile Ile Asn Phe Tyr Asp Pro Leu Val Phe Pro Ser Asp Glu
    450                 455                 460

Phe Asp Ala Ser Ile Ser Gln Val Asn Glu Lys Ile Asn Gln Ser Leu
465                 470                 475                 480
```

```
Ala Phe Ile Arg Lys Ser Asp Glu Leu Leu His Asn Val Asn Ala Gly
            485                 490                 495
Lys Ser Thr Thr Asn
            500

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ttggatctgc aatcgcca                                                   18

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cttttgatct tgttcacttc tccttct                                         27

<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
tggcactgct gtatctaagg tcctgcact                                       29

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Val Pro Arg
1

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Asp Asp Asp Lys
1               5

<210> SEQ ID NO 77
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 77

Arg Ala Arg Lys
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Ala Arg Gln
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Ala Gln Asn
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Glu Gly Arg
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Lys Lys Lys
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Asn Gln Asn
1
```

-continued

```
<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Gln Gln Arg
1

<210> SEQ ID NO 84
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
```

```
                290                 295                 300
Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
        515                 520                 525

Gly Ser Gly His His His His His His
    530                 535

<210> SEQ ID NO 85
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110
```

```
Gln Phe Met Asn Tyr Thr Leu Asn Asn Ala Gln Gln Thr Asn Val Thr
            115                 120                 125

Leu Ser Gln Asn Gln Asn Gln Asn Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
    195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
    515                 520                 525

Gly Ser Gly His His His His His His
```

<210> SEQ ID NO 86
<211> LENGTH: 516
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Gln Gln Asn Gln
            100                 105                 110

Gln Gln Arg Phe Leu Gly Phe Leu Leu Gly Val Gly Ser Ala Ile Ala
        115                 120                 125

Ser Gly Val Ala Val Ser Lys Val Leu His Leu Glu Gly Glu Val Asn
    130                 135                 140

Lys Ile Lys Ser Ala Leu Leu Ser Thr Asn Lys Ala Val Val Ser Leu
145                 150                 155                 160

Ser Asn Gly Val Ser Val Leu Thr Ser Lys Val Leu Asp Leu Lys Asn
                165                 170                 175

Tyr Ile Asp Lys Gln Leu Leu Pro Ile Val Asn Lys Gln Ser Cys Ser
            180                 185                 190

Ile Ser Asn Ile Glu Thr Val Ile Glu Phe Gln Gln Lys Asn Asn Arg
        195                 200                 205

Leu Leu Glu Ile Thr Arg Glu Phe Ser Val Asn Ala Gly Val Thr Thr
    210                 215                 220

Pro Val Ser Thr Tyr Met Leu Thr Asn Ser Glu Leu Leu Ser Leu Ile
225                 230                 235                 240

Asn Asp Met Pro Ile Thr Asn Asp Gln Lys Lys Leu Met Ser Asn Asn
                245                 250                 255

Val Gln Ile Val Arg Gln Gln Ser Tyr Ser Ile Met Ser Ile Ile Lys
            260                 265                 270

Glu Glu Val Leu Ala Tyr Val Val Gln Leu Pro Leu Tyr Gly Val Ile
        275                 280                 285

Asp Thr Pro Cys Trp Lys Leu His Thr Ser Pro Leu Cys Thr Thr Asn
    290                 295                 300

Thr Lys Glu Gly Ser Asn Ile Cys Leu Thr Arg Thr Asp Arg Gly Trp
305                 310                 315                 320

Tyr Cys Asp Asn Ala Gly Ser Val Ser Phe Phe Pro Gln Ala Glu Thr
                325                 330                 335

Cys Lys Val Gln Ser Asn Arg Val Phe Cys Asp Thr Met Asn Ser Leu
            340                 345                 350

```
Thr Leu Pro Ser Glu Val Asn Leu Cys Asn Val Asp Ile Phe Asn Pro
            355                 360                 365

Lys Tyr Asp Cys Lys Ile Met Thr Ser Lys Thr Asp Val Ser Ser Ser
    370                 375                 380

Val Ile Thr Ser Leu Gly Ala Ile Val Ser Cys Tyr Gly Lys Thr Lys
385                 390                 395                 400

Cys Thr Ala Ser Asn Lys Asn Arg Gly Ile Ile Lys Thr Phe Ser Asn
                405                 410                 415

Gly Cys Asp Tyr Val Ser Asn Lys Gly Val Asp Thr Val Ser Val Gly
            420                 425                 430

Asn Thr Leu Tyr Tyr Val Asn Lys Gln Glu Gly Lys Ser Leu Tyr Val
            435                 440                 445

Lys Gly Glu Pro Ile Ile Asn Phe Tyr Asp Pro Leu Val Phe Pro Ser
    450                 455                 460

Asp Glu Phe Asp Ala Ser Ile Ser Gln Val Asn Glu Lys Ile Asn Gln
465                 470                 475                 480

Ser Leu Ala Phe Ile Arg Lys Ser Asp Glu Leu Leu His Asn Val Asn
                485                 490                 495

Ala Gly Lys Ser Thr Thr Asn Gly Gly Ser Ala Gly Ser Gly His His
            500                 505                 510

His His His His
        515

<210> SEQ ID NO 87
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Glu Leu Pro
            100                 105                 110

Gln Phe Met Asn Tyr Thr Leu Asn Asn Ala Gln Gln Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190
```

```
Leu Asp Leu Lys Asn Tyr Ile Asp Lys Gln Leu Pro Ile Val Asn
        195                 200                 205
Lys Gln Ser Cys Ser Ile Ser Asn Ile Glu Thr Val Ile Glu Phe Gln
210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
        450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu His Asn Val Asn Ala Gly Lys Ser Thr Thr Asn Gly Gly Ser Ala
        515                 520                 525
Gly Ser Gly His His His His His His
    530                 535

<210> SEQ ID NO 88
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Glu Leu Leu Ile Leu Lys Ala Asn Ala Ile Thr Thr Ile Leu Thr
```

-continued

```
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
 50                  55                  60
Lys Glu Asn Lys Cys Asn Gly Thr Asp Ala Lys Val Lys Leu Ile Lys
 65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Gln Ala Gln Asn Glu Leu Gln
            100                 105                 110
Arg Phe Met Asn Tyr Thr Leu Asn Asn Ala Asn Asn Thr Asn Val Thr
            115                 120                 125
Leu Ser Gln Asn Gln Asn Gln Asn Phe Leu Gly Phe Leu Leu Gly Val
 130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
            195                 200                 205
Lys Gln Ser Cys Ser Ile Ser Asn Ile Glu Thr Val Ile Glu Phe Gln
 210                 215                 220
Gln Lys Asn Asn Arg Leu Leu Glu Ile Thr Arg Glu Phe Ser Val Asn
 225                 230                 235                 240
Ala Gly Val Thr Thr Pro Val Ser Thr Tyr Met Leu Thr Asn Ser Glu
            245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
            275                 280                 285
Met Ser Ile Ile Lys Glu Glu Val Leu Ala Tyr Val Val Gln Leu Pro
 290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
            325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
            370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
```

```
Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Gly Gly Ser Ala
            515                 520                 525

Gly Ser Gly His His His His His His
            530                 535
```

<210> SEQ ID NO 89
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Glu Leu Pro
            100                 105                 110

Gln Phe Met Asn Tyr Thr Leu Asn Asn Ala Gln Gln Thr Asn Val Thr
        115                 120                 125

Leu Ser Gln Asn Gln Asn Gln Asn Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
```

```
                 245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Thr Asn Gly Gly Ser Ala
    515                 520                 525

Gly Ser Gly His His His His His
    530                 535

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gly Ser Ala Gly Ser Gly His His His His His
1               5                   10

<210> SEQ ID NO 91
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 91

Thr Pro Ala Thr Asn Asn Arg Ala Arg Arg Glu Leu Pro Arg Phe Met
1               5                   10                  15

Asn Tyr Thr Leu Asn Asn Ala Lys Lys Thr Asn Val Thr Leu Ser Lys
            20                  25                  30

Lys Arg Lys Arg Arg Gly Val Gly Ser Ala Ile Ala Ser
        35                  40                  45

<210> SEQ ID NO 92
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Thr Pro Ala Thr Asn Asn Gln Ala Gln Asn Glu Leu Pro Gln Phe Met
1               5                   10                  15

Asn Tyr Thr Leu Asn Asn Ala Gln Gln Thr Asn Val Thr Leu Ser Gln
            20                  25                  30

Asn Gln Asn Gln Asn Phe Leu Gly Phe Leu Leu Gly Val Gly Ser Ala
        35                  40                  45

Ile Ala Ser
    50

<210> SEQ ID NO 93
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Gln Asn Glu Leu Pro
            100                 105                 110

Gln Phe Met Asn Tyr Thr Leu Asn Asn Ala Gln Gln Thr Asn Val Thr
        115                 120                 125

Leu Ser Gln Asn Gln Asn Gln Asn Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val

```
                  180                 185                 190
Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys

Ala Phe Ile Arg Lys Ser Asp Glu Leu Leu His His Val Asn Ala Gly
            20                  25                  30

Lys Ser Thr Thr Asn
        35

<210> SEQ ID NO 95
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Phe Asp Ala Ser Ile Ser Gln Ile Asn Glu Lys Ile Asn Gln Ser Ile
1               5                   10                  15

Ala Phe Ile Arg Lys Ile Asp Glu Leu Leu His His Ile Asn Ala Gly
            20                  25                  30

Lys Ser Thr Thr Asn Gly Ser Gly Ser Gly Asp Asp Asp Lys Gly
        35                  40                  45

Ser Gly Ser Gly
    50

<210> SEQ ID NO 96
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Asp Lys
            20                  25                  30

Ile Glu Glu Ile Leu Ser Lys Ile Tyr His Ile Glu Asn Glu Ile Ala
        35                  40                  45

Arg Ile Lys Lys Leu Ile Gly Glu Gly Ser Gly Ser Gly Asp Asp Asp
    50                  55                  60

Asp Lys Gly Ser Gly Ser Gly
65                  70

<210> SEQ ID NO 97
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Phe Asp Ala Ser Ile Ser Gln Ile Asn Glu Lys Ile Asn Gln Ile Leu
1               5                   10                  15

Ala Phe Ile Arg Lys Ile Asp Glu Leu Leu His His Ile Asn Ala Gly
            20                  25                  30

Lys Ser Thr Thr Asn Gly Ser Gly Ser Gly Ile Glu Gly Arg Gly Ser
        35                  40                  45

Gly Ser Gly
    50

```
<210> SEQ ID NO 98
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His His Val Asn Asp Lys
            20                  25                  30

Ile Glu Glu Ile Leu Ser Lys Ile Tyr His Ile Glu Asn Glu Ile Ala
        35                  40                  45

Arg Ile Lys Lys Leu Ile Gly Glu Gly Ser Gly Ser Gly Ile Glu Gly
    50                  55                  60

Arg Gly Ser Gly Ser Gly
65                  70

<210> SEQ ID NO 99
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Phe Asp Ala Ser Ile Ser Gln Ile Asn Glu Lys Ile Asn Gln Ile Leu
1               5                   10                  15

Ala Phe Ile Arg Lys Ile Asp Glu Leu Leu His Asn Ile Asn Ala Gly
            20                  25                  30

Lys Ser Thr Thr Asn Gly Ser Gly Ser Gly Leu Val Pro Arg Gly Ser
        35                  40                  45

Gly Ser Gly
        50

<210> SEQ ID NO 100
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Asp Lys
            20                  25                  30

Ile Glu Glu Ile Leu Ser Lys Ile Tyr His Ile Glu Asn Glu Ile Ala
        35                  40                  45

Arg Ile Lys Lys Leu Ile Gly Glu Gly Ser Gly Ser Gly Leu Val Pro
    50                  55                  60

Arg Gly Ser Gly Ser Gly
65                  70

<210> SEQ ID NO 101
<211> LENGTH: 12463
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 101

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct cgccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggcc cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg ataccaaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tagacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccacccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctcct tccatgaatt cgcctacgag agtctgagaa    2160
cacgaccagc cgctccttac caagtaccaa ccatagggt gtatggcgtg ccaggatcag    2220
```

```
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg     2340 ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca aacagtgcgg ttttttttaac atgatgtgcc   2520 tgaaagtgca ttttaaccac gagatttgca cacaagtctt ccacaaaagc atctctcgcc    2580
gttgcactaa atctgtgact tcggtcgtct caaccttgtt ttacgacaaa aaaatgagaa    2640
cgacgaatcc gaaagagact aagattgtga ttgacactac cggcagtacc aaacctaagc   2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga   2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca gttttcccg ggtatgcaaa ccgaaatcct     3900
cacttgaaga gacggaagtt ctgtttgtat tcattggggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag   4080
gagtgattat aaatgctgct aacagcaaag acaacctgg cggagggtg tgcggagcgc      4140 tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agcttagac accactgatg     4440 cagatgtagc catatactgc agggacaaga aatgggaaat gactctcaag gaagcagtgg    4500
ctaggagaga agcagtggag gagatatgca tatccgacga ctcttcagtg acagaacctg    4560
```

```
atgcagagct ggtgagggtg catccgaaga gttctttggc tggaaggaag ggctacagca    4620
caagcgatgg caaaacttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tccttttccat   4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga ccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggaggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccacccccgc    5520
caggcgtgaa tagggtgatc actagagagg agctcgaggc gcttacccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acctgctaa    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca agctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
```

-continued

```
aatttaaatt cggagccatg atgaaatctg aatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtcgacgcc    7560
accatggaac tgctgatcct gaaggccaac gccatcacca ccatcctgac cgccgtgacc    7620
ttctgcttcg ccagcggcca gaacataccc gaggaattct accagagcac ctgcagcgcc    7680
gtgagcaagg gctacctgag cgccctgcgg accggctggt acaccagcgt gatcaccatc    7740
gagctgtcca acatcaaaga aaacaagtgc aacggcaccg acgccaaggt gaaactgatc    7800
aagcaggaac tggacaagta caagaacgcc gtgaccgagc tgcagctgct gatgcagagc    7860
acccccgcca ccaacaaccg ggccagaaga gagctgcccc ggttcatgaa ctacaccctg    7920
aacaacgcca agaaaaccaa cgtgacccctg agcaagaagc ggaagcggcg gttcctgggc    7980
ttcctgctgg gcgtgggcag cgccatcgcc agcggggtgg ccgtgtccaa ggtgctgcac    8040
ctggaaggcg aggtgaacaa gatcaagtcc gccctgctgt ccaccaacaa ggccgtggtg    8100
tccctgagca acggcgtgag cgtgctgacc agcaaggtgc tggatctgaa gaactacatc    8160
gacaagcagc tgctgcccat cgtgaacaag cagagctgca gcatcagcaa catcgagacc    8220
gtgatcgagt ccagcagaa gaacaaccgg ctgctggaaa tcacccggga gttcagcgtg    8280
aacgccggcg tgaccacccc cgtgagcacc tacatgctga ccaacagcga gctgctgtcc    8340
ctgatcaatg acatgcccat caccaacgac cagaaaaagc tgatgagcaa caacgtgcag    8400
atcgtgcggc agcagagcta ctccatcatg agcatcatca aagaagaggt gctggcctac    8460
gtggtgcagc tgcccctgta cggcgtgatc gacacccct gctggaagct gcacaccagc    8520
cccctgtgca ccaccaacac caaagagggc agcaacatct gcctgacccg gaccgaccgg    8580
ggctggtact gcgacaacgc cggcagcgtg agcttcttcc ccaagccga cctgcaag    8640 gtgcagagca accgggtgtt ctgcgacacc atgaacagcc tgaccctgcc ctccgaggtg    8700
aacctgtgca acgtggacat cttcaacccc aagtacgact gcaagatcat gacctccaag    8760
accgacgtga gcagctccgt gatcacctcc ctgggcgcca tcgtgagctg ctacggcaag    8820
accaagtgca ccgccagcaa caagaaccgg ggcatcatca gaccttcag caacggctgc    8880 gactacgtga caacaaggg cgtggacacc gtgagcgtgg caacacact gtactacgtg    8940 aataagcagg aaggcaagag cctgtacgtg aagggcgagc ccatcatcaa cttctacgac    9000
cccctggtgt ccccagcga cgagttcgac gccagcatca gccaggtcaa cgagaagatc    9060
aaccagagcc tggccttcat ccggaagagc gacgagctgc tgcacaatgt gaatgccggc    9120
aagagcacca ccaatatcat gatcaccaca atcatcatcg tgatcattgt gatcctgctg    9180
tctctgattg ccgtgggcct gctgctgtac tgcaaggccc gcagccccc tgtgaccctg    9240 tccaaggacc agctgtccgg catcaacaat atcgccttct ccaactgaag tctagacggc    9300
```

```
gcgcccaccc agcggccgca tacagcagca attggcaagc tgcttacata gaactcgcgg    9360
cgattggcat gccgccttaa aattttatt  ttattttct  tttcttttcc gaatcggatt    9420
ttgttttaa  tatttcaaaa aaaaaaaaa  aaaaaaaaa  aaaaaaaa   agggtcggca    9480
tggcatctcc acctcctcgc ggtccgacct gggcatccga aggaggacgc acgtccactc    9540
ggatggctaa gggagagcca cgtttaaacc agctccaatt cgccctatag tgagtcgtat    9600
tacgcgcgct cactggccgt cgttttacaa cgtcgtgact gggaaaaccc tggcgttacc    9660
caacttaatc gccttgcagc acatccccct ttcgccagct ggcgtaatag cgaagaggcc    9720
cgcaccgatc gcccttccca cagttgcgc  agcctgaatg gcgaatggga cgcgccctgt    9780
agcggcgcat taagcgcggc gggtgtggtg ttacgcgca  gcgtgaccgc tacacttgcc    9840
agcgccctag cgcccgctcc tttcgctttc ttcccttcct ttctcgccac gttcgccggc    9900
tttccccgtc aagctctaaa tcgggggctc cctttagggt tccgatttag tgctttacgg    9960
cacctcgacc ccaaaaaact tgattagggt gatggttcac gtagtgggcc atcgccctga   10020
tagacggttt ttcgcccttt gacgttggag tccacgttct ttaatagtgg actcttgttc   10080
caaactggaa caacactcaa ccctatctcg gtctattctt ttgatttata agggattttg   10140
ccgatttcgg cctattggtt aaaaatgag  ctgatttaac aaaaatttaa cgcgaatttt   10200
aacaaaatat taacgcttac aatttaggtg gcacttttcg gggaaatgtg cgcggaaccc   10260
ctatttgttt attttctaa  atacattcaa atatgtatcc gctcatgaga caataaccct   10320
gataaatgct tcaataatat tgaaaaagga agagtatgag tattcaacat ttccgtgtcg   10380
cccttattcc cttttttgcg gcattttgcc ttcctgtttt tgctcaccca gaaacgctgg   10440
tgaaagtaaa agatgctgaa gatcagttgg gtgcacgagt gggttacatc gaactggatc   10500
tcaacagcgg taagatcctt gagagttttc gccccgaaga acgttttcca atgatgagca   10560
cttttaaagt tctgctatgt ggcgcggtat tatcccgtat tgacgccggg caagagcaac   10620
tcggtcgccg catacactat tctcagaatg acttggttga gtactcacca gtcacagaaa   10680
agcatcttac ggatggcatg acagtaagag aattatgcag tgctgccata accatgagtg   10740
ataacactgc ggccaactta cttctgacaa cgatcgagg  accgaaggag ctaaccgctt   10800
ttttgcacaa catgggggat catgtaactc gccttgatcg ttgggaaccg gagctgaatg   10860
aagccatacc aaacgacgag cgtgacacca cgatgcctgt agcaatggca acaacgttgc   10920
gcaaactatt aactggcgaa ctacttactc tagcttcccg gcaacaatta atagactgga   10980
tggaggcgga taaagttgca ggaccacttc tgcgctcggc ccttccggct ggctggttta   11040
ttgctgataa atctggagcc ggtgagcgtg ggtctcgcgg tatcattgca gcactggggc   11100
cagatggtaa gccctcccgt atcgtagtta tctacacgac ggggagtcag gcaactatgg   11160
atgaacgaaa tagacagatc gctgagatag gtgcctcact gattaagcat tggtaactgt   11220
cagaccaagt ttactcatat atactttaga ttgatttaaa acttcatttt taatttaaaa   11280
ggatctaggt gaagatcctt tttgataatc tcatgaccaa aatcccttaa cgtgagtttt   11340
cgttccactg agcgtcagac cccgtagaaa agatcaaagg atcttcttga gatccttttt   11400
ttctgcgcgt aatctgctgc ttgcaaacaa aaaaaccacc gctaccagcg gtggtttgtt   11460
tgccggatca agagctacca actctttttc cgaaggtaac tggcttcagc agagcgcaga   11520
taccaaatac tgttcttcta gtgtagccgt agttaggcca ccacttcaag aactctgtag   11580
caccgcctac atacctcgct ctgctaatcc tgttaccagt ggctgctgcc agtggcgata   11640
agtcgtgtct taccgggttg gactcaagac gatagttacc ggataaggcg cagcggtcgg   11700
```

```
gctgaacggg gggttcgtgc acacagccca gcttggagcg aacgacctac accgaactga    11760
gatacctaca gcgtgagcta tgagaaagcg ccacgcttcc cgaagggaga aaggcggaca    11820
ggtatccggt aagcggcagg gtcggaacag gagagcgcac gagggagctt ccaggggggaa   11880 acgcctggta tctttatagt cctgtcgggt ttcgccacct ctgacttgag cgtcgatttt    11940
tgtgatgctc gtcagggggg cggagcctat ggaaaaacgc cagcaacgcg gccttttac     12000 ggttcctggc cttttgctgg ccttttgctc acatgttctt tcctgcgtta tcccctgatt   12060
ctgtggataa ccgtattacc gcctttgagt gagctgatac cgctcgccgc agccgaacga   12120
ccgagcgcag cgagtcagtg agcgaggaag cggaagagcg cccaatacgc aaaccgcctc   12180
tccccgcgcg ttggccgatt cattaatgca gctggcacga caggtttccc gactggaaag   12240
cgggcagtga gcgcaacgca attaatgtga gttagctcac tcattaggca ccccaggctt   12300
tacactttat gctcccggct cgtatgttgt gtggaattgt gagcggataa caatttcaca   12360
caggaaacag ctatgaccat gattacgcca agcgcgcaat taaccctcac taaagggaac   12420
aaaagctggg taccgggccc acgcgtaata cgactcacta tag                     12463
```

<210> SEQ ID NO 102
<211> LENGTH: 574
<212> TYPE: PRT
<213> ORGANISM: Human respiratory syncytial virus

<400> SEQUENCE: 102

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Ala Thr Val Ile Glu Phe Gln
    210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Ile Asn Ile Met Ile Thr
            515                 520                 525

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 103
<211> LENGTH: 574
<212> TYPE: PRT
<213> ORGANISM: Human respiratory syncytial virus

<400> SEQUENCE: 103

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
```

```
            35                  40                  45
Arg Thr Gly Trp Tyr Thr Ser Val Ile Thr Ile Glu Leu Ser Asn Ile
 50                  55                  60
Lys Glu Thr Lys Cys Asn Gly Thr Asp Thr Lys Val Lys Leu Ile Lys
 65                  70                  75                  80
Gln Glu Leu Asp Lys Tyr Lys Asn Ala Val Thr Glu Leu Gln Leu Leu
                 85                  90                  95
Met Gln Asn Thr Pro Ala Ala Asn Asn Arg Ala Arg Arg Glu Ala Pro
                100                 105                 110
Gln Tyr Met Asn Tyr Thr Ile Asn Thr Thr Lys Asn Leu Asn Val Ser
                115                 120                 125
Ile Ser Lys Lys Arg Lys Arg Arg Phe Leu Gly Phe Leu Leu Gly Val
                130                 135                 140
Gly Ser Ala Ile Ala Ser Gly Ile Ala Val Ser Lys Val Leu His Leu
145                 150                 155                 160
Glu Gly Glu Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asn Asn Gln Leu Leu Pro Ile Val Asn
                195                 200                 205
Gln Gln Ser Cys Arg Ile Ser Asn Ile Gly Thr Val Ile Glu Phe Gln
                210                 215                 220
Gln Lys Asn Ser Arg Leu Leu Glu Ile Asn Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
                260                 265                 270
Leu Met Ser Ser Asn Val Gln Ile Val Arg Gln Gln Ser Tyr Ser Ile
                275                 280                 285
Met Ser Ile Ile Lys Glu Glu Val Leu Ala Tyr Val Val Gln Leu Pro
290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Asp Thr Cys Lys Val Gln Ser Asn Arg Val Phe Cys Asp
                355                 360                 365
Thr Met Asn Ser Leu Thr Leu Pro Ser Glu Val Ser Leu Cys Asn Thr
                370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
                435                 440                 445
Thr Val Ser Val Gly Asn Thr Leu Tyr Tyr Val Asn Lys Leu Glu Gly
450                 455                 460
```

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
        500                 505                 510

Leu His Asn Val Asn Thr Gly Lys Ser Thr Thr Asn Ile Met Ile Thr
            515                 520                 525

Thr Ile Ile Ile Val Ile Ile Val Val Leu Leu Ser Leu Ile Ala Ile
        530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
            565                 570

<210> SEQ ID NO 104
<211> LENGTH: 574
<212> TYPE: PRT
<213> ORGANISM: Human respiratory syncytial virus

<400> SEQUENCE: 104

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys 260                 265                 270
Leu Met Ser Ser Asn Val Gln Ile Val Arg Gln Gln Ser Tyr Ser Ile
                275                 280                 285
Met Ser Ile Ile Lys Glu Glu Val Leu Ala Tyr Val Val Gln Leu Pro
            290                 295                 300
Ile Tyr Gly Val Ile Asp Thr Pro Cys Trp Lys Leu His Thr Ser Pro
305                 310                 315                 320
Leu Cys Thr Thr Asn Ile Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
    370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Leu Glu Gly
    450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Arg Ser Asp Glu Leu
            500                 505                 510
Leu His Asn Val Asn Thr Gly Lys Ser Thr Thr Asn Ile Met Ile Thr
        515                 520                 525
Thr Ile Ile Ile Val Ile Ile Val Val Leu Leu Ser Leu Ile Ala Ile
    530                 535                 540
Gly Leu Leu Leu Tyr Cys Lys Ala Lys Asn Thr Pro Val Thr Leu Ser
545                 550                 555                 560
Lys Asp Gln Leu Ser Gly Ile Asn Asn Ile Ala Phe Ser Lys
                565                 570

<210> SEQ ID NO 105
<211> LENGTH: 574
<212> TYPE: PRT
<213> ORGANISM: Human respiratory syncytial virus

<400> S

```
Lys Glu Asn Lys Cys Asn Gly Thr Asp Ala Lys Val Lys Leu Ile Asn
 65                  70                  75                  80

Gln Glu Leu Asp Lys Tyr Lys Asn Ala Val Thr Glu Leu Gln Leu Leu
                 85                  90                  95

Met Gln Ser Thr Thr Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
```

```
                        485                 490                 495
Glu Lys Ile Asn Gln Ser Leu Ala Phe Ile Arg Lys Ser Asp Glu Leu
                    500                 505                 510

Leu His His Val Asn Ala Gly Lys Ser Thr Thr Asn Ile Met Ile Thr
                515                 520                 525

Thr Ile Ile Ile Val Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 106
<211> LENGTH: 574
<212> TYPE: PRT
<213> ORGANISM: Human respiratory syncytial virus

<400> SEQUENCE: 106

Met Glu Leu Leu Ile His Arg Ser Ser Ala Ile Phe Leu Thr Leu Ala
1               5                   10                  15

Val Asn Ala Le

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 107
<211> LENGTH: 574
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (4)..(4)
<223> OTHER INFORMATION: Leu or Pro
<220> FEATURE:
<221> NAME/KEY: MOD_RES
<222> LOCATION: (6)..(6)
<223> OTHER INFORMATION: His or Leu
<220> FEATURE:
<221> NAME/KEY: MOD_RES
<222> LOCATION: (7)..(7)
<223> OTHER INFORMATION: Arg or Lys
<220> FEATURE:
<221> NAME/KEY: MOD_RES
<222> LOCATION: (8)..(8)
<223> OTHER INFORMATION: Leu, Ser or Ala
<220> FEATURE:

-continued

```
<221> NAME/KEY: MOD_RES
<222> LOCATION: (9)..(9)
<223> OTHER INFORMATION: Ser or Asn
<220> FEATURE:
<221> NAME/KEY: MOD_RES
<222> LOCATION: (12)..(12)
<223> OTHER INFORMATION: Phe or Thr
<220> FEATURE:
<221> NAME/KEY: MOD_RES
<222> LOCATION: (13)..(13)
<223> OTHER INFORMATION: Leu or Thr
<220> FEATURE:
<221> NAME/KEY: MOD_RES
<222> LOCATION: (14)..(14)
<223> OTHER INFORMATION: Thr or Ile
<220> FEATURE:
<221> NAME/KEY: MOD_RES
<222> LOCATION: (16)..(16)
<223> OTHER INFORMATION: Ala or Thr
<220> FEATURE:
<221> NAME/KEY: MOD_RES
<222> LOCATION: (17)..(17)
<223> OTHER INFORMATION: Ile, Val or Ala
<220> FEATURE:
<221> NAME/KEY: MOD_RES
<222> LOCATION: (18)..(18)
<223> OTHER INFORMATION: Asn or Val
<220> FEATURE:
<221> NAME/KEY: MOD_RES
<222> LOCATION: (19)..(19)
<223> OTHER INFORMATION: Ala or Thr
<220> FEATURE:
<221> NAME/KEY: MOD_RES
<222> LOCATION: (20)..(20)
<223> OTHER INFORMATION: Leu or Phe
<220> FEATURE:
<221> NAME/KEY: MOD_RES
<222> LOCATION: (21)..(21)
<223> OTHER INFORMATION: Tyr or Cys
<220> FEATURE:
<221> NAME/KEY: MOD_RES
<222> LOCATION: (22)..(22)
<223> OTHER INFORMATION: Leu or Phe
<220> FEATURE:
<221> NAME/KEY: MOD_RES
<222> LOCATION: (23)..(23)
<223> OTHER INFORMATION: Thr or Ala
<220> FEATURE:
<221> NAME/KEY: MOD_RES
<222> LOCATION: (25)..(25)
<223> OTHER INFORMATION: Ser or Gly
<220> FEATURE:
<221> NAME/KEY: MOD_RES
<222> LOCATION: (42)..(42)
<223> OTHER INFORMATION: Arg or Lys
<220> FEATURE:
<221> NAME/KEY: MOD_RES
<222> LOCATION: (45)..(45)
<223> OTHER INFORMATION: Phe or Leu
<220> FEATURE:
<221> NAME/KEY: MOD_RES
<222> LOCATION: (67)..(67)
<223> OTHER INFORMATION: Thr or Asn
<220> FEATURE:
<221> NAME/KEY: MOD_RES
<222> LOCATION: (74)..(74)
<223> OTHER INFORMATION: Thr or Ala
<220> FEATURE:
<221> NAME/KEY: MOD_RES
<222> LOCATION: (80)..(80)
<223> OTHER INFORMATION: Lys or Asn
<220> FEATURE:
<221> NAME/KEY: MOD_RES
<222> LOCATION: (99)..(99)
<223> OTHER INFORMATION: Asn or Ser
<220> FEATURE:
<221> NAME/KEY: MOD_RES
<222> LOCATION: (101)..(101)
<223> OTHER INFORMATION: Pro or Thr
```

```
<220> FEATURE:
<221> NAME/KEY: MOD_RES
<222> LOCATION: (103)..(103)
<223> OTHER INFORMATION: Ala or Thr
<220> FEATURE:
<221> NAME/KEY: MOD_RES
<222> LOCATION: (111)..(111)
<223> OTHER INFORMATION: Ala or Leu
<220> FEATURE:
<221> NAME/KEY: MOD_RES
<222> LOCATION: (113)..(113)
<223> OTHER INFORMATION: Gln or Arg
<220> FEATURE:
<221> NAME/KEY: MOD_RES
<222> LOCATION: (114)..(114)
<223> OTHER INFORMATION: Tyr or Phe
<220> FEATURE:
<221> NAME/KEY: MOD_RES
<222> LOCATION: (119)..(119)
<223> OTHER INFORMATION: Ile or Leu
<220> FEATURE:
<221> NAME/KEY: MOD_RES
<222> LOCATION: (121)..(121)
<223> OTHER INFORMATION: Thr or Asn
<220> FEATURE:
<221> NAME/KEY: MOD_RES
<222> LOCATION: (122)..(122)
<223> OTHER INFORMATION: Thr or Ala
<220> FEATURE:
<221> NAME/KEY: MOD_RES
<222> LOCATION: (124)..(124)
<223> OTHER INFORMATION: Asn or Lys
<220> FEATURE:
<221> NAME/KEY: MOD_RES
<222> LOCATION: (125)..(125)
<223> OTHER INFORMATION: Leu or Thr
<220> FEATURE:
<221> NAME/KEY: MOD_RES
<222> LOCATION: (128)..(128)
<223> OTHER INFORMATION: Ser or Thr
<220> FEATURE:
<221> NAME/KEY: MOD_RES
<222> LOCATION: (129)..(129)
<223> OTHER INFORMATION: Ile or Leu
<220> FEATURE:
<221> NAME/KEY: MOD_RES
<222> LOCATION: (152)..(152)
<223> OTHER INFORMATION: Ile or Val
<220> FEATURE:
<221> NAME/KEY: MOD_RES
<222> LOCATION: (169)..(169)
<223> OTHER INFORMATION: Asn or Ser
<220> FEATURE:
<221> NAME/KEY: MOD_RES
<222> LOCATION: (200)..(200)
<223> OTHER INFORMATION: Asn or Asp
<220> FEATURE:
<221> NAME/KEY: MOD_RES
<222> LOCATION: (201)..(201)
<223> OTHER INFORMATION: Asn or Lys
<220> FEATURE:
<221> NAME/KEY: MOD_RES
<222> LOCATION: (202)..(202)
<223> OTHER INFORMATION: Gln or Arg
<220> FEATURE:
<221> NAME/KEY: MOD_RES
<222> LOCATION: (209)..(209)
<223> OTHER INFORMATION: Gln or Lys
<220> FEATURE:
<221> NAME/KEY: MOD_RES
<222> LOCATION: (213)..(213)
<223> OTHER INFORMATION: Arg or Ser
<220> FEATURE:
<221> NAME/KEY: MOD_RES
<222> LOCATION: (218)..(218)
<223> OTHER INFORMATION: Gly, Glu or Ala
<220> FEATURE:
<221> NAME/KEY: MOD_RES
<222> LOCATION: (226)..(226)
```

```
<223> OTHER INFORMATION: Lys or Met
<220> FEATURE:
<221> NAME/KEY: MOD_RES
<222> LOCATION: (228)..(228)
<223> OTHER INFORMATION: Ser or Asn
<220> FEATURE:
<221> NAME/KEY: MOD_RES
<222> LOCATION: (234)..(234)
<223> OTHER INFORMATION: Asn or Thr
<220> FEATURE:
<221> NAME/KEY: MOD_RES
<222> LOCATION: (247)..(247)
<223> OTHER INFORMATION: Leu or Val
<220> FEATURE:
<221> NAME/KEY: MOD_RES
<222> LOCATION: (276)..(276)
<223> OTHER INFORMATION: Ser or Asn
<220> FEATURE:
<221> NAME/KEY: MOD_RES
<222> LOCATION: (305)..(305)
<223> OTHER INFORMATION: Ile or Leu
<220> FEATURE:
<221> NAME/KEY: MOD_RES
<222> LOCATION: (326)..(326)
<223> OTHER INFORMATION: Ile or Thr
<220> FEATURE:
<221> NAME/KEY: MOD_RES
<222> LOCATION: (356)..(356)
<223> OTHER INFORMATION: Asp or Glu
<220> FEATURE:
<221> NAME/KEY: MOD_RES
<222> LOCATION: (380)..(380)
<223> OTHER INFORMATION: Ser or Asn
<220> FEATURE:
<221> NAME/KEY: MOD_RES
<222> LOCATION: (384)..(384)
<223> OTHER INFORMATION: Thr or Val
<220> FEATURE:
<221> NAME/KEY: MOD_RES
<222> LOCATION: (389)..(389)
<223> OTHER INFORMATION: Ser or Pro
<220> FEATURE:
<221> NAME/KEY: MOD_RES
<222> LOCATION: (402)..(402)
<223> OTHER INFORMATION: Ile or Val
<220> FEATURE:
<221> NAME/KEY: MOD_RES
<222> LOCATION: (462)..(462)
<223> OTHER INFORMATION: Leu or Gln
<220> FEATURE:
<221> NAME/KEY: MOD_RES
<222> LOCATION: (466)..(466)
<223> OTHER INFORMATION: Asn or Ser
<220> FEATURE:
<221> NAME/KEY: MOD_RES
<222> LOCATION: (477)..(477)
<223> OTHER INFORMATION: Tyr or Phe
<220> FEATURE:
<221> NAME/KEY: MOD_RES
<222> LOCATION: (508)..(508)
<223> OTHER INFORMATION: Arg or Lys
<220> FEATURE:
<221> NAME/KEY: MOD_RES
<222> LOCATION: (515)..(515)
<223> OTHER INFORMATION: Asn or His
<220> FEATURE:
<221> NAME/KEY: MOD_RES
<222> LOCATION: (518)..(518)
<223> OTHER INFORMATION: Thr or Ala
<220> FEATURE:
<221> NAME/KEY: MOD_RES
<222> LOCATION: (523)..(523)
<223> OTHER INFORMATION: Thr or Ile
<220> FEATURE:
<221> NAME/KEY: MOD_RES
<222> LOCATION: (537)..(537)
<223> OTHER INFORMATION: Val or Ile
<220> FEATURE:
<221> NAME/KEY: MOD_RES
```

```
<222> LOCATION: (544)..(544)
<223> OTHER INFORMATION: Ile or Val
<220> FEATURE:
<221> NAME/KEY: MOD_RES
<222> LOCATION: (553)..(553)
<223> OTHER INFORMATION: Lys or Arg
<220> FEATURE:
<221> NAME/KEY: MOD_RES
<222> LOCATION: (554)..(554)
<223> OTHER INFORMATION: Asn or Ser
<220> FEATURE:
<221> NAME/KEY: MOD_RES
<222> LOCATION: (574)..(574)
<223> OTHER INFORMATION: Lys or Asn

<400> SEQUENCE: 107

Met Glu Leu Xaa Ile Xaa Xaa Xaa Xaa Ala Ile Xaa Xaa Xaa Leu Xaa
1               5                   10                  15

Xaa Xaa Xaa Xaa Xaa Xaa Xaa Ser Xaa Gln Asn Ile Thr Glu Glu Phe
            20                  25                  30

Tyr Gln Ser Thr Cys Ser Ala Val Ser Xaa Gly Tyr Xaa Ser Ala Leu
        35                  40                  45

Arg Thr Gly Trp Tyr Thr Ser Val Ile Thr Ile Glu Leu Ser Asn Ile
50                  55                  60

Lys Glu Xaa Lys Cys Asn Gly Thr Asp Xaa Lys Val Lys Leu Ile Xaa
65                  70                  75                  80

Gln Glu Leu Asp Lys Tyr Lys Asn Ala Val Thr Glu Leu Gln Leu Leu
                85                  90                  95

Met Gln Xaa Thr Xaa Ala Xaa Asn Asn Arg Ala Arg Arg Glu Xaa Pro
            100                 105                 110

Xaa Xaa Met Asn Tyr Thr Xaa Asn Xaa Xaa Lys Xaa Xaa Asn Val Xaa
115                 120                 125

Xaa Ser Lys Lys Arg Lys Arg Arg Phe Leu Gly Phe Leu Leu Gly Val
130                 135                 140

Gly Ser Ala Ile Ala Ser Gly Xaa Ala Val Ser Lys Val Leu His Leu
145                 150                 155                 160

Glu Gly Glu Val Asn Lys Ile Lys Xaa Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Xaa Xaa Xaa Leu Leu Pro Ile Val Asn
        195                 200                 205

Xaa Gln Ser Cys Xaa Ile Ser Asn Ile Xaa Thr Val Ile Glu Phe Gln
210                 215                 220

Gln Xaa Asn Xaa Arg Leu Leu Glu Ile Xaa Arg Glu Phe Ser Val Asn
225                 230                 235                 240

Ala Gly Val Thr Thr Pro Xaa Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Xaa Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Xaa Tyr Gly Val Ile Asp Thr Pro Cys Trp Lys Leu His Thr Ser Pro
305                 310                 315                 320

Leu Cys Thr Thr Asn Xaa Lys Glu Gly Ser Asn Ile Cys Leu Thr Arg
                325                 330                 335
```

Thr Asp Arg Gly Trp Tyr Cys Asp Asn Ala Gly Ser Val Ser Phe Phe
            340                 345                 350

Pro Gln Ala Xaa Thr Cys Lys Val Gln Ser Asn Arg Val Phe Cys Asp
            355                 360                 365

Thr Met Asn Ser Leu Thr Leu Pro Ser Glu Val Xaa Leu Cys Asn Xaa
    370                 375                 380

Asp Ile Phe Asn Xaa Lys Tyr Asp Cys Lys Ile Met Thr Ser Lys Thr
385                 390                 395                 400

Asp Xaa Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Xaa Glu Gly
    450                 455                 460

Lys Xaa Leu Tyr Val Lys Gly Glu Pro Ile Ile Asn Xaa Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Xaa Ser Asp Glu Leu
            500                 505                 510

Leu His Xaa Val Asn Xaa Gly Lys Ser Thr Xaa Asn Ile Met Ile Thr
            515                 520                 525

Thr Ile Ile Val Ile Ile Val Xaa Leu Leu Ser Leu Ile Ala Xaa
            530                 535                 540

Gly Leu Leu Leu Tyr Cys Lys Ala Xaa Xaa Thr Pro Val Thr Leu Ser
545                 550                 555                 560

Lys Asp Gln Leu Ser Gly Ile Asn Asn Ile Ala Phe Ser Xaa
            565                 570

<210> SEQ ID NO 108
<211> LENGTH: 51
<212> TYPE: PRT
<213> ORGANISM: Human respiratory syncytial virus

<400> SEQUENCE: 108

Thr Pro Ala Thr Asn Asn Arg Ala Arg Arg Glu Leu Pro Arg Phe Met
1               5                   10                  15

Asn Tyr Thr Leu Asn Asn Ala Lys Lys Thr Asn Val Thr Leu Ser Lys
            20                  25                  30

Lys Arg Lys Arg Arg Phe Leu Gly Phe Leu Leu Gly Val Gly Ser Ala
        35                  40                  45

Ile Ala Ser
    50

<210> SEQ ID NO 109
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Thr Pro Ala Thr Asn Asn Arg Ala Arg Gln Gln Asn Gln Gln Gln Arg
1               5                   10                  15

```
Phe Leu Gly Phe Leu Leu Gly Val Gly Ser Ala Ile Ala Ser
            20                  25                  30

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 110

His His His His His His
1               5

<210> SEQ ID NO 111
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(100)
<223> OTHER INFORMATION: This sequence may encompass 3-100 Lys residues

<400> SEQUENCE: 111

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys Lys
        35                  40                  45

Lys Lys Lys Lys Lys Lys Lys Lys Lys Lys Lys Lys Lys Lys Lys Lys
    50                  55                  60

Lys Lys Lys Lys Lys Lys Lys Lys Lys Lys Lys Lys Lys Lys Lys Lys
65                  70                  75                  80

Lys Lys Lys Lys Lys Lys Lys Lys Lys Lys Lys Lys Lys Lys Lys Lys
                85                  90                  95

Lys Lys Lys Lys
            100

<210> SEQ ID NO 112
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ile Met Ile Thr Thr Ile Ile Val Ile Ile Val Ile Leu Leu Ser
1               5                   10                  15

Leu Ile Ala Val Gly Leu Leu Leu Tyr Cys Lys Ala Arg Ser Thr Pro
            20                  25                  30

Val Thr Leu Ser Lys Asp Gln Leu Ser Gly Ile Asn Asn Ile Ala Phe
        35                  40                  45

Ser Asn
    50
```